US009872846B2

(12) United States Patent
Yu et al.

(10) Patent No.: US 9,872,846 B2
(45) Date of Patent: Jan. 23, 2018

(54) HIGH PENETRATION COMPOSITIONS AND USES THEREOF

(71) Applicant: Techfields Pharma Co., Ltd., Suzhou, Jiangsu (CN)

(72) Inventors: Chongxi Yu, Kensington, MD (US); Lina Xu, Shanghai (CN)

(73) Assignee: Techfields Pharma Co., Ltd., Suzhou, Jiangsu (CN)

( * ) Notice: Subject to any disclaimer, the term of this patent is extended or adjusted under 35 U.S.C. 154(b) by 0 days.

(21) Appl. No.: 15/402,618

(22) Filed: Jan. 10, 2017

(65) Prior Publication Data

US 2017/0209404 A1    Jul. 27, 2017

Related U.S. Application Data

(60) Division of application No. 12/351,804, filed on Jan. 9, 2009, now abandoned, which is a continuation-in-part of application No. PCT/IB2006/052318, filed on Jul. 9, 2006, and a continuation-in-part of application No. PCT/IB2006/052461, filed on Jul. 18, 2006, and a continuation-in-part of application No. PCT/IB2006/052549, filed on Jul. 25, 2006, and a continuation-in-part of application No. PCT/IB2006/052563, filed on Jul. 26, 2006, and a continuation-in-part of application No. PCT/IB2006/052575, filed on Jul. 27, 2006, and a continuation-in-part of application No. PCT/IB2006/052732, filed on Aug. 8, 2006, and a continuation-in-part of application No. PCT/IB2006/052815, filed on Aug. 15, 2006, and a continuation-in-part of application No. PCT/IB2006/053090, filed on Sep. 3, 2006, and a continuation-in-part of application No. PCT/IB2006/053741, filed on Oct. 11, 2006.

(51) Int. Cl.

| A61K 31/625 | (2006.01) |
| A61K 31/60 | (2006.01) |
| A61K 31/216 | (2006.01) |
| A61K 9/14 | (2006.01) |
| A61K 31/24 | (2006.01) |
| A61L 15/44 | (2006.01) |
| A61K 47/48 | (2006.01) |
| A61K 9/00 | (2006.01) |
| A61K 9/70 | (2006.01) |

(52) U.S. Cl.
CPC .......... *A61K 31/216* (2013.01); *A61K 9/0014* (2013.01); *A61K 9/0043* (2013.01); *A61K 9/0073* (2013.01); *A61K 9/703* (2013.01); *A61K 31/24* (2013.01); *A61K 47/48023* (2013.01); *A61L 15/44* (2013.01); *A61L 2300/21* (2013.01)

(58) Field of Classification Search
None
See application file for complete search history.

(56) References Cited

U.S. PATENT DOCUMENTS

| 1,815,802 A | 7/1931 | Schleicher et al. |
| 2,671,805 A | 3/1954 | Krimmel et al. |
| 3,365,483 A | 1/1968 | Jerzmanowska et al. |
| 3,420,871 A | 1/1969 | Scherrer et al. |
| 3,476,791 A | 11/1969 | Newman et al. |
| 3,488,380 A | 1/1970 | Goldhamer et al. |
| 3,704,298 A | 11/1972 | Zinnes et al. |
| 3,787,324 A | 1/1974 | Zinnes et al. |
| 3,821,279 A | 6/1974 | Kurono et al. |

(Continued)

FOREIGN PATENT DOCUMENTS

| AU | 2004201178 A1 | 4/2004 |
| CA | 1246446 | 12/1988 |

(Continued)

OTHER PUBLICATIONS

Schafer et al. Drug Discovery Today, 2008, 13 (21/22), 913-916.*
Horig et al. Journal of Translational Medicine 2004, 2(44), p. 1-8.*
Agawa, T., et al., "Stabilities of Vitamin A Urethans," Kogyo Kagaku Zasshi 58:686-688 (1955).
Allegretti, M. et al., "2-Arylpropionic CXC Chemokine Receptor 1 (CXCR1) Ligands as Novel Noncompetitive CXCL8 Inhibitors," J. Medic. Chem. 48(13):4312-4331 (2005).
Altuntas, T. G., et al., "A Study on the Interation Between p60c-src Receptor Tyrosine Kinase and Arylcarboxylic and Arylacetic Acid Derivatives Based on Docking Modes and In Vitro Activity," Biol. Pharm. Bull. 27(1):61-65 (2004 ).
Amin, R. C., et al., "Diethylaminoethyl Dialkylacetates," J. Amer. Pharma. Association 37:243-245 (1948).
Andrews, J. M., "Determination of Minimum Inhibitory Concentrations," Journal of Antimicrobial Chemotherapy 48, suppl. S1: 5-16 (2001).

(Continued)

*Primary Examiner* — Yong Chu
(74) *Attorney, Agent, or Firm* — Finnegan, Henderson, Farabow, Garrett & Dunner LLP

(57) ABSTRACT

The present invention relates to compositions and uses of novel high penetration compositions or high penetration prodrugs (HPP), in particular HPPs for non-steroidal anti-inflammatory agents (NSAIAs), which are capable of crossing biological barriers with high penetration efficiency. The HPPs herein are capable of being converted to parent active drugs or drug metabolites after crossing the biological barrier and thus can render treatments for the conditions that the parent drugs or metabolites can. Additionally, due to the ability of penetrating biological barriers, the HPPs herein are capable of reaching areas that parent drugs may not be able to access or to render a sufficient concentration at the target areas and therefore render novel treatments. The HPPs herein can be administered to a subject through various administration routes. For example, the HPPs can be locally delivered to an action site of a condition with a high concentration due to their ability of penetrating biological barriers and thus obviate the need for a systematic administration. For another example, the HPPs herein can be systematically administer to a biological subject and enter the general circulation with a faster rate.

20 Claims, 56 Drawing Sheets

(56) References Cited

U.S. PATENT DOCUMENTS

| | | |
|---|---|---|
| 3,822,258 A | 7/1974 | Zinnes et al. |
| 3,956,363 A | 5/1976 | Shen et al. |
| 3,957,754 A | 5/1976 | Lund |
| 3,966,923 A | 6/1976 | Serre |
| 4,006,181 A | 2/1977 | Cousse et al. |
| 4,012,508 A | 3/1977 | Burton |
| 4,035,376 A | 7/1977 | Janssen et al. |
| 4,044,049 A | 8/1977 | Ruyle et al. |
| 4,127,671 A | 11/1978 | Cognacq |
| 4,146,637 A | 3/1979 | Metz et al. |
| 4,180,662 A | 12/1979 | Pfister et al. |
| 4,180,665 A | 12/1979 | Schwander et al. |
| 4,207,332 A | 6/1980 | Hayashi et al. |
| 4,244,948 A | 1/1981 | Boghosian et al. |
| 4,376,768 A | 3/1983 | Ozaki et al. |
| 4,472,431 A | 9/1984 | Toth |
| 4,543,353 A | 9/1985 | Faustini et al. |
| 4,551,452 A | 11/1985 | Marfat |
| 4,623,486 A | 11/1986 | Lombardino |
| 4,640,689 A | 2/1987 | Sibalis |
| 4,640,911 A | 2/1987 | Baschang et al. |
| 4,689,338 A | 8/1987 | Gerster |
| 4,743,704 A | 5/1988 | Nicolini |
| 4,746,509 A | 5/1988 | Haggiage et al. |
| 4,822,773 A | 4/1989 | Alexander et al. |
| 5,081,118 A | 1/1992 | Braisted et al. |
| 5,100,918 A | 3/1992 | Sunshine et al. |
| 5,134,165 A | 7/1992 | Hirsch-Kauffmann |
| 5,190,953 A | 3/1993 | Munson, Jr. et al. |
| 5,192,753 A | 3/1993 | McGeer et al. |
| 5,331,000 A | 7/1994 | Young et al. |
| 5,399,562 A | 3/1995 | Becker |
| 5,570,559 A | 11/1996 | Lewis |
| 5,604,259 A | 2/1997 | Jee |
| 5,607,691 A | 3/1997 | Hale et al. |
| 5,654,337 A | 8/1997 | Roentsch et al. |
| 5,760,261 A | 6/1998 | Guttag |
| 5,861,170 A | 1/1999 | Kissel |
| 5,885,597 A | 3/1999 | Botknecht et al. |
| 5,902,110 A | 5/1999 | Alfano et al. |
| 6,011,049 A | 1/2000 | Whitcomb |
| 6,054,457 A | 4/2000 | Setoi et al. |
| 6,190,690 B1 | 2/2001 | Park et al. |
| 6,193,996 B1 | 2/2001 | Effing et al. |
| 6,262,121 B1 | 7/2001 | Kawaji et al. |
| 6,346,278 B1 | 2/2002 | Macrides et al. |
| 6,368,618 B1 | 4/2002 | Jun et al. |
| 6,416,772 B1 | 7/2002 | Van Engelen et al. |
| 6,444,234 B1 | 9/2002 | Kirby et al. |
| 6,528,040 B1 | 3/2003 | Pearson et al. |
| 6,592,891 B1 | 7/2003 | Donati et al. |
| 6,593,365 B1 | 7/2003 | Yung-Yu Hung et al. |
| 6,635,674 B1 | 10/2003 | Kaneko et al. |
| 6,638,528 B1 | 10/2003 | Kanios |
| 6,693,135 B2 | 2/2004 | Yeager et al. |
| 6,723,337 B1 | 4/2004 | Song et al. |
| 6,773,724 B2 | 8/2004 | Franckowiak et al. |
| 7,052,715 B2 | 5/2006 | Fishman |
| 7,256,210 B2 | 8/2007 | Man et al. |
| 2001/0038861 A1 | 11/2001 | Hsu et al. |
| 2002/0142607 A1 | 10/2002 | Gabriel et al. |
| 2003/0152611 A1 | 8/2003 | Illel et al. |
| 2004/0022837 A1 | 2/2004 | Hsu et al. |
| 2004/0229920 A1 | 11/2004 | Garvey et al. |
| 2004/0254182 A1 | 12/2004 | Mulvihill et al. |
| 2004/0266870 A1 | 12/2004 | Allegretti et al. |
| 2005/0037922 A1 | 2/2005 | Bickers et al. |
| 2005/0049255 A1 | 3/2005 | Bictash et al. |
| 2005/0080067 A1 | 4/2005 | Allegretti et al. |
| 2005/0107463 A1 | 5/2005 | Woodward et al. |
| 2005/0272108 A1 | 12/2005 | Kalra et al. |
| 2006/0003428 A1 | 1/2006 | Tsai |
| 2006/0024365 A1 | 2/2006 | Vaya et al. |
| 2006/0172002 A1 | 8/2006 | Takada et al. |

FOREIGN PATENT DOCUMENTS

| | | | |
|---|---|---|---|
| CA | 2614312 A1 | 1/2007 | |
| DE | 3023206 A1 | 1/1982 | |
| EP | 152379 A2 | 8/1985 | |
| EP | 202062 A2 | 11/1986 | |
| EP | 237495 A2 | 9/1987 | |
| EP | 289262 A2 | 11/1988 | |
| EP | 0208404 B1 | 8/1990 | |
| EP | 208404 B1 | 8/1990 | |
| EP | 469450 A1 | 5/1992 | |
| EP | 659442 A1 | 6/1995 | |
| FR | 5342 M | 9/1967 | |
| FR | 1593024 A | 5/1970 | |
| FR | 2410641 A1 | 6/1979 | |
| GB | 958186 A | 5/1964 | |
| GB | 984471 | 2/1965 | |
| GB | 1000208 | 8/1965 | |
| GB | 1081055 | 8/1967 | |
| GB | 1165300 | 9/1969 | |
| GB | 1187259 A | 4/1970 | |
| GB | 2154585 A | 9/1985 | |
| JP | 53130634 A | 11/1978 | |
| JP | 54003044 A | 1/1979 | |
| JP | 57-183738 A | 11/1982 | |
| JP | 2004-525112 | 8/2004 | |
| JP | 2005-504121 | 2/2005 | |
| WO | WO 1990/02141 A1 | 3/1990 | |
| WO | WO 1990/08128 | 7/1990 | |
| WO | WO 1993/07902 | 4/1993 | |
| WO | WO 1993/14743 A2 | 8/1993 | |
| WO | WO 1993/17677 A1 | 9/1993 | |
| WO | WO 1993/25197 | 12/1993 | |
| WO | WO 1993/25703 A1 | 12/1993 | |
| WO | WO 1994/00449 | 1/1994 | |
| WO | WO 9407471 A1 * | 4/1994 | ............ A61K 31/52 |
| WO | WO 1994/10167 | 5/1994 | |
| WO | WO 1994/20635 A1 | 9/1994 | |
| WO | WO 1995/34813 | 12/1995 | |
| WO | WO 1996/28144 | 9/1996 | |
| WO | WO 1997/44020 A1 | 11/1997 | |
| WO | WO 1997/45113 A1 | 12/1997 | |
| WO | WO 1998/40061 | 9/1998 | |
| WO | WO 1998/47502 A1 | 10/1998 | |
| WO | WO 2001/054481 | 8/2001 | |
| WO | WO 2001/58852 A2 | 8/2001 | |
| WO | WO 2001/85143 A2 | 11/2001 | |
| WO | WO 2002/00167 | 1/2002 | |
| WO | WO 2002/68377 A1 | 9/2002 | |
| WO | WO 2002/85297 A2 | 10/2002 | |
| WO | WO 2003/022270 A1 | 3/2003 | |
| WO | WO 2003/29187 A1 | 4/2003 | |
| WO | WO 2003/61713 | 7/2003 | |
| WO | WO 2004000300 A1 | 12/2003 | |
| WO | WO 2004/004648 A2 | 1/2004 | |
| WO | WO 2005/68421 A1 | 7/2005 | |
| WO | WO 2005/97099 A1 | 10/2005 | |
| WO | WO 2006/74249 A1 | 7/2006 | |
| WO | WO 2006/128184 A2 | 11/2006 | |
| WO | WO 2008/007171 A1 | 1/2008 | |
| WO | WO 2008/010025 A1 | 1/2008 | |
| WO | WO 2008/012602 A1 | 1/2008 | |
| WO | WO 2008/012603 A1 | 1/2008 | |
| WO | WO 2008/012605 A1 | 1/2008 | |
| WO | WO 2008/017903 A1 | 2/2008 | |
| WO | WO 2008/020270 A1 | 2/2008 | |
| WO | WO 2008/026776 | 3/2008 | |
| WO | WO 2008/029199 A1 | 3/2008 | |
| WO | WO 2008/029200 A1 | 3/2008 | |
| WO | WO 2008/041054 A1 | 4/2008 | |
| WO | WO 2008/041059 A1 | 4/2008 | |
| WO | WO 2008/044095 A1 | 4/2008 | |
| WO | WO 2008/056207 A1 | 5/2008 | |
| WO | WO 2008/072032 A1 | 6/2008 | |

(56) References Cited

FOREIGN PATENT DOCUMENTS

| WO | WO 2008/087493 A1 | 7/2008 |
|---|---|---|
| WO | WO 2008/093173 A1 | 8/2008 |
| WO | WO 2008/149181 A1 | 12/2008 |

OTHER PUBLICATIONS

Apt, L., et al., "A Randomized Clinical Trial of the Nonsteroidal Eyedrop Diclofenac After Strabismus Surgery," Ophthalmology 105:1448-1454 (1998).
Arora, P., et al., "Design Development, Physicochemical, and In Vitro and In Vivo Evaluation of Transdermal Patches Containing Diclofenac Diethylammonium Salt," J. Pharm. Sci. 91:2076-2089 (2002).
Barcia, E., et al., "Influence of Medium and Temperature on the Hydrolysis Kenetics of Propacetamol Hydrochloride: Determination Using Derivative Spectrophotometry," Chem. Pharm. Bull. 53(3):277-280 (2005).
Battaglino, R., et al., "Fluoxetine Treatment Increases Trabecular Bone Formation in Mice (Fluoxetine Affects Bone Mass)," J. Cell Biochem. 100(6):1387-1394 (2007).
Berge, S. M., et al., "Pharmaceutical Salts," J. Pharm. Sci. 66:1-19 (1977).
Brown, K., et al., "Nonsteroidal Antiinftammatory Agents. 1.2,4-Diphenylthiazole-5-acetic Acid and Related Compounds," J. Med. Chem.17(11):1177-1181 (1975).
Bundgaard, H., et al., "Prodrugs as Drug Delivery Systems IV: N-Mannich Bases as Potential Novel Prodrugs for Amides, Ureides, Amines, and Other NH-Acidic Compounds," J. Pharm. Sci. 69:44-46 (1980).
Campbell, C. L., et al., "Aspirin Dose for the Prevention of Cardiovascular Disease," JAMA 297(18):2018-2024 (2007).
Cannon, J. G., "Analog Design", Chapter Nineteen in Burger's Medicinal Chemistry and Drug Discovery, Fifth Edition, vol. I: Principles and Practice, Wiley-Interscience 1995, pp. 783-802, 784.
Carrico, D., et al., "In Vitro and In Vivo Antimalarial of Peptidomimetic Protein Farnesyltransferase Inhibitors with Improved Membrane Permeability," Bioorg. Med. Chem. 12(24):6517-6526 (2004).
Cevc, G., et al., "New, Highly Efficient Formulation of Diclofenac for the Topical, Transdermal Administration in Ultradeformable Drug Carriers, Transfersomes," Biochim. Biophys. Acta 1514:191-205 (2001).
Chanal, J. L., et al., "Etude de la Distribution et de L'Elimination Chez le Rat de L'Acetyl Salicylate de Dimethyl Amino Ethyle Influence de la Position du Marquage au Carbone 14," Boll. Chim. Farm. 119:331-338 (1980).
Cwalina, G. E., et al., "Synthesis and Stability Studies of Certain Disubstituted Aminoacetoxybenzoic Acids," J. Organic Chem. 26:3344-3346 (1961).
Dalpiaz, A., et al., "Vitamin C and 6-Amino-Vitamin C Conjugates of Diclofenac: Synthesis and Evaluation," International Journal of Pharmaceutics 291 (1-2):171-181 (2005).
D'Amour, F. E., et al., "A Method for Determining Loss of Pain Sensation," J. Pharmacol. Exp. Ther. 72:74-79 (1941).
Database Caplus [Online] Chemical Abstracts Service, Columbus, OH, US; "Esters of .Omega.-Aminoaliphatic Acids and p-Acetamidophenol," retrieved from STN database accession No. 1969:3537 (Oct. 18, 2010).
Diven, W. F., et al., "Treatment of Experimental Acute Otitis Media with Ibuprofen and Ampicillin," Int. J. Pediatric Otorhinolaryngology 33:127-139 (1995).
Drachman, D. B., et al., "Cyclooxygenase 2 Inhibition Protects Motor Neurons and Prolongs Survival in a Transgenic Mouse Model of ALS," Ann. Neurol. 52:771-778 (2002).
Erlanson-Albertsson, C., et al., "Enterostatin—A Peptide Regulating Fat Intake," Obes. Rev. 5(4):360-372 (1997).
Foye's, W. O., et al., Medicinal Chemistry, 4th Ed., Williams & Wilkins, p. 549 (1995).
Funt, L. S., "Oral Ibuprofen and Minocycline for the Treatment of Resistant Acne Vulgaris," J. Amer. Acad. Dermatol. 13(3):524-525 (1985).
Gamache, D.A., et al., "Nepafenac, A Unique Nonsteroidal Prodrug with Potential Utility in the Treatment of Trauma-Induced Ocular Inflammation: 1. Asssessment of Anti-Inflammatory Efficacy," Inflammation 24(4):357-370 (2000).
Gidoh, M., et al., "Derivatives of Several Acidic Anti-Inflammatory Drugs Showing Local Anesthetic Effects and Their Possible Use in the Treatment of Leprous Neuritis," Nippon Rai Gakkai Zasshi 52(3):156-64 (1983).
Ginaldi, L., et al., "Osteoporosis, Inflammation and Ageing," Immunity & Ageing 2:14 (2005).
Giraud, I., et al., "Application to a Cartilage Targeting Strategy: Synthesis and In Vivo Biodistribution of 14C-Labeled Quaternary Ammonium-Glucosamine Conjugates," Bioconjugate Chem. 11:212-218 (2000).
Google machine translation, obtained Aug. 4, 2016.
Gossel, T.A., "Aspirin's Role in Reducing Cardiac Mortality," U.S. Pharmacitst, Feb. 1988, pp. 34-41.
Gringauz, A., "Certain Disubstituted O-Aminoacetoxy- and Propoxybenzoic and Cinnamic Acids and Their Tert-Butyl Esters," J. Pharma. Sci. 59(3):422-225 (1970).
Hacking, M.A.P.J., et al., "Lipase Catalysed Acylation of Hydroxylamine and Hydrazine Derivatives," Journal of Molecular Catalysis B: Exzymatic 11:315-321 (2001).
Halen et al. "Combining Anticholinergic and Anti-inflammatory Activities into a single moiety: A novel Approach to Reduce Gastrointestinal Toxicity of Ibuprofen and Ketoprofen" Gehm Biol Drug Des, 2007, vol. 70, pp. 450-455.
Halen, P. K., et al., "Synthesis and Pharmacological Evaluation of Some Dual-Acting Amino-Alcohol Ester Derivatives of Flurbiprofen and 2-[1,1'-Biphenyl-4-yl]Acetic Acid: A Potential Approach to Reduce Local Gastrointestinal Toxicity," Chemistry & Biodiversity 3(11):1238-1248 (2006).
Hengesh, E. J., Principles of Medicinal Chemistry, 4th Ed., p. 591, Williams & Wilkins (1995).
Hennekens, C. H., et al., "Final Report on the Aspirin Component of the Ongoing Physicians' Health Study," N. Eng. J. Med. 321:129-135 (1989).
Ho et al. "The percutaneous penetration of prostaglandin E1 and its alkyl esters" Journal of Controlled Release, 1999, vol. 58, pp. 349-355.
Horan, P. J., et al., "Antinociceptive Profile of Biphalin, a Dimeric Enkephalin Analog," J. Pharmacology & Experimental Therapeutics 265(3): 1446-1454 (1993).
Hovgaard, L., et al., "Drug Delivery Studies in Caco-2 Monolayers. Synthesis, Hydrolysis, and Transport of O-Cyclopropane Carboxylic Acid Ester Prodrugs of Various B-Blocking Agents," Pharm. Res. 12(3):387-392 (1995).
Hovgaard, L., et al., "Permeation Studies on O-Cyclopropanoyl Ester Prodrugs of B-Blockers in Caco-2 Cell Monolayers," Proceed. Intern: Symp. Control. Rel. Bioact. Mater. 20:238-239 (1993).
In't Veld, B. A., et al., "Nonsteroidal Antiinflammatory Drugs and the Risk of Alzheimer's Disease," N. Eng. J. Med. 345(21):1515-1521 (2001).
Jona, J. A., et al., "Design of Novel Prodrugs for the Enhancement of the Transdermal Penetration of Indomethacin," International Journal of Pharmaceuticals 123:127-136 (1995).
Jung, Y. J., et al., "Colon-Specific Prodrugs of 5-Aminosalicylic Acid: Synthesis and In Vitro/In Vivo Properties of Acidic Amino Acid Derivatives of 5-Aminosalicylic Acid," J. Pharm. Sci. 90:1767-1775 (2001).
Kawathekar, N., et al., "Synthesis, Biological Evaluation and QSAR Analysis of Some New Derivatives of Ketoprofen and Flurbiprofen," Indian J. Pharmaceutical Sciences 60(6):346-352 (1998).
Kigasawa, K., et al., "Decomposition and Stabilization of Drugs. XVIII. Studies on the Stability of Carboxylic Acid Esters of Phenol and Their Effectiveness as Prodrug," J. Pharm. Soc. Japan 99(4):402-412 (1979).

(56) References Cited

OTHER PUBLICATIONS

Kisel, V.M., et al., "Condensed Isoquinolines. 15. Synthesis of 5,10-Dihydro[1,2,4]Triazolo[1,5-b]-Isoquinolines and Related Spiranes," Chemistry of Heterocyclic Compounds 38(10):1253-1262 (2002).
Knychalska-Kawwan, Z., et al., "The Use of Edan in Stomatodynia," J. Stomatol. 38:10(1985).
Kobayashi, M., et al., "A Model System for Convenient Fluorescent Labeling of Sugar Chain in Taka-Amylase A.," Biosci. Biotechnol. Biochem. 61 (11): 18361839 (1997).
Korean Intellectual Property Office, International Preliminary Report on Patentability for PCT/IB2006/052318 dated May 7, 2007.
Korean Intellectual Property Office, International Preliminary Report on Patentability for PCT/IB2006/052461 dated Mar. 29, 2007.
Korean Intellectual Property Office, International Preliminary Report on Patentability for PCT/IB2006/052549 dated Apr. 23, 2007.
Korean Intellectual Property Office, International Preliminary Report on Patentability for PCT/IB2006/052563 dated Apr. 25, 2007.
Korean Intellectual Property Office, International Preliminary Report on Patentability for PCT/IB2006/052575 dated Apr. 25, 2007.
Korean Intellectual Property Office, International Preliminary Report on Patentability for PCT/IB2006/053090 dated May 12, 2007.
Korean Intellectual Property Office, International Preliminary Report on Patentability for PCT/IB2006/053091 dated May 12, 2007.
Korean Intellectual Property Office, International Preliminary Report on Patentability for PCT/IB2006/053619 dated Jun. 26, 2007.
Korean Intellectual Property Office, International Preliminary Report on Patentability for PCT/IB2006/053594 dated Jun. 20, 2007.
Korean Intellectual Property Office, International Preliminary Report on Patentability for PCT/US2009/066884 dated Jun. 7, 2011.
Korean Intellectual Property Office, International Preliminary Report on Patetability for PCT/IB2007/052090 dated May 31, 2007.
Korean Intellectual Property Office, International Search Report for PCT/IB2006/052732 dated May 2, 2007.
Korean Intellectual Property Office, International Search Report for PCT/IB2006/052815 dated May 3, 2007.
Korean Intellectual Property Office, International Search Report for PCT/IB2006/053741 dated May 29, 2007.
Kovach, I. M., et al., "Amino Acid Esters of Phenols as Prodrugs: Synthesis and Stability of Glycine, beta-Aspartic Acid, and alpha-Aspartic Acid Esters of p-Acetamidophenol," J. Pharm. Sci. 70(8):881-885 (1981).
Machon, Z., et al., "Synthesis of Benzoylcholine Derivatives," Dissertationes Pharmaceuticae 17(4):491-496 (1965).
Madhu, C., et al "Penetration of Natural Prostaglandins and Their Ester Prodrugs and Analogs Across Human Ocular Tissues in Vitro," Journal of Ocular Pharmacology 14(5):389-399 (1998).
Magnette, J.-L., et al., "Diclofenac Systemic Exposure is Not Increased when Topical Diclofenac is Applied to Ultraviolet-Induced Erythema," Eur. J. Clin. Pharmacol. 60:591-594 (2004).
McGeer, P.L., et al., "The Inflammatory Response System of Brain Implications for the Therapy of Alzheimer and Other Neurodegenerative Diseases," Res. Rev. 21:195-218 (1995).
Milosovich, S., et al., "Testosteronyl-4-Dimethylaminobutyrate-HCI: A Prodrug with Improved Skin Penetration Rate," J. Pharm. Sci. 82(2):227-228 (1993).
Mork et al. "Stereoselective Enzymatic Hydrolysis of Various Ester Prodrugs of Ibuprofen and Flurbiprofen in Human Plasma" Pharmaceutical Research, 1992, vol. 9, No. 4, pp. 492-496.
National Center for Biotechnology Information, PubChem Compound Database, create date Jun. 16, 2018, CID=24811342, https://pubchem.ncbi.nlm.nih.gov/compound/24811342, pp. 1-9.

Nebioglu, D., et al., "Synthesis and In Vitro Anti-Inflammatory Activities of Some New Diaryl Amine Derivatives as Prodrug of Diclofenac," J. Fac. Pharm. Gazi 10(1):69-81 (1993).
Nicolas, C., et al., "New Quaternary Ammonium Oxican Derivatives Targeted Toward Cartilage: Synthesis, Pharmacokinetic Studies, and Antiinflammatory Potency," J. Med. Chem. 42:5235-5240 (1999).
Nielsen, N. M., et al., "Evaluation of Glycolamide Esters and Various Other Esters of Aspirin as True Aspirin Prodrugs," J. Med. Chem. 32(3):727-734 (1989).
Non_steroidal_antiinflammatory_dr,2011, http://en.wikipedia.org/wiki/Non-steroidal_anti-inflammatory_drug.
Pan, D.S., et al., "Inhibitory Effect of Progesterone on Inflammatory Factors after Experimental Traumatic Brain Injury," Biomed. Environ. Sci. 20(5):432-438 (2007).
PDR Generics, "Fenoprofen Calcium," 1996, second edition, Medical Economics, Montvale, NJ, p. 1289-1292.
PDR Generics, "Ketoprofen," 1996, second edition, Medical Economics, Montvale, NJ, p. 1810-1815.
PDR Generics, 1996, 2nd Ed., Medical Economics, Montvale, New Jersey, p. 242-243.
Perioli, L., et al., "Potential Prodrugs of Non-Steroidal Anti-Inflammatory Agents for Targeted Drug Delivery to the CNS," European Journal of Medicinal Chemistry 39(8):715-727 (2004).
Ponte, C., et al., "Does Acetaminophen Interfere in the Antibiotic Treatment of Acute Otitis Media Caused by a Penicillin-Resistant Pneumococcus Strain? A Gerbil Model," Pediatric Res. 54(6):913-918 (2003).
Raisz, L., "Pathogenesis of Osteoporosis: Concepts, Conflicts, and Prospects," J. Clin. Invest. 115(12):3318-3325 (2005).
Rolka, D. B., et al., "Aspirin Use Among Adults with Diabetes," Diabetes Care 24(2):197-201 (2001).
Romundstad, L., et al., "Adding propacetamol to Ketorolac Increase the Tolerance to Painful Pressure," European Journal of Pain (Amsterdam, Netherlands) 10(3):177-183, ISSN:1090-3801 (2006).
Roof, R.L., et al., "Gender Differences in Acute CNS Trauma and Stroke: Neuroprotective Effects of Estrogen and Progesterone," J. Neurotrauma 17(5):367-388 (2000).
Rosenberg, E.W., et al., "Effect of Topical Applications of Heavy Suspensions of Killed Malassezia Ovalis on Rabbit Skin," Mycopathologia 72:147-154 (1980).
Roth, H. J., et al., "Synthesis of Polymer Bound Antiphlogistic Agents," Archiv der Pharmazie 321(5):273-276 (1988).
Salimbeni, A., et al., "New Esters of N-Arylanthranilic Acids," Farmaco, Edizione Scientifica 30(4):276-286 (1975).
Santos, C., et al., "Cyclization-Activated Prodrug. Synthesis, Reactivity and Toxicity of Dipeptide Esters of Paracetamol," Bioorganic & Medicial Chemistry Letters 15(6):1595-1598 (2005).
Scott, I. L., "Keystone Symposia: Inflammation and Cancer, Breckenridge, CO, USA, Feb. 27-Mar 3, 2005," Technical Reports 10(13)1-17.
Selim, A. S. M., et al., "A New Method for the Direct Isolation of Glycine from Protein Hydrolyzates," Biochemical Journal 61(2):177-179 (1955).
Shanbhag, V. R., et al., "Ester and Amide Prodrugs of Ibuprofen and Naproxen: Synthesis, Anti-Inflammatory Activity, and Gastrointestinal Toxicity," Journal of Pharmaceutical Sciences 81 (2):149-154 (1992).
Silverman, RB., "The Organic Chemistry of Drug Design and Drug Action," Academic Press Inc. 1992, pp. 355-361.
Sloan, K. B., et al., "Design for Optimized Topical Delivery: Prodrugs and a Paradigm Change," Pharmaceutical Research 23(12):2729-2747 (2006).
Sloan, K. B., et al., "Designing for Topical Delivery: Prodrugs Can Make the Difference," Medicinal Research Reviews 23(6):763-793 (2003).
Soine, T. O., et al., "Antispasmodics. I. Phenyl Esters of Beta-Dialkylaminopropionic Acids," J. Am. Pharm. Assoc. 41:236-238 (1952).
Song, N., et al., "Synthesis of a Derivative of Quaternary Ammonium-Ibuprofen," Journal of Ocean University of Qingdao 32(6):911-913 (2002).

(56) References Cited

OTHER PUBLICATIONS

Sorhede, M., et al., "Enterostatin: A Gut-Brain Peptide Regulating Fat Intake in Rat," J. Physiol. 87:273-275 (1993).
SpinalCordinjury,2011, http://www.mayoclinic.com/health/spinal-cord-injury/DS00460/DSECTION=treatments-and-drugs.
Terry, M. B., et al., "Association of Frequency and Duration of Aspirin Use and Hormone Receptor Status With Breast Cancer Risk," JAMA 291 (21):2433-2489 (2004).
Thun, M.J., et al., "Aspirin Use and Reduced Risk of Fatal Colon Cancer," N. Eng. J. Med., 325(23):1593-1596 (1991).
Tjebbes, G.W.A., et al., "d-Ibuprofen in Ocular Inflammation Induced by Paracentesis of the Rabbit Eye," Prostaglandins, Butterworth, Stoneham, MA, US 40(1):29-33 (1990).
Toyooka, T., et al., "Fluoroescent Chiral Derivatization Reagents for Carboxylic Acid Enantiomers in High-Performance Liquid Chromatography," Caplus an 1992:523750 (1992).
Tozkoparan, B., et al.," 6-Benzylidenethiazolo[3,2-b]-1,24-Triazole-5(6H)-Ones Substituted with Ibprofen: Synthesis, Characterization and Evaluation of AntiInflammatory Activity," Eur. J. Med. Chem. 35(78):743-750 (2000).
Tute, M. S., et al., Principles of Medicinal Chemistry, Eds., Williams & Wilkins, Media, PA, 1995, pp. 52.
Urbanska, H., et al., "Synthesis and Pharmacological Properties of Aminoalkyl Esters of Nicotinic Acid Derivatives," Acta Poloniae Pharmaceutica 36(6):657-665 (1979).
Venuti, M. C., et al., "Synthesis and Biological Evaluation of Omega-(N,N,N-Trialkylammonium)Alkyl Esters and Thioesters of Carboxylic Acid Nonsteroidal Antiinflammatory Agents," Pharmaceutical Research 6(10):867-873 (1989).
Warolin, C., et al.," Sur L'Activite Pharamacodynamique de L'Anhydride Acetylsalicylique et du Chlorhydrate D'Acetylsalicylate de N Diethylaminoethyle (1)," Therapie 21(1):245-59 (1966).
Wiwattanawongsa, K., et al., "Experimental and Computational Studies of Epithelial Transport of Mefenamic Acid Ester Prodrugs," Pharmaceutical Research 22(5):721-727 (2005).
Wolinski, J., et al., "Search for Anticholinargic Compounds. XX. Synthesis of Aminoalkyl O-, M-, and P-Hydroxybenzoates and O-, M-, and P-Acetoxybenzoates," Acta Poloniae Pharmaceutica 37(3):275-280 (1980).
Woods, H. F., et al., "Inhibition by Salicylate of Gluconeogenesis in the Isolated Perfused Rat Liver," Clin. Exp. Pharmacol. Physiol. 1(6):535-540 (1974).
Wright, D.W., et al., "ProTECT: A Randomized Clinical Trial of Progesterone for Acute Traumatic Brain Injury," Ann. Emerg. Med. 49(4):391-402 (2007).
Xiao, G., et al., "Improved Outcomes from the Administration of Progesterone for Patients with Acute Severe traumatic brain injury: A Randomized Controlled Trial," Crit. Care 12:R61 (2008).
Yadav, M.R., et al., "Synthesis and Pharmacological Evaluation of Some Dual-Acting Aminoalcohol Ester Derivatives of Flurbiprofen and 2-[1,1'-Biphenyl-4-yl] Acetic Acid: A Potential Approach to Reduce Local Gastrointestinal Toxicity," Chem. & Biodiversity 3(11):1238-1248 (2006).
Yang, S., et al., "Specificity of RGS10A as a Key Component in the RANKL Signaling Mechanism for Osteoclast Differentiation," J. Cell Sci. 120:3362-3371 (2007).
Zovko, M., et al., "Macromolecular Prodrugs. IX. Synthesis of Polymer-Fenoprofen Conjugates," Int. J. Pharmaceutics 228:129-138 (2001).
Zovko, M., et al., "The Novel Ketoprofenamides: Synthesis and Spectroscopic Characterization," Croatica Chemica Acta 76(4):335-341 (2003).
Sansom, D.N., "Clinical relevance of salicylate drugs pharmacokinetics," Pharmaceutical Information Bulletin, 4: cover, copyright, table of contents, and pp. 21-25 (1984).
Liang, B.W., "Transdermal drug delivery systems," Cover, copyright, table of contents, and pp. 88-89 (1992).
"Experimental reports and attachments," submitted in Chinese Patent Application No. CN200680055301.8.
"Experimental reports," submitted in Chinese Patent Application No. CN200680055467.X.
Database CA [Online] Chemical Abstracts Service, XP002571761, retrieved from STN Database accession No. 1966: 412012.
Knychalska-Karwan, Z., et al., Czasopismo stomatologiczne, 38(10): 732-734 (1985).
Zheng, J.M., "Novel transdermal drug delivery system," Copyright, preface, p. 3-6 (1997).
Indian Patent Office, First Examination Report for Indian Patent Application No. 777/KOLNP/2009, 1 page, dated Apr. 21, 2014.
Prausnitz, M.R., "Transdermal drug delivery," Nat Biotechnol., 26(11):1261-1268 (2008).
Xing, X.X., et al., "Development of transdermal drug delivery system," Anhui Medical and Pharmaceutical Journal, 9(12): 883-885 (2005).
Ma, Q.A., "The physiological characteristics of skin and transdermal absorption," 32(10): 24-26 (1997).
Zhao, Y.J., "The type and biology of transdermal drug delivery system," Shandong Pharmaceutical Industry, 13(2): 29-33 (1994).
Swain, A.R., "Salicylates in foods," J Am Diet Assoc., 85(8):950-960 (1985).
Ding, G.L., "Effects of aspirin on treating unstable angina pectoris (UAP," Foreign Medicine • Geriatrics, 18(6): 275 (1977).
He, N.N., "Aspirin can help preventing colon cancer," Shanghai Medicine, 24(10): 466-467 (2003).
Che, D.F., et al., "Randomized, double-blind and controlled clinical trial of 2% salicylic acid gel on treating Acne vulgaris," Chinese Journal of Aesthetic Medicine, 15(5): 561-563 (2006).
Hou, S.G., et al., Aspirin and glomerulus nephritis, Introduction to Japanese medicine, 17(5): 208-209 (1996).
Sun, L.Q., et al., "The application of aspirin in cardiovascular diseases," Shandong Pharmaceutical Industry, 8(2):38-40 (1989).
Liao, M.S., et al., "Prediction of pre-eclampsia by color doppler ultrasound and prevention of eclampsia with low dose aspirin," Chinese J Ultrasound Med., 17(4): 307-308 (2001).
Li, Y.L., "Effects of combination therapy using aspirin and high dose intravenous immunoglobulin (IVIG) on treating Kawasaki disease," Chin J Prim Med Phamn, 12(8): 1077 (2005).
Fan, B., "Effects of aspirin on cancer treatment," Chinese Journal of Hospital Pharmacy, 11(1):36 (1991).
Pang, S.Q., et al., "Preliminary report on effective doses of aspirin in thrombosis prevention," Journal of Beijing Second Medical College, 7(2): 146 (1986).
Hu, D.Y., "The randomized study of efficiency and safety of antithrombotic therapy in nonvascular atrial fibrillation: warfarin compared with aspirin," Chin J Cardiol, 34(4): 295-298 (2006).
Deng, W.L., et al., "Effects of low dose aspirin on pregnancy-induced hypertension," Shangdong Medicine, 37(9): 9 (1997).
Harter, H.R., et al., "Prevention of thrombosis in patients on hemodialysis by low-dose aspirin," N Engl J Med., 301(11): 577-579 (1979).
Donadio, J.V., et al., "Membranoproliferative glomerulonephritis. A prospective clinical trial of platelet-inhibitor therapy," N Engl J Med., 310(22): 1421-1426 (1979).
Liu, H.Y., et al., "Effects of aspirin on prevention of cataracts," Pharmacy Information Communication, 7(3): 59-60 (1989).
Li, C.Q., Chinese community physician, 16: 21 (2004).
Wang, S.X., et al., "Advances in pharmacology research on aspirin," Journal of Hainan Medical College, 7(1): 61-64 (2001).
Yan, H., et al., "Effects of aspirin on prevention and treatment of cataracts," Chinese Journal of Practical Ophthalmology, 17(19): 582-583 (1999).
Yu, M.Y., et al., "Antithrombotic treatment for atrial fibrillation," Chin J Cardiol., 26(4): 318-319 (1998).
Hou, G.R., et al., "Comparative study of the effect of warfarin with aspirin on preventing atrial fibrillation from thrombo-embolism," Journal of Hangzhou Teachers College ( Natural Science Edition ), 4(6): 441-442 (2005). English Abstract.
Wang, X.Y., et al., "A study of prevention thrombosis with intermittent treatment of aspirin," Henan Medical Information, 2(1): 11-12 (1994).

(56) References Cited

OTHER PUBLICATIONS

Xiong, P., et al., "Effects of combination therapy using clopidogrel and aspirin on unstable angina," Practical Journal of Cardiac Cerebral Pneumal and Vascular Disease, 12(5): 316-317 (2004).

Li, A.P., et al., "Study on antithrombotic effect of low dose aspirin on ischemic cardiovascular and cerebrovascular diseases," Journal of Preventive Medicine of Chinese People's Liberation Army, 12(6): 463-365 (1994).

Li, W.M., et al., "Clinical study of small dose of aspirin in the prevention and treatment of retinopathy in patients with type 2 diabetes mellitus," China Pharmacist, 2(2): 104 (1999).

Mao, S.F., et al., "Effects of combination therapy using low dose Warfarin and aspirin on atrial fibrillation thrombosis," Chinese Journal of Cardiac Arrhythmias, 3(4): 295-296(1999).

Zhang, Q., et al., "Pharmaceutics," Peking University Medical Press, Cover, copyright, table of contents, and pp. 92-101 (2005).

Henderson, J.T., et al., "Low-dose aspirin for prevention of morbidity and mortality from preeclampsia: a systematic evidence review for the U.S. preventive services task force," Annals of Internal Medicine, 160(10): 695-703, Appendix (2014).

Lu, J., et al., "Clinical observation of aspirin on the safety of diabetic retinopathy," Journal of China Traditional Chinese Medicine Information, 2(8): 71 (2010).

Chen, X.B., "Clinical observation of aspirin on the safety of diabetic retinopathy," Strait Pharmaceutical Journal, 24(3): 124-126 (2012).

Bayer aspirin tablet drug label, Revised Nov. 2014.

Sang, X.F., "Experience of treating tinea manuum and tinea pedis with aspirin," Chinese Journal of Current Traditiona and Western Medicine, 6(6): 422-423 (2008).

Yu, W., et al., "Advances in diabetic foot treatment," Medical Innovation of China, 7(5): 177-179 (2010).

Guo, Q.Y., et al., "Aspirin and diabetes," Intern J Endocrinol Metab, 27(5): 306-309 (2007).

Wang, J.L., "Clinical observation of aspirin in the treatment of unstable angina pectoris," Chinese Medicine Guide, 11(4): 158-159 (2013).

Zhiyuan, "Role of aspirin in primary prevention of colorectal cancer," Liaoning Medical Journal, 21(5): 333 (2007).

Li, Y.H., et al., "Efficacy of aspirin in the treatment of herpes zoster neuropathic pain," Chinese Journal of Clinical Healthcare, 7(2): 127-128 (2004).

Qu, L., et al., "Effect of aspirin on thromboembolism in hypertensive patients associated with paroxysmal atrim fibrillation," Chinese Journal of Hypertension, 14(9): 703-706 (2006).

Din, Y.G., et al., "Influence of aspirin to the incidence of cardiovascular and cerebrovascular events after healing of diabetic foot ulcer," Chinese Journal of Primary Medicine and Pharmacy, 17(15): 2061-2062 (2010).

Huang, M.Z., "anti-polymerization effect of aspirin on platelet aggregation," Fujian Medical Journal, 34-35 (1980).

Kearney, D., et al., "Optimal suppression of thromboxane a2formation by aspirin during percutaneous transluminal coronary angioplasty: no additional effect of a selective cyclooxygenase-2 inhibitor," Journal of the American College of Cardiology, 43(4): 526-531 (2004).

He, J.D., "Efficacy and safety of aspirin in preventing thromboembolic disease after arthroplasty," Chinese and Foreign Medical Research, 11(23): 46-47 (2013).

Lin, J.C., et al., "The effect of aspirin on arteriovenous fistula embolization in patients with diabetic nephropathy," Journal of Practical Medicine, 27(3): 497-498 (2011).

Database CA [Online] Chemical Abstracts Service, XP002590079, retrieved from STN Database accession No. 2003:29322.

European Search Report of Application No. 17152505.8-1454, dated Jul. 13, 2017.

* cited by examiner ly than when the drug is administered accurately at the particular site of pain or injury (Fishman; Robert, U.S. Pat. No. 7,052,715).

HIGH PENETRATION COMPOSITIONS AND USES THEREOF

PRIORITY CLAIM

The present application is a divisional of U.S. patent application Ser. No. 12/351,804, filed Jan. 9, 2009, which is a continuation-in-part application of International Application PCT/IB2006/052318, with an international filing date of Jul. 9, 2006; a continuation-in-part application of International Application PCT/IB2006/052461, with an international filing date of Jul. 18, 2006; a continuation-in-part application of International Application PCT/IB2006/052549, with an international filing date of Jul. 25, 2006; a continuation-in-part application of International Application PCT/IB2006/052563, with an international filing date of Jul. 26, 2006; a continuation-in-part application of International Application PCT/IB2006/052575, with an international filing date of Jul. 27, 2006; a continuation-in-part application of International Application PCT/IB2006/052732, with an international filing date of Aug. 8, 2006; a continuation-in-part application of International PCT/IB2006/052815, with an international filing date of Aug. 15, 2006; a continuation-in-part application of International Application PCT/IB2006/053090, with an international filing date of Sep. 3, 2006; and a continuation-in-part application of International Application PCT/IB2006/053741, with an international filing date of Oct. 11, 2006; and designating the U.S., all of which are incorporated herein by reference. The present application also claims priority to U.S. Provisional Application 61/120,052, filed Dec. 4, 2008, which is incorporated herein by reference.

FIELD OF THE INVENTION

This invention relates to the field of pharmaceutical compositions and method of using the pharmaceutical compositions for penetrating one or more biological barriers, treating conditions, diagnosing conditions or screening for new compositions.

BACKGROUND

Active agents or drugs that are effective in vitro may not be as effective in vivo due to the delivery difficulties in vivo, in particular, their limited penetration ability across one or more biological barriers before reaching the site of action where diseases occur in vivo.

Currently many drugs are administered through systematic route, such as oral or parenteral administration, to reach the action site of a condition or disease. Since higher dosage of drugs is required to reach a distal location in the systematic administration, drugs delivered by such a route may cause adverse reactions. For example, non-steroidal anti-inflammatory agents (NSAIAs) are widely used for treatment of acute or chronic conditions where pain and inflammation are present. Although NSAIAs are absorbed in the stomach and intestinal mucosa, oral administration usually accompany adverse drug reactions such as gastrointestinal (GI) effects and renal effects. For instance, aspirin is known to cause gastric mucosal cell damage. The side effects of NSAIAs appear to be dose-dependent, and in many cases severe enough to pose the risk of dyspepsia, gastroduodenal bleeding, gastric ulcerations, gastritis, ulcer perforation, and even death.

Modifications of the known NSAIAs have been reported to improve their efficacy and decrease their side effects. However, to treat inflammation or pain at distal areas, a much higher plasma concentration of the active agent is required when the drug is administered orally than when the drug is administered accurately at the particular site of pain or injury (Fishman; Robert, U.S. Pat. No. 7,052,715).

Fishman and many others (Van Engelen et al. U.S. Pat. No. 6,416,772; Macrides et al. U.S. Pat. No. 6,346,278; Kirby et al. U.S. Pat. No. 6,444,234, Pearson et al. U.S. Pat. No. 6,528,040, and Botknecht et al. U.S. Pat. No. 5,885,597) have attempted to develop a delivery system for transdermal application by drug formulation to reduce the side effect associating with oral administration and achieve localized drug administrations with reduced systematic exposure. It is very difficult, however, to deliver therapeutically effective plasma levels of these drugs by the formulation.

Therefore, there is a need to develop novel compositions that are capable of being delivered efficiently and effectively to the action site of a condition (e.g., a disease) to prevent, reduce or treat conditions and minimize side effects.

SUMMARY OF THE INVENTION

One aspect of the invention relates to a high penetration prodrug (HPP) or a high penetration composition (HPC) comprising a functional unit covalently linked to a transportational unit through a linker.

In certain embodiments, the functional unit comprises a moiety of an agent wherein the delivery of the agent into a biological subject or transportation across a biological barrier is desired. In certain embodiments, the agent comprises an active agent or an agent that can be metabolized into an active agent or active metabolite.

In certain embodiments, the functional unit may be hydrophilic, lipophilic, or amphiphilic (hydrophilic and lipophilic). For example, the lipophilic nature of the function unit may be inherent or achieved by converting its hydrophilic moieties to lipophilic moieties.

In certain embodiments, the functional unit comprises a moiety of an agent wherein the agent is a non-steroidal anti-inflammatory agent (NSAIA), an active NSAIA metabolite or an agent that can be metabolized into a NSAIA or NSAIA metabolite after the HPP penetrates one or more BBs. Examples of NSAIA include, but are not limited to, aspirin, diflunisal, salsalate, salicylic acid, ibuprofen, ketoprofen, fenoprofen, naproxen, suprofen, acetaminophen, α-methyl-(p-chlorobenzoyl)-5-methoxy-2-methylindole 3-acetic acid, flurbiprofen, carprofen, pranoprofen, benoxaprofen, alminoprofen, tiaprofenic acid, pirprofen, zaltoprofen, bermoprofen, loxoprofen, indoprofen, fenclorac, oxaprozin, fenbufen, orpanoxin, ketorolac, clidanac, tolmetin, zomepirac, etodolac, amfenac, bromofenac, alclofenac, fenclofenac, acemetacin, fentiazac, indomethacin, sulindac, lonazolac, bendazac, 6MNA, diclofenac, mefenamic acid, meclofenamic acid, flufenamic acid, niflumic acid, flunixin, piroxicam, sudoxicam, lomoxicam, tenoxicam, ampiroxicam, lomoxicam, isoxicam, cinnoxicam, and meloxicam.

In certain embodiments, the transportational unit of the HPP comprises a protonatable amine group that is capable of facilitating the transportation or crossing of the HPP through one or more biological barriers (>100 times faster than the parent drug). In certain embodiments, the protonatable amine group is substantially protonated at the pH of the BBs the HPP penetrates through. In certain embodiment, the amine group can be reversibly protonated.

In certain embodiments, the linker covalently linking the functional unit and the transportational unit comprises a bond that is capable of being cleaved after the HPP penetrates across one or more BBs. The cleavable bond comprises, for example, a covalent bond, an ether, thioether, amide, ester, thioester, carbonate, carbamate, phosphate or oxime bond.

Another aspect of the invention relates to a pharmaceutical composition comprising one HPP and a pharmaceutically acceptable carrier.

Another aspect of the invention relates to the use of a composition of the invention in penetrating a biological barrier.

Another aspect of the invention relates to method for diagnosing the onset, development, or remission of a condition in a biological subject by using a HPP (or a HPC) of the invention. In certain embodiments, the HPP or the functional unit of the HPP of the composition is detectable. In certain embodiments, the HPP or the functional unit of the HPP is inherently labeled, or labeled or conjugated to a detectable agent.

Another aspect of the invention relates methods for screening a test functional unit, a test linker, or a test transportational unit with desired characters.

Another aspect of the invention relates to methods for preventing, ameliorating, or treating a condition in a biological subject by administering a composition of the present invention. In certain embodiments, the method relates to treating a condition treatable by an NSAIA by administering the NSAIA HPP. In certain embodiment, the composition of the present invention is administrated to a biological subject through various delivery routes such as oral, enteral, buccal, nasal, topical, rectal, vaginal, aerosol, transmucosal, epidermal, transdermal, dermal, ophthalmic, pulmonary, subcutaneous, and/or parenteral administration. In certain embodiments, the composition of the present invention is administered orally, transdermally, topically, subcutaneously and/or parenterally.

Another aspect of the invention relates to the advantages of HPP or HPC according to the present invention. The advantages include, for example, location administration of a HPP to the site of condition with less dosage but higher concentration, avoidance of systematic administration and reduction of adverse effects (e.g., pain of injection, gastrointestinal/renal effects, and other side effect), possible novel treatment due to high local concentration of the HPP or active agent. The advantages further include, for example, systematic administration of a HPP to a biological subject to achieve faster and more efficient bioavailability, penetration of biological barriers (e.g., the blood brain barrier) which have not been crossed by parent agents, and new indications thereof.

DESCRIPTION OF THE DRAWINGS

FIG. 1e-2: Cumulative amounts of diethylaminoethyl α-methyl-5H-[1]benzopyrano[2,3-b]pyridine-7-acetate.AcOH (A, 20% solution), diethylaminoethyl 2-(4-chlorophenyl)-α-methyl-5-benzoxazoleacetate.AcOH (B, 20% solution), diethylaminoethyl α-methyl-4-[(2-methyl-2-propenyl)amino]benzeneacetate.AcOH (C, 20% solution), diethylaminoethyl 5-benzoyl-α-methyl-2-thiopheneacetate.AcOH (D, 20% solution), diethylaminoethyl 3-chloro-4-(2,5-dihydro-1H-pyrrol-1-yl)-α-methyl benzeneacetate.AcOH (E, 20% solution), pranoprofen (F, 20% suspension), benoxaprofen (G, 20% suspension), alminoprofen (H, 20% suspension), tiaprofenic acid (I, 20% suspension), or pirprofen (J, 20% suspension) crossing isolated human skin tissue in Franz cells (n=5). In each case, the vehicle was pH 7.4 phosphate buffer (0.2 M).

FIG. 1e-3: Cumulative amounts of diethylaminoethyl 2-(10, 11-dihydro-10-oxodibenzo(b,f)thiepin-2-yl)propionate.AcOH (A, 20% solution), diethylaminoethyl 2-(8-methyl-10,11-dihydro-11-oxodibenz(b,f)oxepin-2-yl)propionate.AcOH (B, 20% solution), diethylaminoethyl 2-[4-(2-oxocyclopentyl-methyl)phenyl]propionate.AcOH (C, 20% solution), diethylaminoethyl 4-(1,3-dihydro-1-oxo-2H-isoindol-2-yl)-α-methylbenzeneacetate.AcOH (D, 20% solution), diethylaminoethylα,3-dichloro-4-cyclohexylbenzeneacetate.AcOH (E, 20% solution), zaltoprofen (F, 20% suspension), bermoprofen (G, 20% suspension), loxoprofen (H, 20% suspension), indoprofen (I, 20% suspension), or fenclorac (J, 20% suspension) crossing isolated human skin tissue in Franz cells (n=5). In each case, the vehicle was pH 7.4 phosphate buffer (0.2 M).

FIG. 1e-4: Cumulative amounts of diethylaminoethyl 4,5-Diphenyl-2-oxazole propionate.AcOH (A, 20% solution), diethylaminoethyl 3-(4-biphenylylcarbonyl)propionate.AcOH (B, 20% solution), diethylaminoethyl 5-(4-chlorophenyl)-beta-hydroxy-2-furanpropionate.AcOH (C, 20% solution), diethylaminoethyl 5-benzoyl-2,3-dihydro-1H-pyrrolizine-1-carboxylate.AcOH (D, 20% solution), diethylaminoethyl 6-chloro-5-cyclohexyl-2,3-dihydro-1H-indene-1-carboxylate.AcOH (E, 20% solution), oxaprozin (F, 20% suspension), fenbufen (G, 20% suspension), orpanoxin (H, 20% suspension), ketorolac (I, 20% suspension), or clidanac (J, 20% suspension) crossing isolated human skin tissue in Franz cells (n=5). In each case, the vehicle was pH 7.4 phosphate buffer (0.2 M).

FIG. 1*f*-1: Cumulative amounts of diethylaminoethyl 1-(p-chlorobenzoyl)-5-methoxy-2-methylindole 3-acetate.AcOH (A, 20% solution), diethylaminoethyl (Z)-5-fluoro-2-methyl-1-[(4-methylsulfinyl) phenylmethylene]-1H-indene-3-acetate.AcOH (B, 20% solution), diethylaminoethyl 1-methyl-5-(4-methylbenzoyl)-1H-pyrrole-2-acetate.AcOH (C, 20% solution), diethylaminoethyl 5-(4-Chlorobenzoyl)-1,4-dimethyl-1H-pyrrole-2-acetate.AcOH (D, 20% solution), diethylaminoethyl 1,8-diethyl-1,3,4,9-tetrahydropyrano-[3,4-b]indole-1-acetate.AcOH (E, 20% solution), indomethacin (F, 20% suspension), sulindac (G, 20% suspension), tolmetin (H, 20% suspension), zomepirac (I, 20% suspension), or etodolac (J, 20% suspension), crossing isolated human skin tissue in Franz cells (n=5), the vehicle was pH 7.4 phosphate buffer (0.2 M).

FIG. 1*f*-2: Cumulative amounts of diethylaminoethyl 2-amino-3-benzoylbenzeneacetate.AcOH (A, 20% solution), diethylaminoethyl 2-amino-3-(4-bromo-benzoyl)benzeneacetate.AcOH (B, 20% solution), diethylaminoethyl 3-chloro-4-(2-propenyloxy)benzeneacetate.AcOH (C, 20% solution), diethylaminoethyl 2-(2,4-dichlorophenoxy) benzeneacetate.AcOH (D, 20% solution), diethylaminoethyl 1-(4-chlorobenzoyl-5-methoxy-2-methyl-1H-indole-3-acetoxyacetate.AcOH (E, 20% solution), diethylaminoethyl 4-(4-chlorophenyl)-2-phenyl-5-thiazoleacetate.AcOH (F, 20% solution), amfenac (G, 20% suspension), bromofenac (H, 20% suspension), alclofenac (I, 20% suspension), fenclofenac (J, 20% suspension), acemetacin (K, 20% suspension), or fentiazac (L, 20% suspension), crossing isolated human skin tissue in Franz cells (n=5). In each case, the vehicle was pH 7.4 phosphate buffer (0.2 M).

FIG. 2*b*-1: Total plasma levels of diflunisal after topical application of 300 mg of a 20% solution of diethylaminoethyl 5-(2,4-difluorophenyl) salicylate.AcOH, (A) or 5-(2,4-difluorophenyl) salicylic acid (diflunisal, B) in isopropanol to the backs of hairless mice (n=5).

FIG. 2*b*-2 Total plasma levels of salsalate after topical application of 300 mg of a 20% solution of diethylaminoethyl salsalate. AcOH, (A) or salsalate (B) in isopropanol to the backs of hairless mice (n=5).

FIG. 2*b*-3: Total plasma levels of salicylic acid after topical application of 300 mg of a 20% solution of diethylaminoethyl salicylate.AcOH (A), or salicylic acid (B) in isopropanol to the backs of hairless mice (n=5).

FIG. 2*d*-1: Total plasma levels of ketoprofen after topical application of 1 ml of a 10% solution of diethylaminoethyl 2-(3-benzoylphenyl) propionate.AcOH, (A) or 2-(3-benzoylphenyl) propionic acid (ketoprofen, B) in isopropanol to the backs of hairless mice (n=5).

FIG. 2*d*-2: Total plasma levels of fenoprofen after topical application of 1 ml of a 10% solution of diethylaminoethyl 2-(3-phenoxyphenyl) propionate.AcOH, (A) or fenoprofen (B) in isopropanol to the backs of hairless mice (n=5).

FIG. 2*e*-1: Total plasma levels of naproxen, suprofen, α-methyl-(p-chlorobenzoyl)-5-methoxy-2-methylindole 3-acetic acid, flurbiprofen, carprofen after topical application of 1 ml of a 20% solution of diethylaminoethyl 2-(6-methoxy-2-naphthyl)propionate.AcOH (A), diethylaminoethyl α-methyl-4-(2-thienylcarbonyl)benzeneacetate.AcOH (B), diethylaminoethyl α-methyl-(p-chlorobenzoyl)-5-methoxy-2-methylindole 3-acetate.AcOH (C), diethylaminoethyl 2-(2-fluoro-4-biphenylyl)propionate.AcOH (D), diethylaminoethyl 6-chloro-α-methyl-9H-carbazole-2-acetate.AcOH (E), naproxen (F), suprofen (G), α-methyl-(p- chlorobenzoyl)-5-methoxy-2-methylindole 3-acetic acid (H), flurbiprofen (I), or carprofen (J) in isopropanol to the backs of hairless mice (n=5).

Figure 1A:
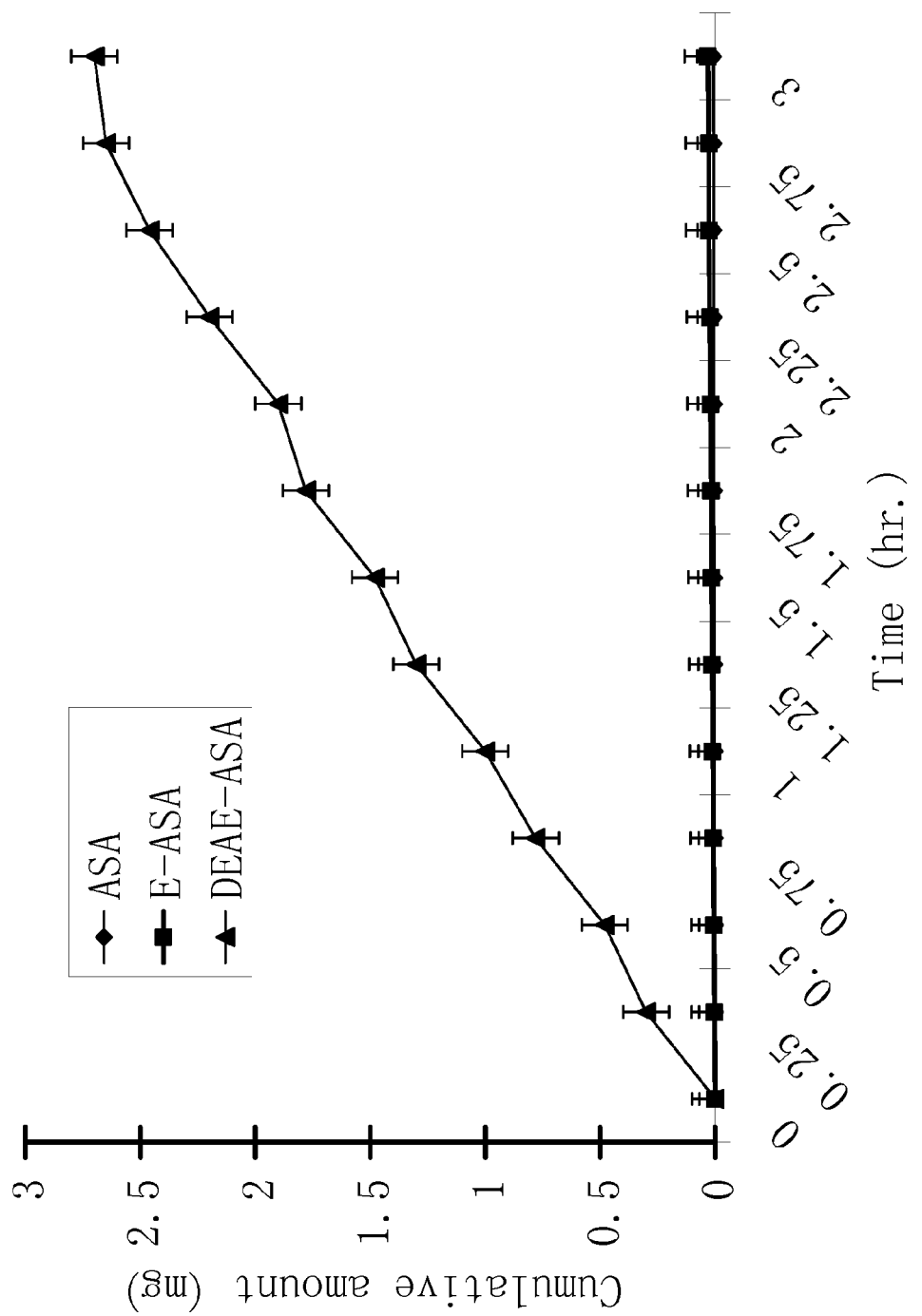
FIG. 1a: Cumulative amounts of acetylsalicylic acid (ASA), ethyl acetylsalicylate (E-ASA), and diethylaminoethyl acetylsalicylate.AcOH (DEAE-ASA) crossing isolated human skin tissue in Franz cells (n=5). ASA and E-ASA were applied as 20% suspensions. DEAE-ASA was applied as a 20% solution. In each case, the vehicle was pH 7.4 phosphate buffer (0.2 M).
Figure 1B:
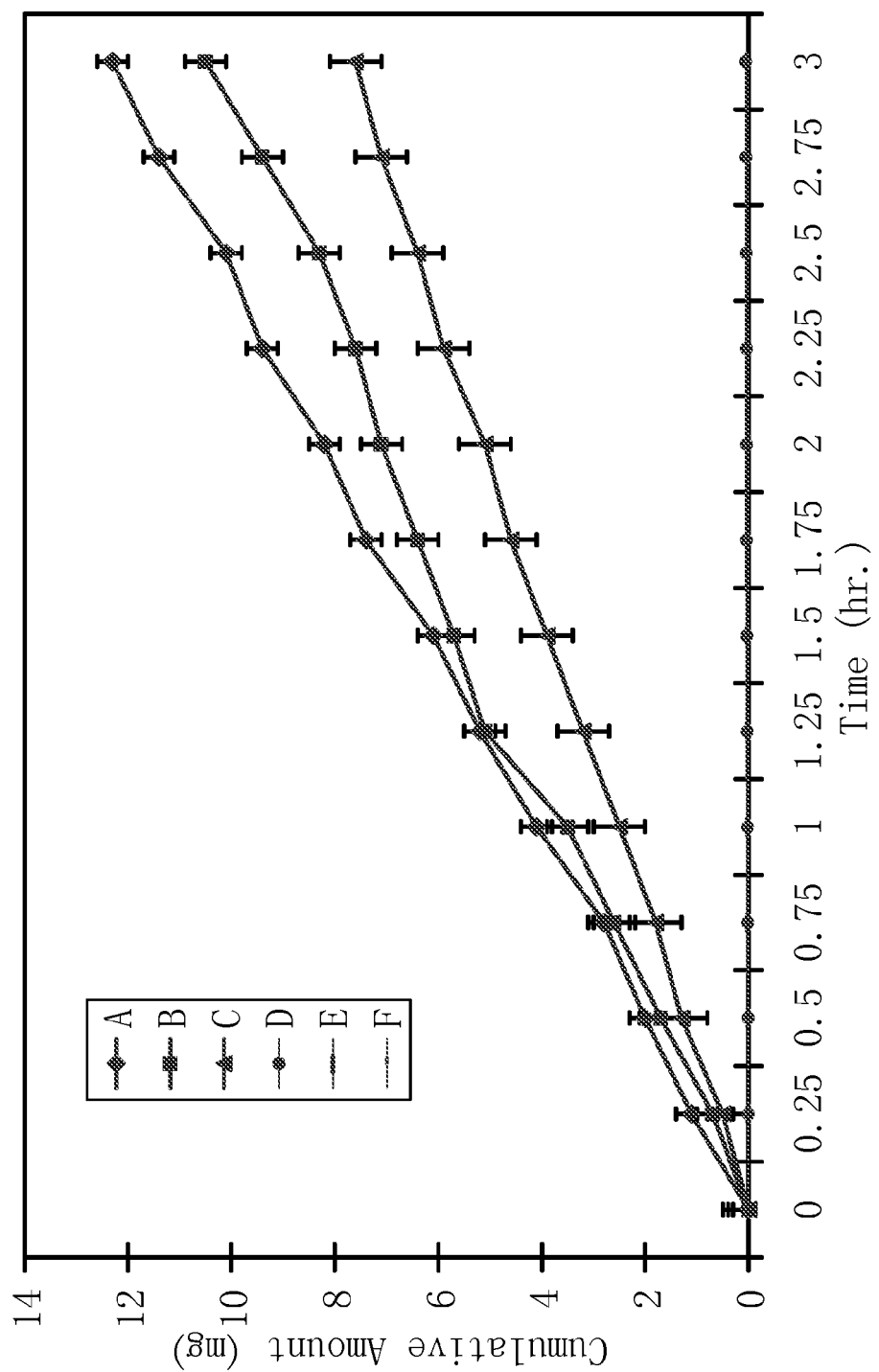
FIG. 1b: Cumulative amounts of diethylaminoethyl 5-(2, 4-difluorophenyl) salicylate.AcOH (A, 20% solution), diethylaminoethyl salicylsalicylate.AcOH (B, 20% solution), diethylaminoethyl salicylate.AcOH (C, 20% solution), diflunisal (D, 20% suspension), salsalate (E, 20% suspension), and salicylic acid (F, 20% suspension) crossing isolated human skin tissue in Franz cells (n=5). In each case, the vehicle was pH 7.4 phosphate buffer (0.2 M).
Figure 1C:
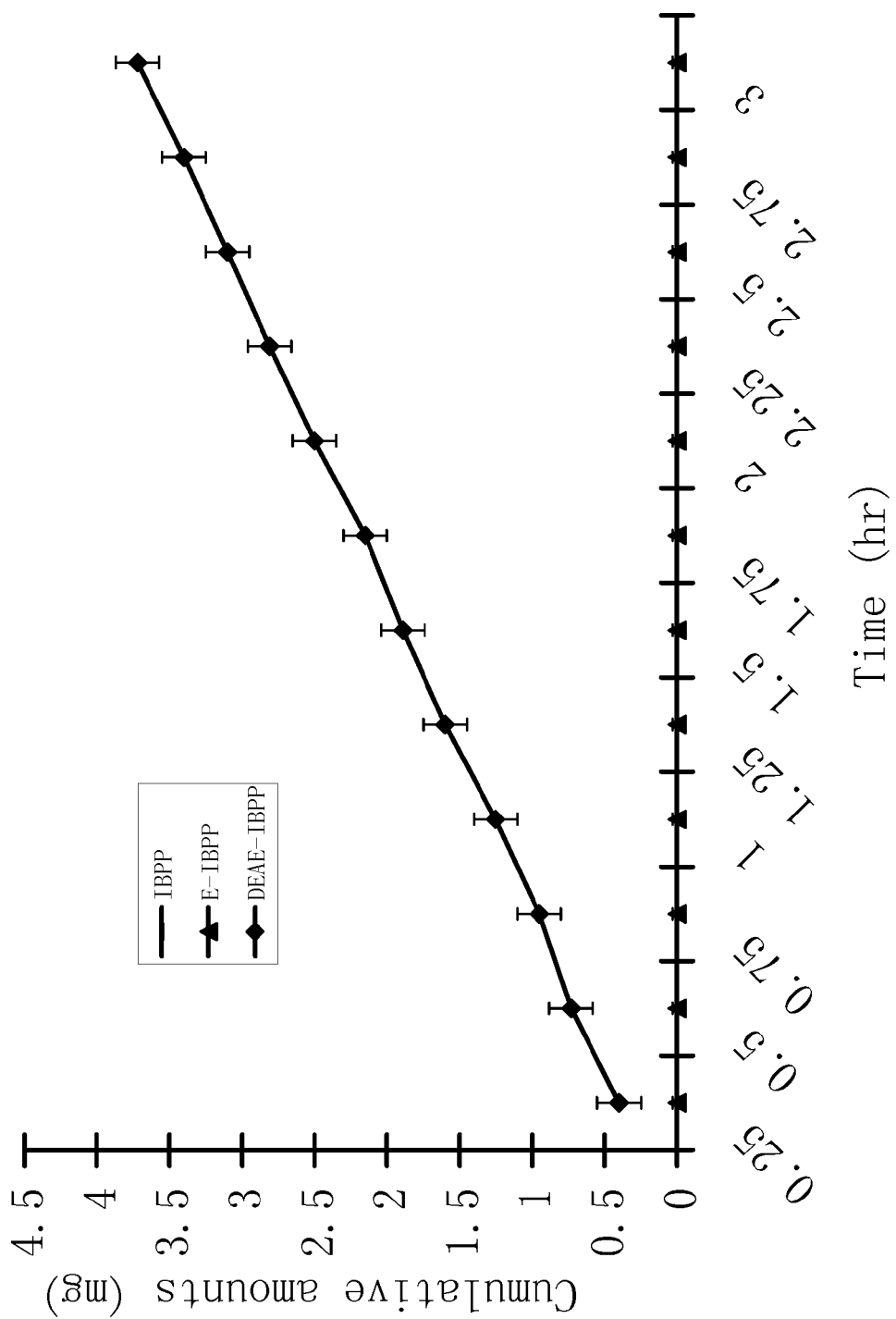
FIG. 1c: Cumulative amounts of 2-(p-isobutylphenyl) propionic acid (IBPP), ethyl 2-(p-isobutylphenyl) propionate (E-IBPP), and diethylaminoethyl 2-(p-isobutylphenyl) propionate.AcOH (DEAE-IBPP) crossing isolated human skin tissue in Franz cells (n=5). IBPP and E-IBPP were applied as a 30% suspension. DEAE-IBPP was applied as 30% solution. In each case, the vehicle was pH 7.4 phosphate buffer (0.2 M).
Figure 1D:
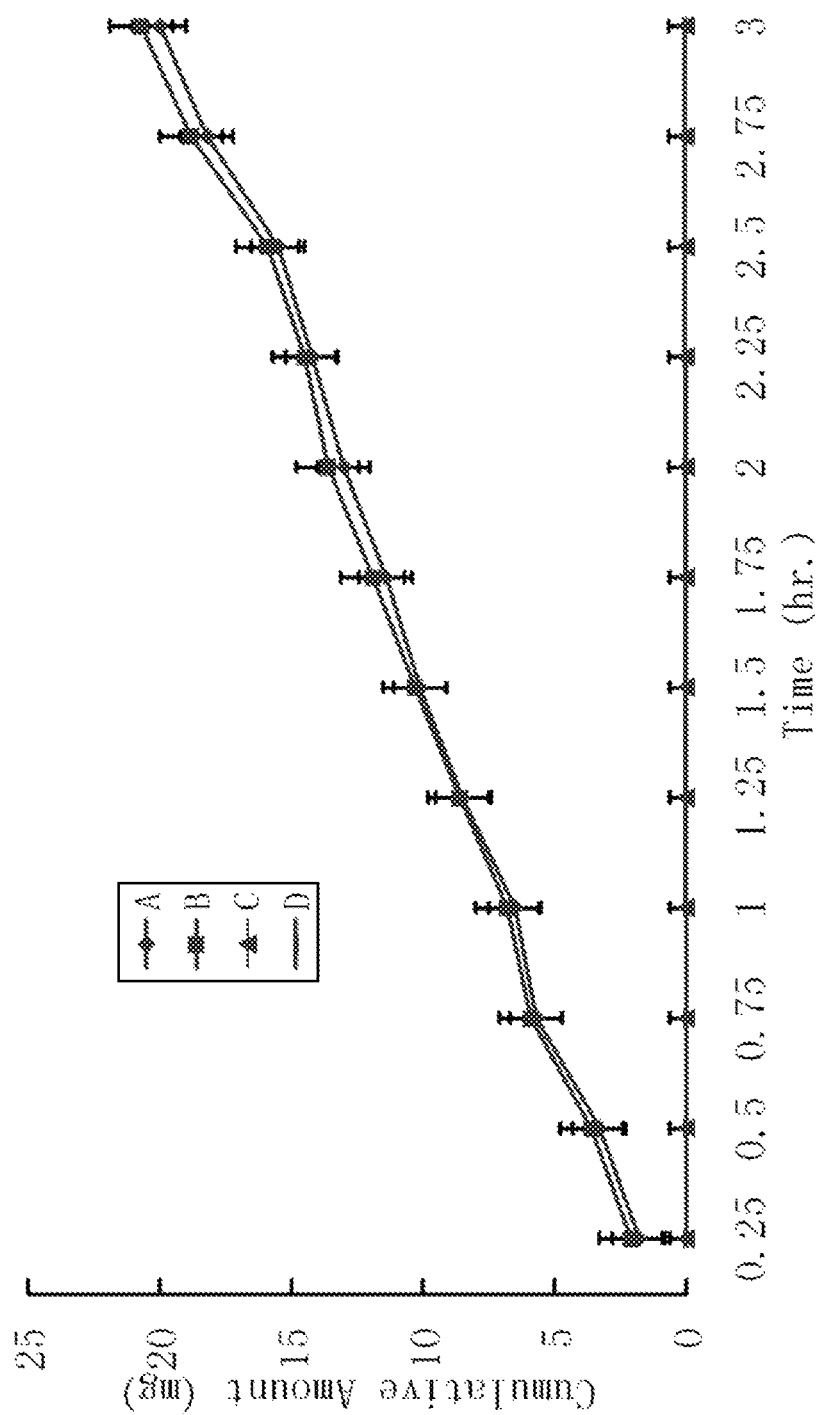
FIG. 1d: Cumulative amounts of diethylaminoethyl 2-(3-benzoylphenyl) propionate.AcOH (A, 20% solution), diethylaminoethyl 2-(3-phenoxyphenyl) propionate.AcOH (B, 20% solution), ketoprofen (C, 20% suspension), and fenoprofen (D, 20% suspension) crossing isolated human skin tissue in Franz cells (n=5). In each case, the vehicle was pH 7.4 phosphate buffer (0.2 M).
Figures 1, 1E:
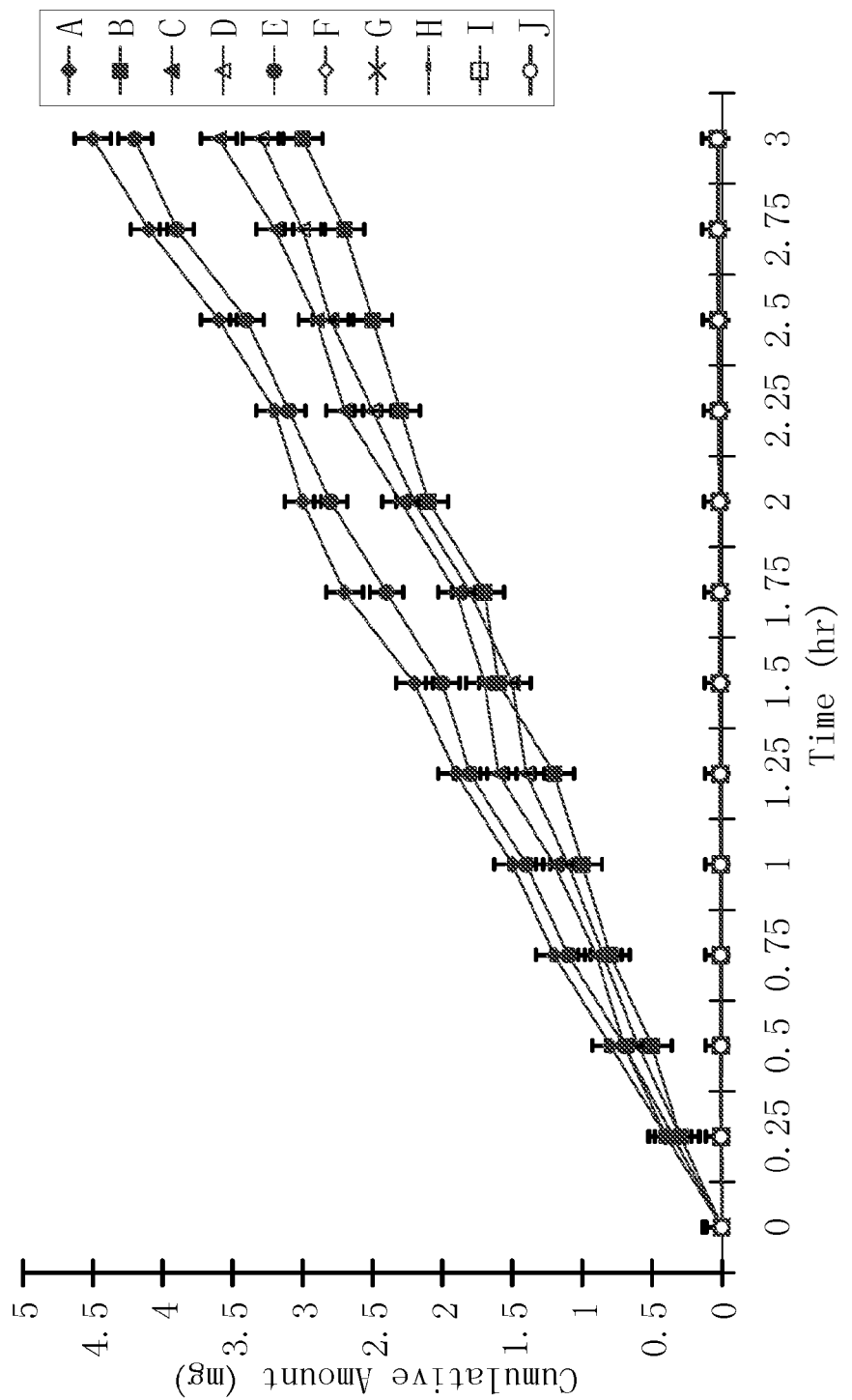
FIG. 1e-1: Cumulative amounts of diethylaminoethyl 2-(6-methoxy-2-naphthyl)propionate.AcOH (A, 20% solution), diethylaminoethyl α-methyl-4-(2-thienylcarbonyl) benzeneacetate.AcOH (B, 20% solution), diethylaminoethyl α-methyl-(p-chlorobenzoyl)-5-methoxy-2-methylindole 3-acetate.AcOH (C, 20% solution), diethylaminoethyl 2-(2-fluoro-4-biphenylyl)propionate.AcOH (D, 20% solution), diethylaminoethyl 6-chloro-α-methyl-9H-carbazole-2-acetate.AcOH (E, 20% solution), naproxen (F, 20% suspension), suprofen (G, 20% suspension), α-methyl-(p-chlorobenzoyl)-5-methoxy-2-methylindole 3-acetic acid (H, 20% suspension), flurbiprofen (I, 20% suspension), or carprofen (J, 20% suspension) crossing isolated human skin tissue in Franz cells (n=5). In each case, the vehicle was pH 7.4 phosphate buffer (0.2 M).
Figures 1, 1E, 2:
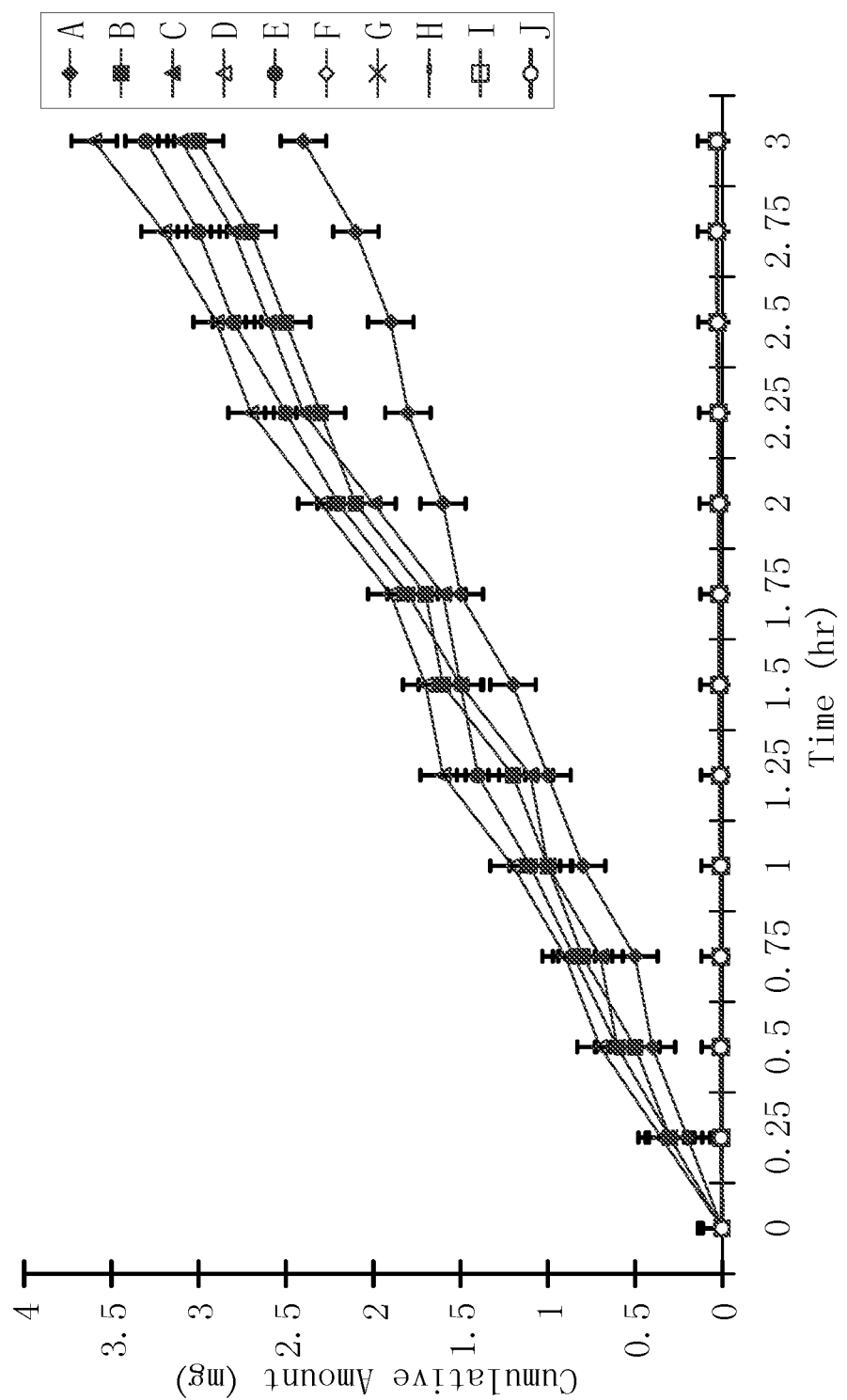
Figure 2A:
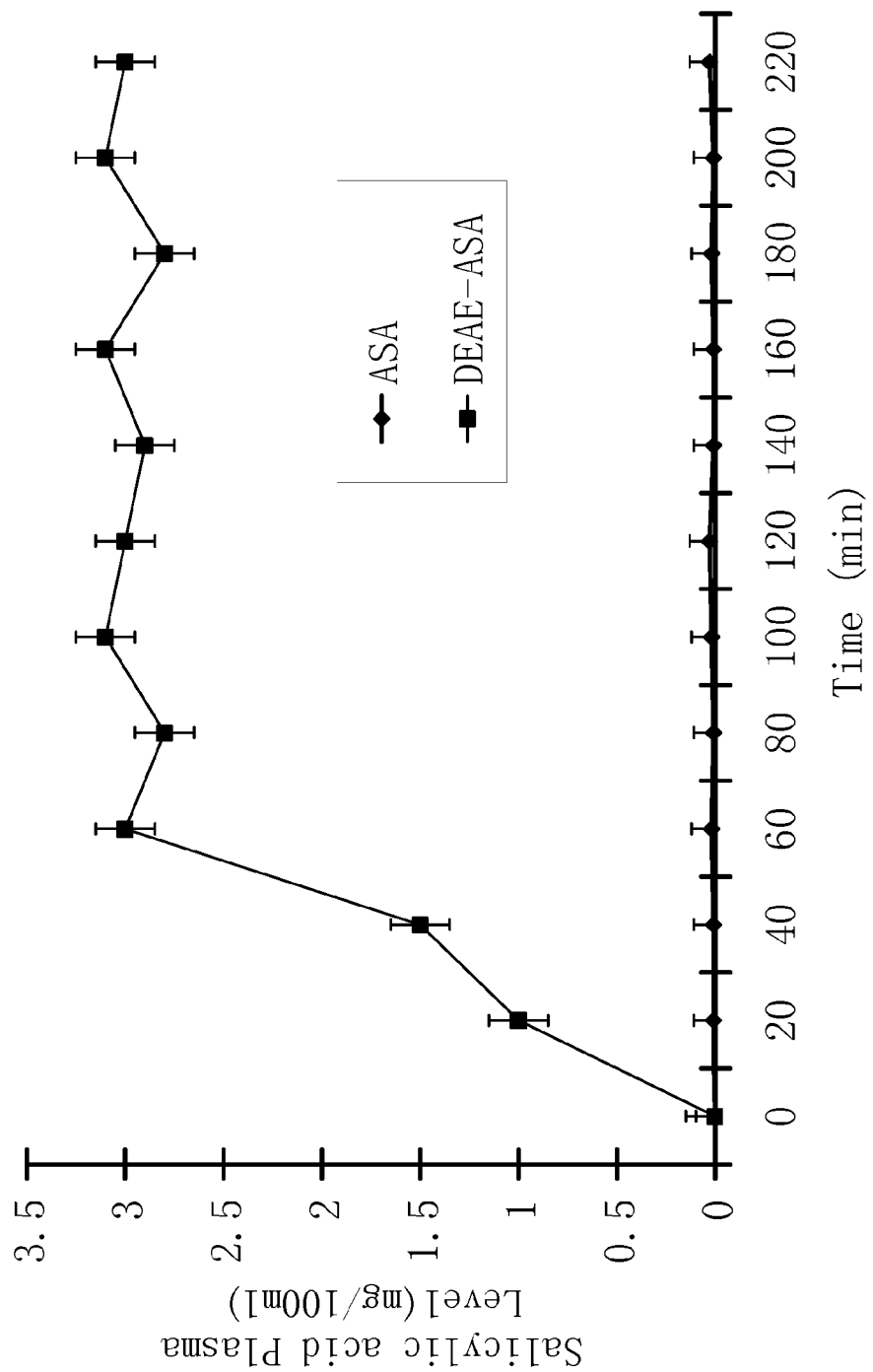
FIG. 2*a*: Total plasma levels of salicylic acid (SA) after topical application of 300 mg of acetylsalicylic acid (ASA) or diethylaminoethyl acetylsalicylate.AcOH (DEAE-ASA) to the backs of hairless mice (n=5).
Figures 1, 2B:
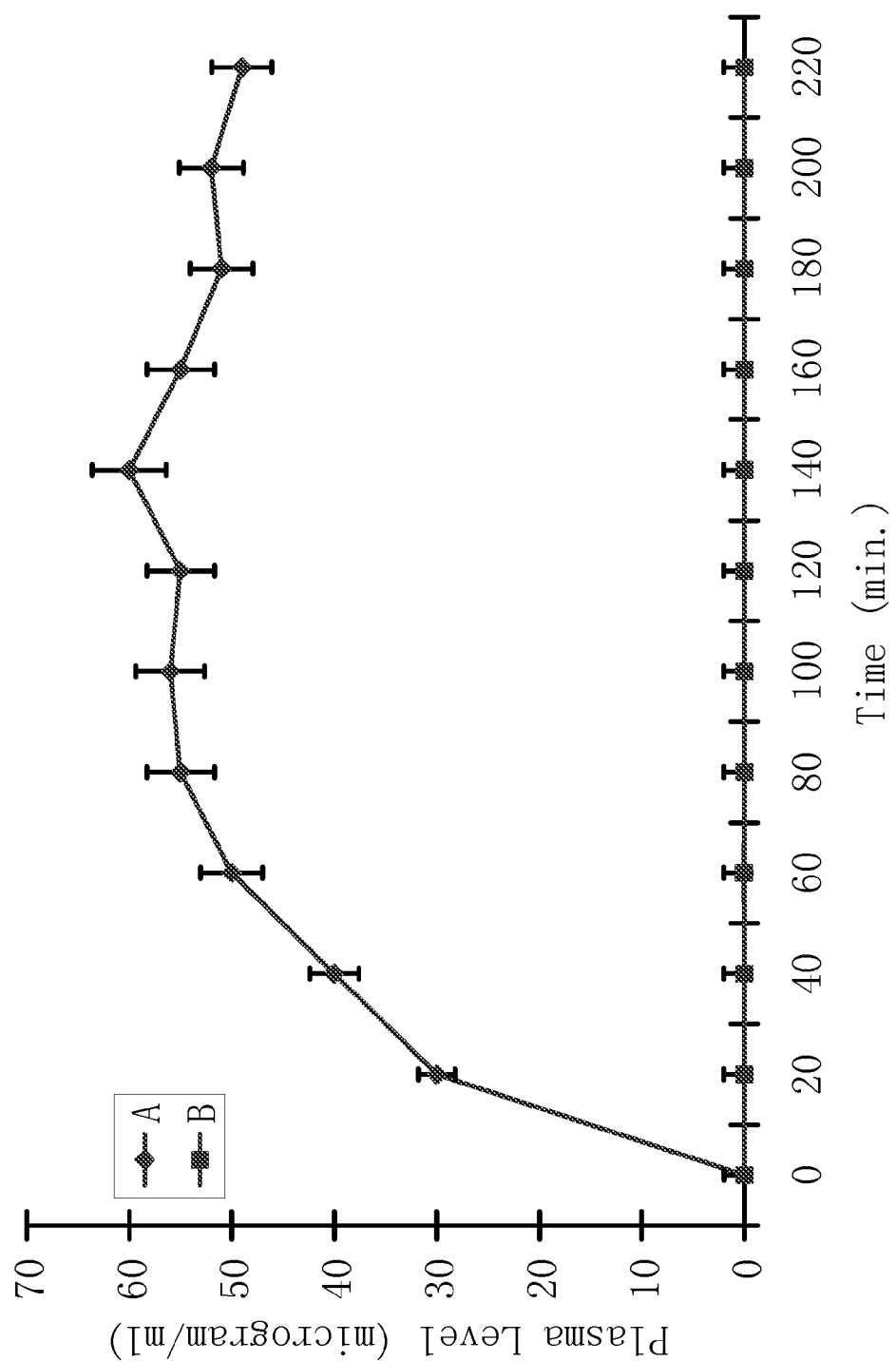
Figures 2, 2B:
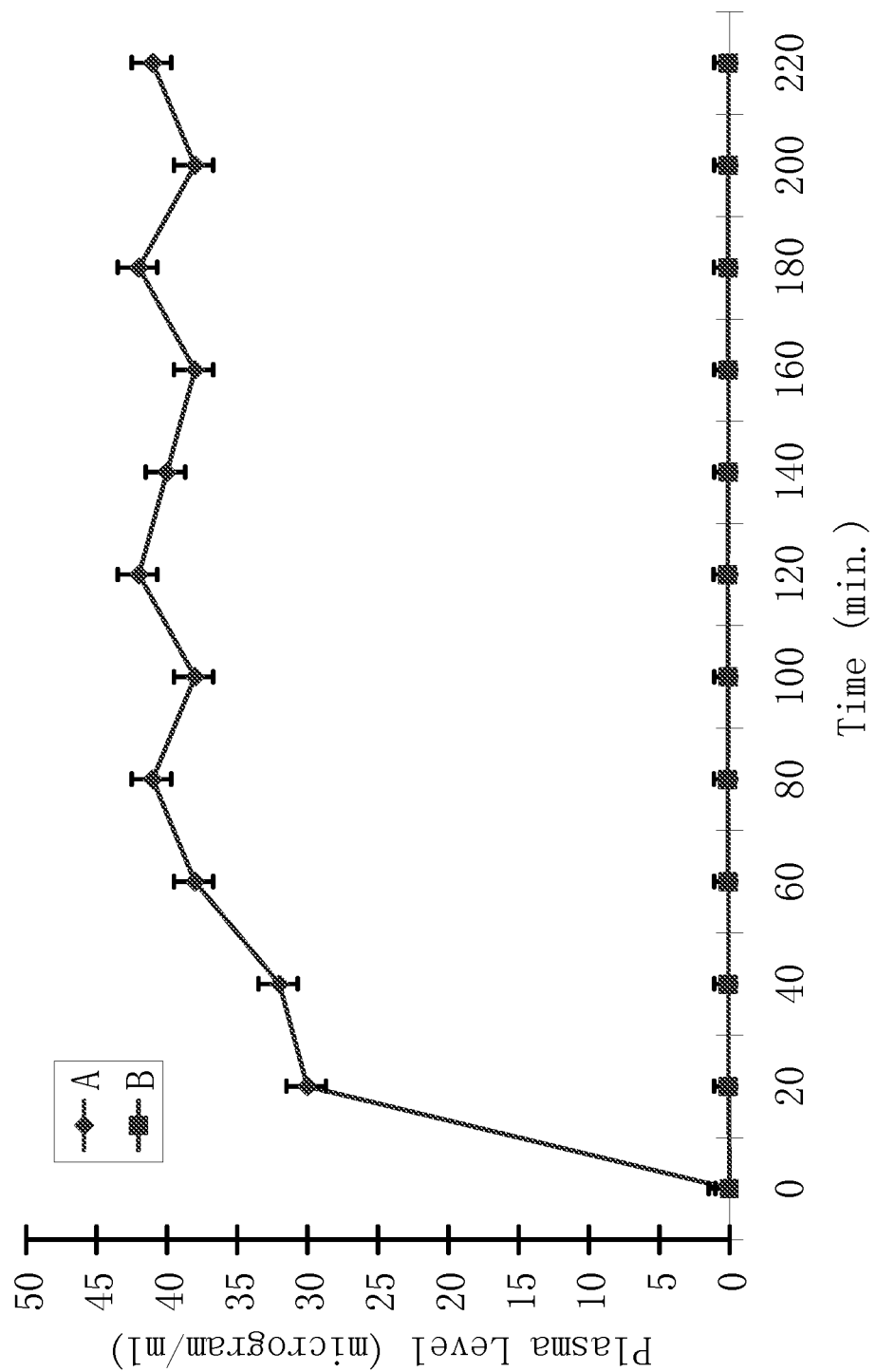
Figures 2, 2B, 3:
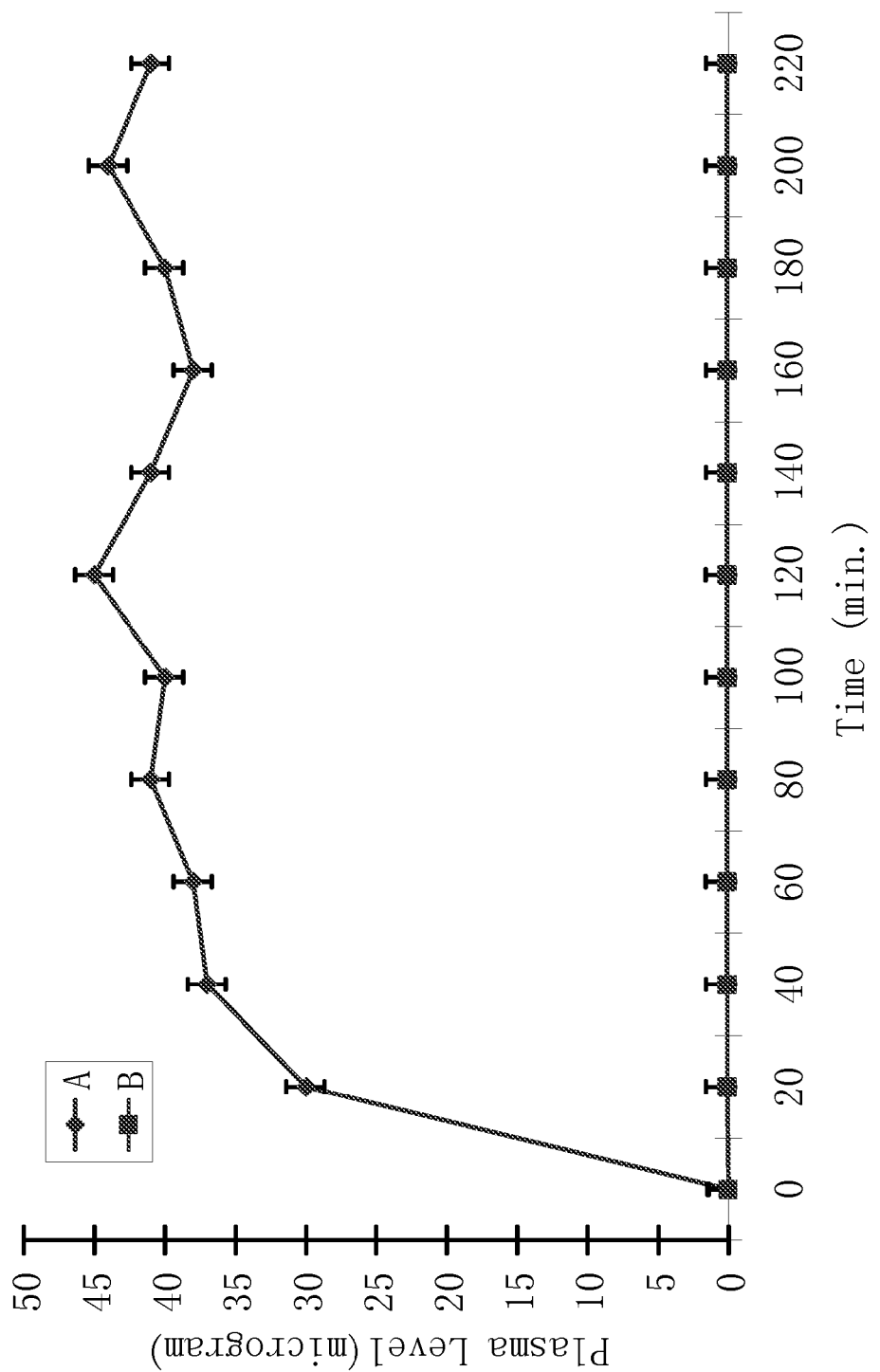
Figure 2C:
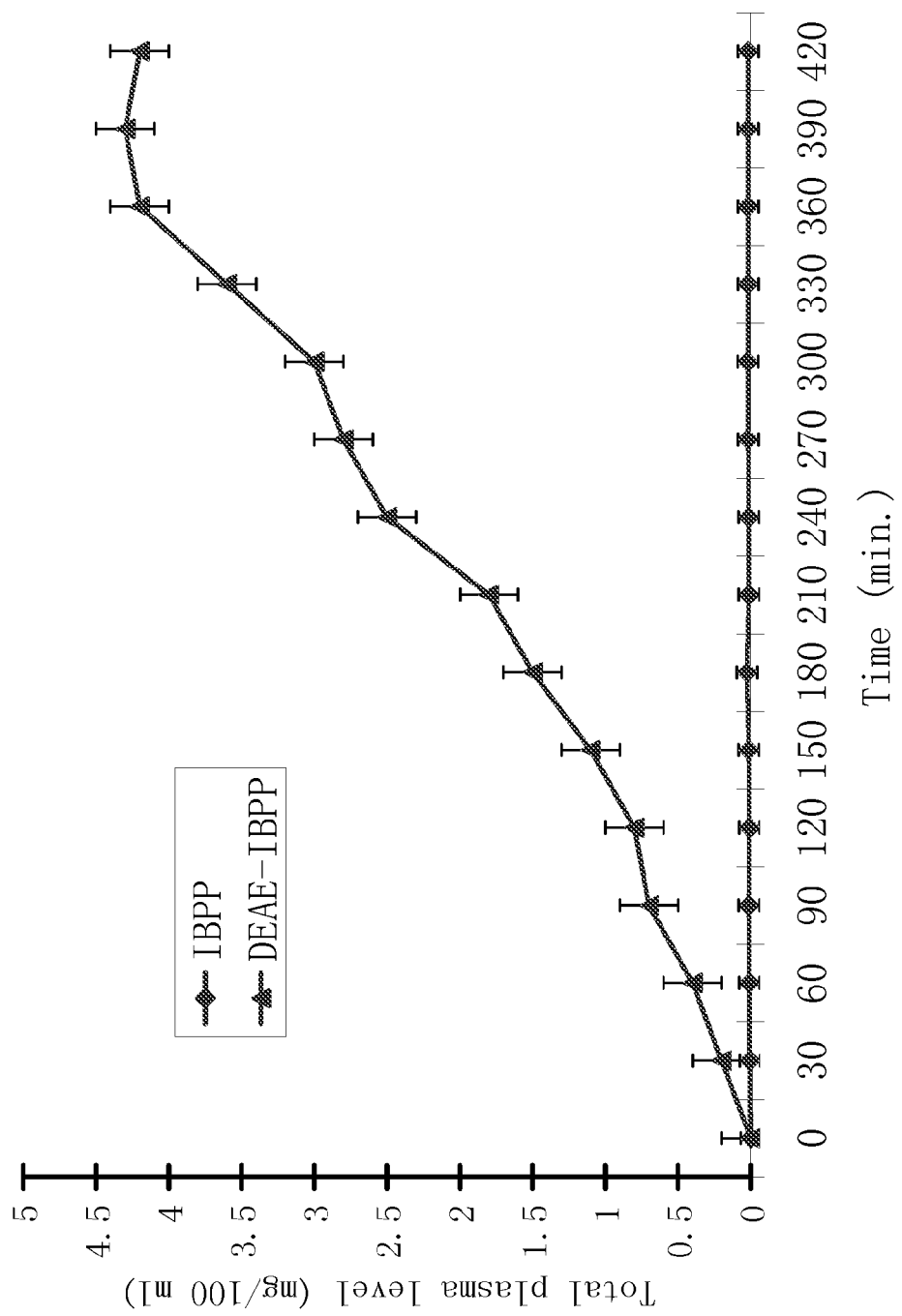
FIG. 2*c*: Total plasma levels of 2-(ρ-isobutylphenyl) propionic acid (IBPP) after topical application of 1 ml of a 20% suspension of 2-(ρ-isobutylphenyl) propionic acid (IBPP) or 20% solution of diethylaminoethyl 2-(ρ-isobutylphenyl) propionate.AcOH (DEAE-IBPP) to the backs of hairless mice (n=5).
Figures 1, 2D:
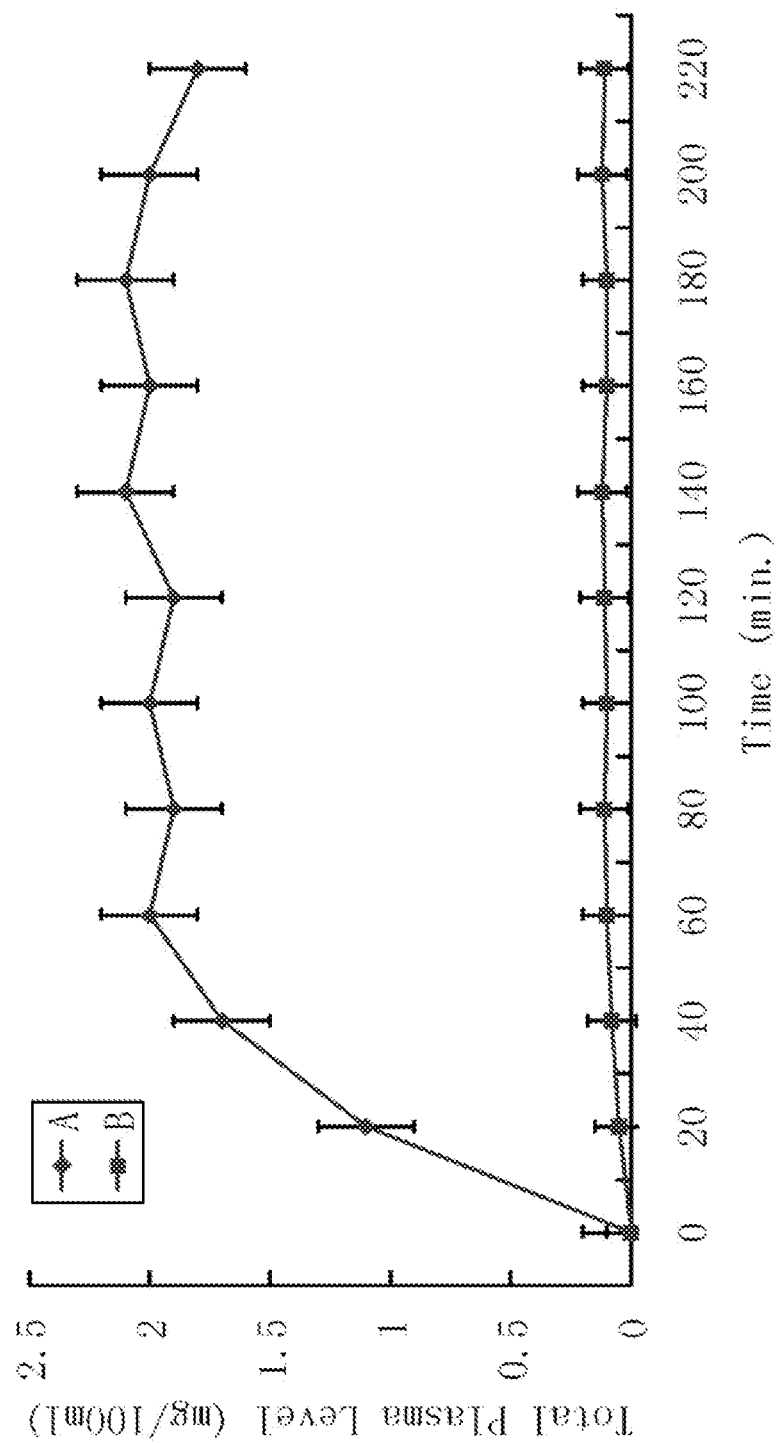
Figures 2, 2D:
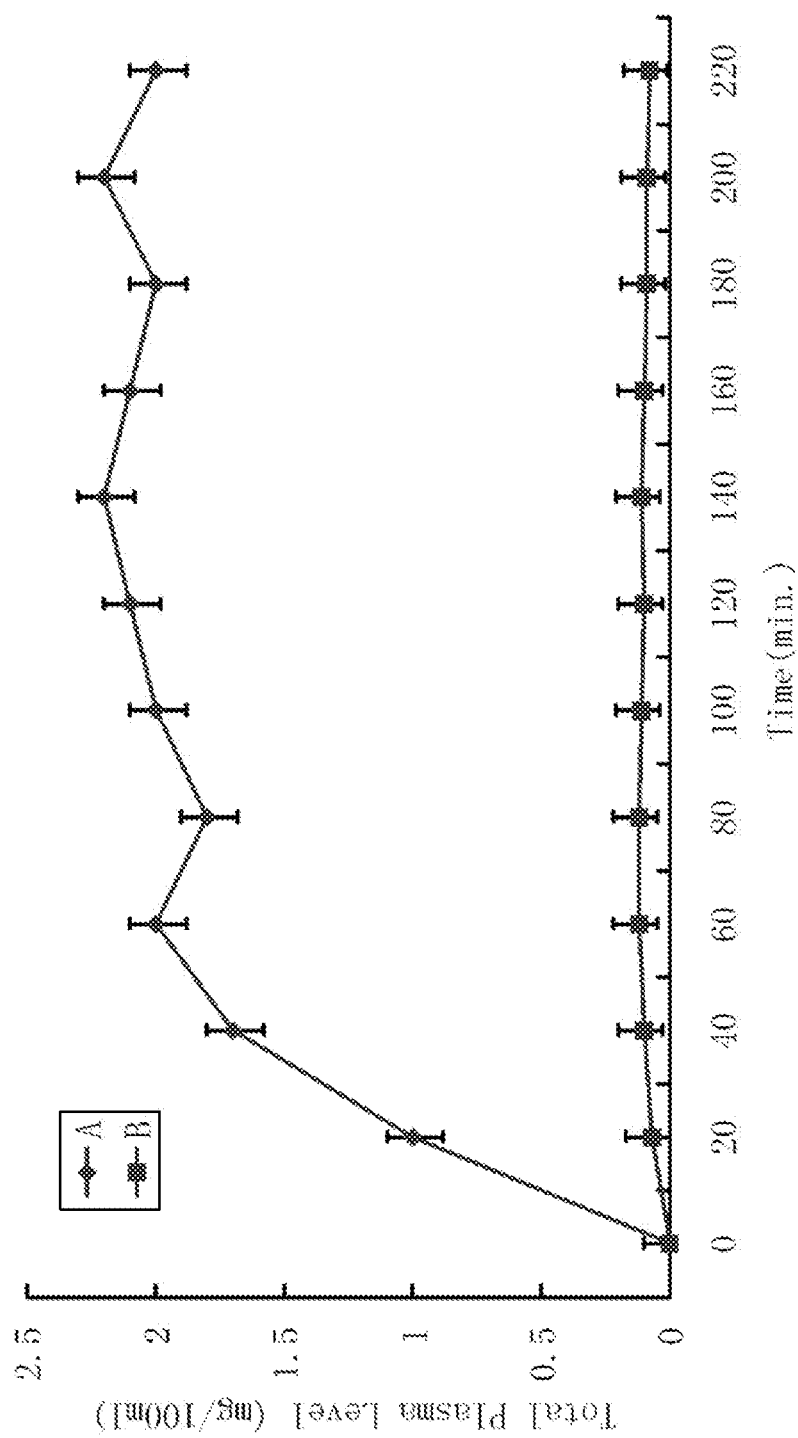
Figures 1, 2E:
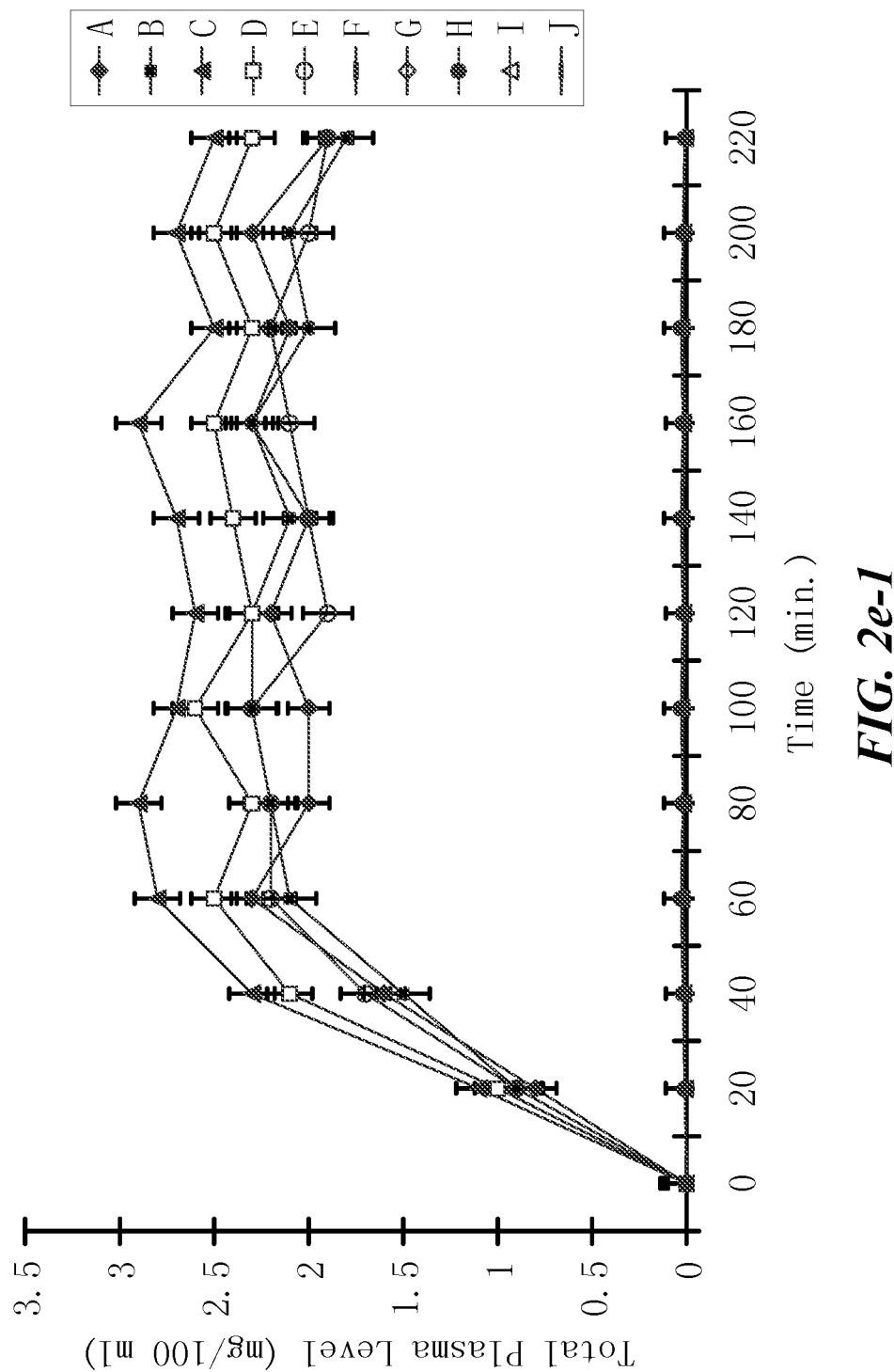
Figures 2, 2E:
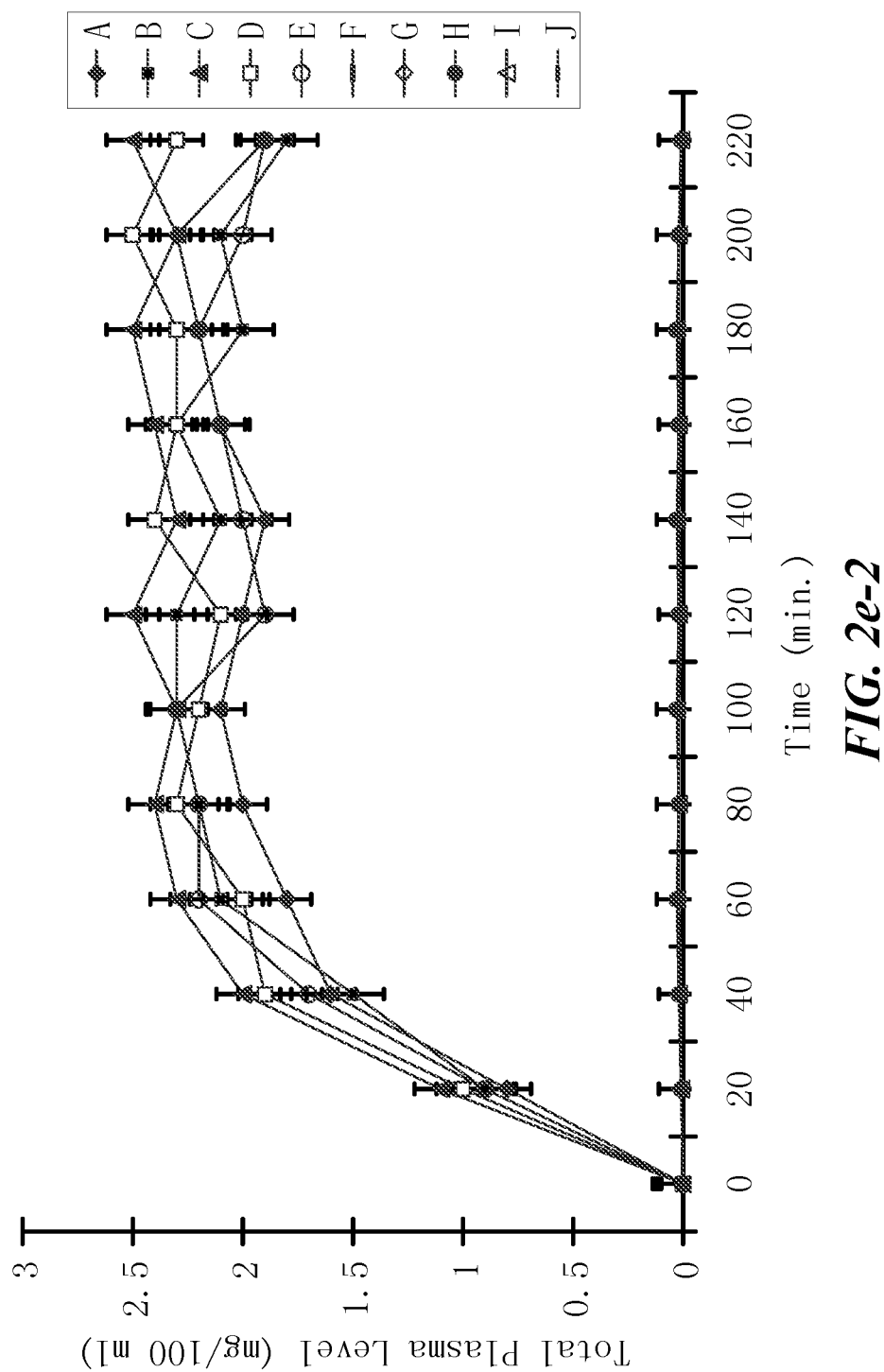
Figures 2, 2E, 3:
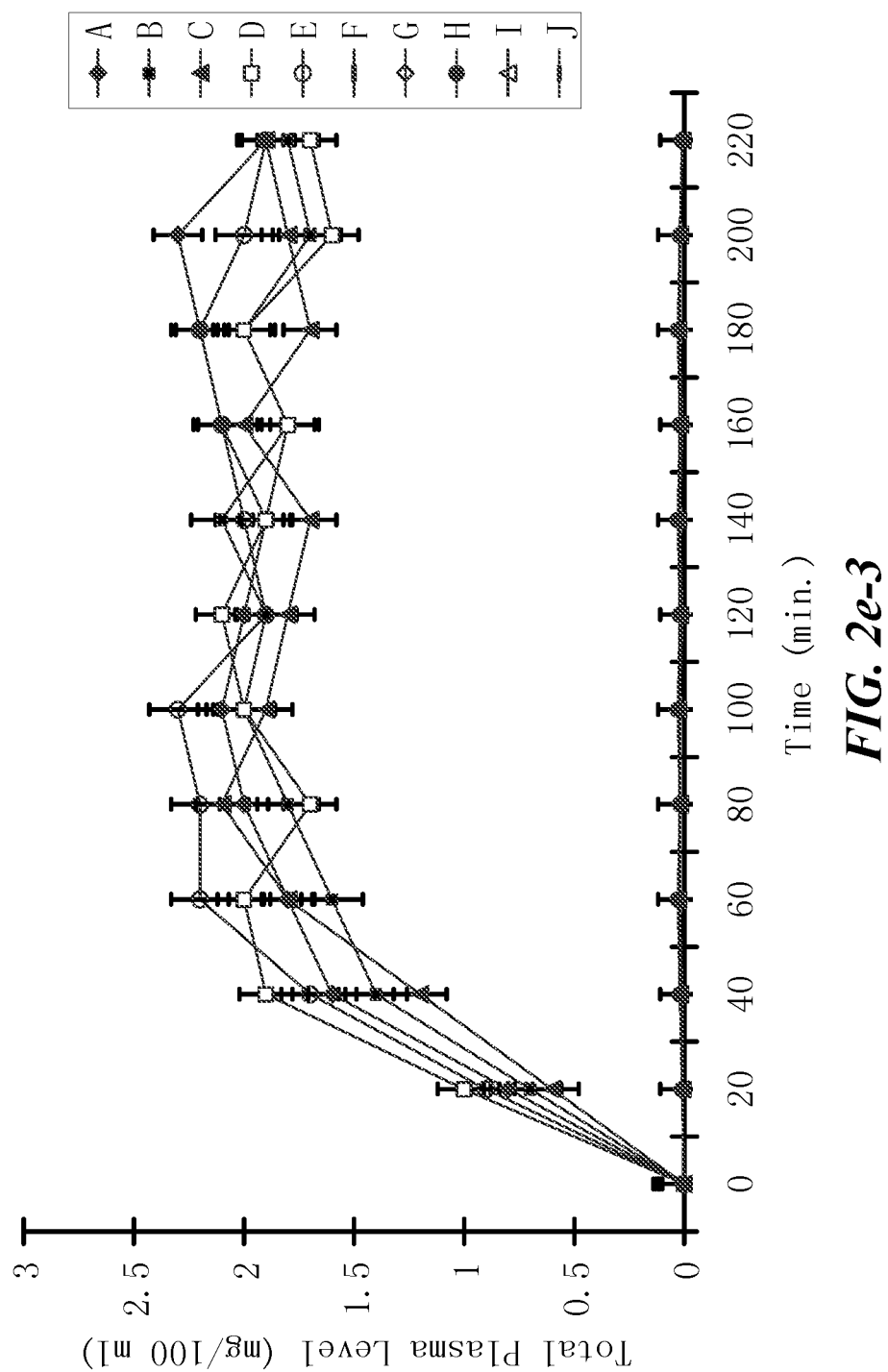
Figures 2, 2E, 3, 4:
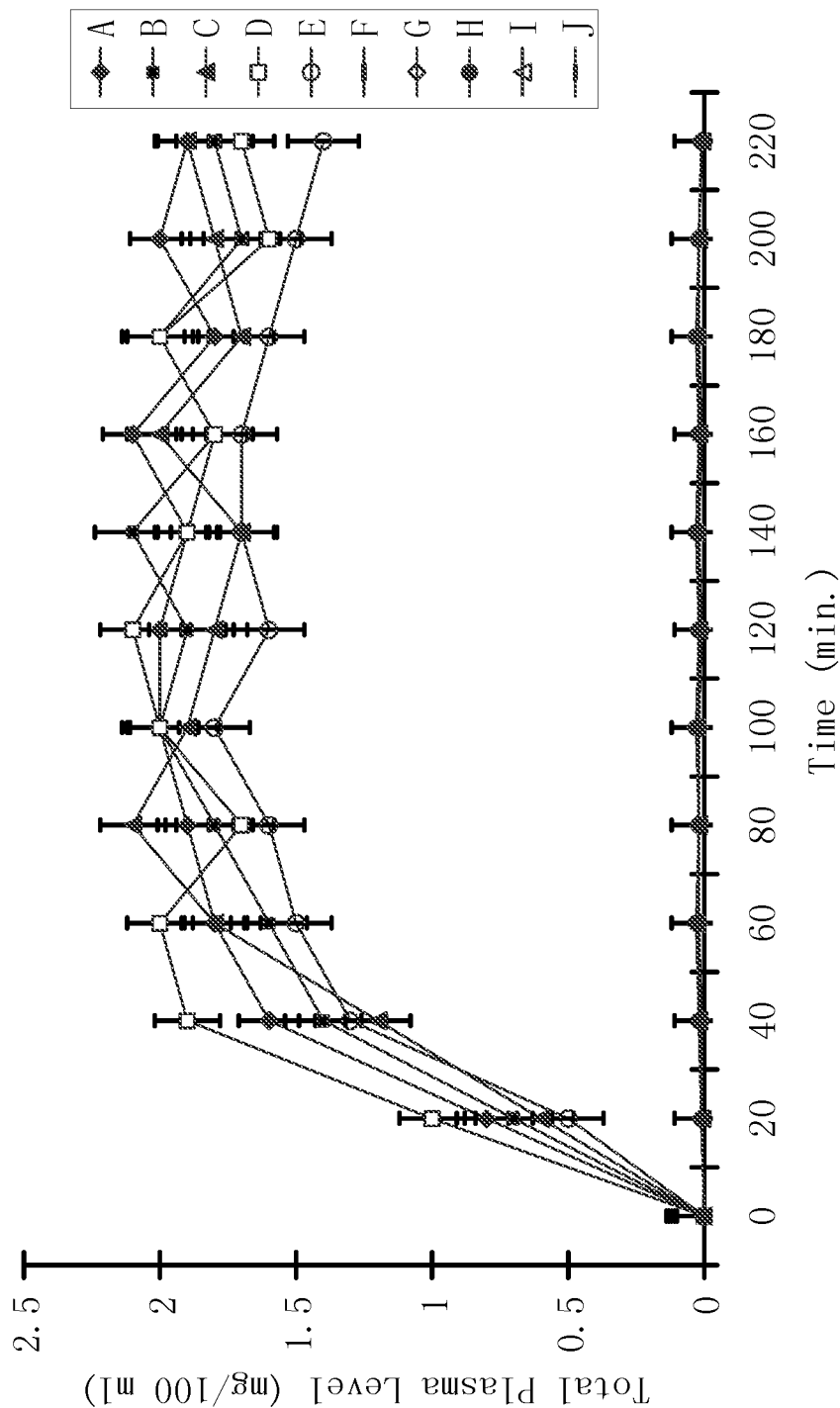

FIG. 2e-2: Total plasma levels of pranoprofen, benoxaprofen, alminoprofen, tiaprofenic acid, or pirprofen after topical application of diethylaminoethyl α-methyl-5H-[1]benzopyrano[2,3-b]pyridine-7-acetate.AcOH (A), diethylaminoethyl 2-(4-chlorophenyl)-α-methyl-5-benzoxazoleacetate.AcOH (B), diethylaminoethyl α-methyl-4-[(2-methyl-2-propenyl)amino]benzeneacetate.AcOH (C), diethylaminoethyl 5-benzoyl-α-methyl-2-thiopheneacetate.AcOH (D), diethylaminoethyl 3-chloro-4-(2,5-dihydro-1H-pyrrol-1-yl)-α-methyl benzeneacetate.AcOH (E), pranoprofen (F), benoxaprofen (G), alminoprofen (H), tiaprofenic acid (I), or pirprofen (J) 1 ml of a 20% solution of in isopropanol to the backs of hairless mice (n=5).

Figures 1, 1E, 2, 3:
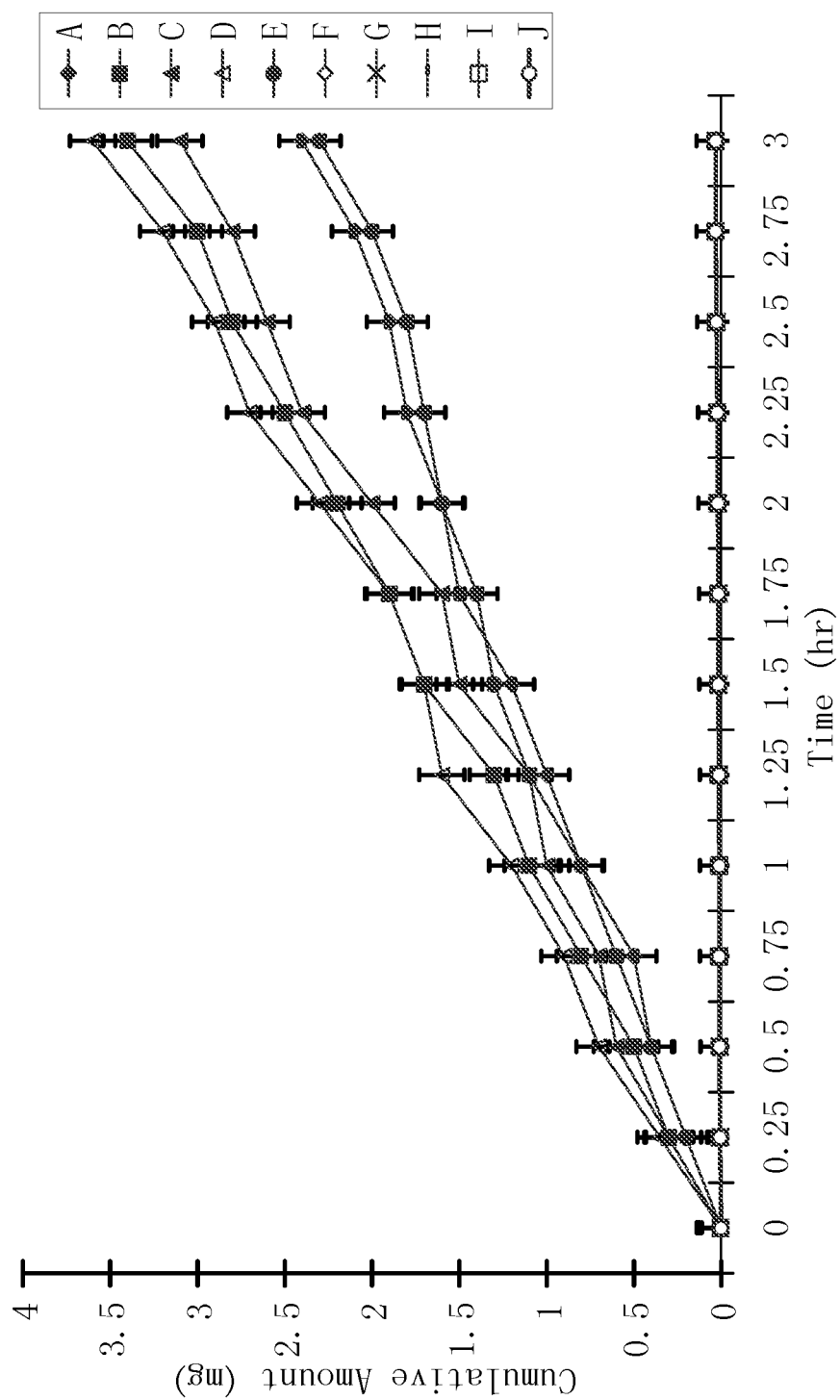

FIG. 2e-3: Total plasma levels of zaltoprofen, bermoprofen, loxoprofen, indoprofen, fenclorac after topical application of diethylaminoethyl 2-(10, 11-dihydro-10-oxodibenzo(b,f)thiepin-2-yl)propionate.AcOH (A), diethylaminoethyl 2-(8-methyl-10,11-dihydro-11-oxodibenz(b,f)oxepin-2-yl)propionate.AcOH (B), diethylaminoethyl 2-[4-(2-oxocyclopentyl-methyl)phenyl]propionate.AcOH (C), diethylaminoethyl 4-(1,3-dihydro-1-oxo-2H-isoindol-2-yl)-α-methylbenzeneacetate.AcOH (D), diethylaminoethylα,3-dichloro-4-cyclohexylbenzeneacetate.AcOH (E), zaltoprofen (F), bermoprofen (G), loxoprofen (H), indoprofen (I), fenclorac (J) 1 ml of a 20% solution of in isopropanol to the backs of hairless mice (n=5).

FIG. 2e-4: Total plasma levels of oxaprozin, fenbufen, orpanoxin, ketorolac, and clidanac after topical application of diethylaminoethyl 4,5-Diphenyl-2-oxazole propionate.AcOH (A), diethylaminoethyl 3-(4-biphenylylcarbonyl)propionate.AcOH (B), diethylaminoethyl 5-(4-chlorophenyl)-beta-hydroxy-2-furanpropionate.AcOH (C), diethylaminoethyl 5-benzoyl-2,3-dihydro-1H-pyrrolizine-1-carboxylate.AcOH (D), diethylaminoethyl 6-chloro-5-cyclohexyl-2,3-dihydro-1H-indene-1-carboxylate.AcOH (E), oxaprozin (F), fenbufen (G), orpanoxin (H), ketorolac (I), or clidanac (J) 1 ml of a 20% solution of in isopropanol to the backs of hairless mice (n=5).

Figures 1, 2F:
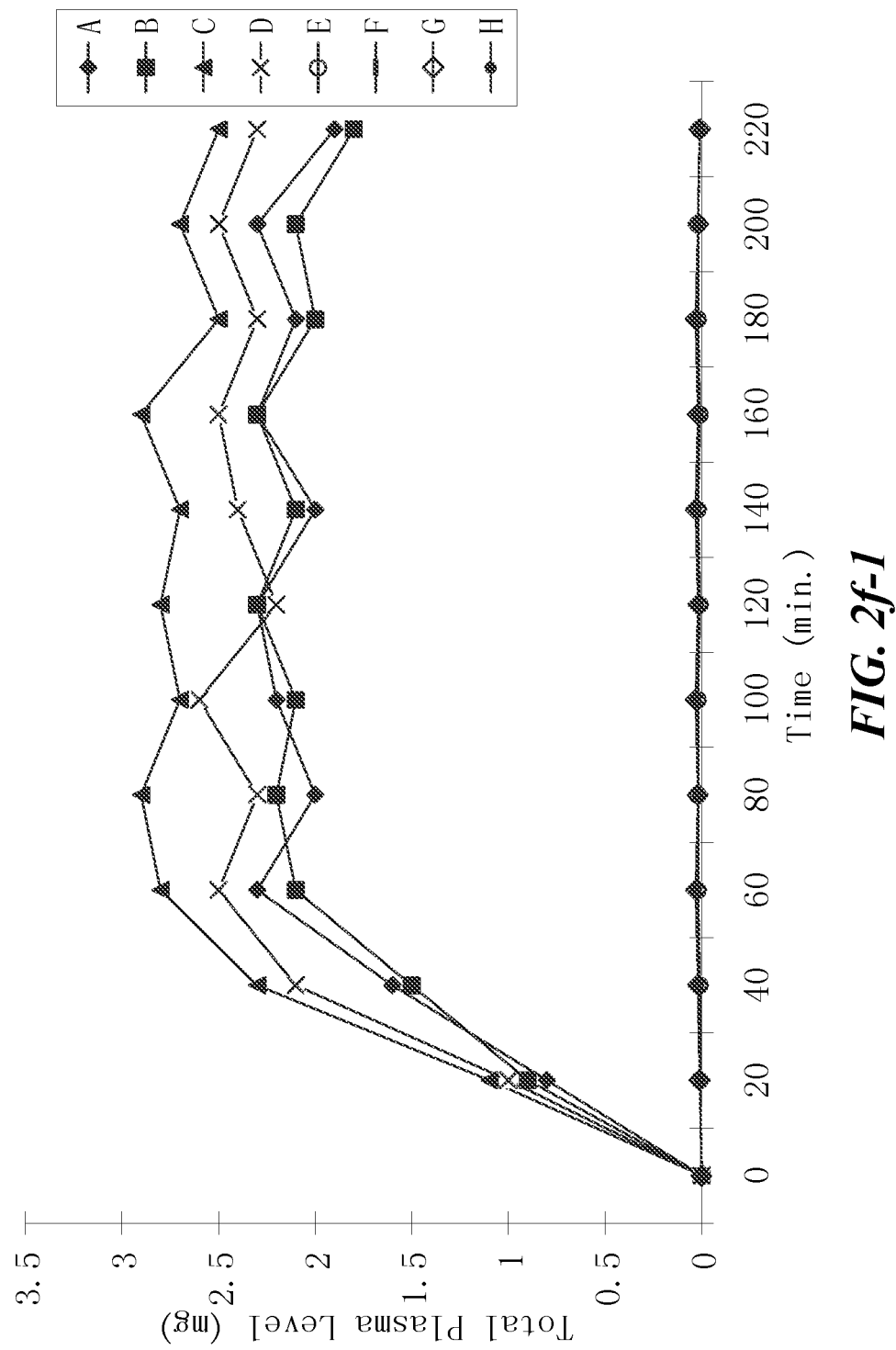
Figures 2, 2F:
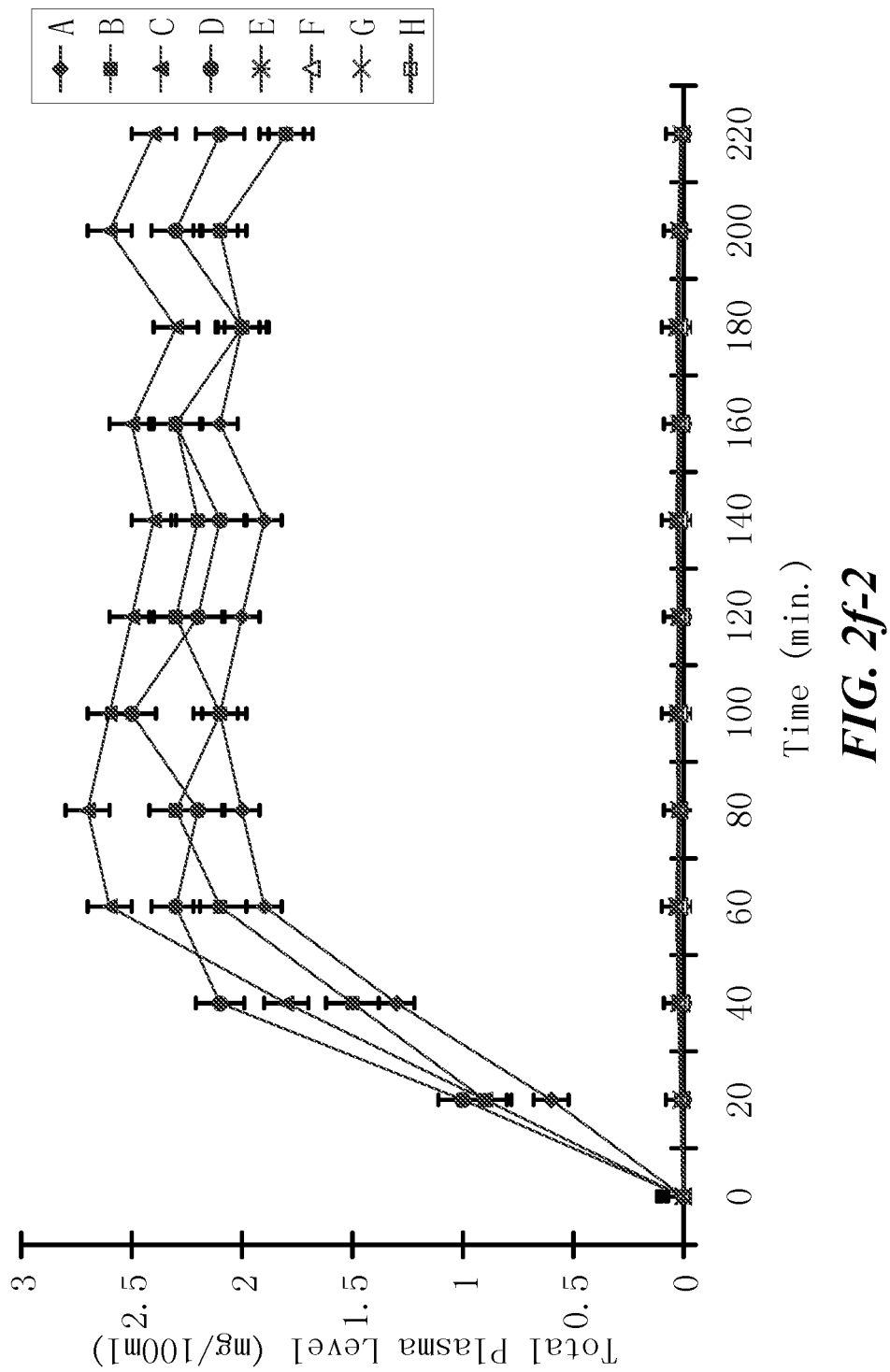
Figures 2, 2F, 3:
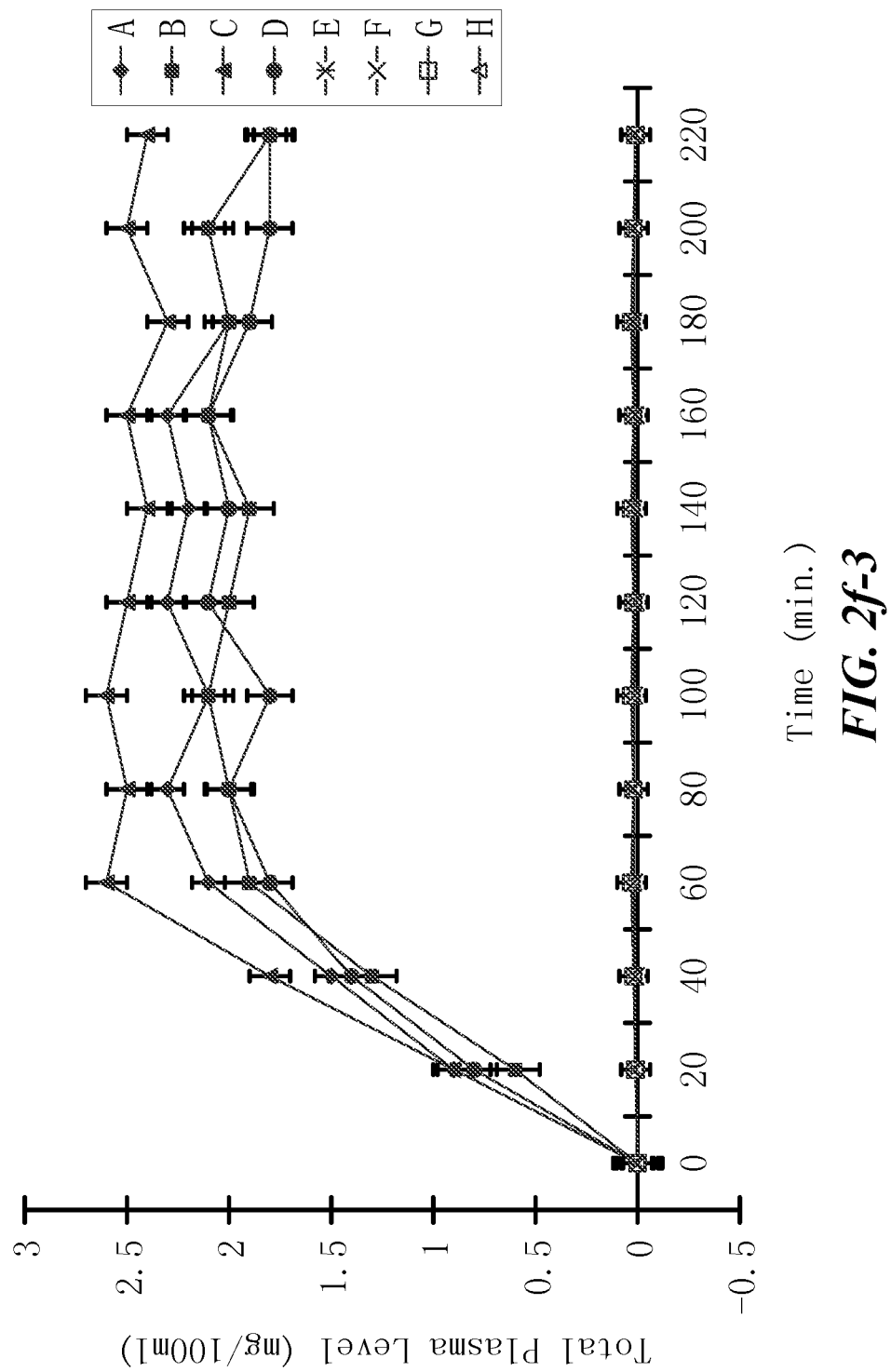

FIG. 2f-1: Total plasma levels of indomethacin. sulindac. tolmetin. or zomepirac after topical application of 1 ml of a 20% solution of diethylaminoethyl 1-(p-chlorobenzoyl)-5-methoxy-2-methylindole 3-acetate.AcOH (A), diethylaminoethyl (Z)-5-fluoro-2-methyl-1-[(4-methysulfinyl phenyl-methylene]-1H-indene-3-acetate.AcOH (B), diethylaminoethyl 1-methyl-5-(4-methylbenzoyl)-1H-pyrrole-2-acetate.AcOH (C), diethylaminoethyl 5-(4-Chlorobenzoyl)-1,4-dimethyl-1H-pyrrole-2-acetate.AcOH (D), indomethacin (E). sulindac (F), tolmetin (G), or zomepirac (H) in isopropanol to the backs of hairless mice (n=5). Total plasma levels of diclofenac after topical application of 1 ml of a 30% solution of diethylaminoethyl 2[(2,6-dichlorophenyl)amino]benzene acetate.AcOH and 2[(2.6-dichlorophenyl)amino]benzene acetic acid (diclofenac) in isopropanol to the backs of hairless mice (n=5).

FIG. 2f-2: Total plasma levels of etodolac. amfenac. bromofenac, or alclofenac after topical application of diethylaminoethyl 1,8-diethyl-1,3,4,9-tetrahydropyrano-[3,4-b]indole-1-acetate.AcOH (A), diethylaminoethyl 2-amino-3-benzoylbenzeneacetate.AcOH (B), diethylaminoethyl 2-amino-3-(4-bromo-benzoyl)benzeneacetate.AcOH (C). diethylaminoethyl 3-chloro-4-(2-propenyloxy) benzeneacetate.AcOH (D), etodolac (E), amfenac (F), bromofenac (G), or alclofenac (H) 1 ml of a 20% solution of in isopropanol to the backs of hairless mice (n=5).

FIG. 2f-3: Total plasma levels of fenclofenac. acemetacin, fentiazac. or lonazolac after topical application of diethylaminoethyl 2-(2,4-dichlorophenoxy)benzeneacetate.AcOH (A), diethylaminoethyl 1-(4-chlorobenzoyl-5-methoxy-2-methyl-1H-indole-3-acetoxyacetate.AcOH (B), diethylaminoethyl 4-(4-chlorophenyl)-2-phenyl-5-thiazoleacetate.AcOH (C), diethylaminoethyl 3-(4-chlorophenyl)-1-phenyl-1H-pyrazole-4-acetate.AcOH (D), fenclofenac (E), acemetacin (F). fentiazac (G), or lonazolac)H) 1 ml of a 20% solution of in isopropanol to the backs of hairless mice (n=5).

Figure 2G:
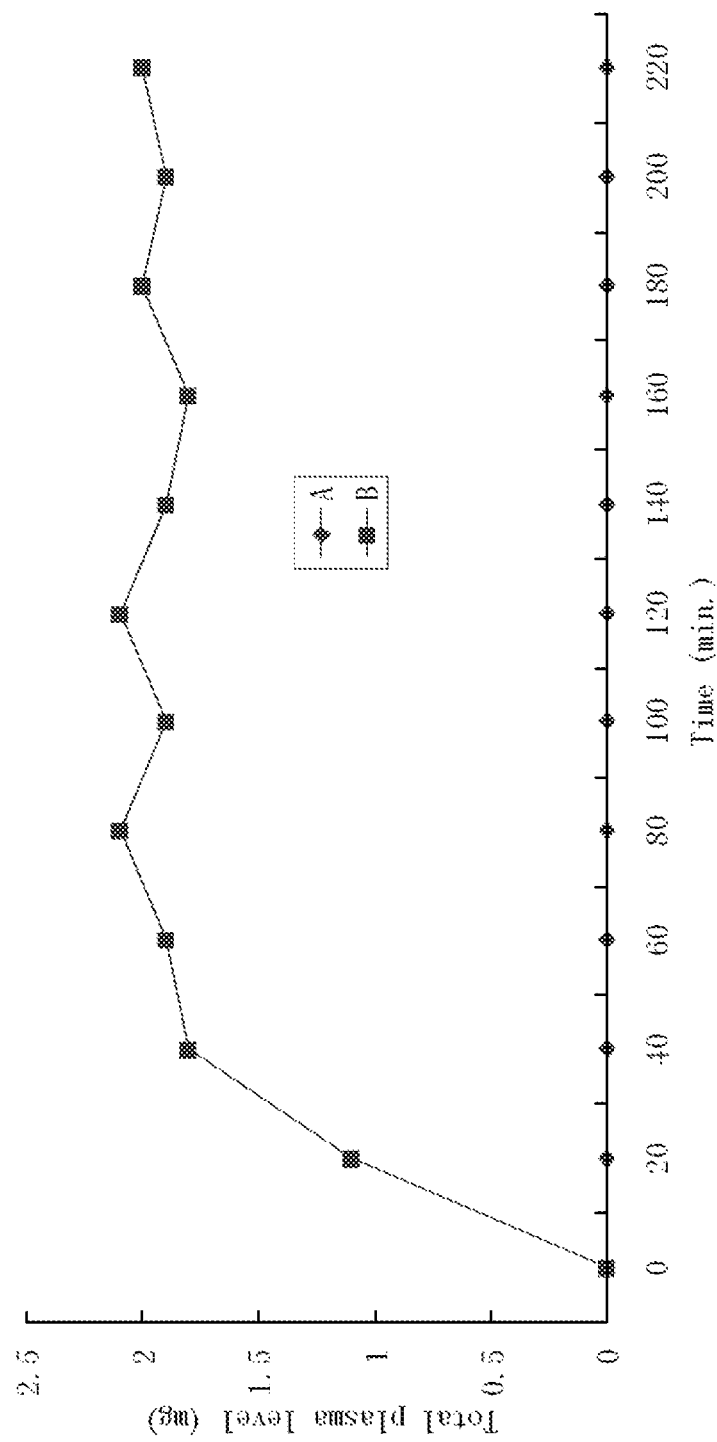

FIG. 2g: Total plasma levels of diclofenac after topical application of 1 ml of a 30% solution of diethylaminoethyl 2[(2,6-dichlorophenyl)amino]benzene acetate.AcOH and 2[(2,6-dichlorophenyl)amino]benzene acetic acid (diclofenac) in isopropanol to the backs of hairless mice (n=5).

Figure 2H:
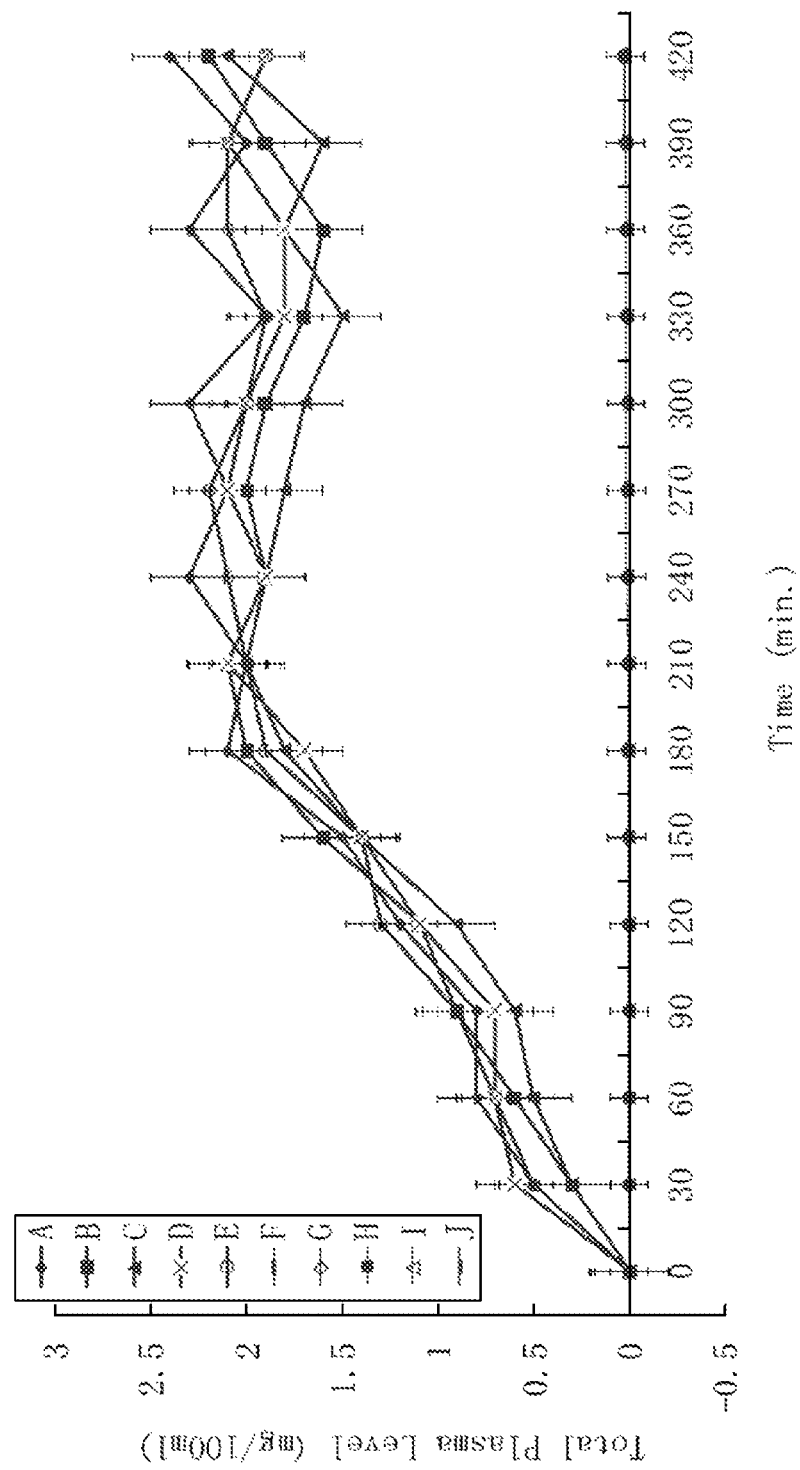

FIG. 2h: Total plasma levels of mefenamic acid, meclofenamic acid, flufenamic acid, niflumic acid, and flunixin after topical application of 1 ml of a 20% solution of diethylaminoethyl 2-[(2,3-dimethylphenyl)amino]benzoate.AcOH (A), diethylaminoethyl 2-[(2,6-dichloro-3-methylphenyl)amino]benzoate.AcOH (B), diethylaminoethyl 2-[[(3-(trifluoromethyl)phenyl)amino]benzoate.AcOH (C), diethylaminoethyl 2-[[3-(trifluoromethyl)phenyl]amino]-3-pyridinecarboxylate.AcOH (D), diethylaminoethyl 2-[[2-methyl-3-(trifluoromethyl)phenyl]amino]-3-pyridinecarboxylate.AcOH (E), mefenamic acid (F), meclofenamic acid (G), flufenamic acid (H), niflumic acid (I), and flunixin (J) in ethanol to the backs of hairless mice (n=5).

Figure 2I:
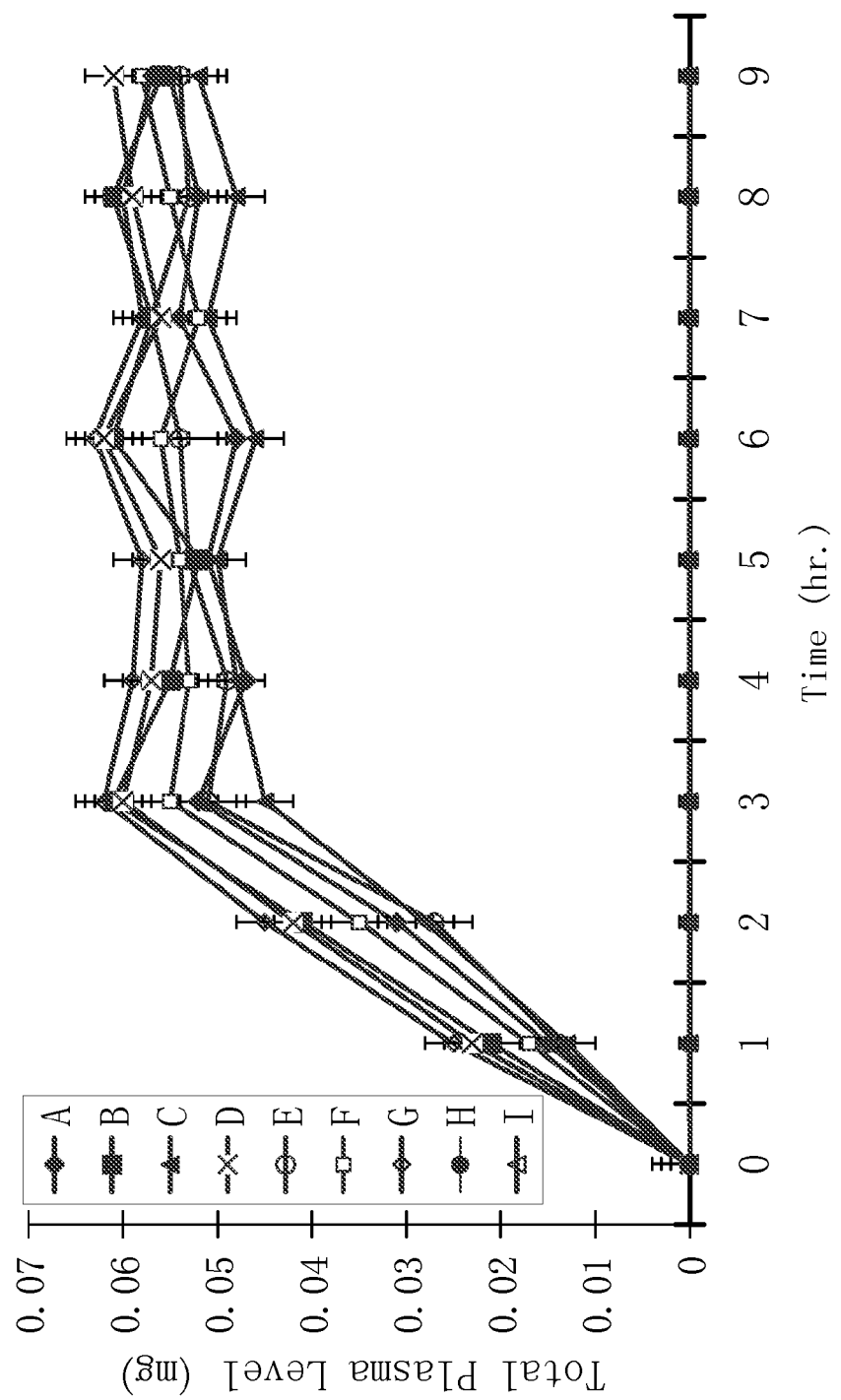

FIG. 2i: Total plasma levels of drugs after topical application of 1 ml of 4-N,N-dimethylaminobutyryloxy-2-methyl-N-2-pyridinyl-2H, 1,2-benzothiazine-3-carboxamide 1,1-dioxide.HCl, N-(2-thiazolyl)-4-N,N-dimethylaminobutyryloxy-2-methyl-2H, 1,2-benzothiazine-3-carboxamide 1,1-dioxide.HCl, 6-chloro-4-N,N-dimethylaminobutyryloxy-2-methyl-N-2-pyridinyl-2H-thieno[2,3-e]-1,2-thiazine-3-carboxamide 1,1-dioxide.HCl, 4-N,N-dimethylaminobutyryloxy-2-methyl-N-2-pyridinyl-2H-thieno[2,3-e]-1,2-thiazine-3-carboxamide 1,1-dioxide-.HCl, 8-chloro-(4-N,N-dimethylaminobutyryloxy-pyridine-2-ylamino-methylidene)-3-methyl-2,2-dioxo-2$\lambda^{6}$7-dithia-3-azabicyclo[4,3,0]nona-8,10-dien-5-one.HCl, 4-N,N-dimethylaminobutyryloxy-2-methyl-N-[5-Methyl-3-isoxolyl-2H-1,2-benzothiazine-3-carboxamide 1,1-dioxide].HCl, 4-N,N-dimethylaminobutyryloxy-2-methyl-N-(5-methyl-2-thiazolyl)-2H-1,2-benzothiazine-3-carboxamide-1,1-dioxide.HCl, Piroxicam, and sudoxiam in isopropanol to the backs of hairless mice (n=5).

Figure 2J:
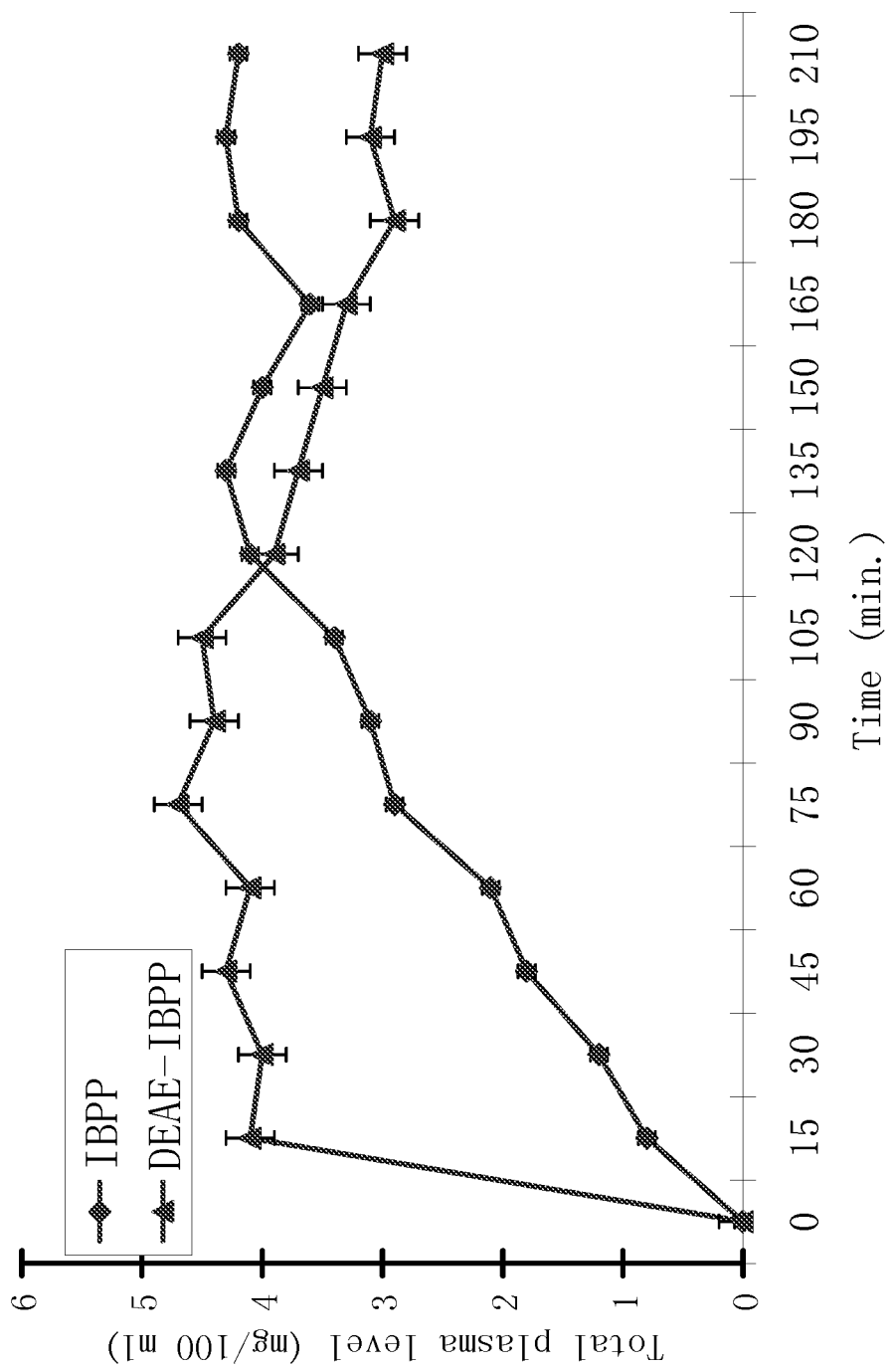

FIG. 2j: Total plasma levels of 2-(p-isobutylphenyl) propionic acid and diethylaminoethyl 2-(p-isobutylphenyl) propionate after 1 ml of a 10% suspension of 2-(p-isobutylphenyl) propionic acid (IBPP) or 10% solution of diethylaminoethyl 2-(p-isobutylphenyl) propionate.AcOH (DEAE-IBPP) in pH 7.4 phosphate buffer were administrated orally to rats (n=5).

Figure 3A:
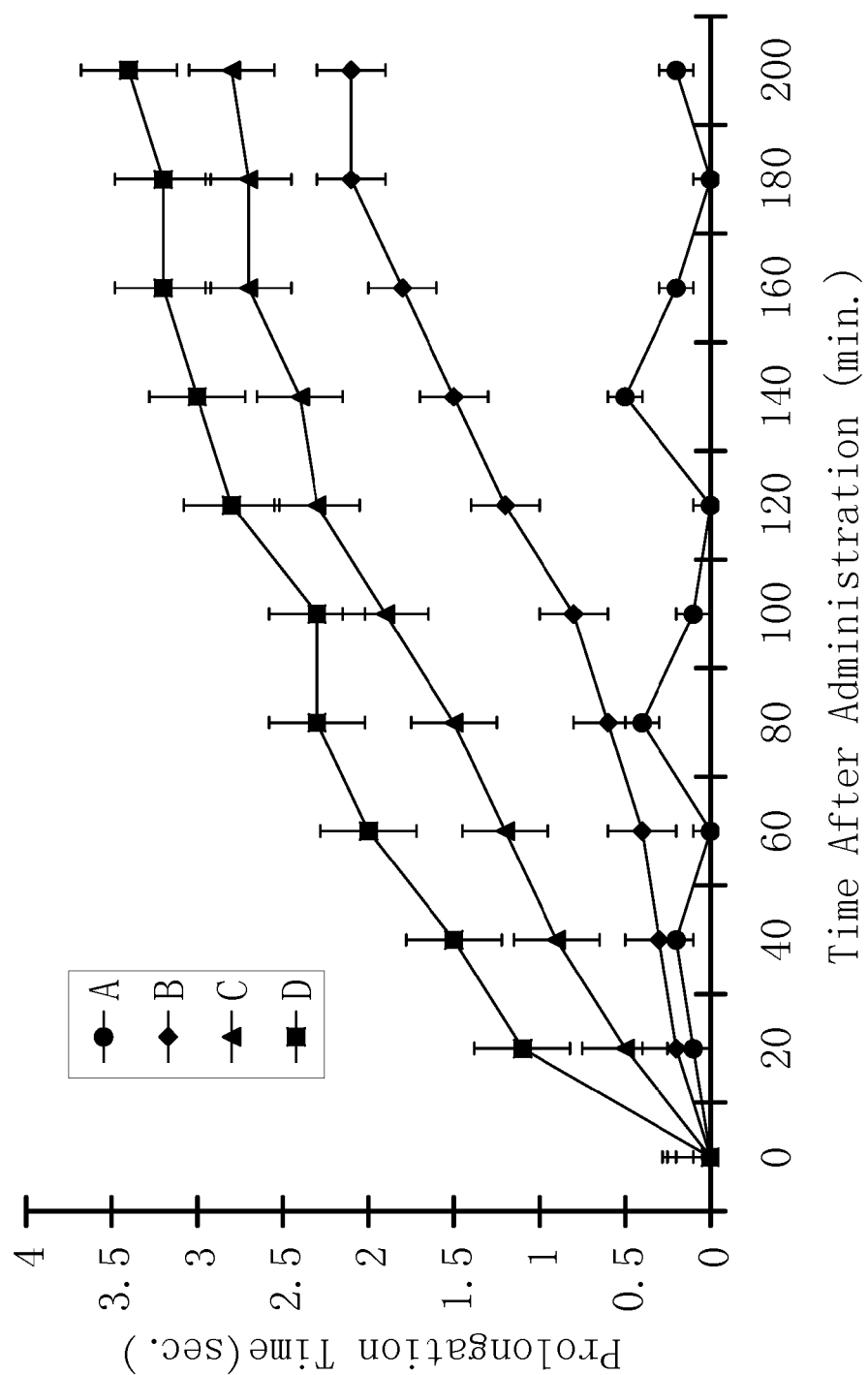

FIG. 3a. The prolongation time of the pain threshold of the mice tails after 200 mg/kg of aspirin (B) was administered orally, 200 mg/kg of diethylaminoethylsalicylate.AcOH was administered orally (C) and transdermally (D). A is the control line.

Figure 3B:
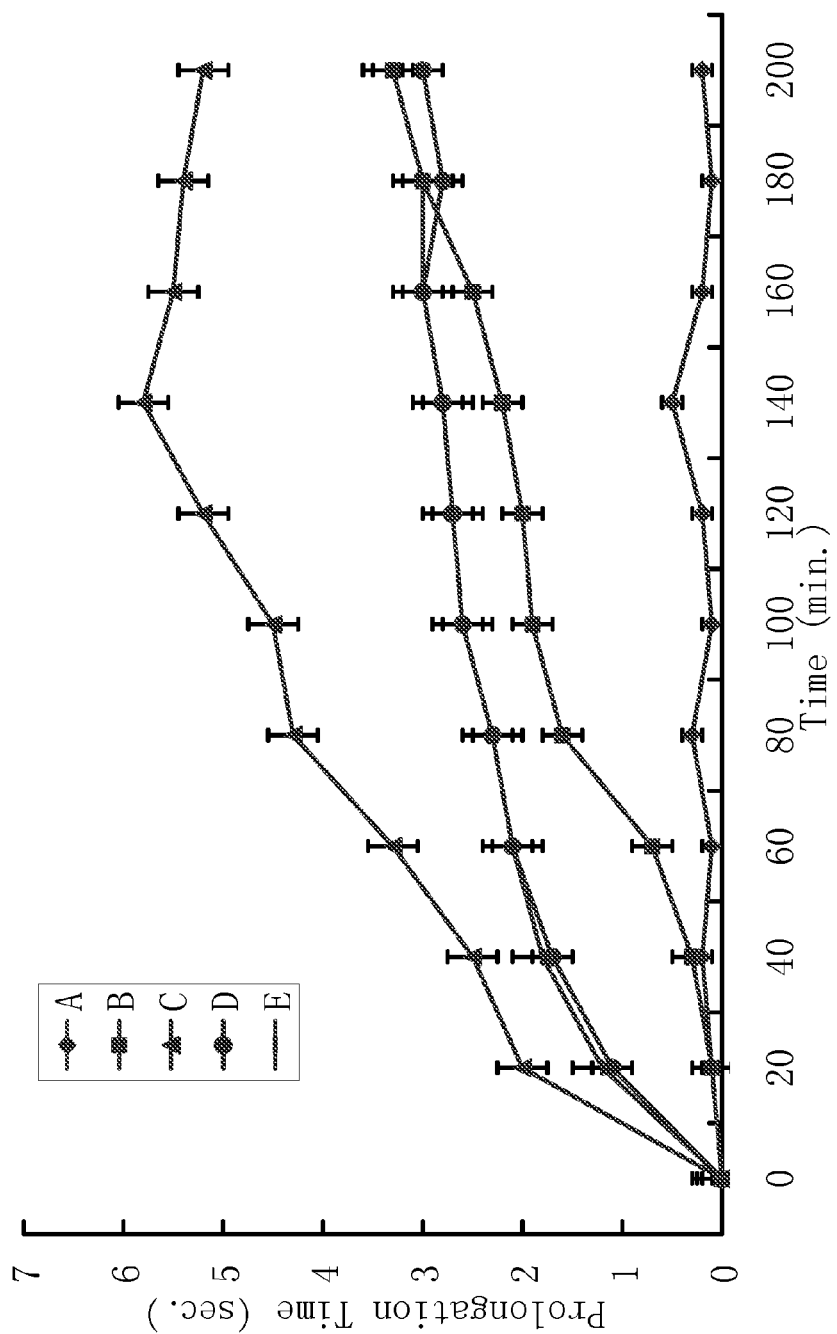

FIG. 3b: The prolongation time of the pain threshold of mice tails after 200 mg/kg of diflunisal (B) was administered orally, 200 mg/kg of diethylaminoethyl 5-(2,4-difluorophenyl) salicylate.AcOH (C), diethylaminoethyl salicylsalicylate.AcOH (D), and diethylaminoethyl salicylate.AcOH (E) were administered transdermally. A is the control line. The groups administered 200 mg/kg of diethylaminoethyl 5-(2,4-difluorophenyl) salicylate.AcOH (C), diethylaminoethyl salicylsalicylate.AcOH (D), and diethylaminoethyl salicylate.AcOH (E) transdermally were shown to exhibit stronger analgesic activity than the group administered 200 mg/kg of diflunisal.

Figure 3C:
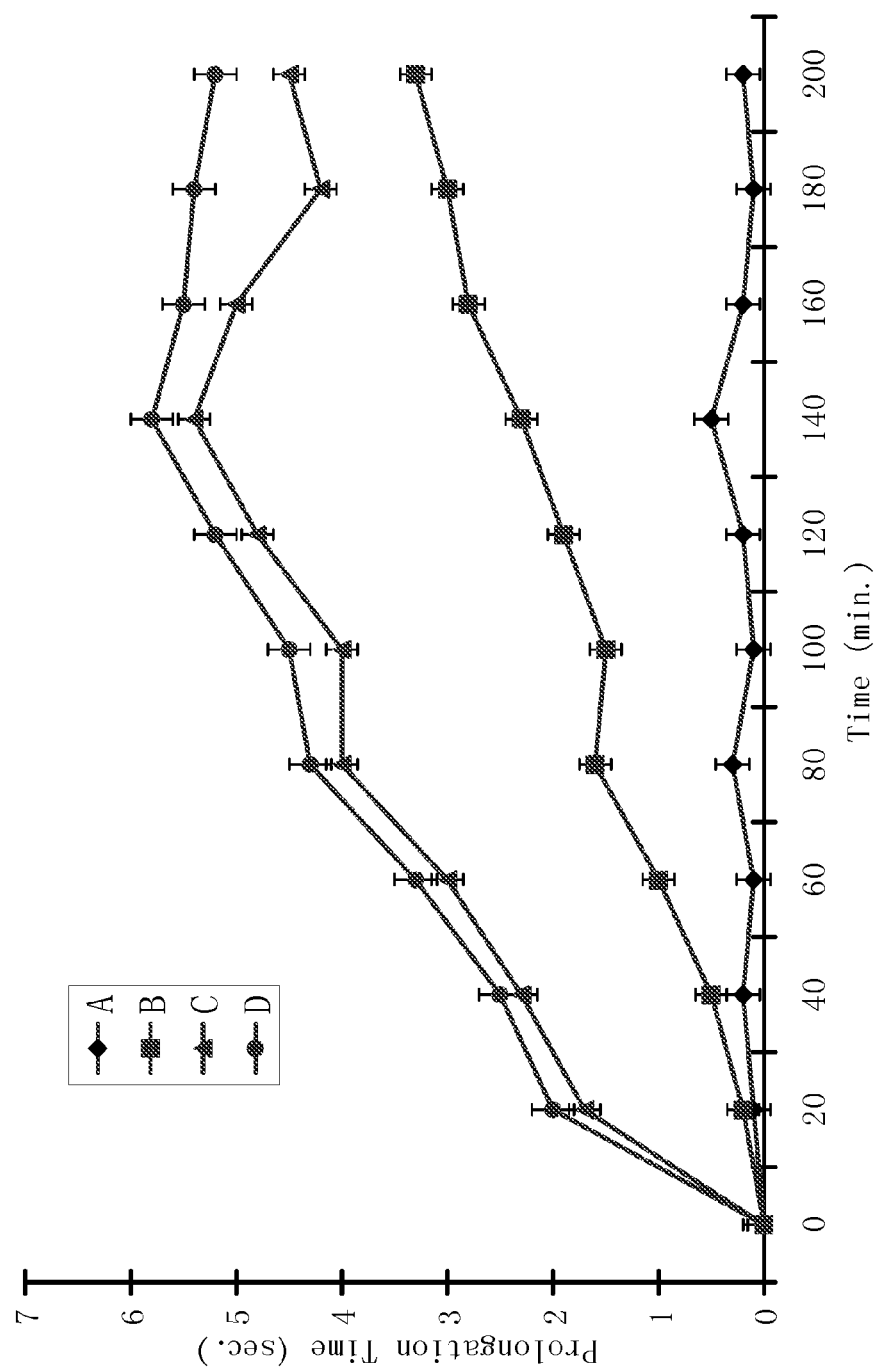

FIG. 3c: The prolongation time of the pain threshold of mice tails after 200 mg/kg of ibuprofen (B) was administered orally, 200 mg/kg of diethylaminoethyl 2-(p-isobutylphenyl) propionate.AcOH was administered orally (C) and transdermally (D). A is the control line.

Figure 3D:
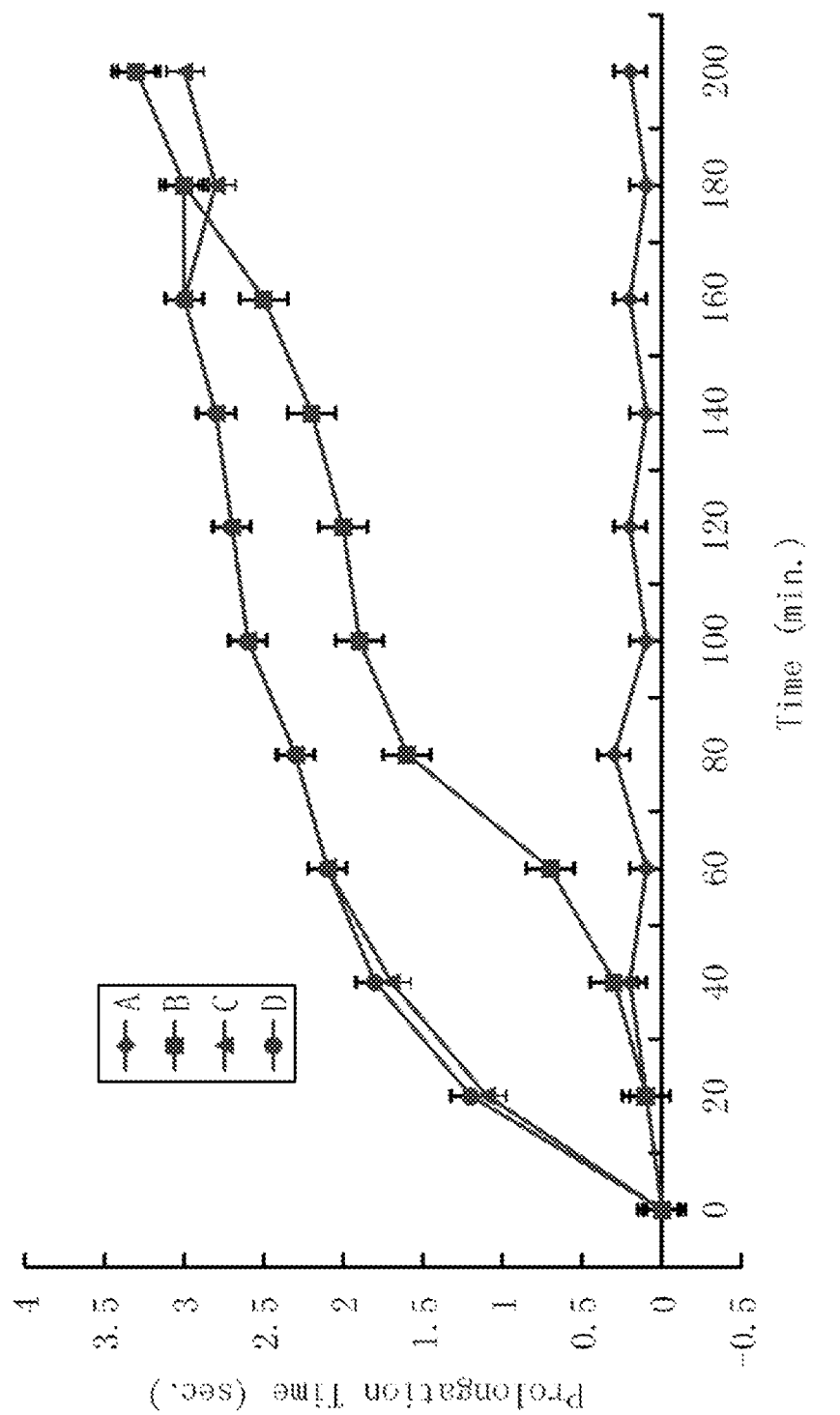

FIG. 3d: The prolongation time of the pain threshold of mice tails after 50 mg/kg of ketoprofen (B) was administered orally, 50 mg/kg of diethylaminoethyl 2-(3-benzoyphenyl) propionate.AcOH (C) and diethylaminoethyl 2-(3-phenoxyphenyl) propionate.AcOH (D) were administered transdermally. A group is the control group.

Figures 1, 3E:
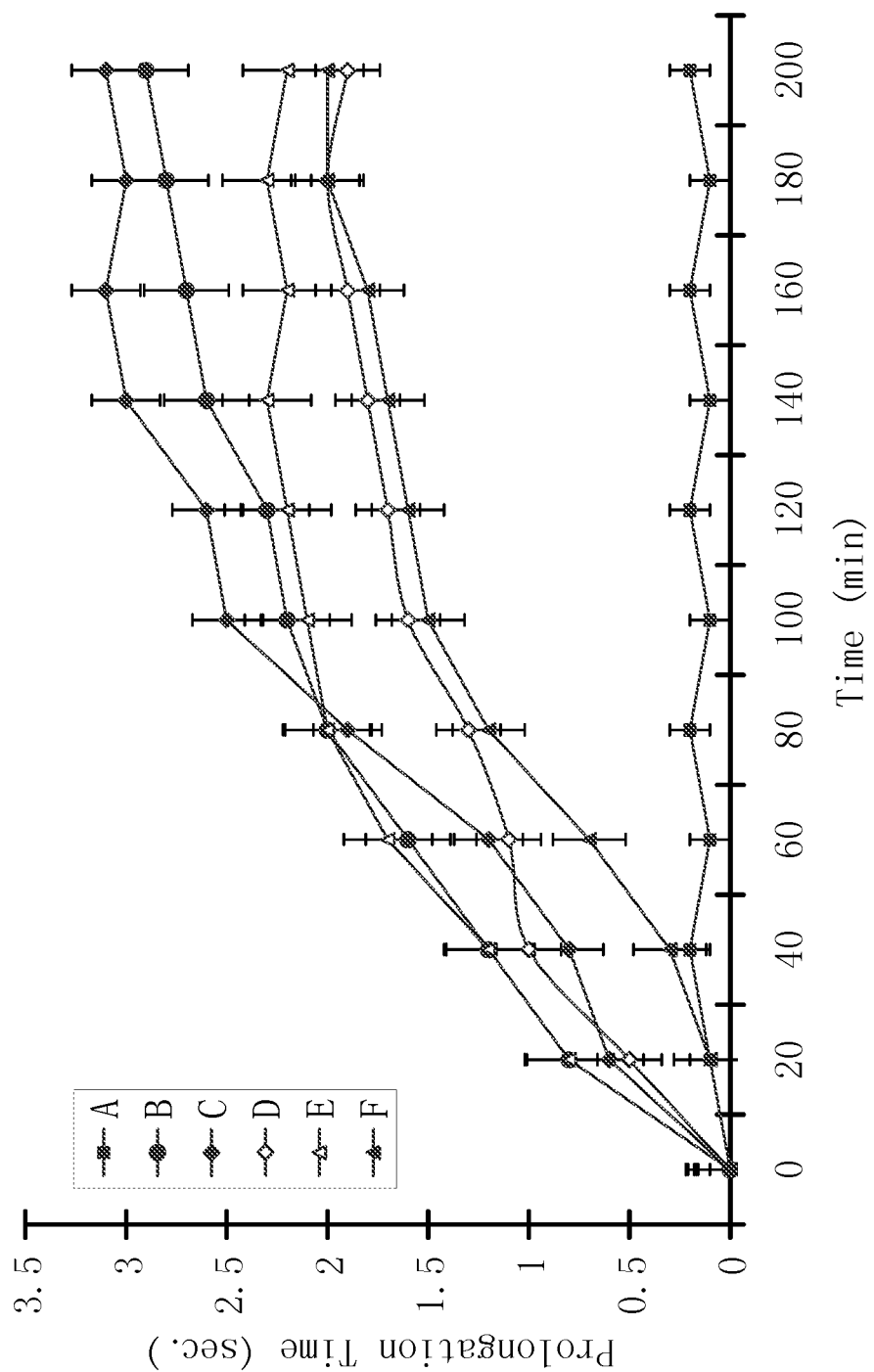
Figures 2, 3E:
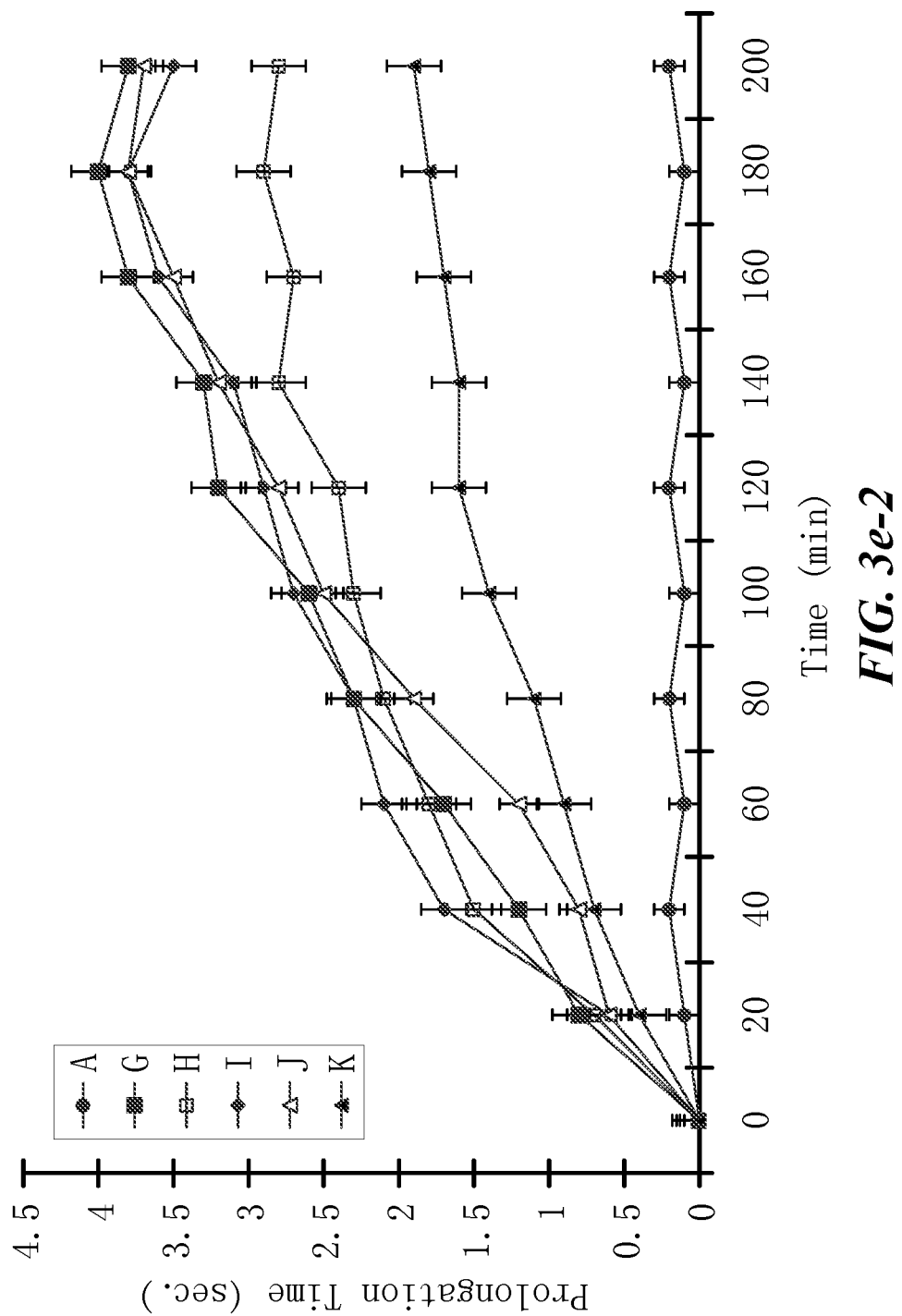
Figures 3, 3E:
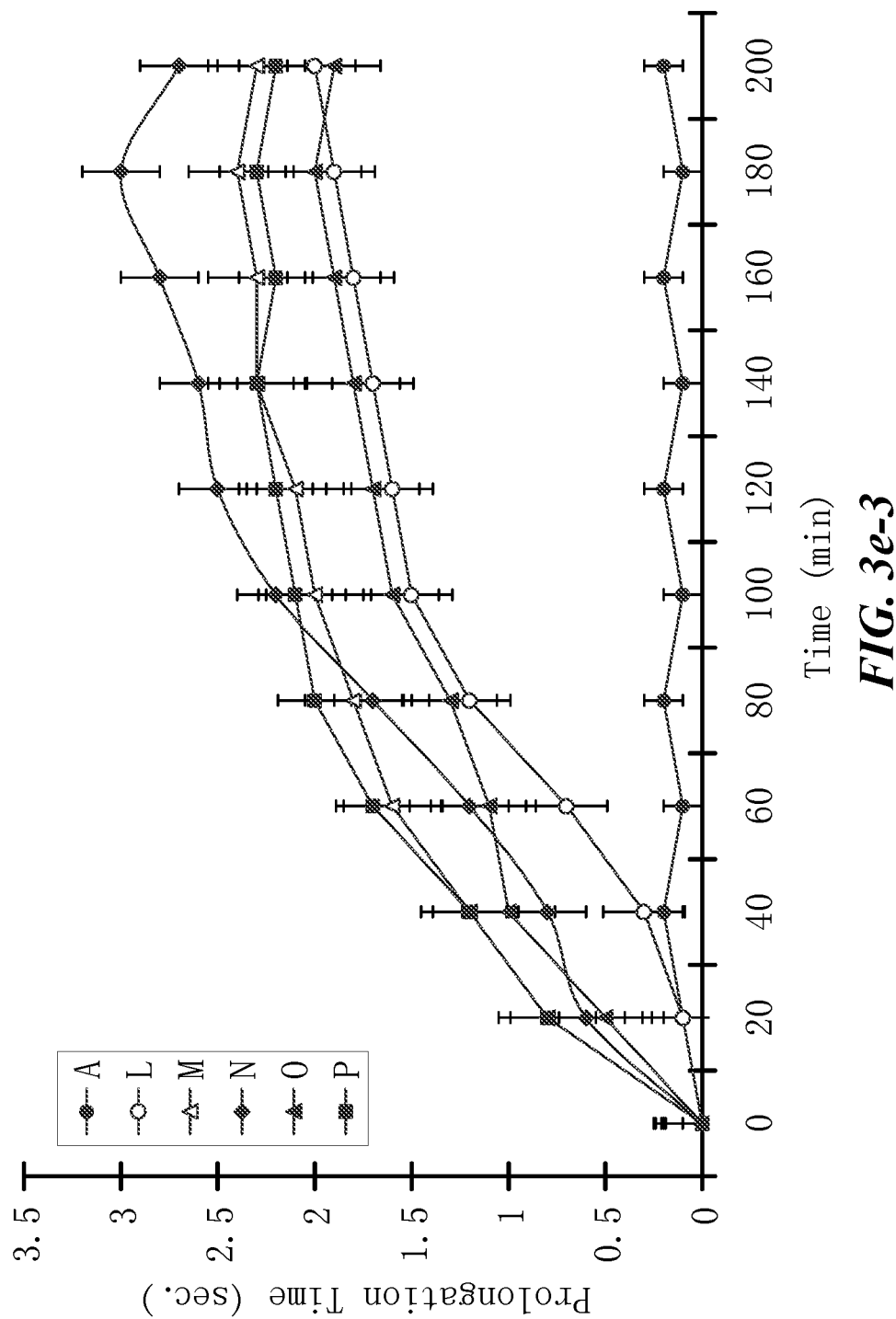
Figures 3, 3E, 4:
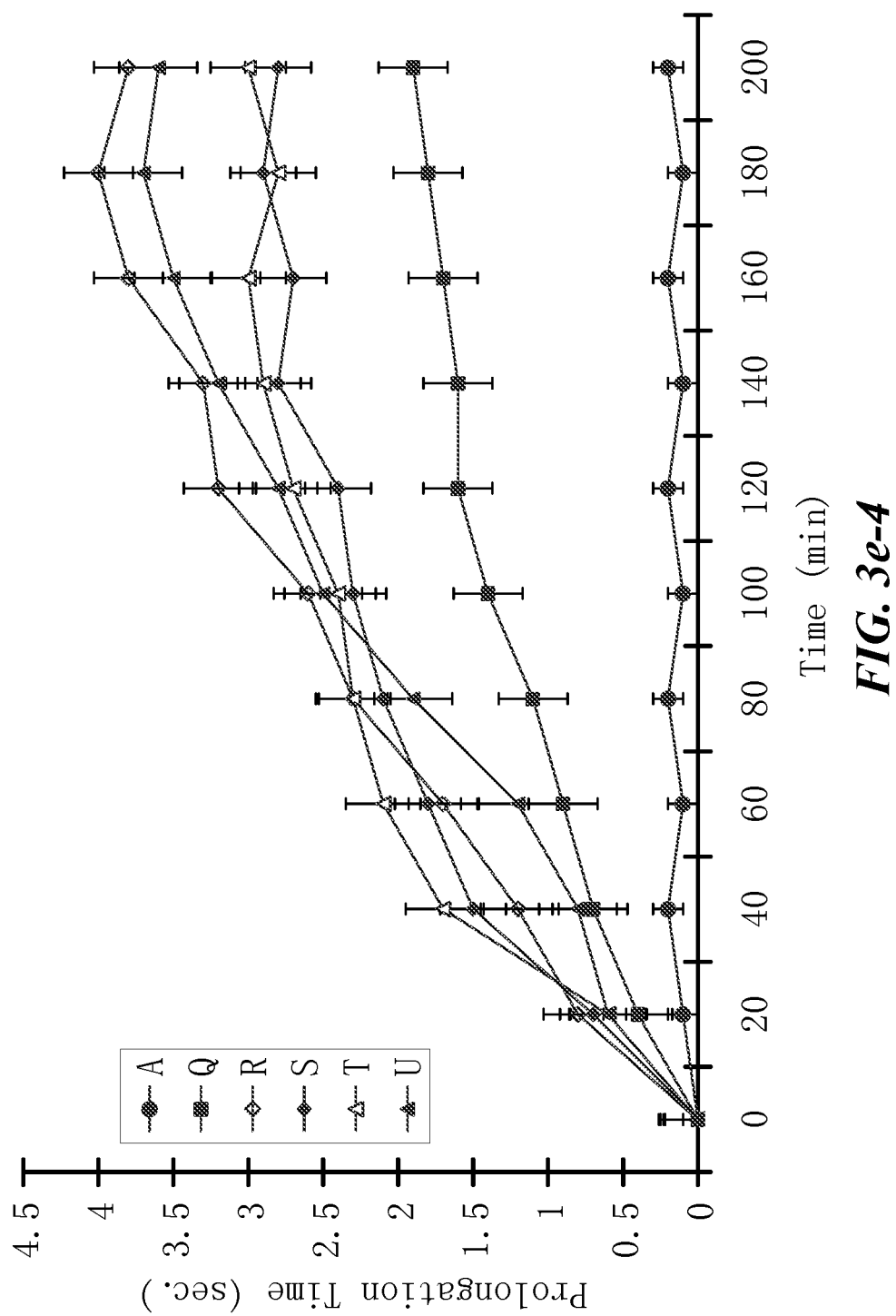

FIG. 3e-1: The prolongation time of the pain threshold of mice tails after 50 mg/kg of diethylaminoethyl 2-(6-methoxy-2-naphthyl)propionate.AcOH (B), diethylaminoethyl α-methyl-4-(2-thienylcarbonyl)benzeneacetate.AcOH (C), diethylaminoethyl α-methyl-(p-chlorobenzoyl)-5-methoxy-2-methylindole 3-acetate.AcOH (D), diethylaminoethyl 2-(2-fluoro-4-biphenylyl)propionate.AcOH (E), diethylaminoethyl 6-chloro-α-methyl-9H-carbazole-2-acetate.AcOH (F) were administered transdermally. Group A is the control group.

FIG. 3e-2: The prolongation time of the pain threshold of mice tails after 50 mg/kg of diethylaminoethyl α-methyl-5H-[1]benzopyrano[2,3-b]pyridine-7-acetate.AcOH (G), diethylaminoethyl 2-(4-chlorophenyl)-α-methyl-5-benzoxazoleacetate.AcOH (H), diethylaminoethyl α-methyl-4-[(2-methyl-2-propenyl)amino]benzeneacetate.AcOH (I), diethylaminoethyl 5-benzoyl-α-methyl-2-thiopheneacetate.AcOH (J), diethylaminoethyl 3-chloro-4-(2,5-dihydro-1H-pyrrol-1-yl)-α-methyl benzeneacetate.AcOH (K) were administered transdermally. Group A is the control group.

FIG. 3e-3: The prolongation time of the pain threshold of mice tails after 50 mg/kg of diethylaminoethyl 2-(10, 11-dihydro-10-oxodibenzo(b,f)thiepin-2-yl)propionate.AcOH (L), diethylaminoethyl 2-(8-methyl-10,11-dihydro-11-oxodibenz(b,f)oxepin-2-yl)propionate.AcOH (M), diethylaminoethyl 2-[4-(2-oxocyclopentyl-methyl)phenyl]propionate.AcOH (N), diethylaminoethyl 4-(1,3-dihydro-1-oxo-2H-isoindol-2-yl)-α-methylbenzeneacetate.AcOH (O), diethylaminoethyl α,3-dichloro-4-cyclohexylbenzeneacetate.AcOH (P), were administered transdermally. Group A is the control group.

Figures 1, 1E, 2, 3, 4:
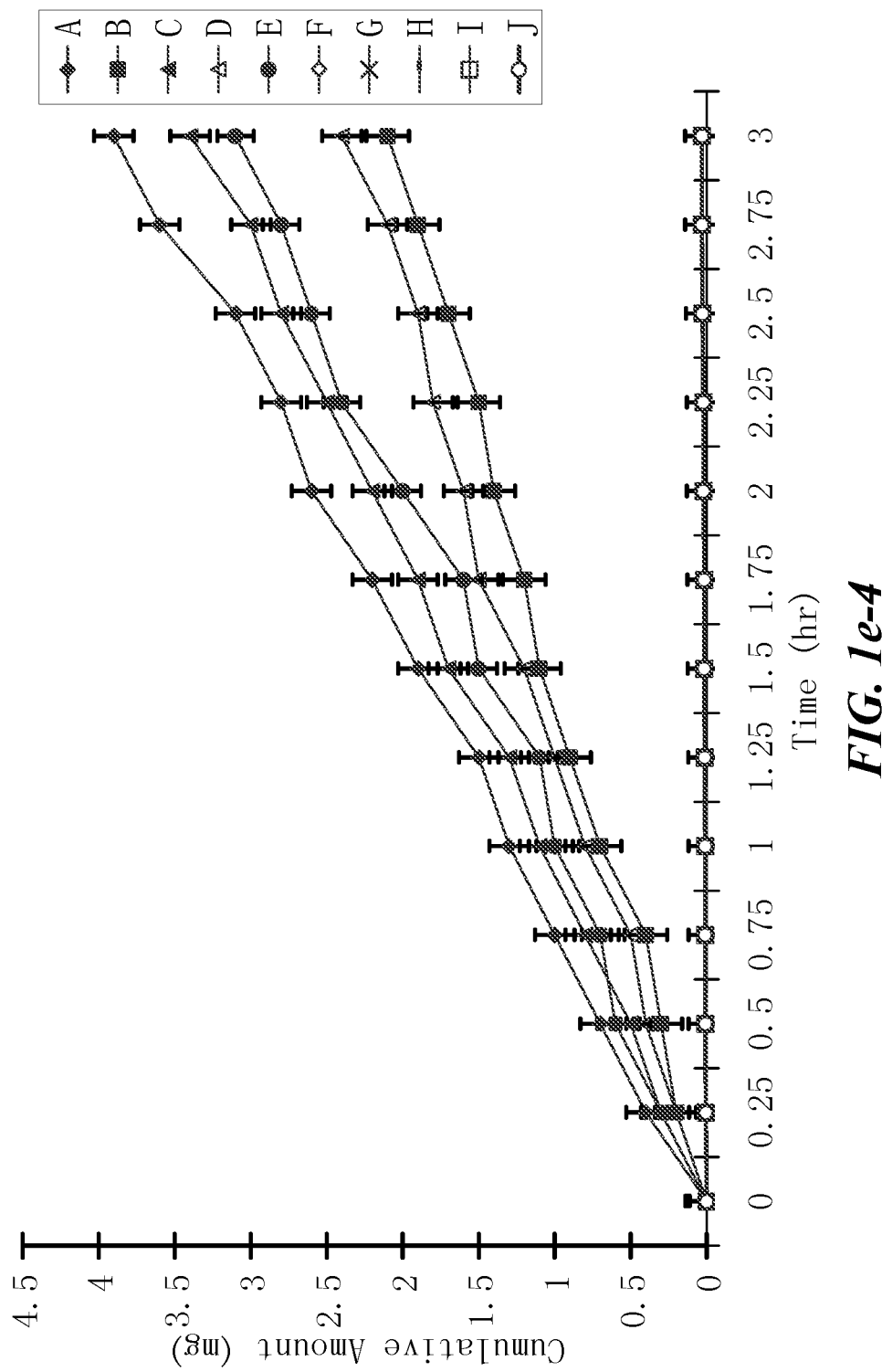
Figures 1, 1F:
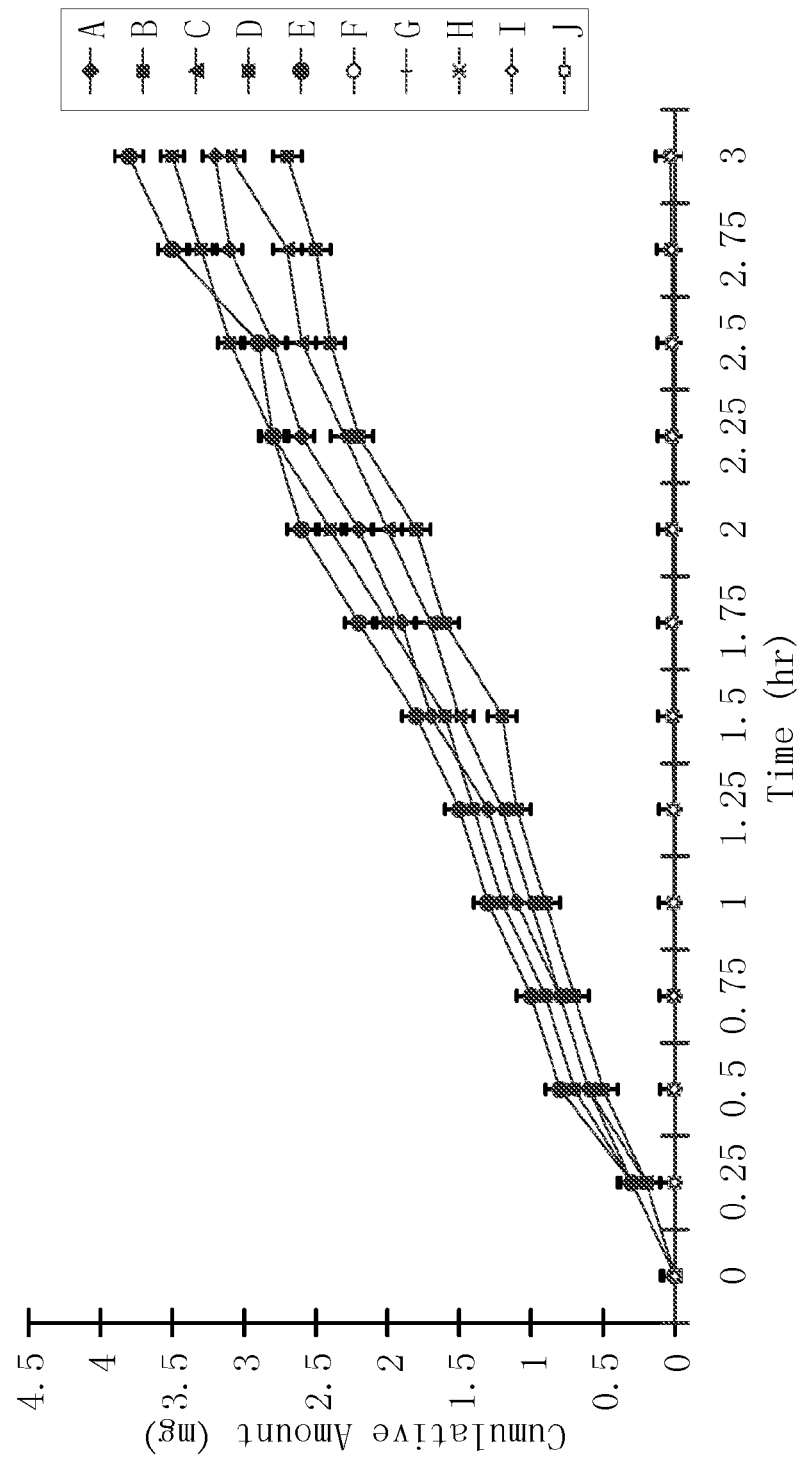
Figures 1, 1F, 2:
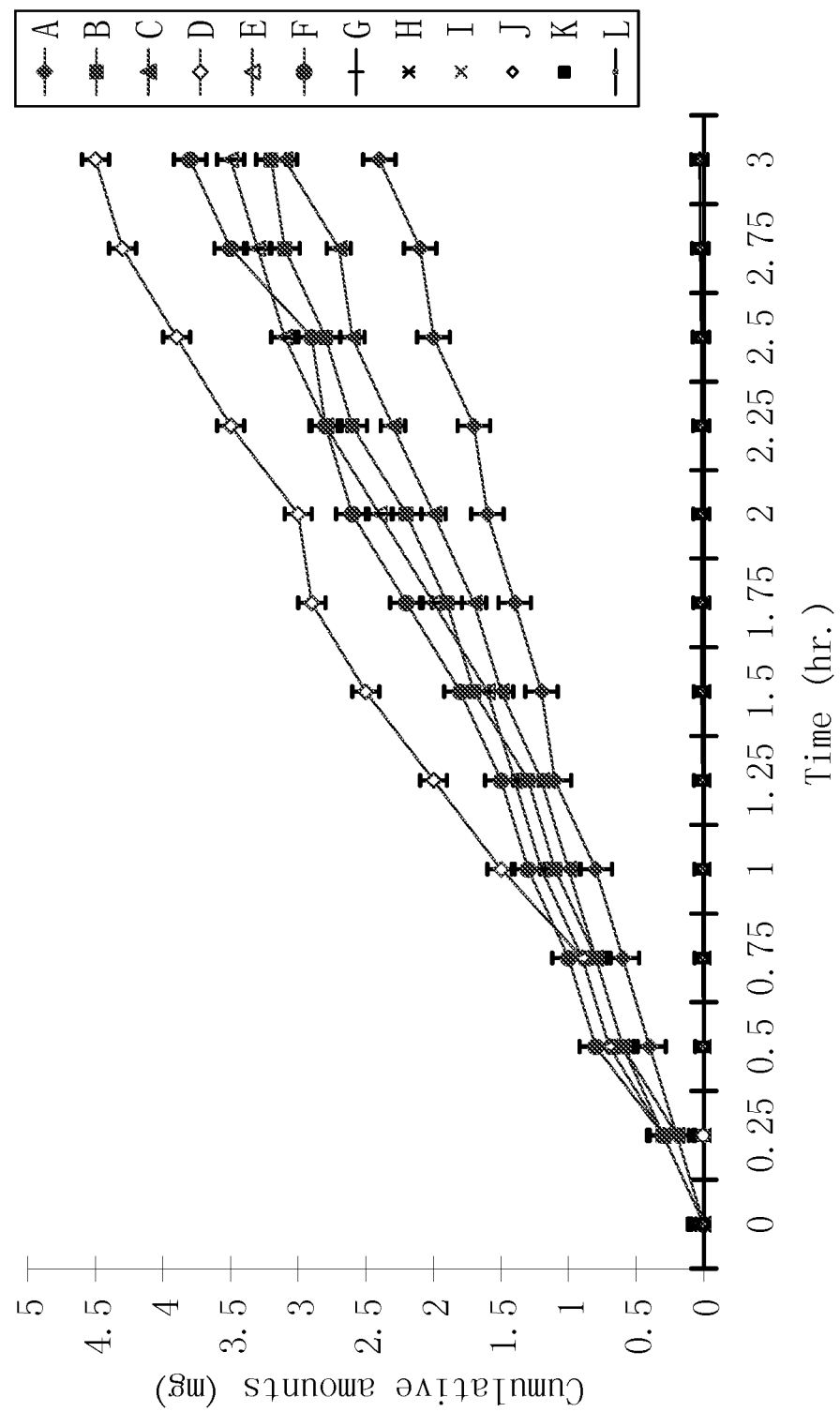
Figure 1G:
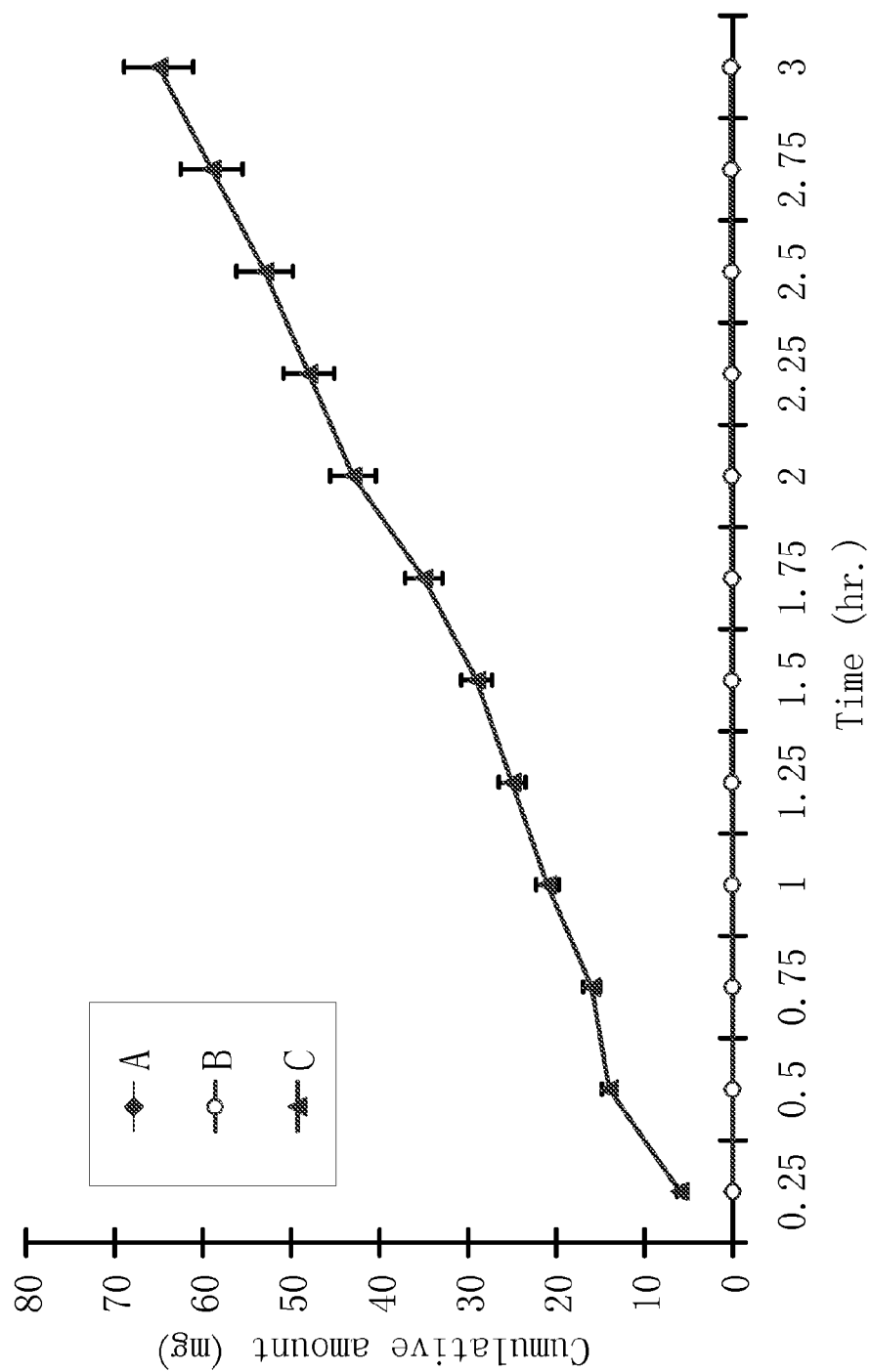
FIG. 1*g*: Cumulative amounts of 2[(2,6-dichlorophenyl) amino]benzene acetic acid (diclofenac, A), ethyl 2[(2,6-dichlorophenyl) amino]benzene acetate (the non positive charged normal ester of diclofenac, B) and diethylaminoethyl 2[(2,6-dichlorophenyl) amino]benzene acetate.AcOH (C) crossing isolated human skin tissue in Franz cells (n=5). Diclofenac and ethyl 2-[(2,6-dichlorophenyl) amino]benzene acetate were applied as a 20% suspension; diethylaminoethyl 2-[(2,6-dichlorophenyl) amino]benzene acetate.AcOH was applied as 20% solution. In each case, the vehicle was pH 7.4 phosphate buffer (0.2 M).
Figure 1H:
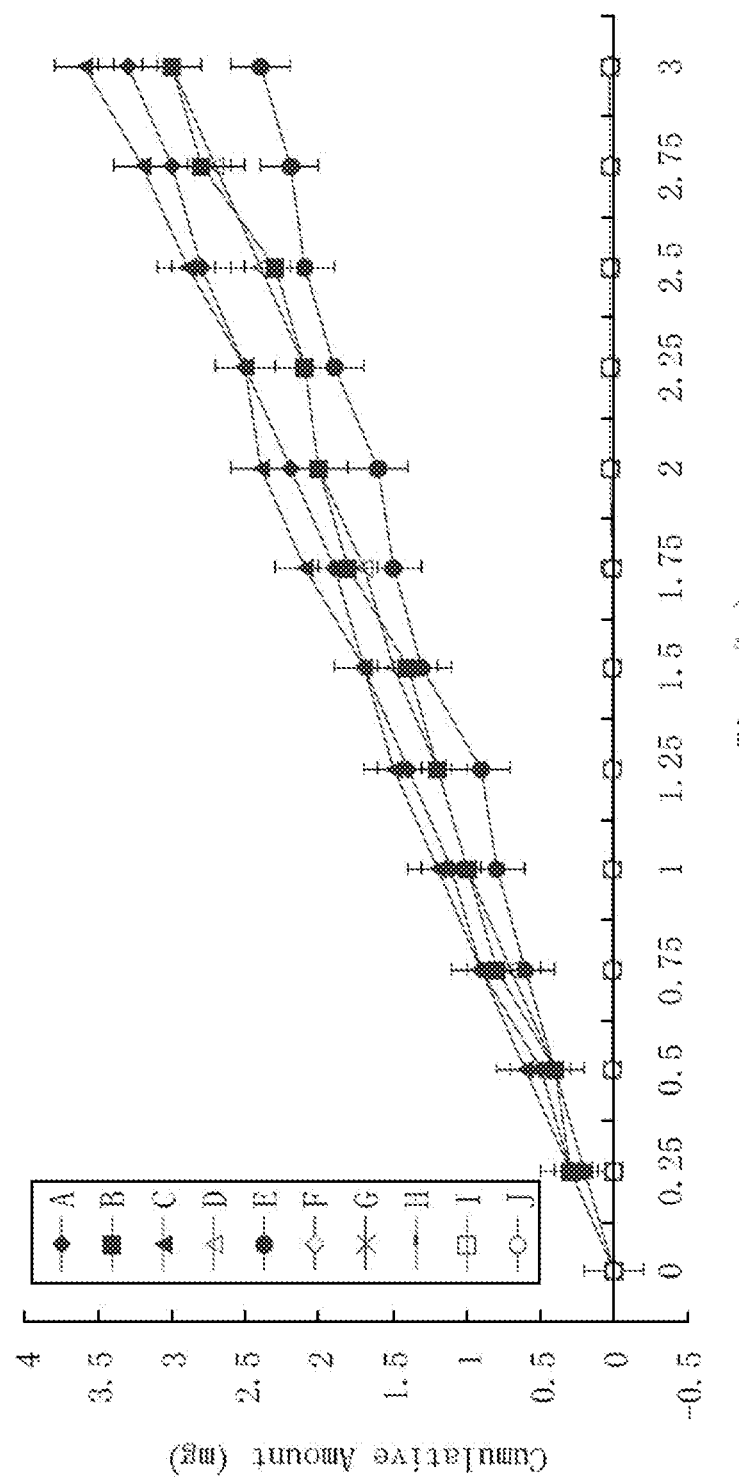
FIG. 1*h*: Cumulative amounts of diethylaminoethyl 2-[(2,3-dimethylphenyl) amino]benzoate.AcOH (A, 20% solution), diethylaminoethyl 2-[(2,6-dichloro-3-methylphenyl) amino]benzoate.AcOH (B, 20% solution), diethylaminoethyl 2-[[(3-(trifluoromethyl) phenyl) amino]benzoate.AcOH(C, 20% solution), diethylaminoethyl 2-[[3-(trifluoromethyl) phenyl]amino]-3-pyridinecarboxylate.AcOH (D, 20% solution), diethylaminoethyl 2-[[2-methyl-3-(trifluoromethyl) phenyl]amino]-3-pyridinecarboxylate.AcOH (E, 20% solution), mefenamic acid (F, 20% suspension), meclofenamic acid (G, 20% suspension), flufenamic acid (H, 20% suspension), niflumic acid (I, 20% suspension), flunixin (J, 20% suspension), crossing isolated human skin tissue in Franz cells (n=5). In each case, the vehicle was pH 7.4 phosphate buffer (0.2 M).
Figure 1I:
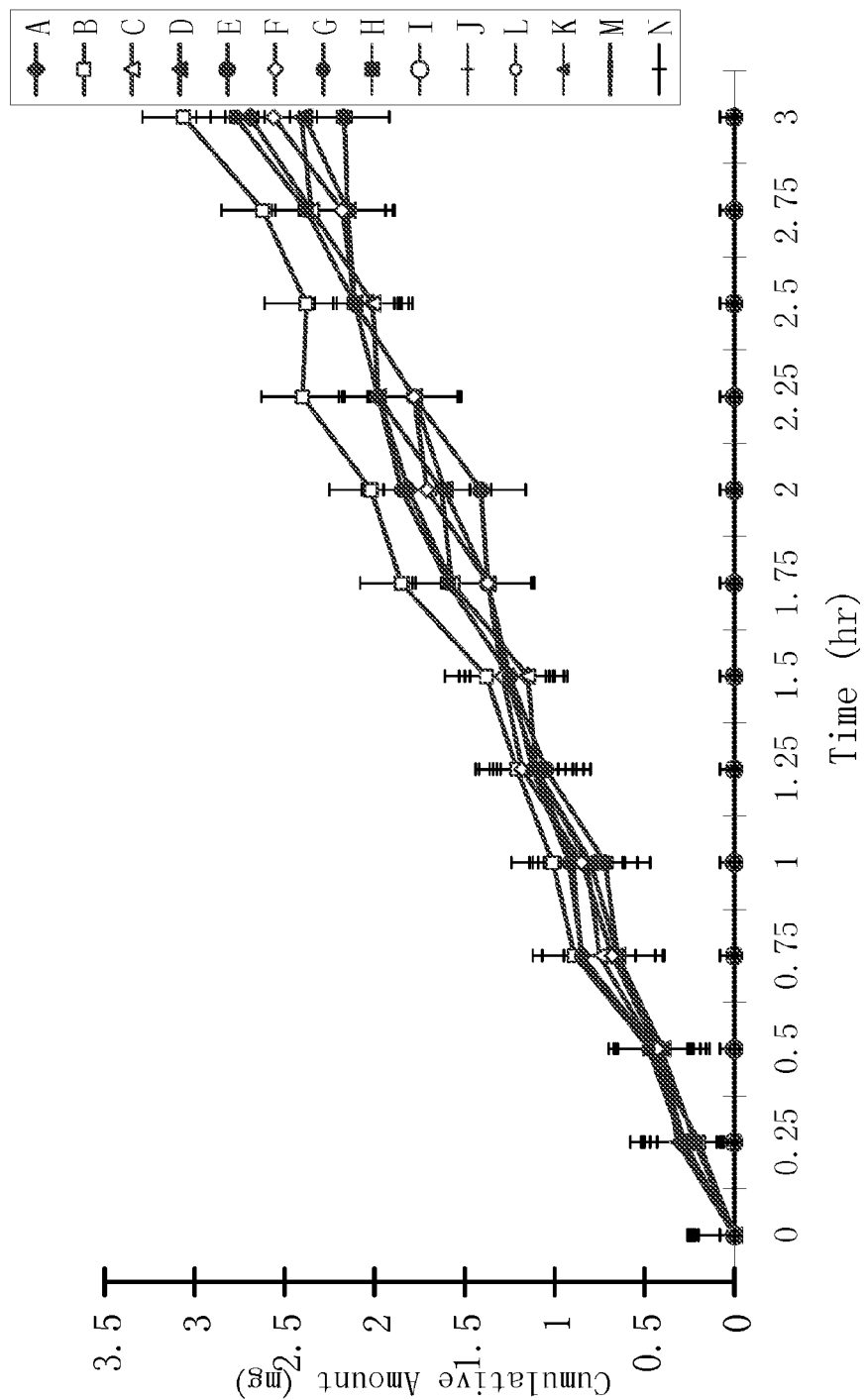
FIG. 1*i*: Cumulative amounts of 4-N,N-dimethylaminobutyryloxy-2-methyl-N-2-pyridinyl-2H, 1,2-benzothiazine-3-carboxamide 1,1-dioxide.HCl (A, 20% solution), N-(2-thiazolyl)-4-N,N-dimethylaminobutyryloxy-2-methyl-2H, 1,2-benzothiazine-3-carboxamide 1,1-dioxide.HCl (B, 20% solution), 6-chloro-4-N,N-dimethylaminobutyryloxy-2-methyl-N-2-pyridinyl-2H-thieno[2,3-e]-1,2-thiazine-3-carboxamide 1,1-dioxide.HCl (C, 20% solution), 4-N,N-dimethylaminobutyryloxy-2-methyl-N-2-pyridinyl-2H-thieno[2,3-e]-1,2-thiazine-3-carboxamide 1,1-dioxide.HCl (D, 20% solution), 8-chloro-(4-N,N-dimethylaminobutyryloxy-pyridine-2-ylamino-methylidene)-3-methyl-2,2-dioxo-2λ$^6$,7-dithia-3-azabicyclo[4,3,0]nona-8,10-dien-5-one.HCl (E, 20% solution), 4-N,N-dimethylaminobutyryloxy-2-methyl-N-[5-Methyl-3-isoxolyl-2H-1,2-benzothiazine-3-carboxamide 1,1-dioxide].HCl (F, 20% solution), 4-N,N-dimethylaminobutyryloxy-2-methyl-N-(5-methyl-2-thiazolyl)-2H-1,2-benzothiazine-3-carboxamide-1,1-dioxide.HCl (G, 20% solution), Piroxicam (H, 20% suspension), sudoxiam (I, 20% suspension), lomoxicam (J, 20% suspension), tenoxicam (K, 20% suspension), lomoxicam (L, 20% suspension), isoxicam (M, 20% suspension), and meloxicam (N, 20% suspension) crossing isolated human skin tissue in Franz cells (n=5). In each case, the vehicle was pH 7.4 phosphate buffer (0.2 M).

FIG. 3e-4: The prolongation time of the pain threshold of mice tails after 50 mg/kg of diethylaminoethyl 4,5-Diphenyl-2-oxazole propionate.AcOH (Q), diethylaminoethyl 3-(4-biphenylylcarbonyl)propionate.AcOH (R), diethylaminoethyl 5-(4-chlorophenyl)-beta-hydroxy-2-furanpropionate.AcOH (S), diethylaminoethyl 5-benzoyl-2,3-dihydro-1H-pyrrolizine-1-carboxylate.AcOH (T), diethylaminoethyl 6-chloro-5-cyclohexyl-2,3-dihydro-1H-indene-1-carboxylate.AcOH (U) were administered transdermally. Group A is the control group.

Figures 1, 3F:
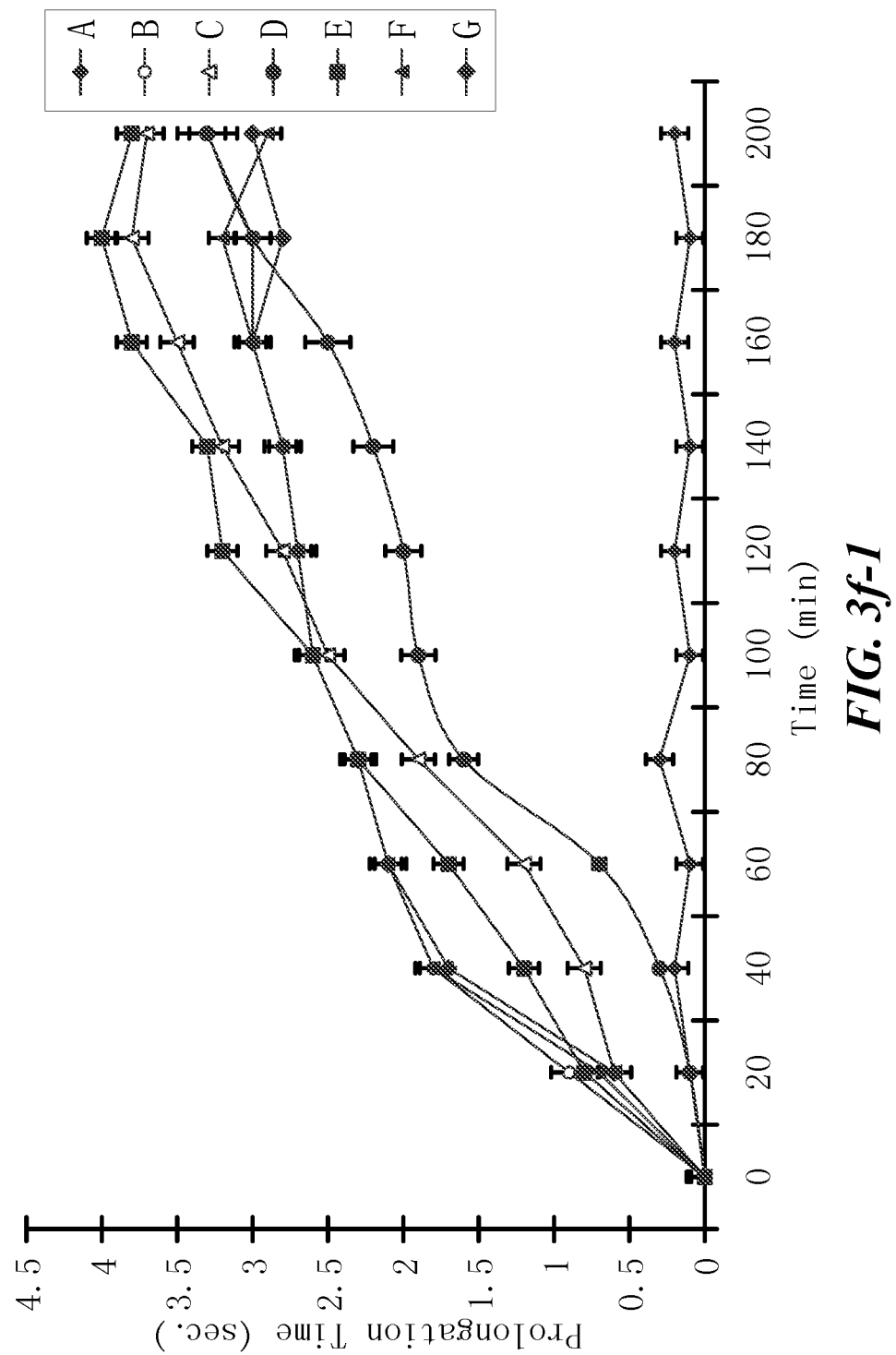
Figures 2, 3F:
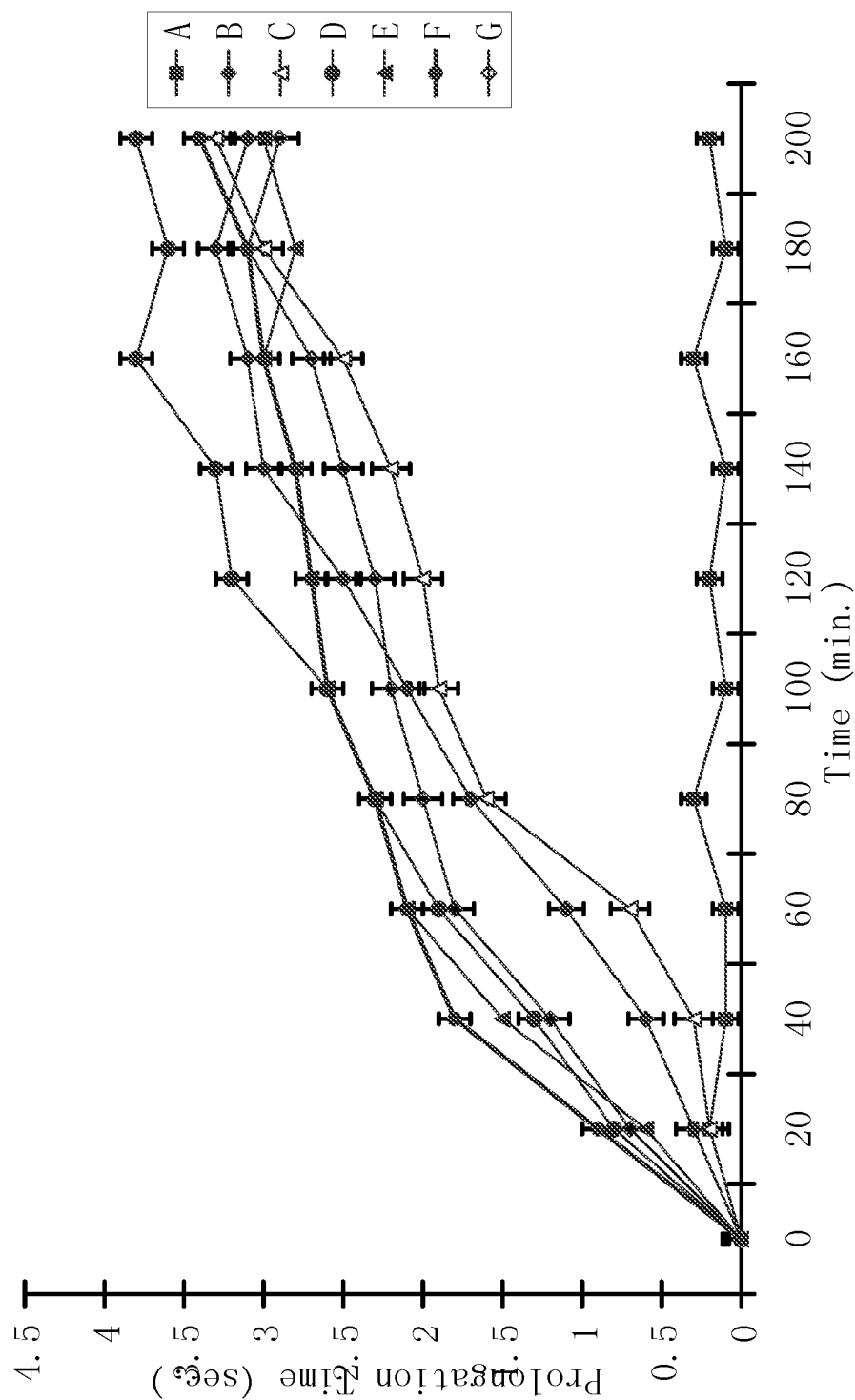

FIG. 3f-1: The prolongation time of the pain threshold of mice tails after 50 mg/kg of diethylaminoethyl 1-(p-chlorobenzoyl)-5-methoxy-2-methylindole 3-acetate.AcOH (B), diethylaminoethyl (Z)-5-fluoro-2-methyl-1-[(4-methylsulfinyl) phenylmethylene]-1H-indene-3-acetate.AcOH (C), diethylaminoethyl 1-methyl-5-(4-methylbenzoyl)-1H-pyrrole-2-acetate.AcOH (D), diethylaminoethyl 5-(4-Chlorobenzoyl)-1.4-dimethyl-1H-pyrrole-2-acetate.AcOH (E), diethylaminoethyl 1,8-diethyl-1,3,4,9-tetrahydropyrano-[3,4-b]indole-1-acetate.AcOH (F). diethylaminoethyl 2-amino-3-benzoylbenzeneacetate.AcOH (G) were administered transdermally. A group is the control group.

FIG. 3f-2: The prolongation time of the pain threshold of mice tails after 50 mg/kg of diethylaminoethyl 2-amino-3-(4-bromo-benzoyl)benzeneacetate.AcOH (B), diethylaminoethyl 3-chloro-4-(2-propenyloxy)benzeneacetate.AcOH (C), diethylaminoethyl 2-(2,4-dichlorophenoxy)benzeneacetate.AcOH (D), diethylaminoethyl 1-(4-chlorobenzoyl-5-methoxy-2-methyl-1H-indole-3-acetoxyacetate.AcOH (E), diethylaminoethyl 4-(4-chlorophenyl)-2-phenyl-5-thiazoleacetate.AcOH (F), diethylaminoethyl 3-(4-chlorophenyl)-1-phenyl-1H-pyrazole-4-acetate.AcOH (G), were administered transdermally. A group is the control group.

Figure 3G:
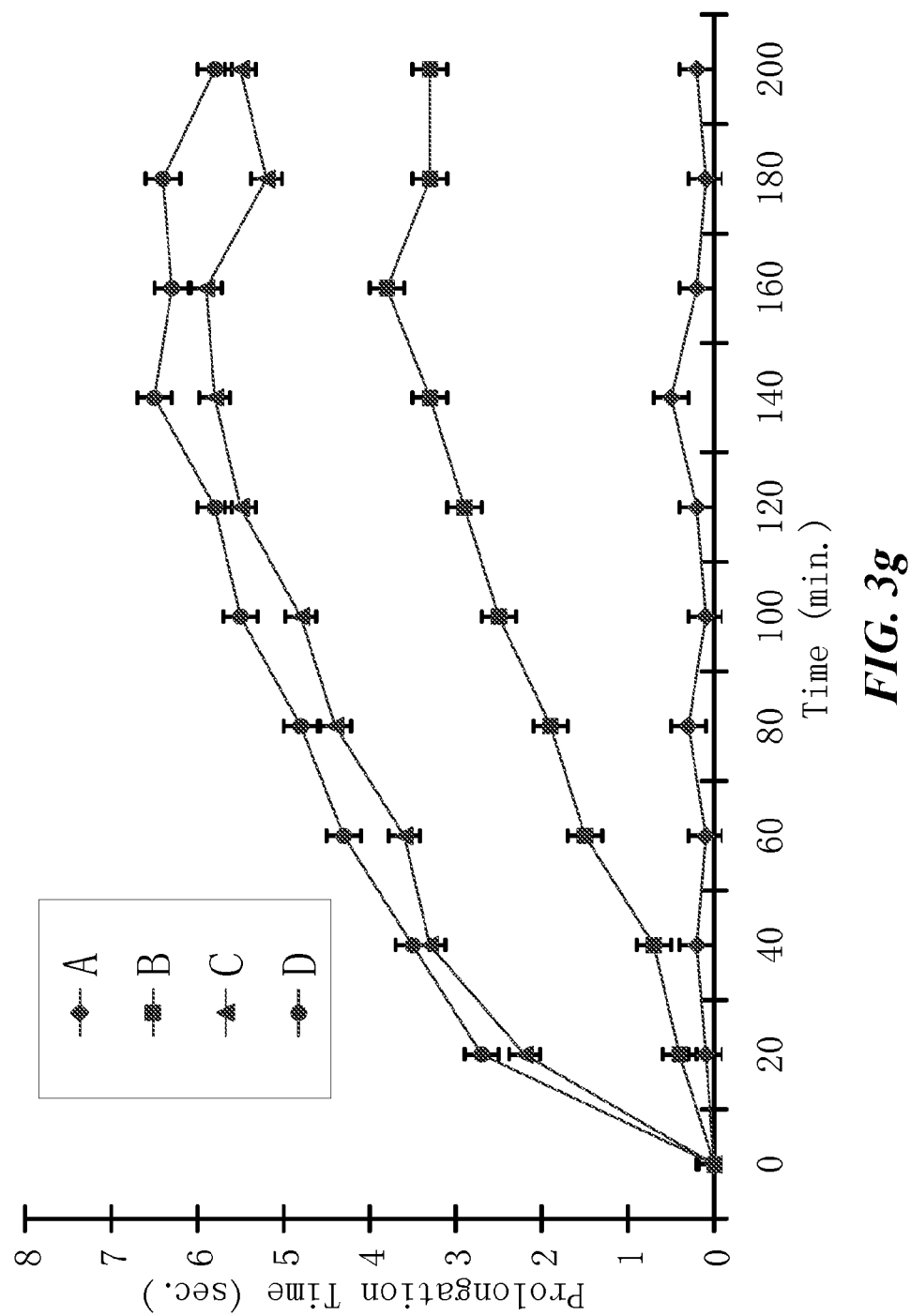

FIG. 3g: The prolongation time of the pain threshold of mice tails after 25 mg/kg of diclofenac (B) was administered orally. 25 mg/kg of diethylaminoethyl 2[(2,6-dichlorophenyl)amino]benzene acetate.AcOH was administered orally (C) and transdermally (D). A is the control line.

Figure 3H:
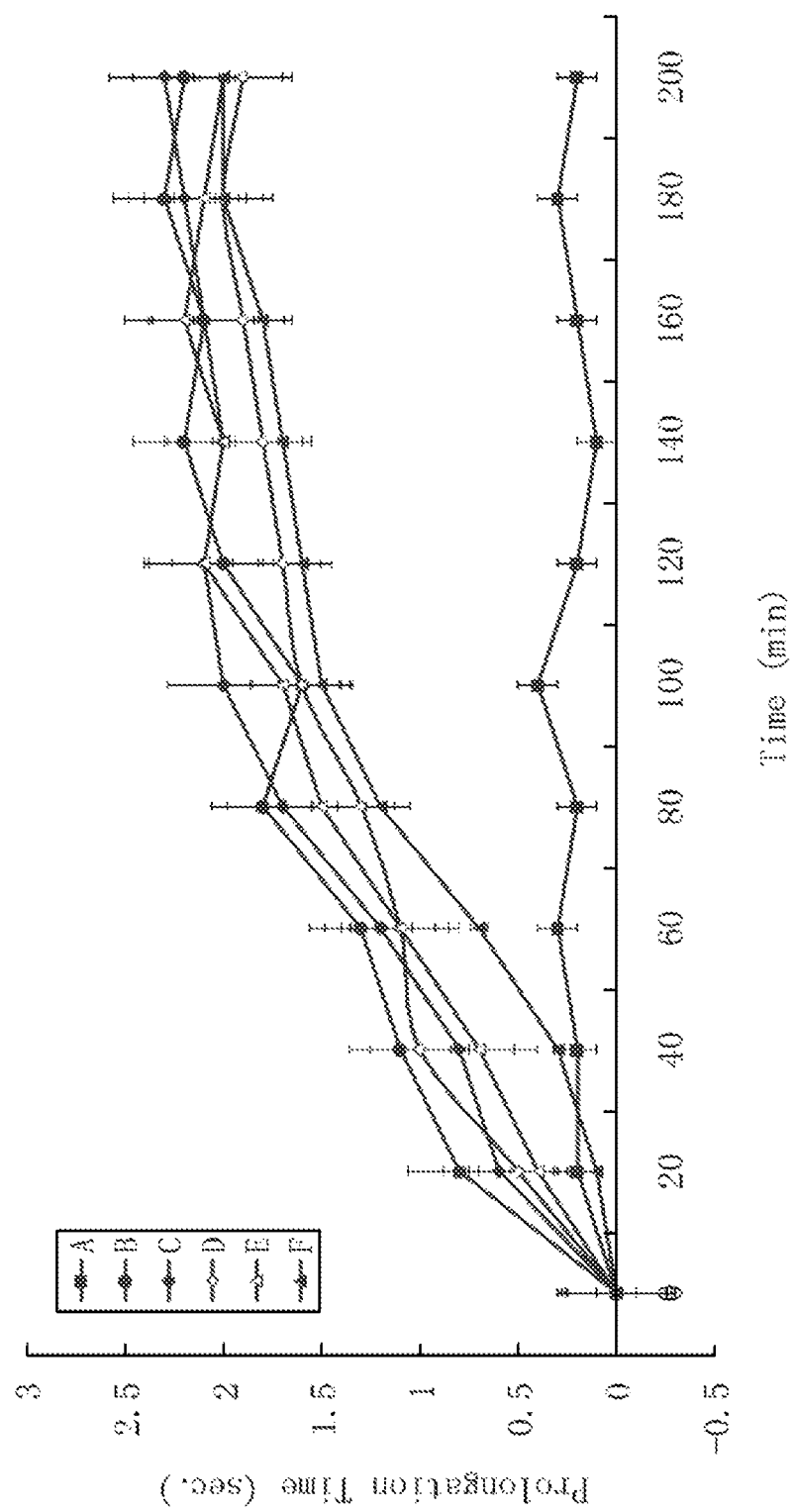

FIG. 3h: The prolongation time of the pain threshold of mice tails after 20 mg/kg of 4-N,N-dimethylaminobutyryloxy-2-methyl-N-2-pyridinyl-2H, 1,2-benzothiazine-3-carboxamide 1,1-dioxide.HCl (B), N-(2-thiazoyl)-4-N,N-dimethylaminobutyryloxy-2-methyl-2H, 1,2-benzothiazine-3-carboxamide 1,1-dioxide. HCl (C), 6-chloro-4-N,N-dimethylaminobutyryloxy-2-methyl-N-2-pyridinyl-2H-thieno[2,3-e]-1,2-thiazine-3-carboxamide 1,1-dioxide.HCl (D), 4-N,N-dimethylaminobutyryloxy-2-methyl-N-2-pyridinyl-2H-thieno[2,3-e]-1,2-thiazine-3-carboxamide 1,1-dioxide.HCl (E), 8-chloro-(4-N,N-dimethylaminobutyryloxy-pyridine-2-ylamino-methylidene)-3-methyl-2,2-dioxo-$2\lambda^{6}$'7-dithia-3-azabicyclo[4,3,0]nona-8,10-dien-5-one. HCl (F), 4-N,N-dimethylaminobutyryloxy-2-methyl-N-[5-Methyl-3-isoxolyl-2H-1,2-benzothiazine-3-carboxamide 1,1-dioxide]. HCl (G), and 4-N,N-dimethylaminobutyryloxy-2-methyl-N-(5-methyl-2-thiazolyl)-2H-1,2-benzothiazine-3-carboxamide-1,1-dioxide.HCl (H) were administered transdermally. Group A is the control group.

Figure 3I:
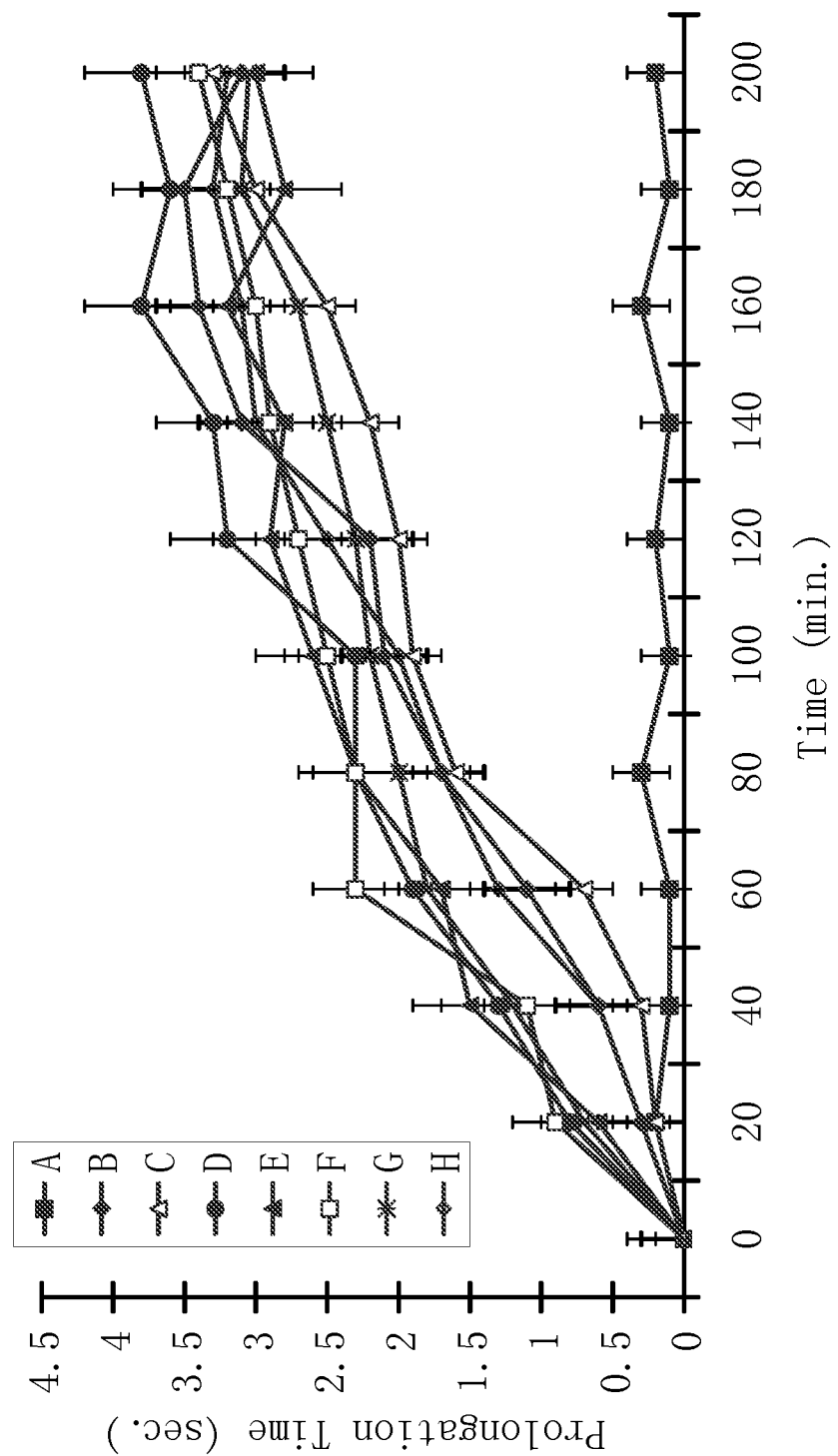

FIG. 3i: The prolongation time of the pain threshold of mice tails after 20 mg/kg of 4-N,N-dimethylaminobutyryloxy-2-methyl-N-2-pyridinyl-2H, 1,2-benzothiazine-3-carboxamide 1,1-dioxide.HCl (B), N-(2-thiazoyl)-4-N,N-dimethylaminobutyryloxy-2-methyl-2H, 1,2-benzothiazine-3-carboxamide 1,1-dioxide.HCl (C), 6-chloro-4-N,N-dimethylaminobutyryloxy-2-methyl-N-2-pyridinyl-2H-thieno[2,3-e]-1,2-thiazine-3-carboxamide 1,1-dioxide.HCl (D), 4-N,N-dimethylaminobutyryloxy-2-methyl-N-2-pyridinyl-2H-thieno[2,3-e]-1,2-thiazine-3-carboxamide 1,1-dioxide.HCl (E), 8-chloro-(4-N,N-dimethylaminobutyryloxy-pyridine-2-ylamino-methylidene)-3-methyl-2,2-dioxo-$2\lambda^{6}$'7-dithia-3-azabicyclo[4,3,0]nona-8,10-dien-5-one. HCl (F), 4-N,N-dimethylaminobutyryloxy-2-methyl-N-[5-Methyl-3-isoxolyl-2H-1,2-benzothiazine-3-carboxamide 1,1-dioxide].HCl (G), and 4-N,N-dimethylaminobutyryloxy-2-methyl-N-(5-methyl-2-thiazolyl)-2H-1,2-benzothiazine-3-carboxamide-1,1-dioxide.HCl (H) were administered transdermally. Group A is the control group.

Figure 4A:
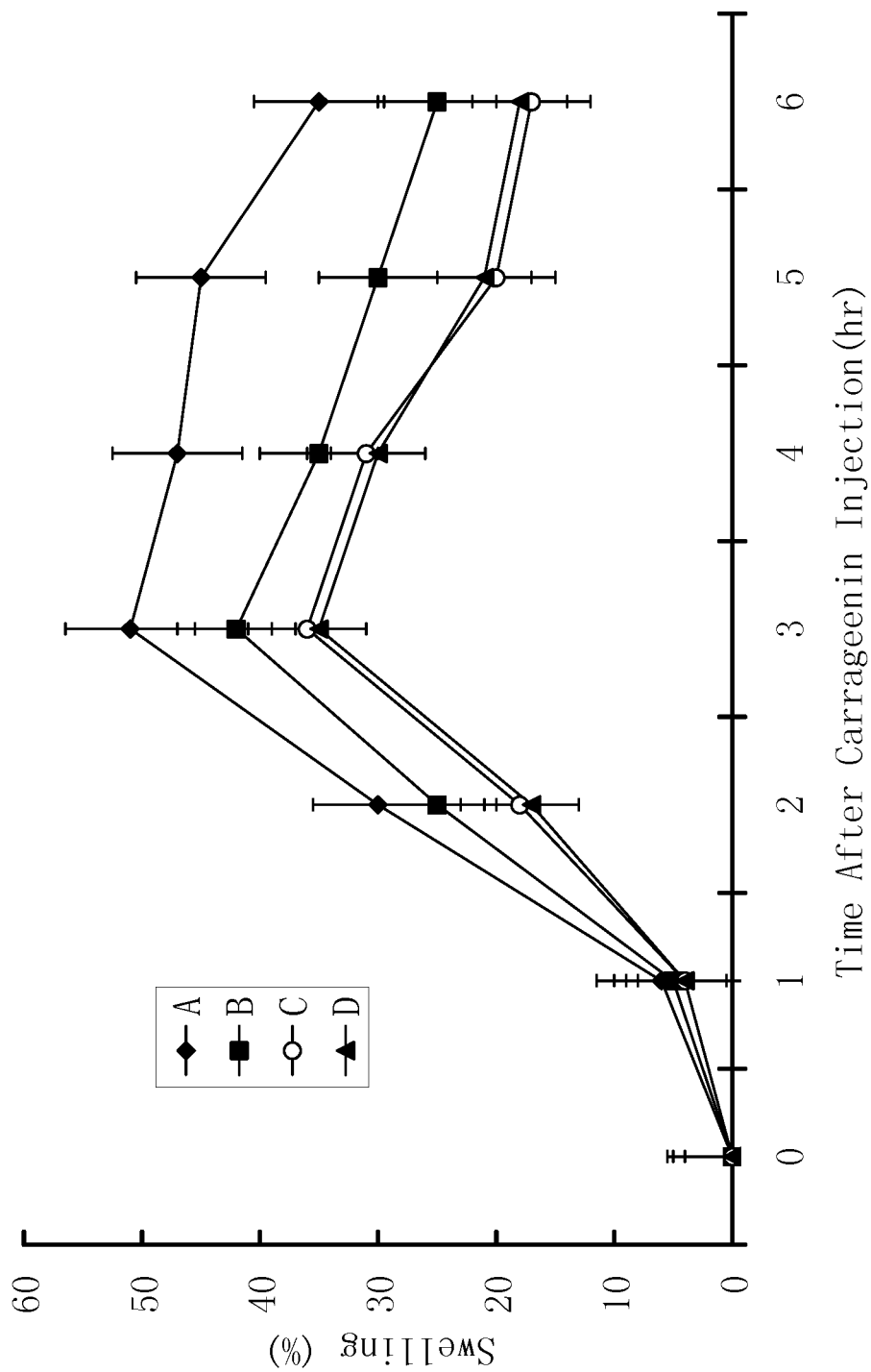

FIG. 4a. The rate of swelling (%) after a carrageenin injection. 1 hour before the carrageenin injection, 100 mg/kg of aspirin was administered orally (B), 100 mg/kg of diethylaminoethyl salicylate.AcOH (C) was administered orally and transdermally (D). A is the control line.

Figure 4B:
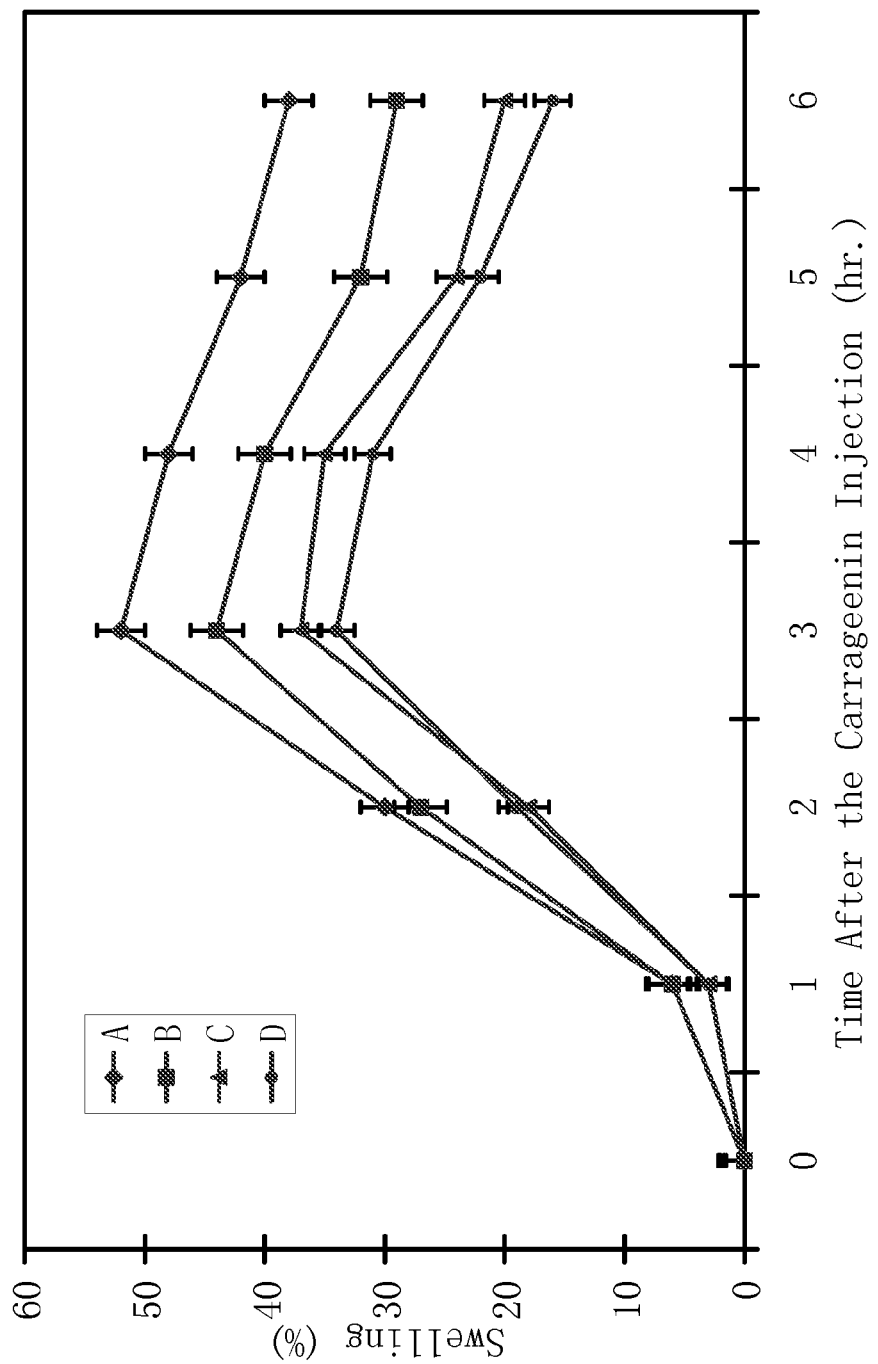

FIG. 4b. The rate of swelling (%) after a carrageenin injection. 1 hour before the carrageenin injection, 50 mg of 5-(2,4-difluorophenyl) salicylic acid (diflunisal, B) was administered orally, 50 mg of diethylaminoethyl 5-(2,4- difluorophenyl) salicylate.AcOH (C) was administered orally, and transdermally (D). A is the control group.

Figure 4C:
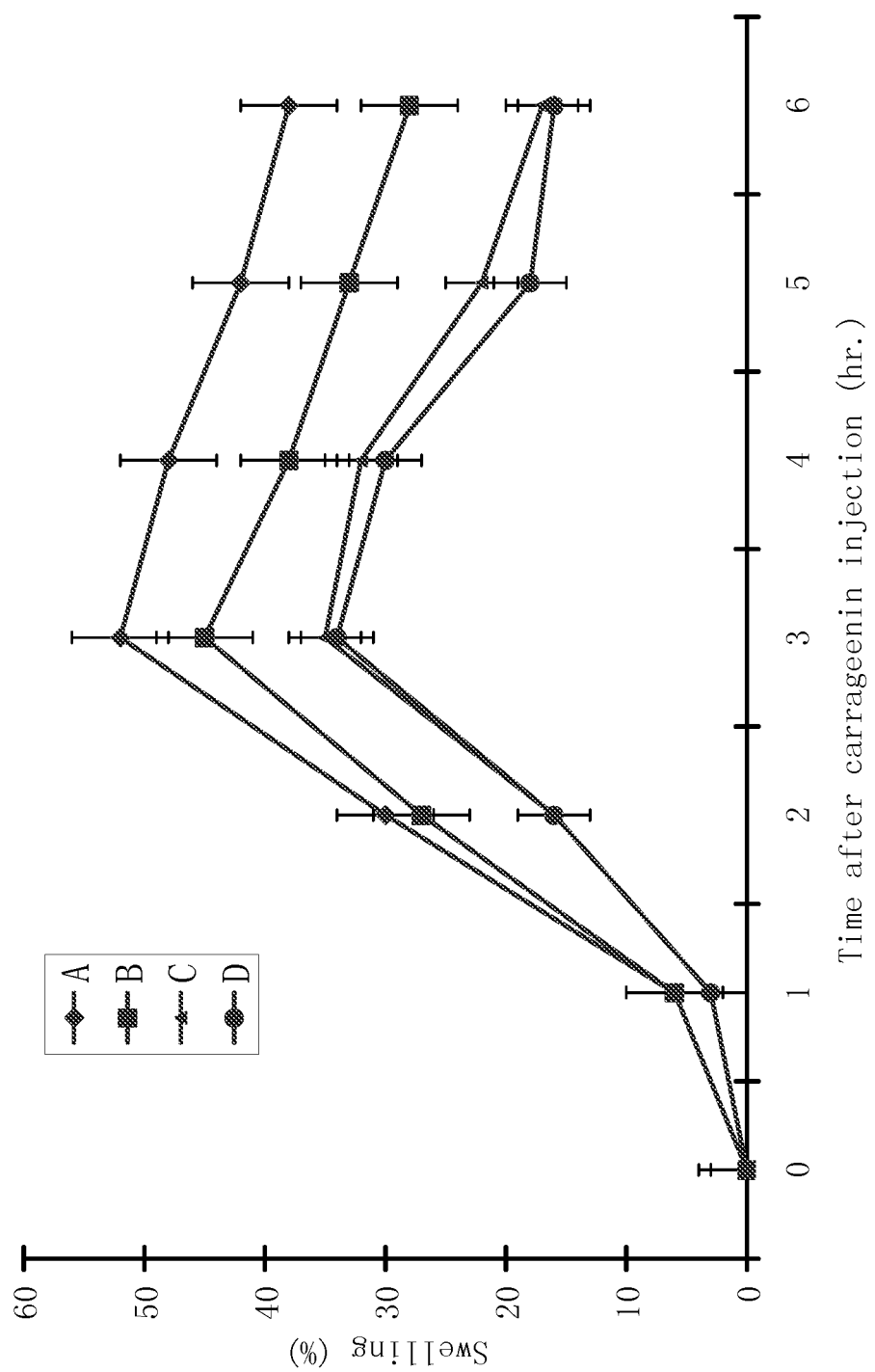

FIG. 4c. The rate of swelling (%) after a carrageenin injection. 1 hour before the carrageenin injection, 50 mg/kg of ibuprofen was administered orally (B), 50 mg/kg of diethylaminoethyl 2-(p-isobutylphenyl) propionate.AcOH was administered orally (C), and transdermally (D). A is the control group.

Figure 4D:
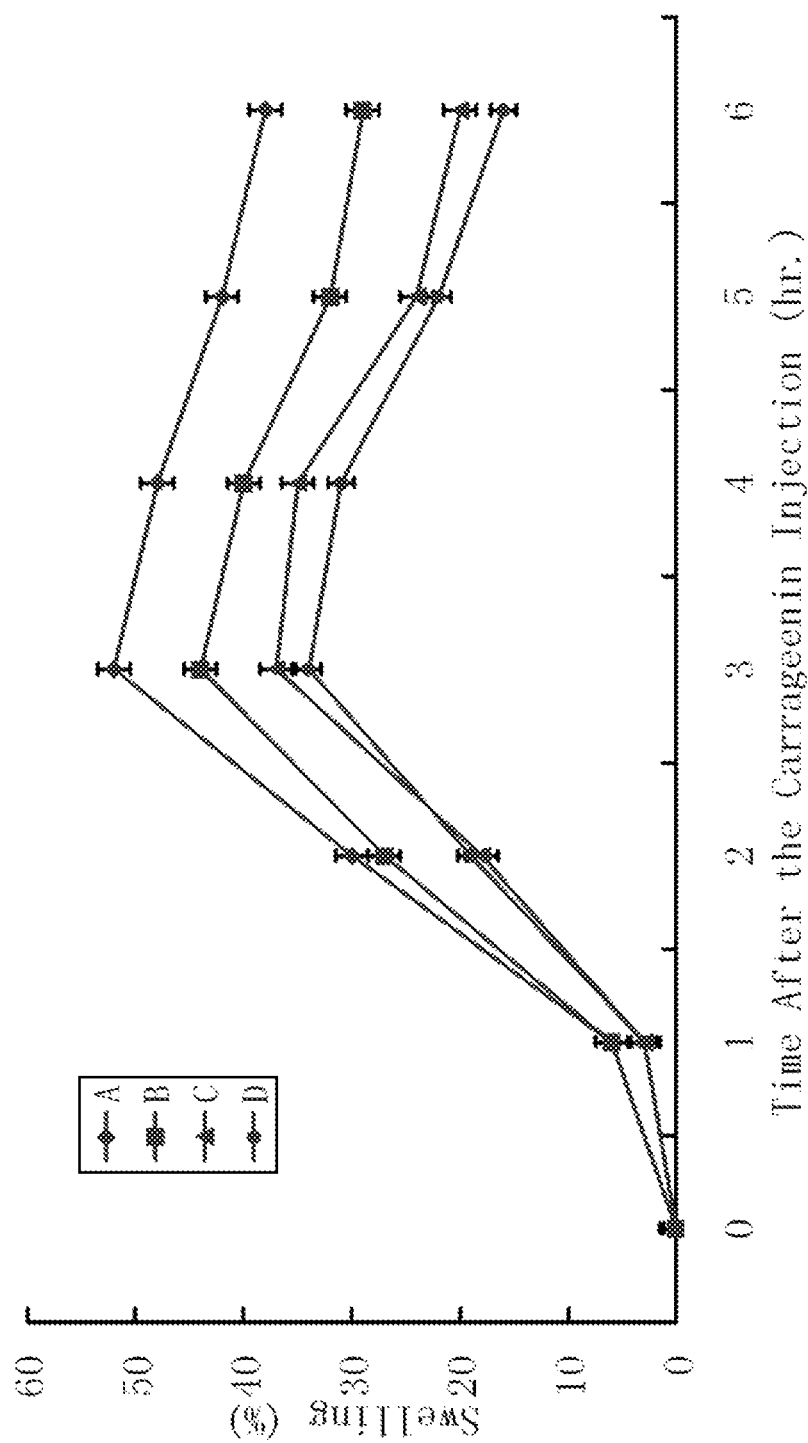

FIG. 4d. The rate of swelling (%) after a carrageenin injection. 1 hour before the carrageenin injection, 50 mg of 2-(3-benzoyphenyl) propionic acid (ketoprofen, B) was administered orally, 50 mg of diethylaminoethyl 2-(3-benzoyphenyl) propionate.AcOH was administered orally (C), and transdermally (D). A is the control group.

Figures 1, 4E:
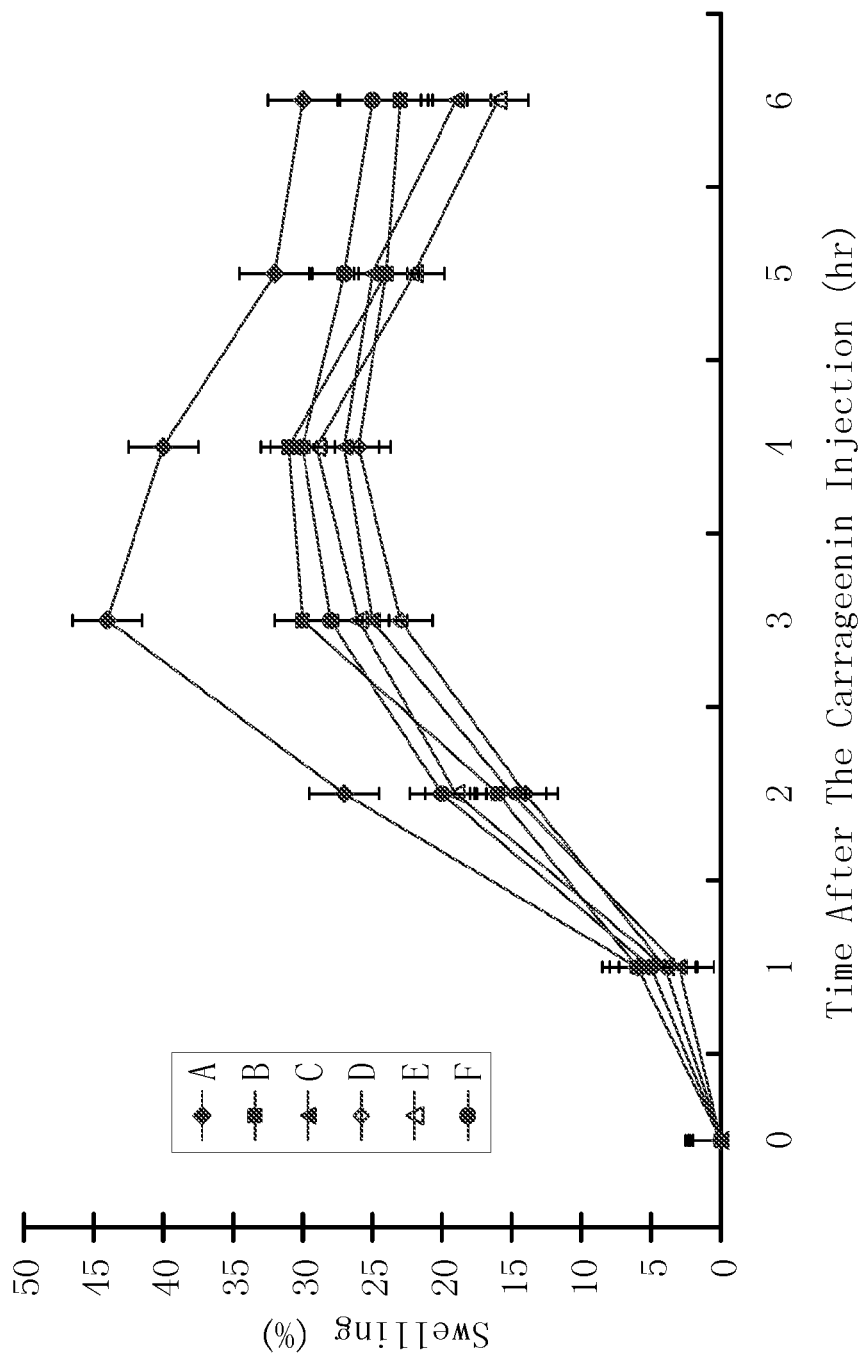
Figures 2, 4E:
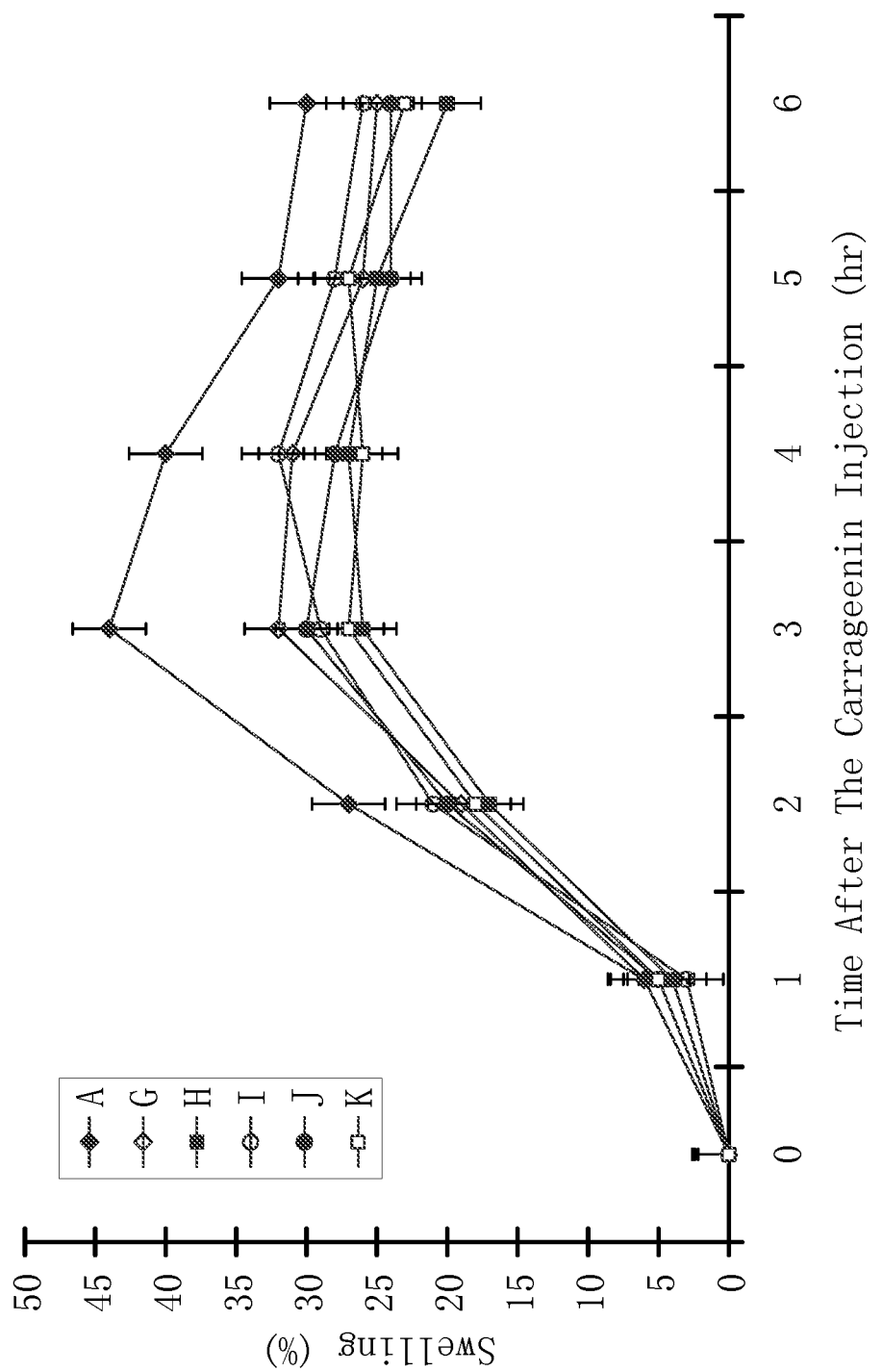
Figures 3, 4E:
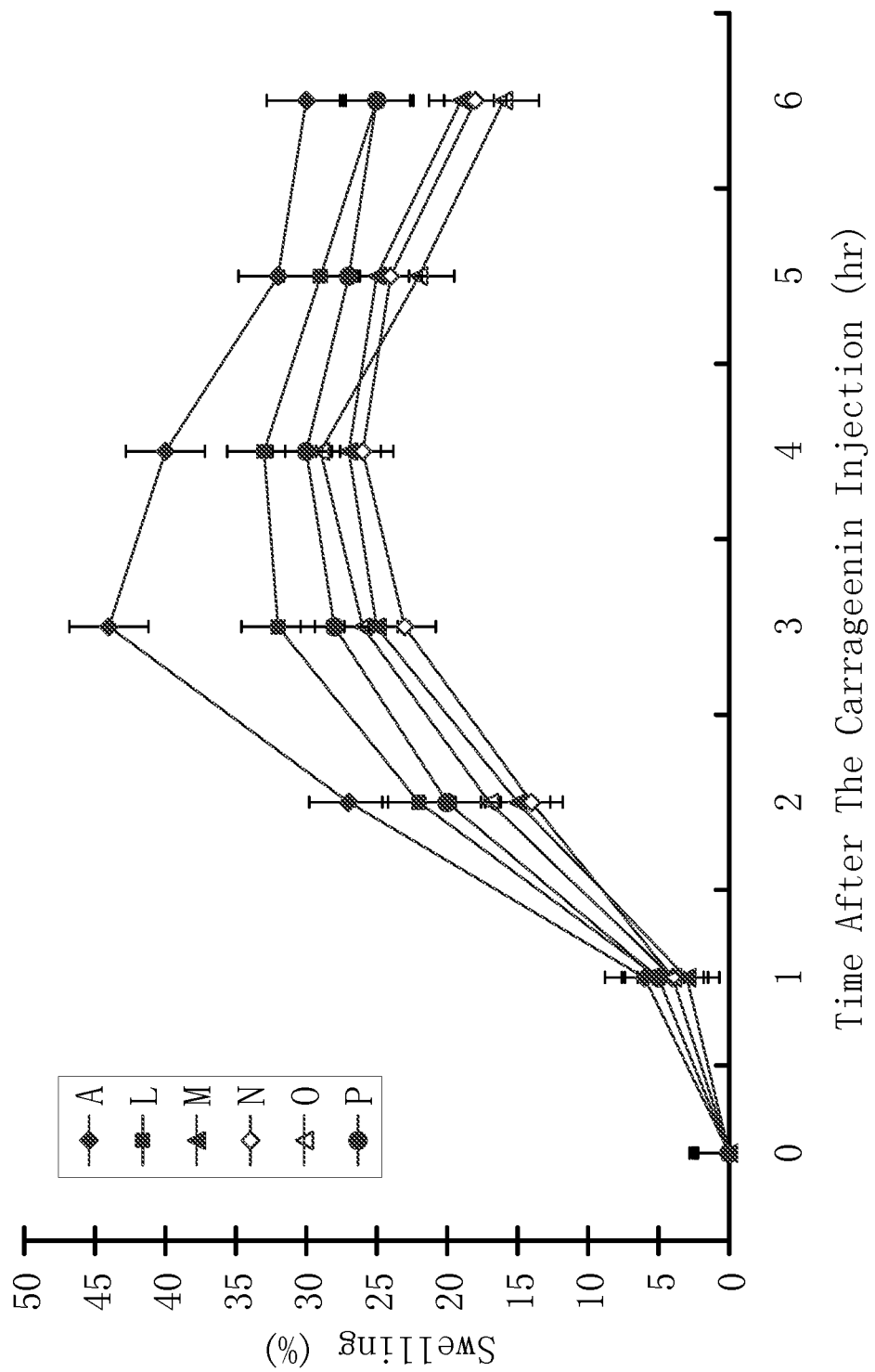
Figures 4, 4E:
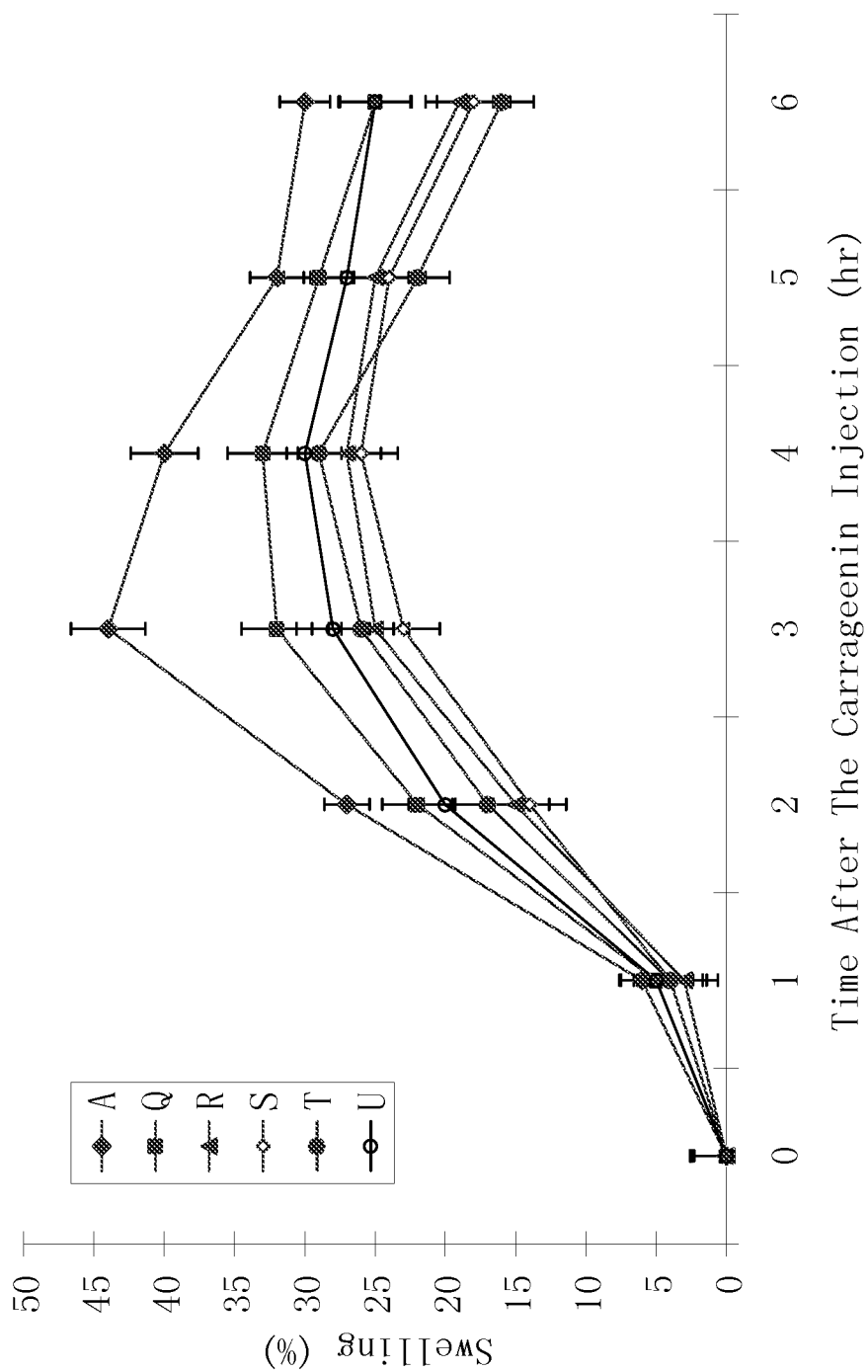

FIG. 4e-1. The rate of swelling (%) after a carrageenin injection. 1 Hour before the carrageenin injection, diethylaminoethyl 2-(6-methoxy-2-naphthyl)propionate.AcOH (100 mg/kg, B), diethylaminoethyl α-methyl-4-(2-thienylcarbonyl)benzeneacetate.AcOH (100 mg/kg, C), diethylaminoethyl α-methyl-(p-chlorobenzoyl)-5-methoxy-2-methyl-indole 3-acetate.AcOH (100 mg/kg, D), diethylaminoethyl 2-(2-fluoro-4-biphenylyl)propionate.AcOH (100 mg/kg, E); diethylaminoethyl 6-chloro-α-methyl-9H-carbazole-2-acetate.AcOH (100 mg/kg, F) were administered transdermally. Group A is the control group.

FIG. 4e-2. The rate of swelling (%) after a carrageenin injection. 1 Hour before the carrageenin injection, diethylaminoethyl α-methyl-5H-[1]benzopyrano[2,3-b]pyridine-7-acetate.AcOH (100 mg/kg, G), diethylaminoethyl 2-(4-chlorophenyl)-α-methyl-5-benzoxazoleacetate.AcOH (100 mg/kg, H), diethylaminoethyl α-methyl-4-[(2-methyl-2-propenyl)amino]benzeneacetate.AcOH (100 mg/kg, I), diethylaminoethyl 5-benzoyl-α-methyl-2-thiopheneacetate.AcOH (100 mg/kg, J), diethylaminoethyl 3-chloro-4-(2,5-dihydro-1H-pyrrol-1-yl)-α-methyl benzeneacetate.AcOH (100 mg/kg, K) were administered transdermally. Group A is the control group.

FIG. 4e-3. The rate of swelling (%) after a carrageenin injection. 1 Hour before the carrageenin injection, diethylaminoethyl 2-(10,11-dihydro-10-oxodibenzo(b,f)thiepin-2-yl)propionate.AcOH (100 mg/kg, L), diethylaminoethyl 2-(8-methyl-10,11-dihydro-11-oxodibenz(b,f)oxepin-2-yl)propionate.AcOH (100 mg/kg, M), diethylaminoethyl 2-[4-(2-oxocyclopentyl-methyl)phenyl]propionate.AcOH (100 mg/kg, N), diethylaminoethyl 4-(1,3-dihydro-1-oxo-2H-isoindol-2-yl)-α-methylbenzeneacetate.AcOH (100 mg/kg, O), diethylaminoethyl α,3-dichloro-4-cyclohexylbenzeneacetate.AcOH (100 mg/kg, P) were administered transdermally. Group A is the control group.

FIG. 4e-4. The rate of swelling (%) after a carrageenin injection. 1 Hour before the carrageenin injection, diethylaminoethyl 4,5-Diphenyl-2-oxazole propionate.AcOH (100 mg/kg, Q), diethylaminoethyl 3-(4-biphenylylcarbonyl)propionate.AcOH (100 mg/kg, R), diethylaminoethyl 5-(4-chlorophenyl)-beta-hydroxy-2-furanpropionate.AcOH (100 mg/kg, S), diethylaminoethyl 5-benzoyl-2,3-dihydro-1H-pyrrolizine-1-carboxylate.AcOH (100 mg/kg, T), diethylaminoethyl 6-chloro-5-cyclohexyl-2,3-dihydro-1H-indene-1-carboxylate.AcOH (100 mg/kg, U) were administered transdermally. Group A is the control group.

Figures 1, 4F:
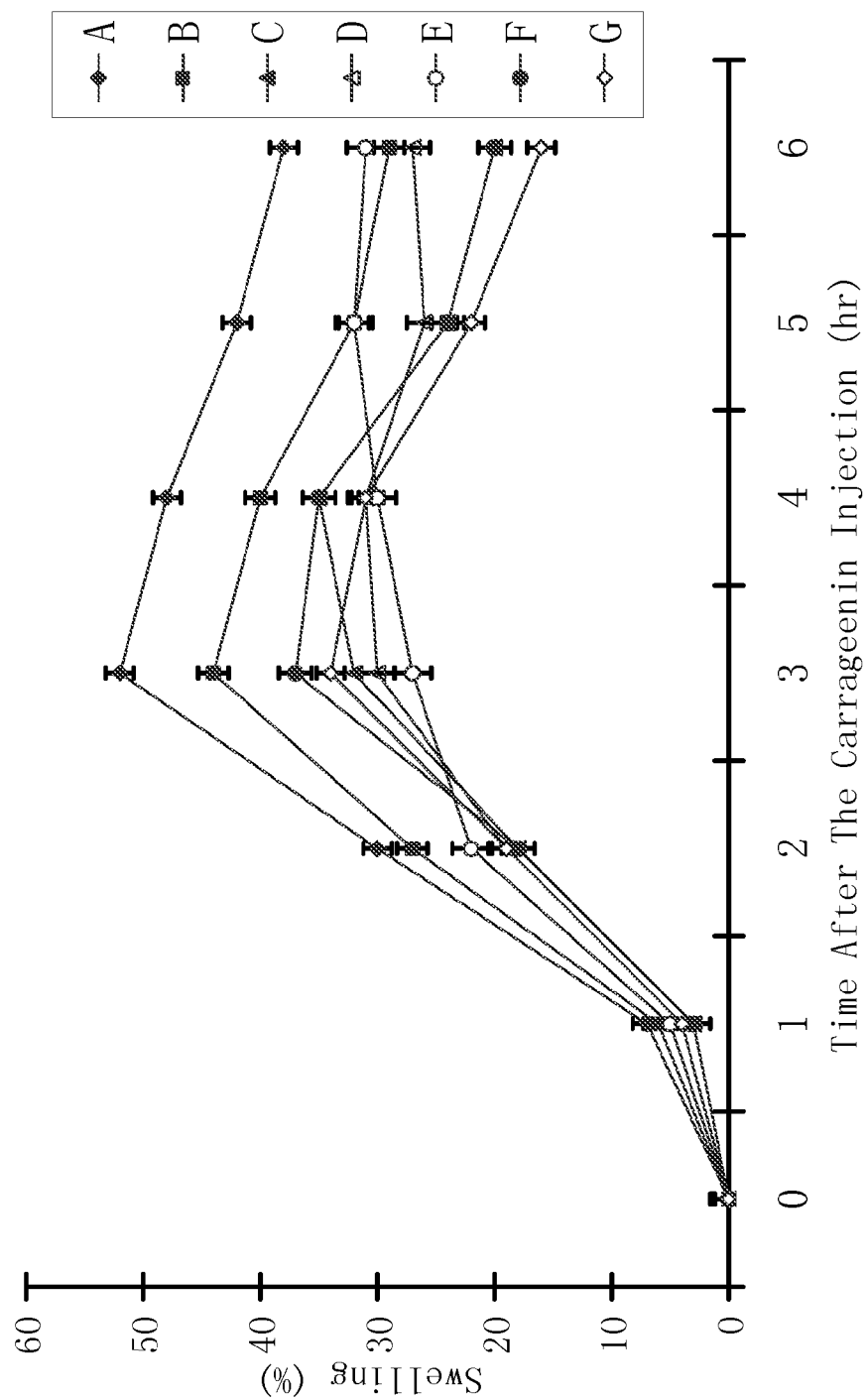
Figures 2, 4F:
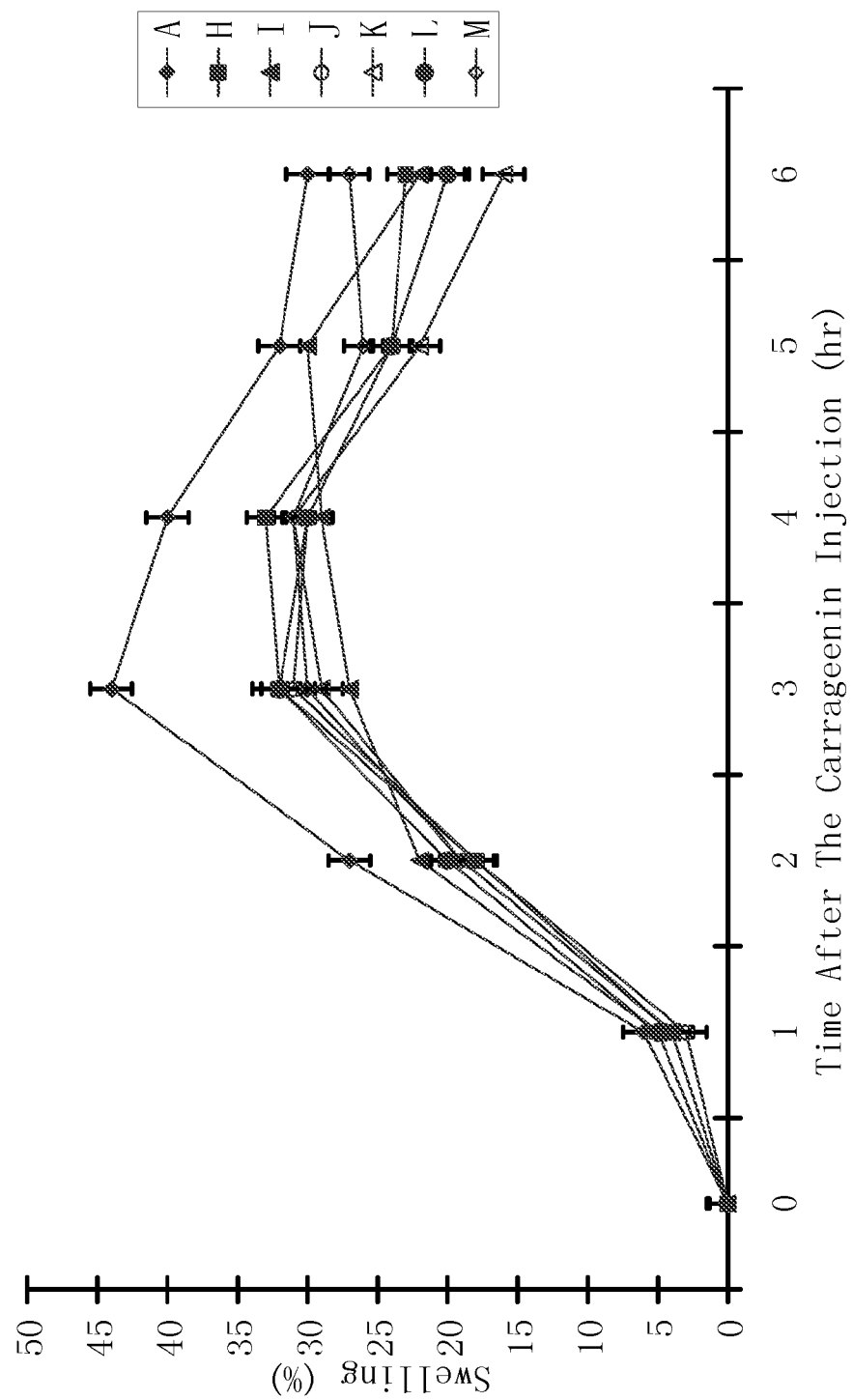

FIG. 4f-1: The rate of swelling (%) after a carrageenin injection. 1 hour before the carrageenin injection, diethylaminoethyl 1-(p-chlorobenzoyl)-5-methoxy-2-methylindole 3-acetate.AcOH (100 mg/kg, B), diethylaminoethyl (Z)-5-fluoro-2-methyl-1-[(4-methylsulfinyl) phenylmethylene]-1H-indene-3-acetate.AcOH (100 mg/kg, C), diethylaminoethyl 1-methyl-5-(4-methylbenzoyl)-1H-pyrrole-2-acetate.AcOH (100 mg/kg, D), diethylaminoethyl 5-(4-Chlorobenzoyl)-1,4-dimethyl-1H-pyrrole-2-acetate.AcOH (100 mg/kg, E), diethylaminoethyl 1.8-diethyl-1,3,4,9-tetrahydropyrano-[3.4-b]indole-1-acetate.AcOH (100 mg/kg, F), diethylaminoethyl 2-amino-3-benzoylbenzeneacetate.AcOH (100 mg/kg, G) were administered transdermally. A group is the control group.

FIG. 4f-2: The rate of swelling (%) after a carrageenin injection. 1 hour before the carrageenin injection, diethylaminoethyl 2-amino-3-(4-bromo-benzoyl)benzeneacetate.AcOH (100 mg/kg, H), diethylaminoethyl 3-chloro-4-(2-propenyloxy)benzeneacetate.AcOH (100 mg/kg. I), diethylaminoethyl 2-(2,4-dichlorophenoxy)benzeneacetate.AcOH (100 mg/kg. J), diethylaminoethyl 1-(4-chlorobenzoyl-5-methoxy-2-methyl-1H-indole-3-acetoxyacetate.AcOH (100 mg/kg. K), diethylaminoethyl 4-(4-chlorophenyl-2-phenyl-5-thiazoleacetate.AcOH (100 mg/kg, L), or diethylaminoethyl 3-(4-chlorophenyl)-1-phenyl-1H-pyrazole-4-acetate.AcOH (100 mg/kg. M) were administered transdermally. A is the control group.

Figure 4G:
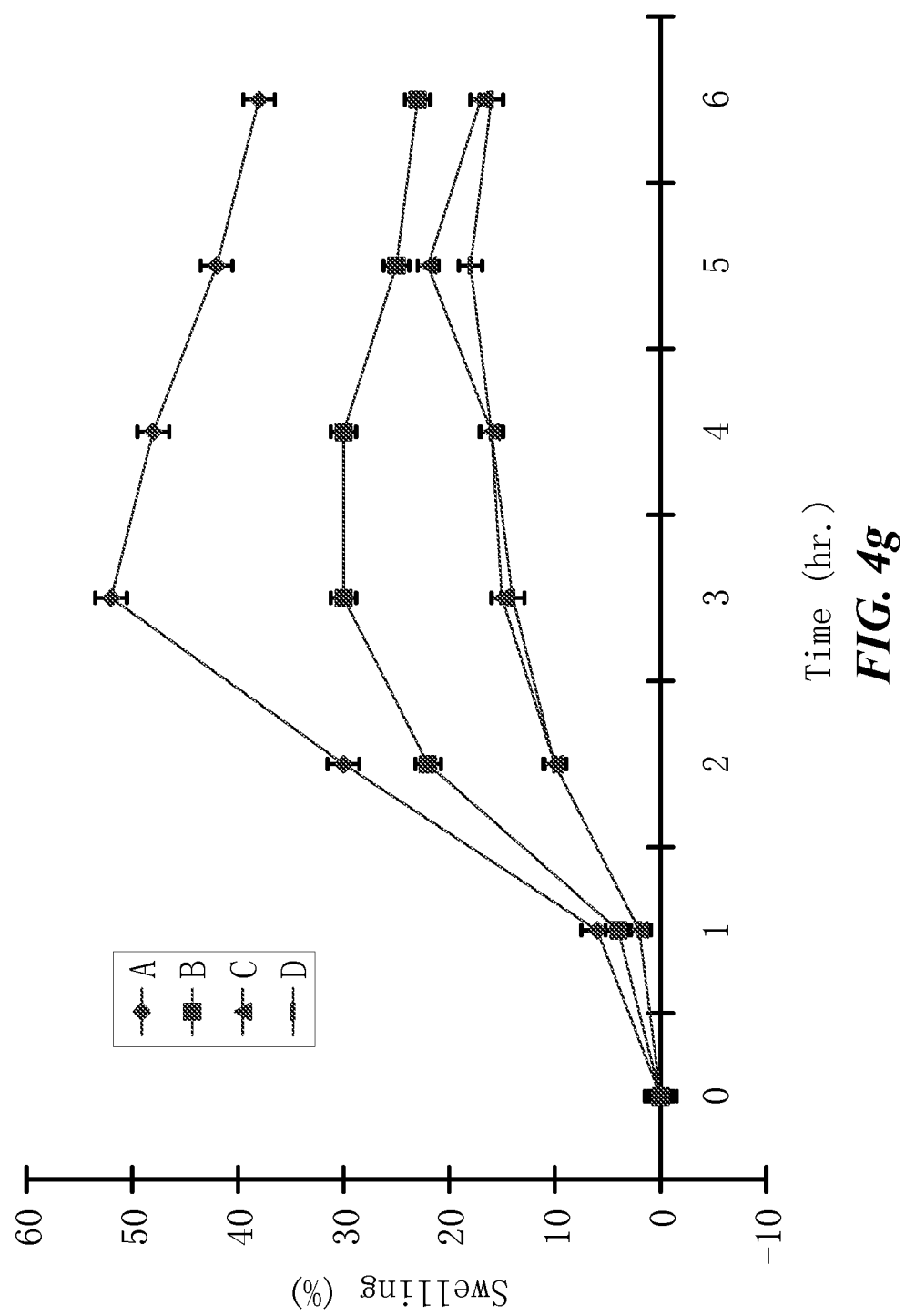

FIG. 4g. The rate of swelling (%) after a carrageenin injection. 1 hour before the carrageenin injection, 10 mg/kg of diclofenac was administered orally (B), 10 mg/kg of diethylaminoethyl 2[(2,6-dichlorophenyl)amino]benzene acetate.AcOH was administered orally (C), and transdermally (D). A is the control group.

Figure 4H:
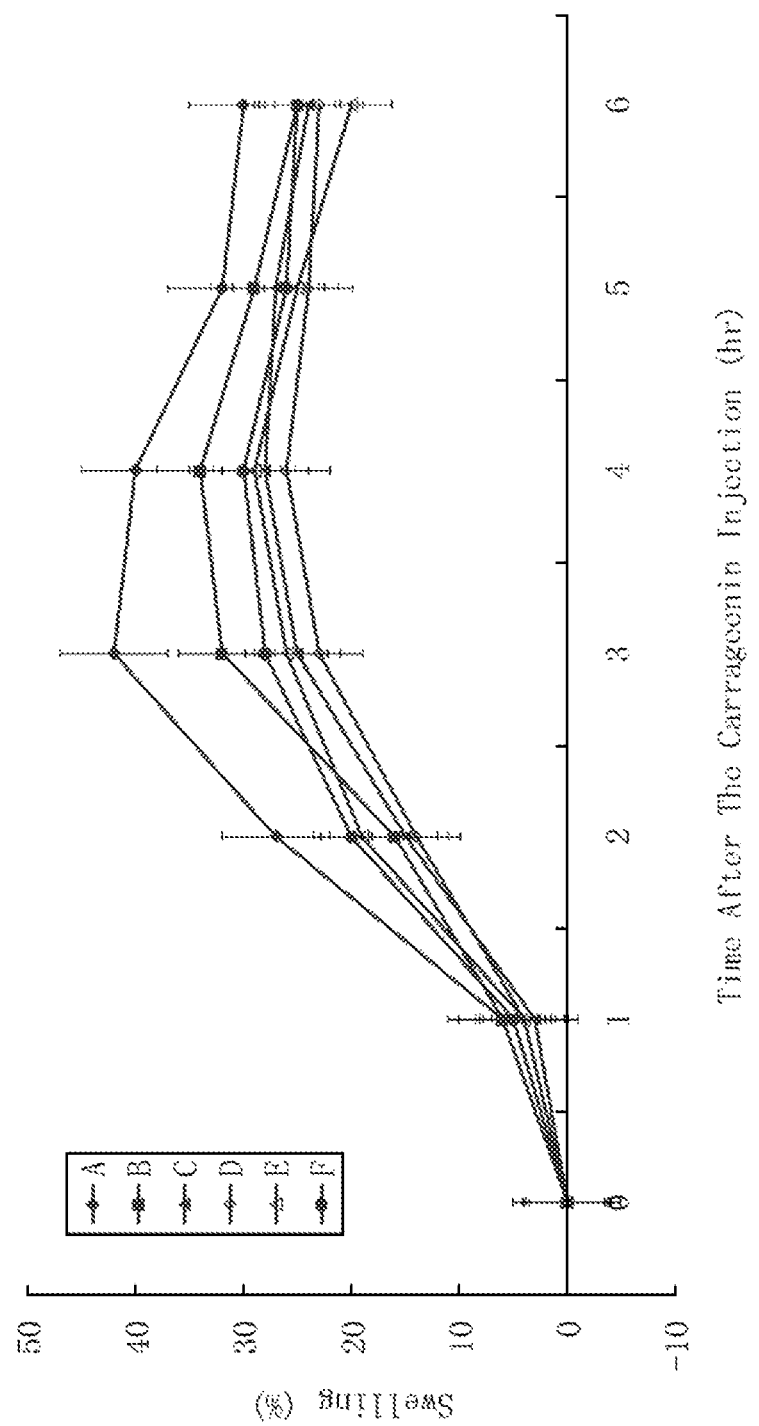

FIG. 4h. The rate of swelling (%) after a carrageenin injection. 2 hour before the carrageenin injection, diethylaminoethyl 2-[(2,3-dimethylphenyl)amino]benzoate.AcOH (100 mg/kg, B), diethylaminoethyl 2-[(2,6-dichloro-3-methylphenyl)amino]benzoate.AcOH (100 mg/kg, C), diethylaminoethyl 2-[[(3-(trifluoromethyl)phenyl)amino]benzoate.AcOH (100 mg/kg, D), diethylaminoethyl 2-[[3-(trifluoromethyl)phenyl]amino]-3-pyridinecarboxylate.AcOH (100 mg/kg, E), diethylaminoethyl 2-[[2-methyl-3-(trifluoromethyl)phenyl]amino]-3-pyridinecarboxylate.AcOH (100 mg/kg, F) were administered transdermally. Group A the control group.

EXEMPLARY EMBODIMENTS OF THE INVENTION

I. Structure of High Penetration Prodrug (HPP) or High Penetration Composition (HPC)

One aspect of the invention relates to a high penetration prodrug (HPP) or a high penetration composition (HPC). The term "high penetration prodrug" or "HPP" or "high penetration composition" or "HPC" as used herein refers to a composition comprising a functional unit covalently linked to a transportational unit through a linker. The functional unit comprises a moiety of an agent (e.g., a drug). The functional unit has the properties including that 1) the delivery of the agent or the HPP into a biological subject or transportation across a biological barrier is desired, 2) the HPP is capable of penetrating or crossing a biological barrier, and 3) the HPP is capable of being cleaved so as to turn the moiety of the agent into an agent or active agent after cleavage. In certain embodiments, the agent comprises an active agent or an agent that can be metabolized into an active agent or active metabolite.

In certain embodiments, the functional unit may be hydrophilic, lipophilic, or amphiphilic (hydrophilic and lipophilic). The lipophilic moiety of the function unit may be inherent or achieved by converting its hydrophilic moieties to lipophilic moieties. For example, the lipophilic moiety of a functional unit is produced by converting one or more hydrophilic groups of the functional unit to lipophilic groups via traditional organic synthesis. Examples of the hydrophilic groups are carboxylic, hydroxyl, thiol, amine, phosphate/phosphonate and carbonyl groups. The lipophilic moieties produced via the modification of these hydrophilic groups are ethers, thioethers, esters, thioesters, carbonates, carbamates, amides, phosphates and oximes.

In certain embodiments, the agent is a non-steroidal anti-inflammatory agent (NSAIA), an active NSAIA metabolite, an agent that can be metabolized into a NSAIA or an active NSAIA metabolite after the HPP (NSAIA-HPP) penetrates one or more BBs. The agent of the functional unit can be further converted to lipophilic motif as described supra.

The term "non-steroidal anti-inflammatory agent" or "NSAIA" is well known in the art and is a non-steroidal agent used to treat inflammation related conditions. NSAIA has anti-inflammatory effect, and some examples of NSAIA also have analgesic and/or antipyretic effects. Examples of NSAIA include, but are not limited to, acetylsalicylic acid (aspirin), 5-(2,4-difluorophenyl)salicylic acid (diflunisal), salicylsalicylic acid (salsalate), salicylic acid, N-Acetyl-p-aminophenol (acetaminophen), 2-(ρ-isobutylphenyl) propionic acid (ibuprofen), 2-(3-benzoylphenyl) propionic acid (ketoprofen), 2-(3-phenoxyphenyl) propionic acid (fenoprofen), 2-(6-methoxy-2-naphthyl) propionic acid (naproxen), α-methyl-4-(2-thienylcarbonyl) benzeneacetic acid (suprofen), α-methyl-(p-chlorobenzoyl)-5-methoxy-2-methylindole 3-acetic acid, 2-(2-fluoro-4-biphenylyl) propionic acid (flurbiprofen), 6-chloro-α-methyl-9H-carbazole-2-acetic acid (carprofen), α-methyl-5H-[1]benzopyrano[2,3-b]pyridine-7-acetic acid (pranoprofen), 2-(4-chlorophenyl)-α-methyl-5-benzoxazoleacetic acid (benoxaprofen), α-methyl-4-[(2-methyl-2-propenyl)amino]benzeneacetic acid (alminoprofen), 5-benzoyl-α-methyl-2-thiopheneacetic acid (tiaprofenic acid), 3-chloro-4-(2,5-dihydro-1H-pyrrol-1-yl)-α-methyl benzeneacetic acid (pirprofen), 2-(10,11-dihydro-10-oxodibenzo(b,f)thiepin-2-yl)propionic acid (zaltoprofen), 2-(8-methyl-10,11-dihydro-11-oxodibenz(b,f)oxepin-2-yl)propionic acid (bermoprofen), 2-[4-(2-oxocyclopentyl-methyl)phenyl]propionic acid (loxoprofen), 4-(1,3-dihydro-1-oxo-2H-isoindol-2-yl)-α-methylbenzeneacetic acid (indoprofen), α,3-dichloro-4-cyclohexylbenzeneacetic acid (fenclorac), 2-aryl and heteroarylpropionic acids, 4,5-Diphenyl-2-oxazole propionic acid (oxaprozin), 3-(4-biphenylylcarbonyl)propionic acid (fenbufen), 5-(4-chlorophenyl)-beta-hydroxy-2-furanpropionic acid (orpanoxin), and related compounds are members of 3-aryl and heteroarylpropionic acid group of NSAIA. 5-benzoyl-2,3-dihydro-1H-pyrrolizine-1-carboxylic acid (ketorolac), 6-chloro-5-cyclohexyl-2,3-dihydro-1H-indene-1-carboxylic acid (clidanac), 1-Methyl-5-(4-methylbenzoyl)-1H-pyrrole-2-acetic acid (tolmetin), 5-(4-Chlorobenzoyl)-1,4-dimethyl-1H-pyrrole-2-acetic acid (zomepirac), 1,8-diethyl-1,3,4,9-tetrahydropyrano-[3,4-b]indole-1-acetic acid (etodolac), 2-amino-3-benzoylbenzeneacetic acid (amfenac), 2-amino-3-(4-bromo-benzoyl)benzeneacetic acid (bromofenac), 3-chloro-4-(2-propenyloxy)benzeneacetic acid (alclofenac), 2-(2,4-dichlorophenoxy)benzeneacetic acid (fenclofenac), 1-(4-chlorobenzoyl-5-methoxy-2-methyl-1H-indole-3-acetic acid carboxymethyl ester (acemetacin), 4-(4-chlorophenyl)-2-phenyl-5-thiazoleacetic acid (fentiazac), 1-(p-chlorobenzoyl)-5-methoxy-2-methylindole 3-acetic acid (indomethacin), (Z)-5-fluoro-2-methyl-1-[(4-methylsulfinyl)phenylmethylene]-1H-indene-3-acetic acid (sulindac), 3-(4-chlorophenyl)-1-phenyl-1H-pyrazole-4-acetic acid (lonazolac), [(1-benzyl-1H-indazol-3-yl)oxy]acetic acid (bendazac), 6-methoxyl-2-naphthalene-2-acetic acid (6MNA), 2[(2,6-dichlorophenyl)amino]benzene acetic acid (diclofenac), 2-[(2,3-Dimethylphenyl)amino]benzoic acid (mefenamic acid), 2-[(2,6-dichloro-3-methylphenyl)amino]benzoic acid (meclofenamic acid), 2-[[(3-trifluoromethyl)phenyl]amino]benzoic acid (flufenamic acid), 2-[[3-(trifluoromethyl)phenyl]amino]-3-pyridinecarboxylic acid (niflumic acid), 2-[[2-methyl-3-(trifluoromethyl)phenyl]amino]-3-pyridinecarboxylic acid (flunixin), 4-hydroxy-2-methyl-N-2-pyridinyl-2H, 1,2-benzothiazine-3-carboxamide 1,1-dioxide (piroxicam), sudoxiam, 6-chloro-4-hydroxy-2-methyl-N-2-pyridinyl-2H-thieno[2,3-e]-1,2-thiazine-3-carboxamide 1,1-dioxide (lomoxicam), 4-hydroxy-2-methyl-N-2-pyridinyl-2H-thieno[2,3-e]-1,2-thiazine-3-carboxamide 1,1-dioxide (tenoxicam), ethyl 1-[2-methyl-1,1-dioxo-3-(pyridin-2-ylcarbamoyl)benzo[e]thiazin-4-yl] oxyethyl carbonate (ampiroxicam), 8-chloro-(4-hydroxyl-4-pyridine-2-ylamino-methyl idene)-3-methyl-2,2-dioxo-2λ$^6$, 7-dithia-3-azabicyclo[4,3,0]nona-8,10-dien-5-one (lomoxicam), 4-hydroxy-2-methyl-N-[5-Methyl-3-isoxolyl-2H-1,2-benzothiazine-3-carboxamide 1,1-dioxide] (isoxicam), cinnoxicam and N-(2-thiazolyl)-4-hydroxy-2-methyl-2H, 1,2-benzothiazine-3-arboxamide 1,1-dioxide (meloxicam).

In one embodiment, the functional unit of a NSAIA-HPP comprises a moiety having a structure selected from Group F-1 and Group F-2, wherein Group F-1 includes the following structures;

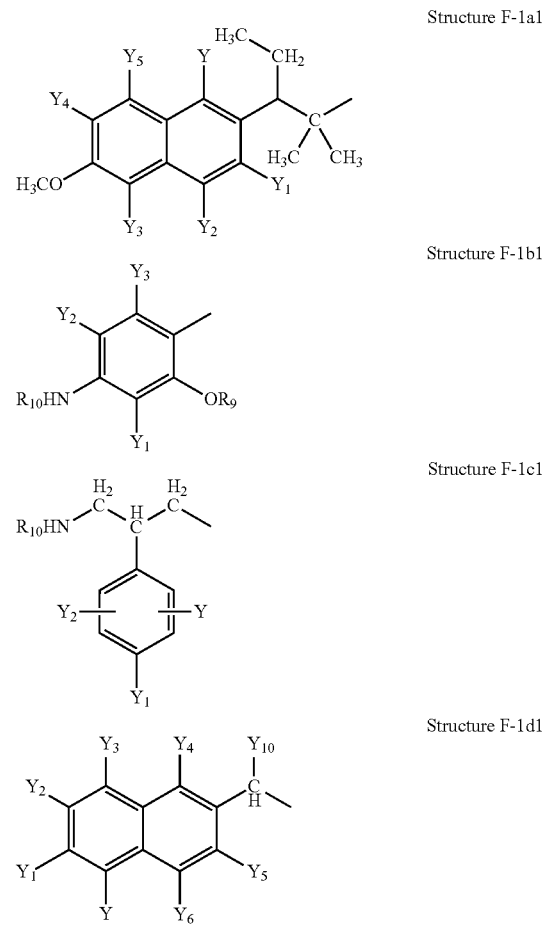

-continued
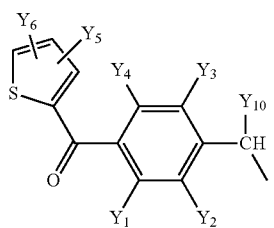
Structure F-1e1
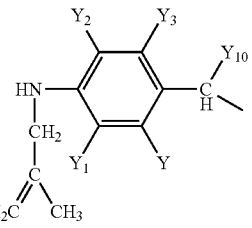
Structure F-1l1
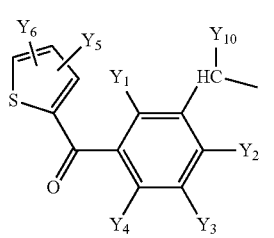
Structure F1f1
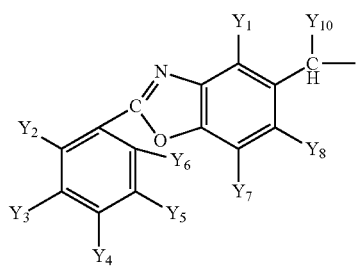
Structure F-1m1
Structure F-1g1
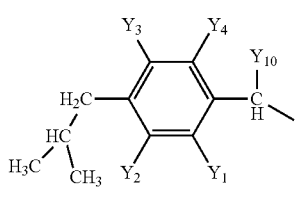
Structure F-1n1
Structure F-1h1
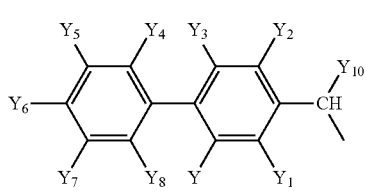
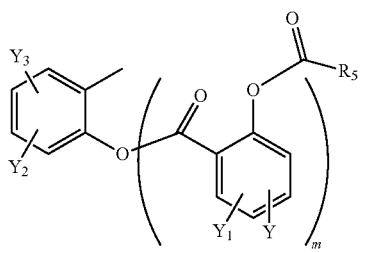
Structure F-1i1
Structure F-1o1
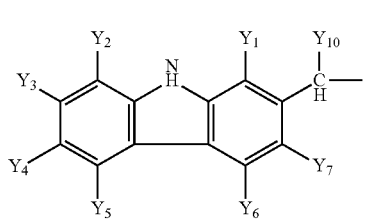
Structure F-1j1
Structure F-1p1
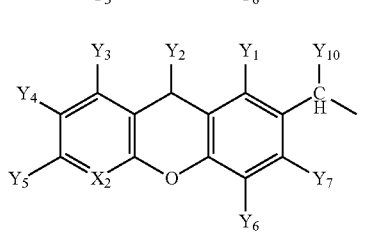
Structure F-1k1
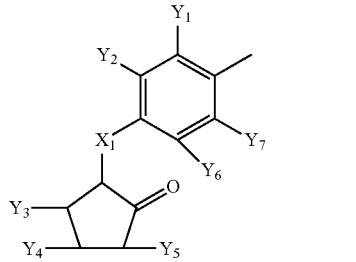
Structure F-1q1

Structure F-1r1
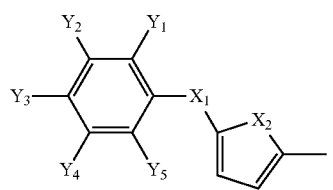
Structure F-1s1
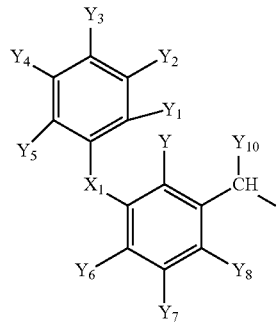
Structure F-1t1
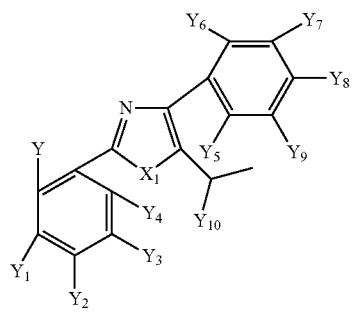
Structure F-1u1
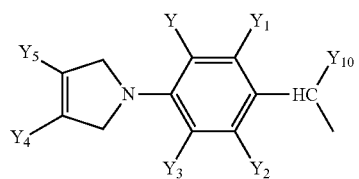
Structure F-1v1
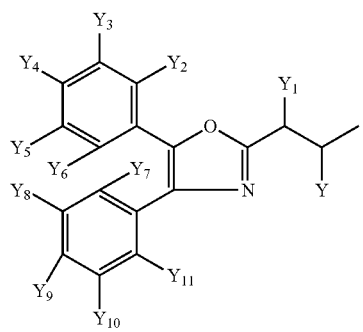
Structure F-1w1
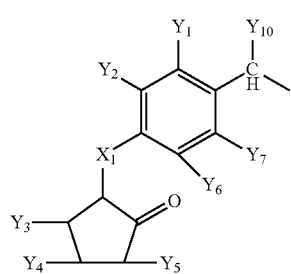
Structure F-1x1
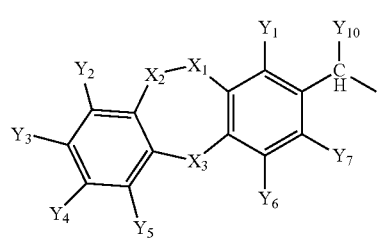
Structure F-1y1
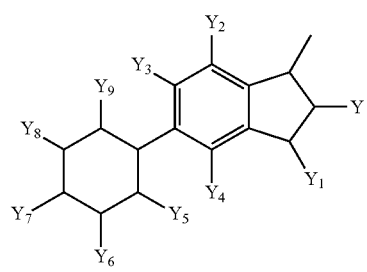
Structure F-1z1
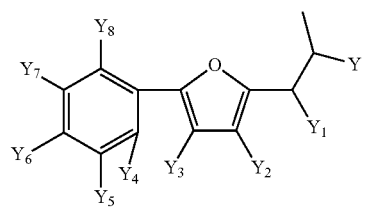
Structure F-1a2
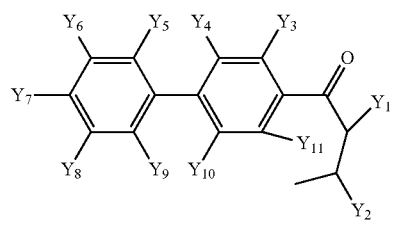
Structure F-1b2
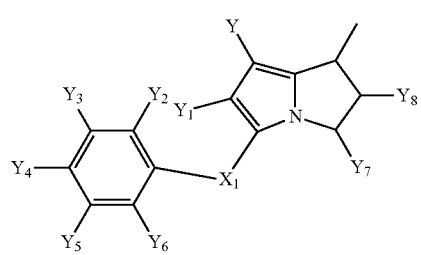
Structure F-1c2
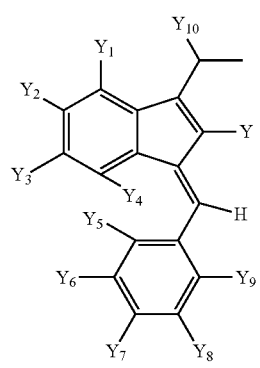

-continued

Structure F-1d2

Structure F-1e2

Structure F-1f2

Structure F-1g2

Structure F-1h2

Structure F-1i2

Structure F-1j2

Structure F-1k2

Structure F-1l2

Structure F-1m2

Structure F-1n2

-continued
Structure F-1o2
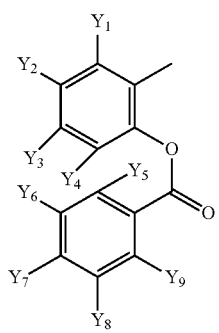
Structure F-1p2
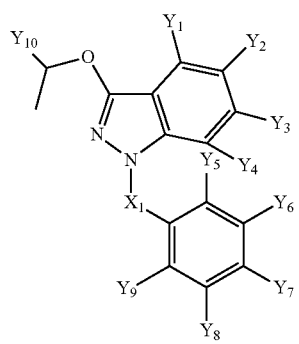
Structure F-1q2
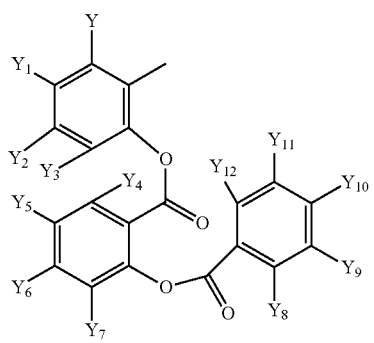
Structure F-1r2
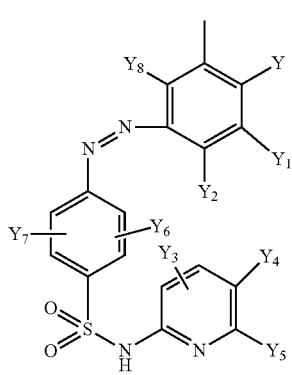
-continued
Structure F-1s2
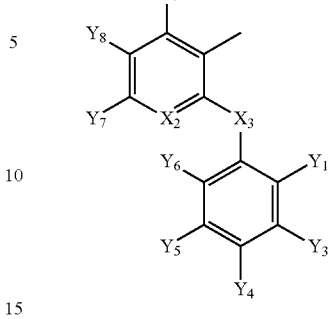
Structure F-1t2
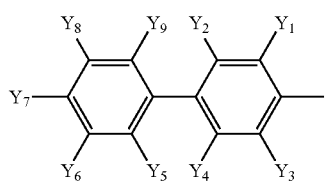
Structure F-1u2
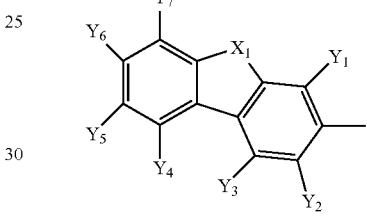
Structure F-1v2
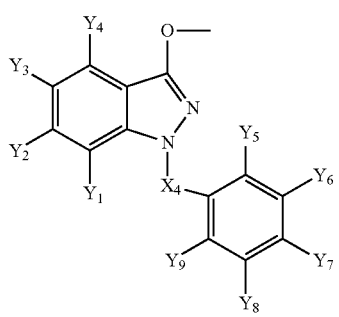
Structure F-1w2
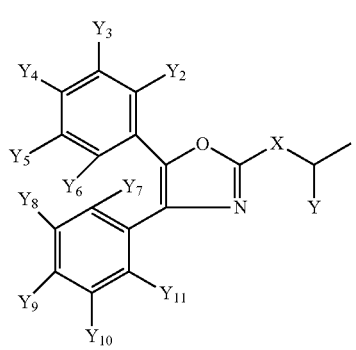
Structure F-1x2
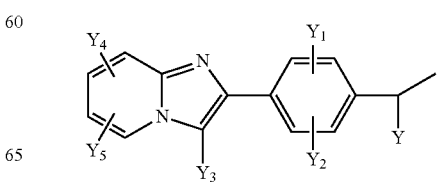

-continued
Structure F-1y2
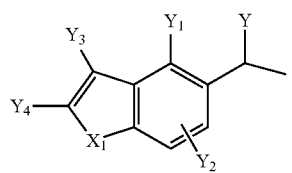
Structure F-1z2
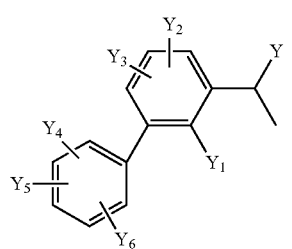
Structure F-1a3
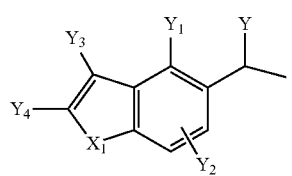
Structure F-1b3
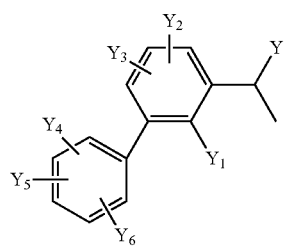
Structure F-1c3
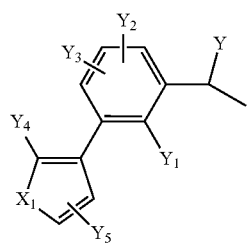
Structure F-1d3
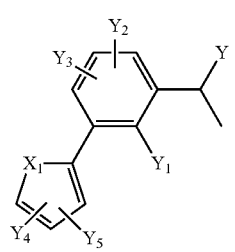
Structure F-1e3
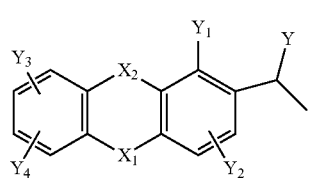
-continued
Structure F-1f3
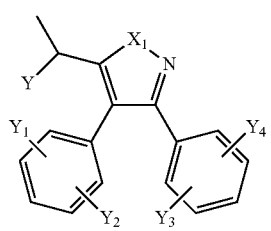
Structure F-1g3
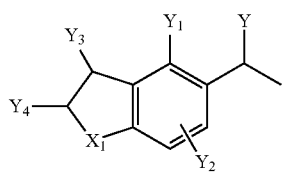
Structure F-1h3
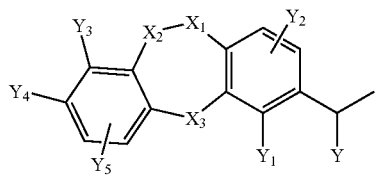
Structure F-1i3
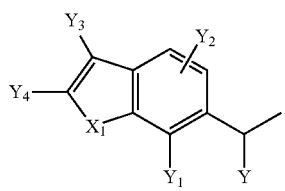
Structure F-1j3
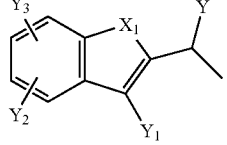
Structure F-1k3
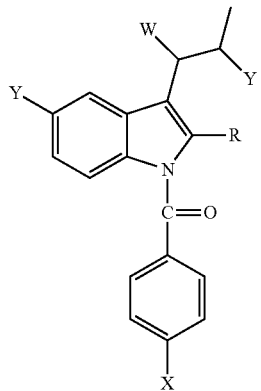
Structure F-1l3
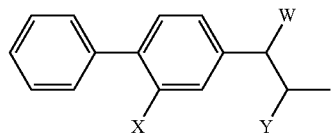

-continued
Structure F-1m3
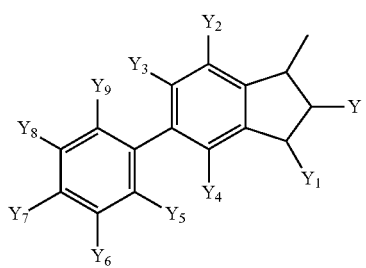
Structure F-1n3
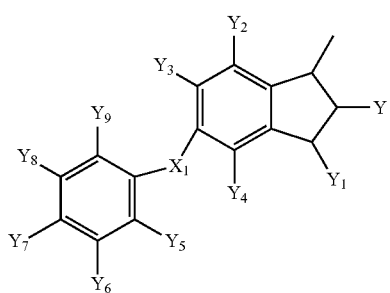
Structure F-1o3
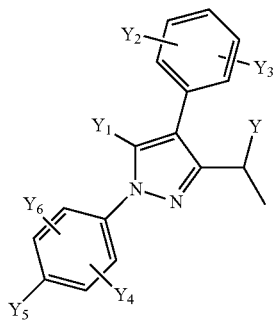
Structure F-1p3
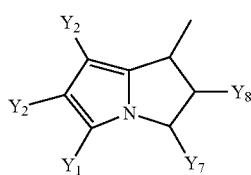
Structure F-1q3
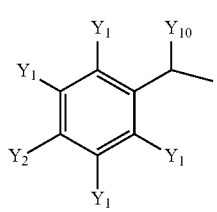
Structure F-1r3
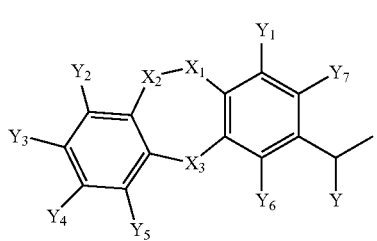
-continued
Structure F-1s3
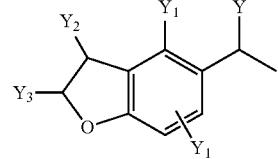
Structure F-1t3
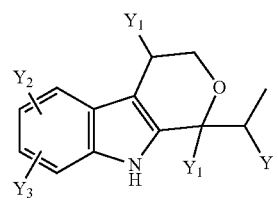
Structure F-1u3
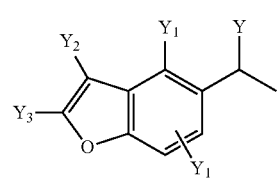
Structure F-1v3
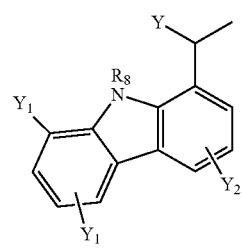
Structure F-1w3
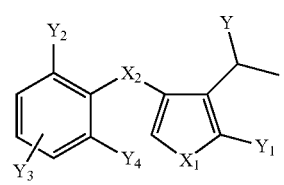
Structure F-1x3
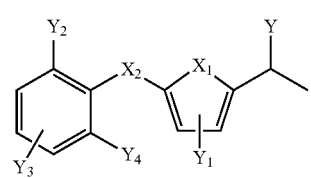
Structure F-1y3
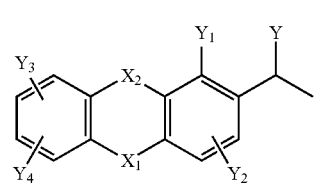
Structure F-1z3
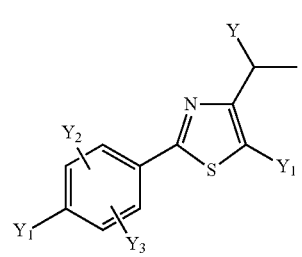

Structure F-1a4
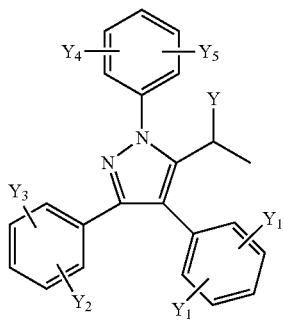
Structure F-2d1
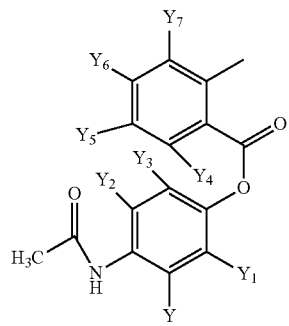
Structure F-1b4
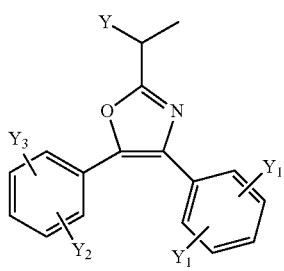
and Group F-2 includes the following structures;
Structure F-2e1
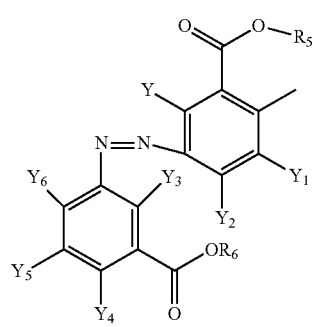
Structure F-2a1
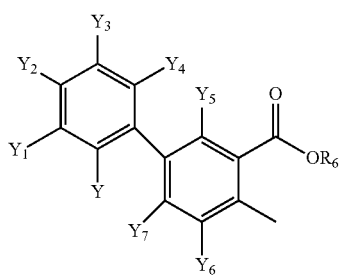
Structure F-2f1
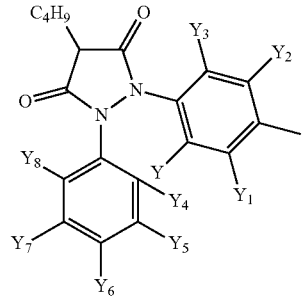
Structure F-2b1
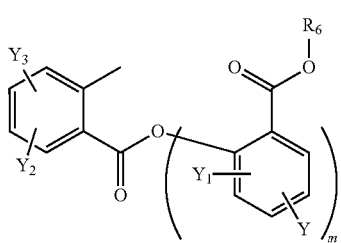
Structure F-2g1
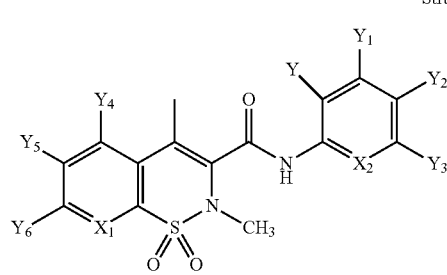
Structure F-2c1
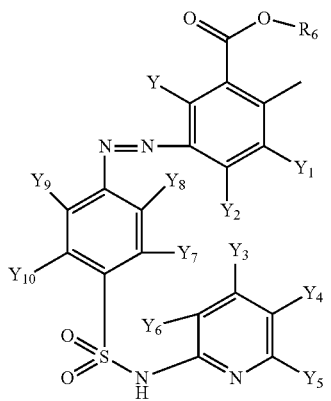
Structure F-2h1
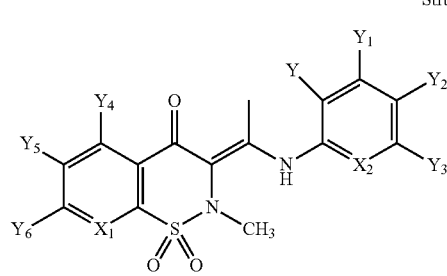

Structure F-2i1
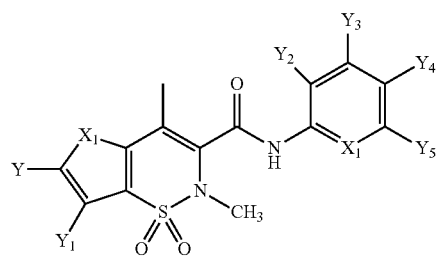
Structure F-2j1
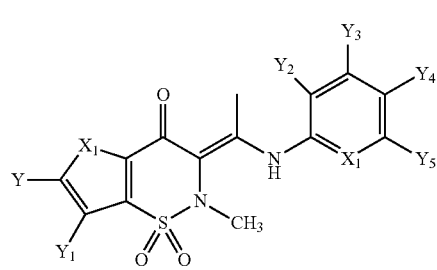
Structure F-2k1
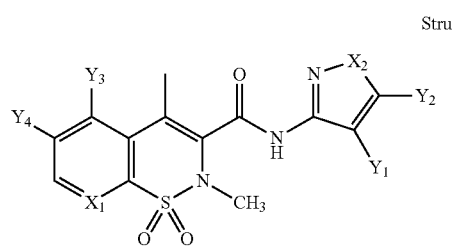
Structure F-2l1
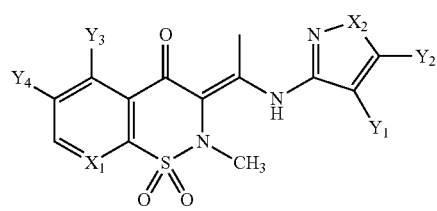
Structure F-2m1
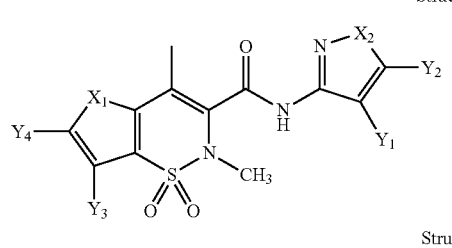
Structure F-2n1
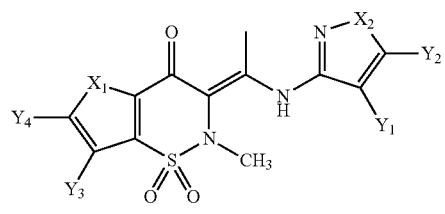
Structure F-2o1
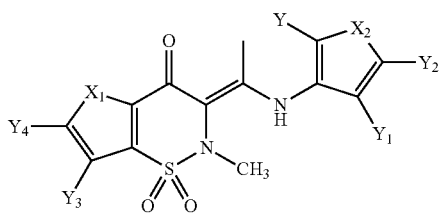
Structure F-2p1
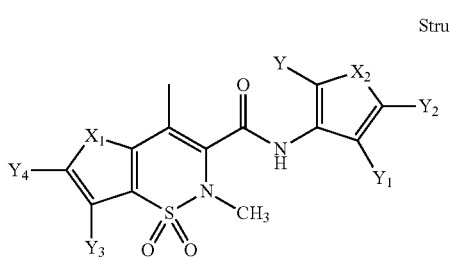
Structure F-2q1
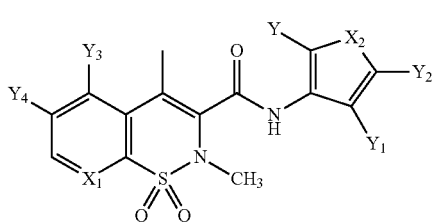
Structure F-2r1
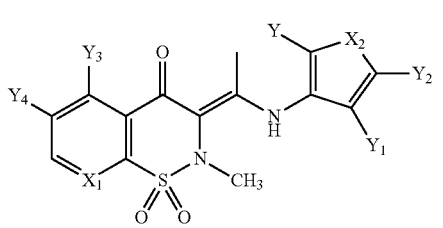
Structure F-2s1
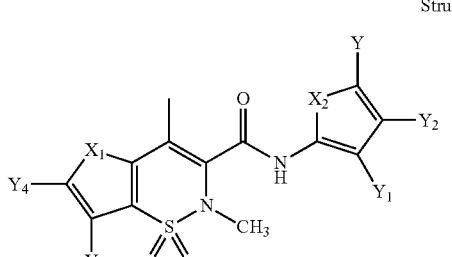
Structure F-2t1
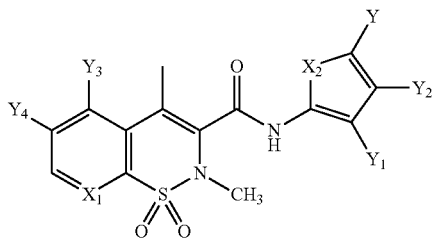

Structure F-2u1
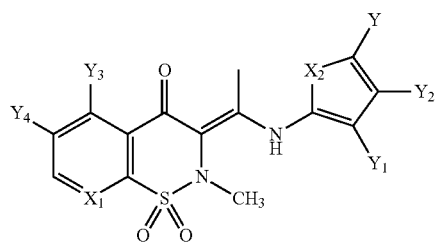
Structure F-2v1
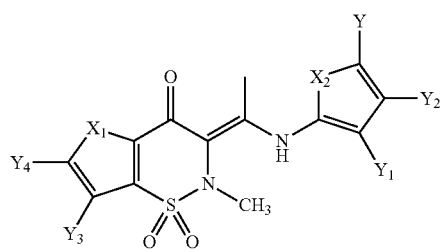
Structure F-2w1
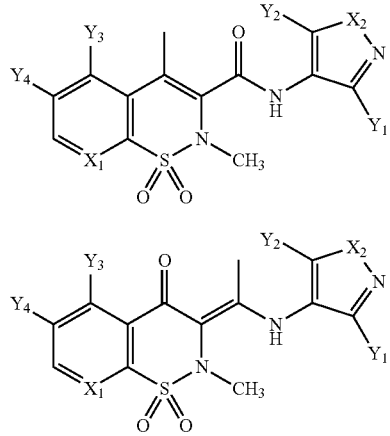
Structure F-2x1
Structure F-2y1
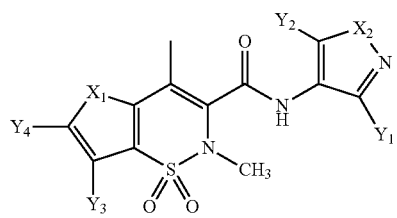
Structure F-2z1
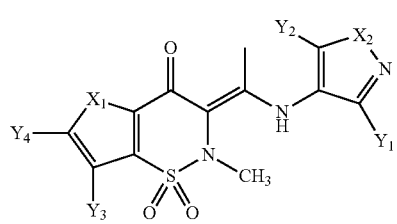
Structure F-2a2
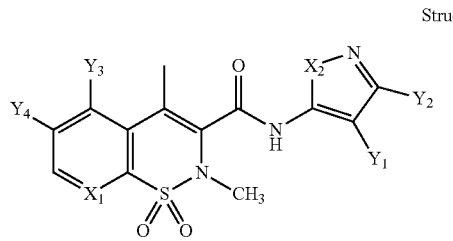
Structure F-2b2
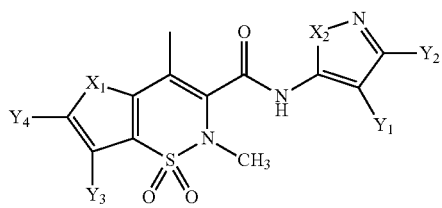
Structure F-2c2
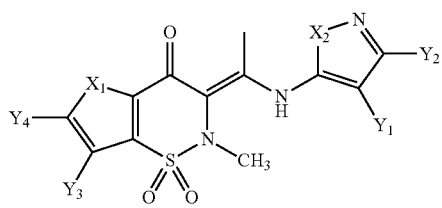
Structure F-2d2
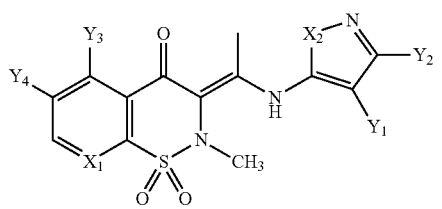
Structure F-2e2
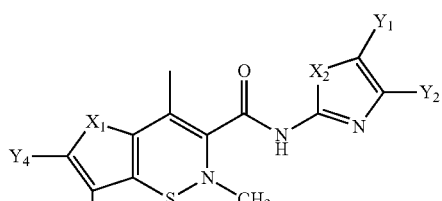
Structure F-2f2
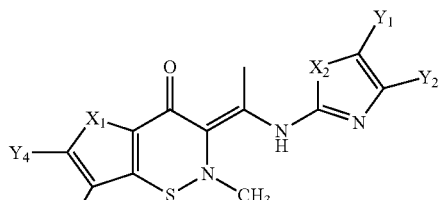
Structure F-2g2
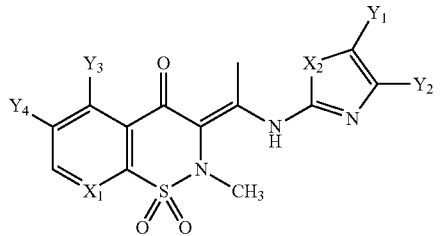

Structure F-2h2
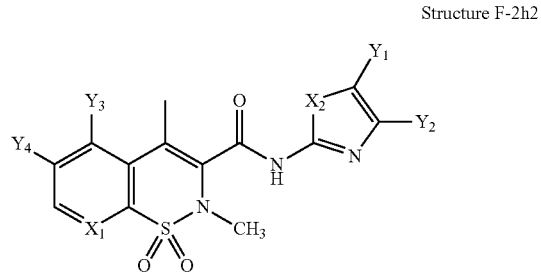
Structure F-2i2
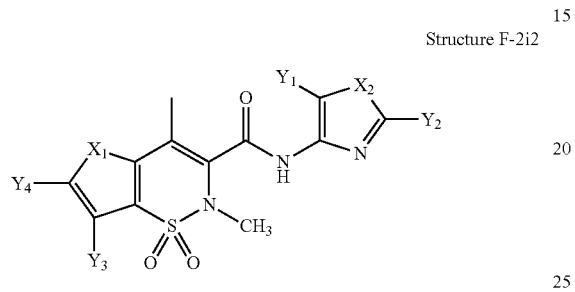
Structure F-2j2
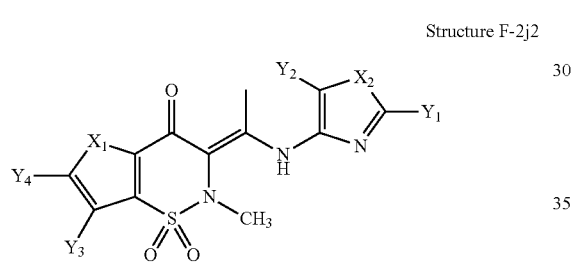
Structure F-2k2
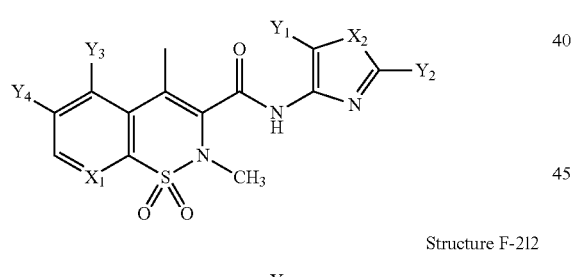
Structure F-2l2
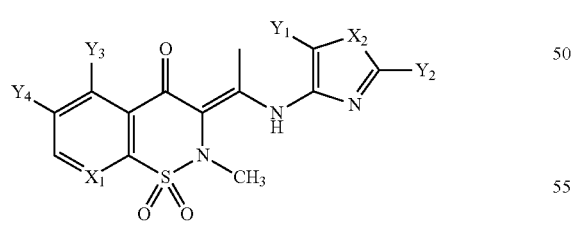
Structure F-2m2
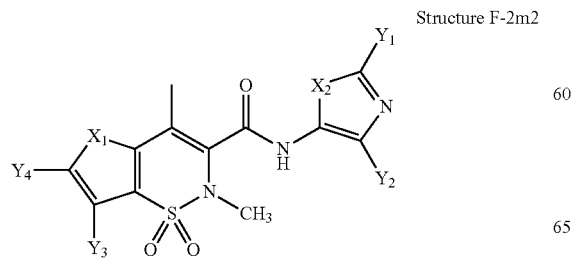
Structure F-2n2
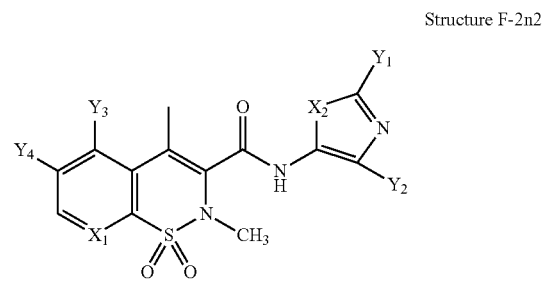
Structure F-2o2
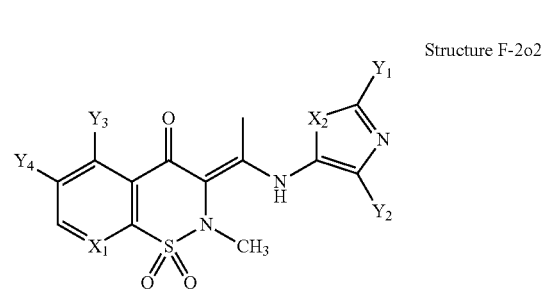
Structure F-2p2
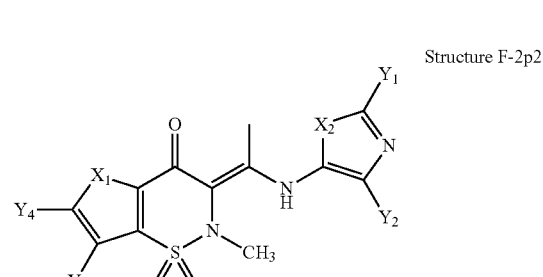
Structure F-2q2
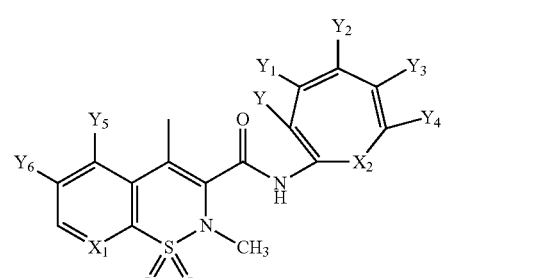
Structure F-2r2
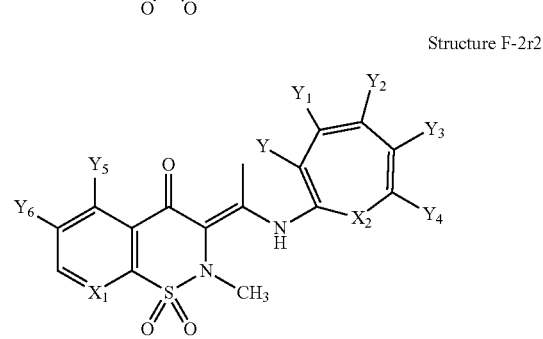

-continued

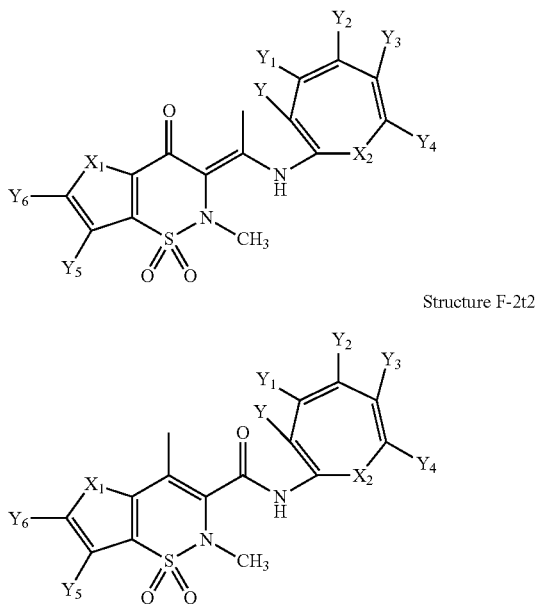

Structure F-2s2

Structure F-2t2 including stereoisomers and pharmaceutically acceptable salts thereof.

As used herein, unless specified otherwise, each R, $R_1$, $R_2$, $R_5$-$R_7$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, substituted and unsubstituted alkyl halide, wherein any carbon or hydrogen may be further independently replaced with O, S, N, P(O)OR$_6$, CH=CH, C≡C, CHR$_6$, CR$_5$R$_6$, aryl, heteroaryl, and cyclic groups;

each $R_8$-$R_{10}$ is independently selected from the group consisting of nothing, H, $R_6$, $R_6$C(=O)—, $R_6$NH(C=O), $R_6$O(C=O), $R_6$C(=NH)—, $R_6$C(=S)—, CNR$_6$ and $R_6$OCO(CH$_2$)nC(=O), wherein n is selected from the group of natural numbers;

each Y and $Y_1$ to $Y_{13}$ is independently selected from the group consisting of H, halogen, CN, $R_{10}$, CH$_3$C≡C, CR$_6$=C, P(O)OR$_6$, CF$_3$, CF$_3$O, CH$_3$, CF$_3$CF$_2$, CF$_3$CF$_2$O, CH$_3$CH$_2$, CH$_3$CH$_2$CH$_2$, (CH$_3$)$_2$CH, (CH$_3$)$_2$CHCH$_2$, CH$_3$CH$_2$CH(CH$_3$), (CH$_3$)$_3$C, C$_4$H$_9$, C$_5$H$_{11}$, CH$_3$CO, CH$_3$CH$_2$CO, R$_5$CO, CH$_3$COO, R$_5$COO, R$_5$COOCH$_2$, R$_6$NHCOOCH$_2$, CH$_3$COS, CH$_3$O, R$_5$O, HO, R$_{10}$O, CF$_3$CH$_2$SCH$_2$, CHCl$_2$, CH$_2$COOR$_6$, CH$_3$S, R$_5$S, HS, R$_{10}$S, CH$_3$OCH$_2$CH$_2$, R$_5$OCH$_2$, R$_{10}$OCH$_2$CH$_2$, R$_5$OC(=O), C$_2$H$_5$OCONH, CH$_2$NHR$_8$, CH$_3$OCONH, CH$_3$SO$_2$, CH$_3$SO, R$_5$SO$_2$, R$_5$SO, NH$_2$SO$_2$, C$_6$H$_5$CH$_2$, NH$_2$, NHR$_{10}$, cyclobutyl, cyclopropyl, 4-chlorophenyl, 4-fluorophenyl, CH$_2$=CH, CH$_2$=CHCH$_2$, CH$_3$CH=CH, NHR$_5$SO$_2$, N(R$_5$)$_2$SO$_2$, R$_5$OCH$_2$CH$_2$CH$_2$, and NO$_2$;

each X and $X_1$ to $X_5$ is independently selected from the group consisting of nothing, CH$_3$SO, S, ONR$_6$, C=O, R$_6$, P(O)OR$_6$;

$X_6$ is selected from the group consisting of R$_6$, CONH, CSNH, COO, OCO, COS, COCH$_2$, and CH$_2$CO;

m is selected from the group of integers; and

W is selected from the group consisting of H, OH and halogen.

As used herein, unless specified otherwise, the term "alkyl" means a branched or unbranched, saturated or unsaturated, monovalent or multivalent hydrocarbon group. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene, In certain embodiments, the hydrocarbon group contains 1 to 30 carbons. In certain embodiments, the hydrocarbon group contains 1 to 20 carbons.

As used herein, unless specified otherwise, the term "cycloalkyl" means an alkyl which contains at least one ring and no aromatic rings. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon chain contains 1 to 30 carbons. In certain embodiments, the hydrocarbon group contains 1 to 20 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, —CH$_2$—OH, —OCH$_3$, —O-alkyl, -alkyl-OH, -alkyl-O-alkyl-, wherein the two alkyls can be the same or different.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, -alkyl-F, -alkyl-Cl, -alkyl-Br, -alkyl-I, -alkyl(F)—, -alkyl(Cl)—, -alkyl(Br)— and -alkyl(I)—.

As used herein, unless specified otherwise, the term "alkylthio" means an alkyl, cycloalkyl or heterocycloalkyl, which contains one or more sulfur atoms. Examples of alkylthio include, but are not limited to, —CH$_2$—SH, —SCH$_3$, —S-alkyl, -alkyl-SH, -alkyl-S-alkyl-, wherein the two alkyls can be the same or different.

As used herein, unless specified otherwise, the term "alkylamino" means an alkyl, cycloalkyl or heterocycloalkyl, which contains one or more nitrogen atoms. Examples of alkylamino include, but are not limited to, —CH$_2$—NH, —NCH$_3$, —N(alkyl)-alkyl, —N-alkyl, -alkyl-NH$_2$, -alkyl-N-alkyl and -alkyl-N(alkyl)-alkyl wherein the alkyls can be the same or different.

As used herein, unless specified otherwise, the term "perfluoroalkyl" means an alkyl, cycloalkyl or heterocycloalkyl, which contains one or more perfluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur. Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl and benzothiazolyl.

In certain embodiments, the transportational unit of the HPP comprises a protonatable amine group that is capable of facilitating the transportation or crossing of the HPP through one or more biological barriers (>100 times faster than the parent drug). In certain embodiments, the protonatable amine group is substantially protonated at a physiological pH. In certain embodiment, the amine group can be reversibly protonated. In certain embodiment, the transportational unit may or may not be cleaved from the functional unit after the penetration of HPP through one or more biological barriers.

In certain embodiments, the protonatable amine group is selected from the group consisting of pharmaceutically acceptable substituted or unsubstituted primary amine groups, pharmaceutically acceptable substituted or unsubstituted secondary amine groups, and pharmaceutically acceptable substituted or unsubstituted tertiary amine groups.

In certain embodiments, the protonatable amine group is selected from Group N, wherein Group N includes Structure Na, Structure Nb, Structure Nc, Structure Nd, Structure Ne, Structure Nf, Structure Ng, Structure Nh, Structure Ni, Structure Nj, Structure Nk, Structure Nl, Structure Nm, Structure Nn, Structure No, Structure Np, Structure Nq and Structure Nr:

Group N:

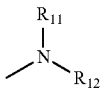

Structure Na

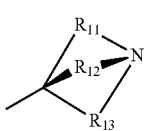

Structure Nb

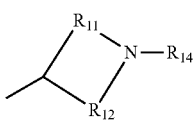

Structure Nc

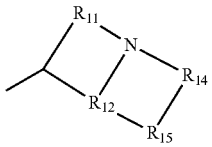

Structure Nd

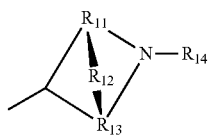

Structure Ne

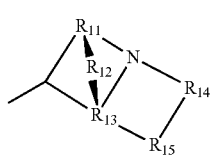

Structure Nf

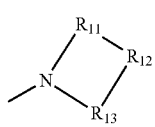

Structure Ng

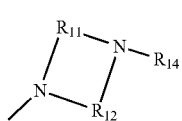

Structure Nh

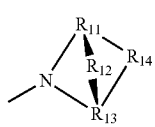

Structure Ni

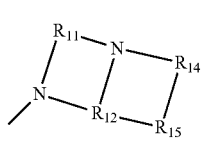

Structure Nj

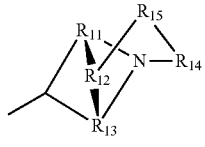

Structure Nk

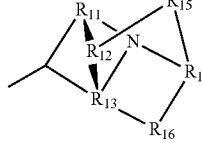

Structure Nl

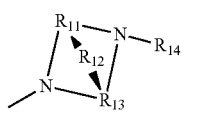

Structure Nm

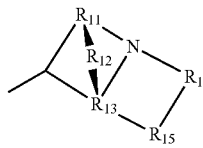

Structure Nn

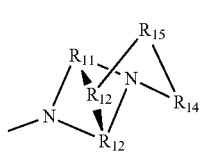

Structure No

Structure Np

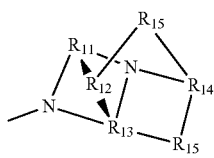

Structure Nq

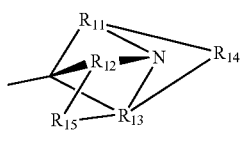

Structure Nr

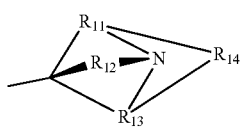

including stereoisomers and pharmaceutically acceptable salts thereof.

As used herein, unless specified otherwise, each $R_{11}$-$R_{16}$ is independently selected from the group consisting of nothing, H, $CH_2COOR_{11}$, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, substituted and unsubstituted alkyl halide, wherein any carbon or hydrogen may be further independently replaced with O, S, P, $NR_{11}$, or any other pharmaceutically acceptable groups.

As used herein, the term "HA" is nothing or a pharmaceutically acceptable acid, e.g. hydrochloride, hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid.

As used herein, "A" or "A⁻" is nothing or a pharmaceutically acceptable anion, e.g. Cl—, Br—, F—, I—, acetylsalicylate, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate or any pharmaceutically acceptable anion.

In certain embodiments, the linker covalently linking the functional unit and the transportational unit comprises a bond that is capable of being cleaved after the HPP penetrates across one or more BBs. The cleavable bond comprises, for example, a covalent bond, an ether, thioether, amide, ester, thioester, carbonate, carbamate, phosphate or oxime bond.

In certain embodiments, HPP of NSAIA has the following Structure L:

Structure L

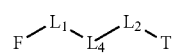

including stereoisomers and pharmaceutically acceptable salts thereof, wherein:

F is selected from Group F1 and Group F2;

T is selected from Group N;

$L_1$ is selected from the group consisting of nothing, O, S, —N($L_3$)-, —N($L_3$)-$CH_2$—O, —N($L_3$)-$CH_2$—N($L_3$)-, —O—$CH_2$—O—, —O—CH($L_3$)-O, —S—CH($L_3$)-O—;

$L_2$ is selected from the group consisting of $L_1$, —O-$L_3$-, —N-$L_3$-, —S-$L_3$-, —N($L_3$)-$L_3$- and $L_3$;

$L_4$ is selected from the group consisting of C=O, C=S,

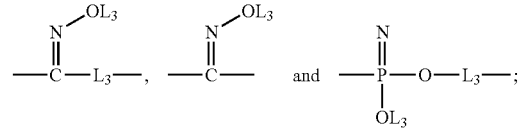

each $L_3$ is independently selected from the group consisting of nothing, H, $CH_2COOR_1$, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, substituted and unsubstituted alkyl halide, wherein any carbon or hydrogen may be further independently replaced with O, S, P, N $L_3$, or any other pharmaceutically acceptable groups.

I-1. Examples of HPP of Aspirin and Related Compounds.

In certain embodiments, the HPP has the following Structure 1 or Structure 2:

Structure 1

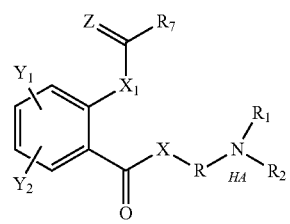

Structure 2

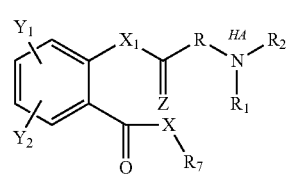

including stereoisomers and pharmaceutically acceptable salts thereof.

In certain embodiments, the HPP has Structure 1 or Structure 2, including stereoisomers and pharmaceutically acceptable salts thereof wherein:

Z is selected from the group consisting of O, S, N;

X is selected from the group consisting of nothing, O, P(O)OR$_1$, NH, NR$_1$ and S;

R is a substituted or unsubstituted —(CH$_2$)$_n$—, n=1, 2, 3, 4, 5, 6, 7, 8, 9, 10, 11, 12, . . . , in —(CH$_2$)$_n$—, any CH$_2$ may be independently replaced with O, S, NR$_5$, CH=CH, C≡C, CHR$_5$, CR$_5$R$_6$, aryl or heteroaryl residues, and any other moieties which are pharmaceutically acceptable;

R$_1$ and R$_2$ are independently selected from the group consisting of H, one of any alkyl, cycloalkyl, alkyloxyl, cycloalkyloxyl, alkenyl, cycloalkenyl, perfluoroalkyl, cyclo-perfluoroalkyl, alkyl halide, cycloalkyl halide, alkynyl, or cycloalkynyl residues having 1 to 12 carbon atoms, aryl or heteroaryl moieties, wherein, any CH$_2$ may be independently replaced with O, S, CH=CH, C≡C, CHR$_5$, CR$_5$R$_6$, aryl or heteroaryl moieties, any other moieties which are pharmaceutically acceptable;

R$_5$ and R$_6$ are independently selected from the group consisting of H, OH, Cl, F, Br, I, alkyl, cycloalkyl, alkyloxyl, cycloalkyloxyl, alkenyl, cycloalkenyl, perfluoroalkyl, cyclo-perfluoroalkyl, alkyl halide, cycloalkyl halide, alkynyl, or cycloalkynyl residues having 1 to 12 carbon atoms, aryl or heteroaryl moieties;

R$_7$ is selected from the group consisting of one of any alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, or cycloalkynyl residues having 1 to 12 carbon atoms, aryl or heteroaryl moieties;

X$_1$ is selected from the group consisting of O, and the following structures:

X$_1$-1

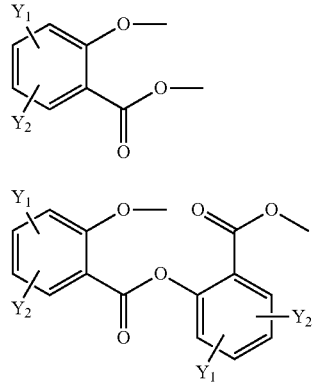

X$_1$-2

Y$_1$ and Y$_2$ are independently selected from the group consisting of H, HO, CH$_3$COO, R$_8$COO, HS, NO$_2$, CN, CH$_3$COS, NH$_2$, CH$_3$CONH, R$_8$CONH, CH$_3$, CH$_3$CH$_2$, C$_3$H$_7$, C$_4$H$_9$, CH$_3$O, CH$_3$CH$_2$O, C$_3$H$_7$O, Cl, F, Br, I, CH$_3$S, CHF$_2$O, CF$_3$O, CF$_3$CF$_2$O, C$_3$F$_7$O, CF$_3$, CF$_3$CF$_2$, C$_3$F$_7$, C$_4$F$_9$, CH$_3$SO$_2$, R$_8$SO$_2$, CH$_3$SO, R$_8$SO, CH$_3$CO, CH$_3$CH$_2$CO;

all R, R$_1$, R$_2$, R$_5$, R$_6$, R$_7$, R$_8$, Y$_1$, Y$_2$, and —(CH$_2$)$_n$— groups are branched or straight chains and may include C, H, O, Cl, Br, F, I, P, S, N or any other atoms which are pharmaceutically acceptable and may have single, double, or/and triple bonds.

In certain embodiments, the HPP of aspirin has the following Structure 1-b:

Structure 1a

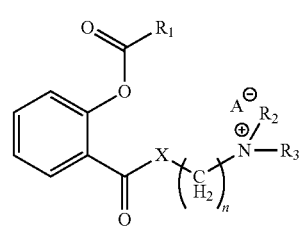

including stereoisomers and pharmaceutically acceptable salts thereof.

In certain embodiments, the HPP has Structure 1a, including stereoisomers and pharmaceutically acceptable salts thereof wherein:

R1 represents CH3, C2H5, C3H7, or other lower alkyl groups;

R2 represents H, one of any alkyl, alkyloxyl, or alkenyl residues having 1 to 6 carbon atoms, or aryl residues;

R$_3$ represents H, one of any alkyl, alkyloxyl, or alkenyl residues having 1 to 6 carbon atoms, or aryl residues;

R$_4$ represents H, one of any alkyl, alkyloxyl, or alkenyl residues having 1 to 6 carbon atoms, or aryl residues;

X represents O, S or N.

1-2. HPP of Diflunisal and Related Compounds

In certain embodiments, the HPP has the following Structure 3 or Structure 4:

Structure 3

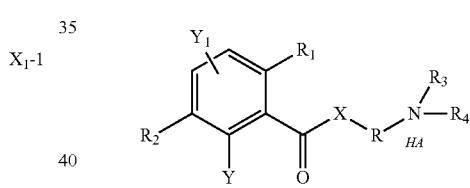

including stereoisomers and pharmaceutically acceptable salts thereof, wherein:

R represents a branched or straight chain —(CH$_2$)$_n$—, n=0, 1, 2, 3, 4, 5, 6, 7, 8, 9, 10, 11, 12, . . . , in —(CH$_2$)$_n$—, any CH$_2$ may be independently replaced with O, S, NR$_5$, CH=CH, C≡C, CHR$_5$, CR$_5$R$_6$, aryl or heteroaryl residues, or any other moieties which are pharmaceutically acceptable;

R$_1$ represents OH, OCOR$_5$, OCSR$_5$, 2-hydroxylbenzoyloxyl (salicyloyloxyl, 2-OCO—C$_6$H$_4$—OH), 2-R$_5$COO-benzoyloxyl (salicyloyloxyl, 2-OCO—C$_6$H$_4$—OCOR$_5$), 2-R$_5$CSO-benzoyloxyl (salicyloyloxyl, 2-OCO—C$_6$H$_4$—OCSR$_5$), 2-OCO—C$_6$H$_4$—OCO—C$_6$H$_4$—OCOR$_5$, or 2-OCO—C$_6$H$_4$—OCO—C$_6$H$_4$—OCSR$_5$;

R$_2$ represents H, 2-fluorophenyl, 4-fluorophenyl, 2-chloro-4-fluorophenyl, 2-fluoro-4-chlorophenyl, 2,4-difluorophenyl, substituted 2,4-difluorophenyl, or substituted phenyl;

R$_3$ and R$_4$ are independently selected from the group consisting of H, any alkyl, alkyloxyl, alkenyl, perfluoroalkyl, alkyl halide or alkynyl residues having 1 to 12 carbon atoms, aryl or heteroaryl moieties, wherein, any CH$_2$ may be independently replaced with O, S, CH=CH, C≡C, CHR$_5$, CR$_5$R$_6$, aryl or heteroaryl moieties, and any other moieties which are pharmaceutically acceptable;

X is selected from the group consisting of O, NH, NR$_5$, S and nothing;

R$_5$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

R$_6$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

R$_8$ represents one of any alkyl, alkyloxyl, alkenyl, perfluoroalkyl, alkyl halide or alkynyl residues having 1 to 12 carbon atoms, aryl or heteroaryl moieties;

Y or Y$_1$ represents independently H, HO, CH$_3$COO, R$_8$COO, HS, NO$_2$, CN, CH$_3$COS, NH$_2$, CH$_3$CONH, R$_8$CONH, CH$_3$, CH$_3$CH$_2$, C$_3$H$_7$, C$_4$H$_9$, CH$_3$O, CH$_3$CH$_2$O, C$_3$H$_7$O, Cl, F, Br, I, CH$_3$S, CHF$_2$O, CF$_3$O, CF$_3$CF$_2$O, C$_3$F$_7$O, CF$_3$, CF$_3$CF$_2$, C$_3$F$_7$, C$_4$F$_9$, CH$_3$SO$_2$, R$_8$SO$_2$, CH$_3$SO, R$_8$SO, CH$_3$CO, CH$_3$CH$_2$CO;

all R, R$_1$, R$_2$, R$_3$, R$_4$, R$_5$, R$_6$, R$_8$, or —(CH$_2$)$_n$— groups are branched or straight chains and may include C, H, O, Cl, Br, F, I, P, S, N or any other atoms which are pharmaceutically acceptable and may have single, double, or/and triple bonds;

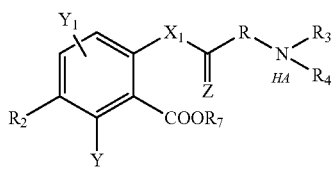

Structure 4 in structure 4, Z represents O or S;

X1 represents O, 2-OCO—C$_6$H$_4$—O, or 2-OCO—C$_6$H$_4$—OCO—C$_6$H$_4$—O;

R represents a branched or straight chain —(CH$_2$)$_n$—, n=1, 2, 3, 4, 5, 6, 7, 8, 9, 10, 11, 12, . . . , in —(CH$_2$)$_n$—, any CH$_2$ may be replaced with O, S, NR$_5$, CH=CH, C≡C, CHR$_5$, CR$_5$R$_6$, aryl or heteroaryl residues, or any other moieties which are pharmaceutically acceptable;

R$_2$ represents H, 2-fluorophenyl, 4-fluorophenyl, 2-chloro-4-fluorophenyl, 2-fluoro-4-chlorophenyl, 2,4-difluorophenyl, or substituted 2,4-difluorophenyl;

R$_3$ represents H, one of any alkyl, alkyloxyl, alkenyl, perfluoroalkyl, alkyl halide or alkynyl residues having 1 to 12 carbon atoms, aryl or heteroaryl moieties, wherein, any CH$_2$ may be independently replaced with O, S, CH=CH, C≡C, CHR$_5$, CR$_5$R$_6$, aryl or heteroaryl moieties, or any other moieties which are pharmaceutically acceptable;

R$_4$ represents H, one of any alkyl, alkyloxyl, alkenyl, perfluoroalkyl, alkyl halide or alkynyl residues having 1 to 12 carbon atoms, aryl or heteroaryl moieties, wherein, any CH$_2$ may be independently replaced with O, S, CH=CH, C≡C, CHR$_5$, CR$_5$R$_6$, aryl or heteroaryl moieties, or any other moieties which are pharmaceutically acceptable; X represents O, NH, NR$_5$, S, or none;

R$_5$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

R$_6$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

R$_7$ represents one of any alkyl, alkyloxyl, alkenyl, perfluoroalkyl, alkyl halide or alkynyl residues having 1 to 12 carbon atoms, aryl or heteroaryl moieties;

R$_8$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

Y, or Y$_1$ represents independently H, HO, CH$_3$COO, R$_8$COO, HS, NO$_2$, CN, CH$_3$COS, NH$_2$, CH$_3$CONH, R$_8$CONH, CH$_3$, CH$_3$CH$_2$, C$_3$H$_7$, C$_4$H$_9$, CH$_3$O, CH$_3$CH$_2$O, C$_3$H$_7$O, Cl, F, Br, I, CH$_3$S, CHF$_2$O, CF$_3$O, CF$_3$CF$_2$O, C$_3$F$_7$O, CF$_3$, CF$_3$CF$_2$, C$_3$F$_7$, C$_4$F$_9$, CH$_3$SO$_2$, R$_8$SO$_2$, CH$_3$SO, R$_8$SO, CH$_3$CO, CH$_3$CH$_2$CO; and all R, R$_1$, R$_2$, R$_3$, R$_4$, R$_5$, R$_6$, R$_7$, R$_8$, Y, Y$_1$, or —(CH$_2$)$_n$— groups are branched or straight chains and may include C, H, O, Cl, Br, F, I, P, S, N or any other atoms which are pharmaceutically acceptable and may have single, double, or/and triple bonds.

In certain embodiments, the HPP has the Structure 3 or Structure 4, including stereoisomers and pharmaceutically acceptable salts thereof, wherein all the substitutions are defined as the general definition.

In certain embodiments, the HPP has the following Structure 3-a:

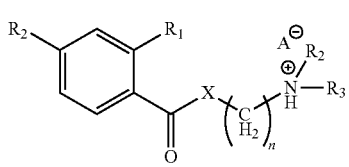

Structure 3-a including stereoisomers and pharmaceutically acceptable salts thereof.

In certain embodiments, the HPP has the Structure 3-1, including stereoisomers and pharmaceutically acceptable salts thereof, wherein:

R$_1$ represents OH, OCOCH$_3$, OCOC$_2$H$_5$, OCOC$_3$H$_7$, OCOC$_4$H$_9$, OCOC$_5$H$_{11}$, OCOC$_6$H$_{13}$, 2-hydroxylbenzoyloxyl (salicyloyloxyl, 2-OCO—C$_6$H$_4$—OH), 2-acetyloxylbenzoyloxyl (acetylsalicyloyloxyl, 2-OCO—C$_6$H$_4$—OCOCH$_3$), 2-propionyloxylbenzoyloxyl (propionylsalicyloyloxyl, 2-OCO—C$_6$H$_4$—OCOC$_2$H$_5$), or 2-butyryloxylbenzoyloxyl (butyrylsalicyloyloxyl, 2-OCO—C$_6$H$_4$—OCOC$_3$H$_7$);

R$_2$ represents H or 2,4-difluorophenyl;

R$_3$ represents H, one of any alkyl, alkyloxy, alkenyl or alkynyl residues having 1 to 12 carbon atoms, or aryl residues;

R$_4$ represents H, one of any alkyl, alkyloxy, alkenyl or alkynyl residues having 1 to 12 carbon atoms, or aryl residues;

R$_5$ represents H, one of any alkyl, alkyloxy, alkenyl, or alkynyl residues having 1 to 12 carbon atoms, or aryl residues; X represents O, S or NH; A$^-$ represents Cl$^-$, Br$^-$, F$^-$, I$^-$, AcO$^-$, citrate, or any negative ions; and n=0, 1, 2, 3, 4, 5, 6, 7, 8, 9, 10, . . . . All R groups may include C, H, O, S, N atoms and may have single, double, and treble bonds; and any CH$_2$ groups may be independently replaced with O, S, or NH.

In certain embodiments, the HPP has the following Structure 4-a

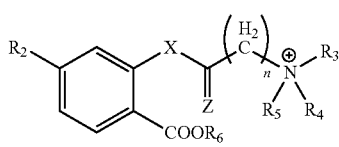

Structure 4-a including stereoisomers and pharmaceutically acceptable salts thereof, wherein:

X represents O or 2-OCO—$C_6H_4$—OH); $R_2$ represents H or 2,4-difluorophenyl;

$R_3$ is H;

$R_4$-$R_6$ represents H, one of any alkyl, alkyl, alkenyl, or alkynyl residues having 1 to 12 carbon atoms, or aryl residues;

Z represents O or S; $A^-$ represents $Cl^-$, $Br^-$, $F^-$, $I^-$, $AcO^-$, citrate, or any negative ions; and n=0, 1, 2, 3, 4, 5, 6, 7, 8, 9, 10, . . . ; and all R groups may include C, H, O, S, N atoms and may have single, double, and treble bonds. Any $CH_2$ groups may be independently replaced with O, S, or NH.

I-3. HPP of Ibuprofen and Related Compounds

In certain embodiments, the HPP has the following Structure 5

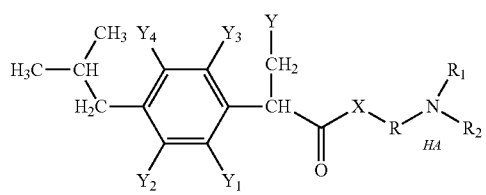

Structure 5 including stereoisomers and pharmaceutically acceptable salts thereof.

In certain embodiments, the HPP has the Structure 5, including stereoisomers and pharmaceutically acceptable salts thereof, wherein:

R represents nothing, linear or branched 1-20 carbon atoms alkyl, 1-20 carbon atoms alkyloxyl, 1-20 carbon atoms perfluoroalkyl, 1-20 carbon atoms alkyl halide, 2-20 carbon atoms alkenyl, 2-20 carbon atoms alkynyl moieties, aryl or heteroaryl moieties having 6-20 carbon atoms which are pharmaceutically acceptable, wherein, any $CH_2$ may be independently replaced with O, S, $NR_5$, or other groups;

$R_1$ represents H, one of any alkyl, alkyloxyl, alkenyl, perfluoroalkyl, alkyl halide or alkynyl residues having 1 to 20 carbon atoms, aryl or heteroaryl moieties, wherein, any $CH_2$ may be independently replaced with O, S, CH=CH, C≡C, $CHR_5$, $CR_5R_6$, aryl or heteroaryl moieties, or any other moieties which are pharmaceutically acceptable;

$R_2$ represents H, one of any alkyl, alkyloxyl, alkenyl, perfluoroalkyl, alkyl halide or alkynyl residues having 1 to 20 carbon atoms, aryl or heteroaryl moieties, wherein, any $CH_2$ may be independently replaced with O, S, CH=CH, C≡C, $CHR_5$, $CR_5R_6$, aryl or heteroaryl moieties, or any other moieties which are pharmaceutically acceptable; X represents O, NH, $NR_5$, S, or none;

$R_5$ represents H, OH, Cl, F, Br, I, one of any alkyl, alkyloxyl, alkenyl, perfluoroalkyl, alkyl halide or alkynyl residues having 1 to 20 carbon atoms, aryl or heteroaryl moieties;

$R_6$ represents H, OH, Cl, F, Br, I, one of any alkyl, alkyloxyl, alkenyl, perfluoroalkyl, alkyl halide or alkynyl residues having 1 to 20 carbon atoms, aryl or heteroaryl moieties;

$R_7$ represents one of any alkyl, alkyloxyl, alkenyl, perfluoroalkyl, alkyl halide or alkynyl residues having 1 to 20 carbon atoms, aryl or heteroaryl moieties;

HA represents none, HCl, HBr, HF, HI, HOAc, citric acid, or any acids which are pharmaceutically acceptable;

Y, $Y_1$, $Y_2$, $Y_3$, or $Y_4$ represents independently H, HO, $CH_3COO$, $R_7COO$, HS, $NO_2$, CN, $R_7COS$, $NH_2$, $CH_3CONH$, $R_7CONH$, $CH_3$, $CH_3CH_2$, $C_3H_7$, $C_4H_9$, $CH_3O$, $CH_3CH_2O$, $C_3H_7O$, Cl, F, Br, I, $CH_3S$, $CHF_2O$, $CF_3O$, $CF_3CF_2O$, $C_3F_7O$, $CF_3$, $CF_3CF_2$, $C_3F_7$, $C_4F_9$, $CH_3SO_2$, $R_7SO_2$, $CH_3SO$, $R_7SO$, $CH_3CO$, or $CH_3CH_2CO$;

all R, $R_1$, $R_2$, $R_5$, $R_6$, $R_7$, or —$(CH_2)_n$— groups are branched or linear chains and may include C, H, O, Cl, Br, F, I, P, S, N or any other atoms which are pharmaceutically acceptable and may have single, double, or/and triple bonds.

I-4. HPP of Ketoprofen, Fenoprofen and Related Compounds.

In certain embodiments, the HPP has the following Structure 6:

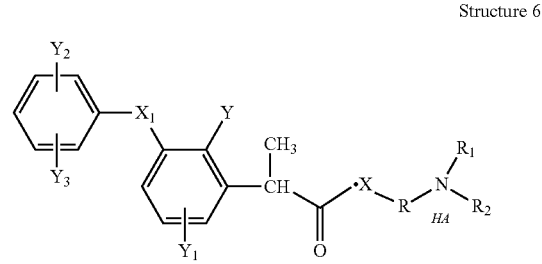

Structure 6 including stereoisomers and pharmaceutically acceptable salts thereof.

In certain embodiments, the HPP has the Structure 6, including stereoisomers and pharmaceutically acceptable salts thereof, wherein:

R represents a branched or straight chain —$(CH_2)_n$—, n=0, 1, 2, 3, 4, 5, 6, 7, 8, 9, 10, 11, 12, . . . , in —$(CH_2)_n$—, any $CH_2$ may be replaced with O, S, $NR_5$, CH=CH, C≡C, $CHR_5$, $CR_5R_6$, aryl or heteroaryl residues, or any other moieties which are pharmaceutically acceptable;

$R_1$ represents H, one of any alkyl, alkyloxyl, alkenyl, perfluoroalkyl, alkyl halide or alkynyl residues having 1 to 12 carbon atoms, aryl or heteroaryl moieties, wherein, any $CH_2$ may be independently replaced with O, S, CH=CH, C≡C, $CHR_5$, $CR_5R_6$, aryl or heteroaryl moieties, or any other moieties which are pharmaceutically acceptable;

$R_2$ represents H, one of any alkyl, alkyloxyl, alkenyl, perfluoroalkyl, alkyl halide or alkynyl residues having 1 to 12 carbon atoms, aryl or heteroaryl moieties, wherein, any $CH_2$ may be independently replaced with O, S, CH=CH, C≡C, $CHR_5$, $CR_5R_6$, aryl or heteroaryl moieties, or any other moieties which are pharmaceutically acceptable;

X represents O, NH, NR$_5$, S, or none; X$_1$ represents O or CO;

R$_5$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

R$_6$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

R$_7$ represents one of any alkyl, alkyloxyl, alkenyl, perfluoroalkyl, alkyl halide or alkynyl residues having 1 to 12 carbon atoms, aryl or heteroaryl moieties;

HA represents none, HCl, HBr, HF, HI, HOAc, citric acid, or any acids which are pharmaceutically acceptable;

Y$_1$, Y$_2$, or Y$_3$ represents independently H, HO, CH$_3$COO, R$_7$COO, HS, NO$_2$, CN, CH$_3$COS, NH$_2$, CH$_3$CONH, R$_7$CONH, CH$_3$, CH$_3$CH$_2$, C$_3$H$_7$, C$_4$H$_9$, CH$_3$O, CH$_3$CH$_2$O, C$_3$H$_7$O, Cl, F, Br, I, CH$_3$S, CHF$_2$O, CF$_3$O, CF$_3$CF$_2$O, C$_3$F$_7$O, CF$_3$, CF$_3$CF$_2$, C$_3$F$_7$, C$_4$F$_9$, CH$_3$SO$_2$, R$_7$SO$_2$, CH$_3$SO, R$_7$SO, CH$_3$CO, CH$_3$CH$_2$CO; and all R, R$_1$, R$_2$, R$_5$, R$_6$, R$_7$, or —(CH$_2$)$_n$— groups are branched or straight chains and may include C, H, O, Cl, Br, F, I, P, S, N or any other atoms which are pharmaceutically acceptable and may have single, double, or/and triple bonds.

In certain embodiments, the HPP has the following Structure 6-a:

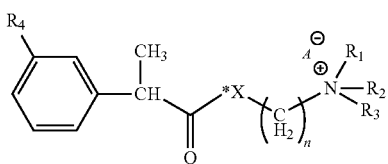

Structure 6-a including stereoisomers and pharmaceutically acceptable salts thereof, wherein:

R$_1$ is H;

R$_2$-R$_3$ are independently selected from the group consisting of H, one of any alkyl, alkyl, alkenyl or alkynyl residues having 1 to 12 carbon atoms, or aryl residues;

R$_4$ represents

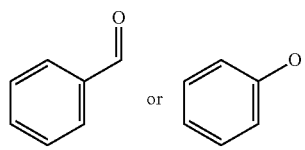 [SMILES: O=Cc1ccccc1 ; Oc1ccccc1]

X represents O, S or NH; A$^-$ represents Cl$^-$, Br$^-$, F$^-$, I-, AcO$^-$, citrate, or any negative ions; and n=0, 1, 2, 3, 4, 5, 6, 7, 8, 9, 10 . . . ; and all R groups may include C, H, O, S, N atoms and may have single, double, and treble bonds, and any CH$_2$ groups may be independently replaced with O, S, or NH.

I-5. HPP of Aryl- and Heteroaryl Propionic Acids and Related Compounds

A. HPP of 2-Aryl Propionic Acids

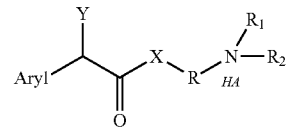

Structure 7

In certain embodiments, the HPP has the following Structure 7: including stereoisomers and pharmaceutically acceptable salts thereof.

In certain embodiments, the HPP has the Structure 7, including stereoisomers and pharmaceutically acceptable salts thereof, wherein:

R represents a branched or straight chain —(CH$_2$)$_n$—, n=1, 2, 3, 4, 5, 6, 7, 8, 9, 10, 11, 12, . . . , in —(CH$_2$)$_n$—, any CH$_2$ may be replaced with O, S, NR$_5$, CH=CH, C≡C, CHR$_5$, CR$_5$R$_6$, aryl or heteroaryl residues, or any other moieties which are pharmaceutically acceptable;

R$_1$ represents H, one of any alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, or cycloalkynyl residues having 1 to 12 carbon atoms, aryl or heteroaryl moieties, wherein, any CH$_2$ may be independently replaced with O, S, CH=CH, C≡C, CHR$_5$, CR$_5$R$_6$, aryl or heteroaryl moieties, or any other moieties which are pharmaceutically acceptable;

R$_2$ represents H, one of any alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, or cycloalkynyl residues having 1 to 12 carbon atoms, aryl or heteroaryl moieties, wherein, any CH$_2$ may be independently replaced with O, S, CH=CH, C≡C, CHR$_5$, CR$_5$R$_6$, aryl or heteroaryl moieties, or any other moieties which are pharmaceutically acceptable;

X represents O, OCR$_5$R$_6$COO, OCR$_5$R$_6$COS, OCR$_5$R$_6$CONR$_5$, NR$_5$, NR$_5$O, NR$_5$NR$_6$, S, or none;

Y represents H, CH$_3$, CH$_3$CH$_2$, C$_3$H$_7$, C$_4$H$_9$, OH, OCOR$_7$, Cl, F, I, or Br; R$_5$ represents H, OH, Cl, F, Br, I, one of any alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, or cycloalkynyl residues having 1 to 12 carbon atoms, aryl or heteroaryl moieties;

R$_6$ represents H, OH, Cl, F, Br, I, one of any alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, or cycloalkynyl residues having 1 to 12 carbon atoms, aryl or heteroaryl moieties;

R$_7$ represents one of any alkyl, cycloalkyl, alkyloxyl, cycloalkyloxyl, alkenyl, cycloalkenyl, perfluoroalkyl, cycloperfluoroalkyl, alkyl halide, cycloalkyl halide, alkynyl, or cycloalkynyl residues having 1 to 12 carbon atoms, aryl or heteroaryl moieties;

HA represents none, HCl, HBr, HF, HI, HOAc, citric acid, or any acids which are pharmaceutically acceptable;

all R, R$_1$, R$_2$, R$_5$, R$_6$, R$_7$, or —(CH$_2$)$_n$— groups are branched or straight chains and may include C, H, O, Cl, Br, F, I, P, S, N or any other atoms which are pharmaceutically acceptable and may have single, double, or/and triple bonds;

aryl- represents:

Structure 7-1
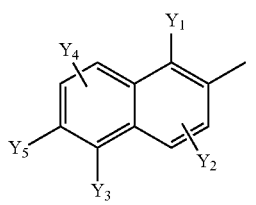
Structure 7-2
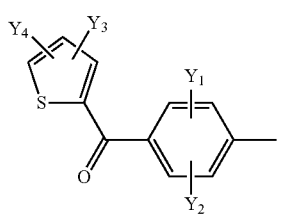
Structure 7-3
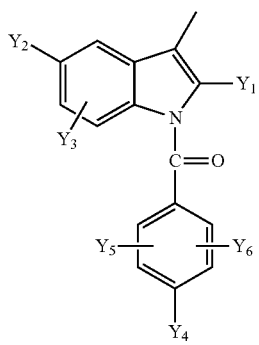
Structure 7-4
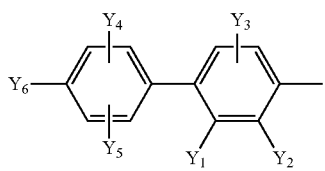
Structure 7-5
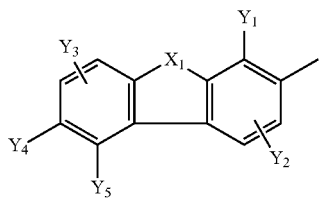
Structure 7-6
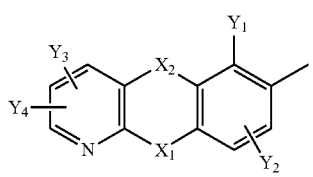
Structure 7-7
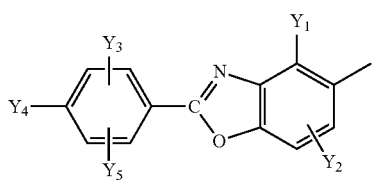
Structure 7-8
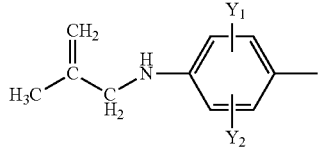
Structure 7-9
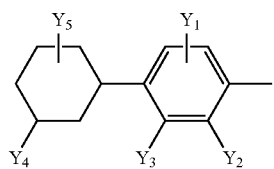
Structure 7-10
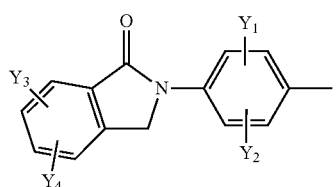
Structure 7-11
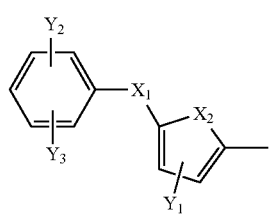
Structure 7-12
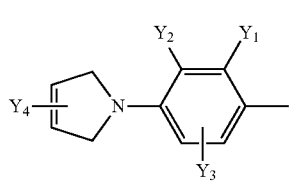
Structure 7-13
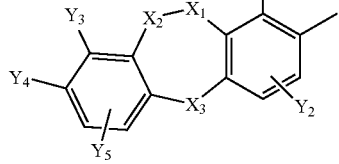
Structure 7-14
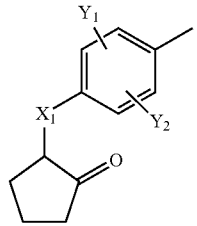
Structure 7-15
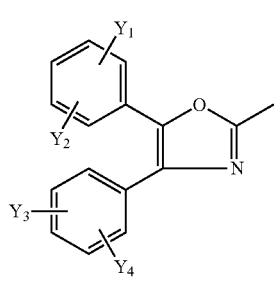

-continued
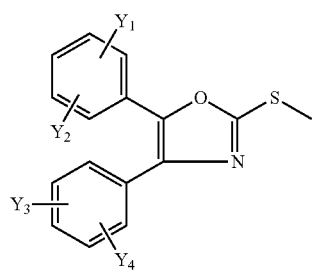
Structure 7-16
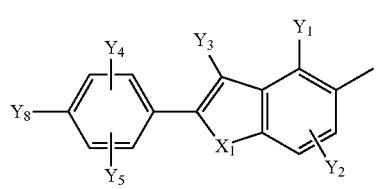
Structure 7-17
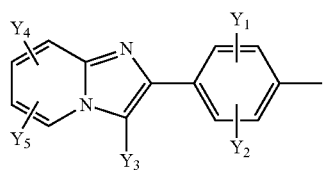
Structure 7-18
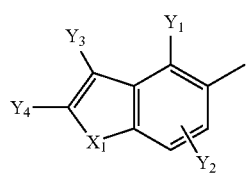
Structure 7-19
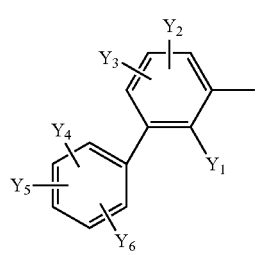
Structure 7-20
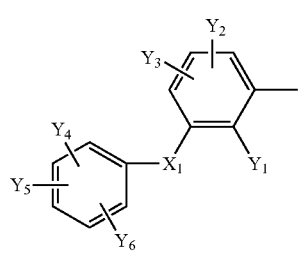
Structure 7-21
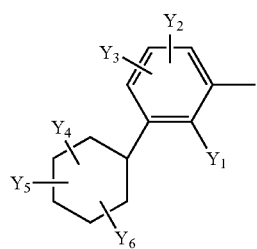
Structure 7-22
-continued
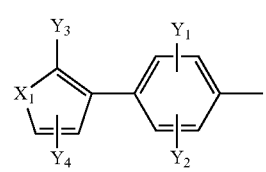
Structure 7-23
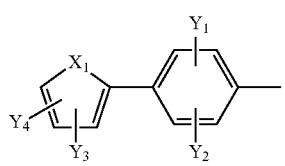
Structure 7-24
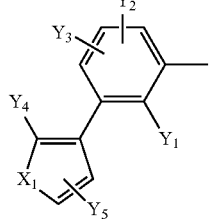
Structure 7-25
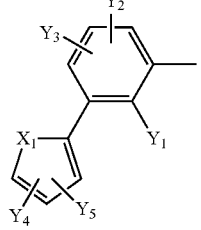
Structure 7-26
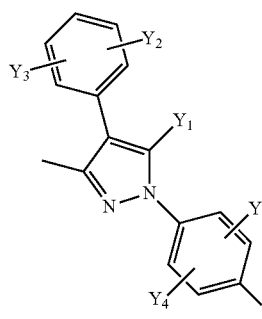
Structure 7-27
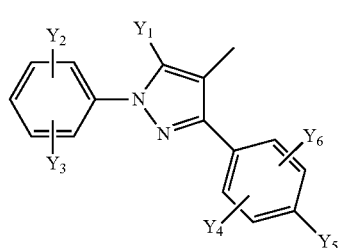
Structure 7-28
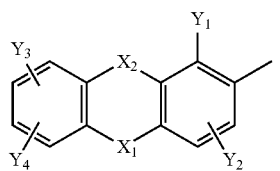
Structure 7-29

-continued

Structure 7-30
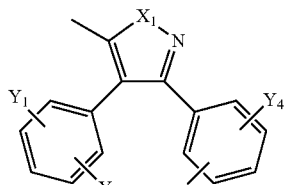

Structure 7-31
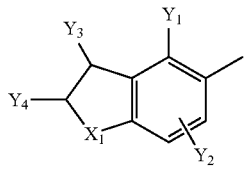

Structure 7-32
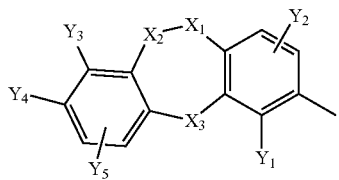

Structure 7-33
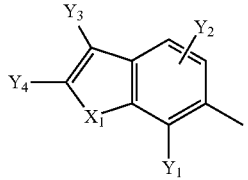

Structure 7-34
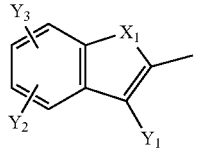

including stereoisomers and pharmaceutically acceptable salts thereof, wherein:

$Y_1, Y_2, Y_3, Y_4, Y_5,$ or $Y_6$ represents independently H, HO, $CH_3COO$, $R_7COO$, HS, $NO_2$, CN, =N—OH, =$NOR_8$, $NR_5OR_8$, $NR_5OH$, $CH_3COS$, $R_7COS$, $NH_2$, $CH_3CONH$, $R_7CONH$, $CH_3$, $CH_3CH_2$, $C_3H_7$, $C_4H_9$, $CH_3O$, $CH_3CH_2O$, $C_3H_7O$, Cl, F, Br, I, $CH_3S$, $CHF_2O$, $CF_3O$, $CF_3CF_2O$, $C_3F_7O$, $CF_3$, $CF_3CF_2$, $C_3F_7$, $C_4F_9$, $CH_3SO_2$, $R_7SO_2$, $CH_3SO$, $R_7SO$, $CH_3CO$, $CH_3CH_2CO$, $C_3H_7CO$, $(CH_3)_2N$, $CH_2$=CH—$CH_2$, $CH_2$=CH—$CH_2O$, $CH_3(CH_2)_3O$, $C_3H_7O$, $C_4H_9O$, cycloalkyl, cycloalkenyl, cycloalkynyl, benzyl, substituted benzyl, phenyl, 4-chlorophenyl, 4-fluorophenyl, 4-bromophenyl, 4-iodophenyl, 3-chlorophenyl, 3-fluorophenyl, 3-bromophenyl, 3-iodophenyl, 2-chlorophenyl, 2-fluorophenyl, 2-bromophenyl, 2-iodophenyl, or other substituted phenyl;

$R_8$ represents $CH_3CO$, $CH_3CH_2CO$, $C_3H_7CO$, $C_4H_9CO$, $CH_3CH_3CH_2C_3H_7C_4H_9$;

$X_1$ represents $CH_2$, CO, O, $NR_5$, or S;

$X_2$ represents $CH_2$, CO, $NR_5$, O, or S;

$X_3$ represents $CH_2$, CO, $NR_5$, O, or S;

all $Y_1, Y_2, Y_3, Y_4, Y_5, Y_6, R_5, R_6, R_7, R_8,$ or —$(CH_2)_n$— groups are branched or straight chains and may include C, H, O, Cl, Br, F, I, P, S, N or any other atoms which are pharmaceutically acceptable and may have single, double, or/and triple bonds.

In certain embodiments, the HPP has the following Structure 7-a:

Structure 7-a
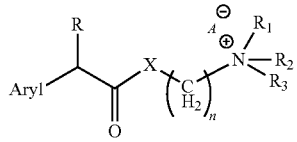

including stereoisomers and pharmaceutically acceptable salts thereof, wherein:

R represents $CH_3$, $CH_3CH_2$, $C_3H_7$, $C_4H_9$, OH, Cl, F, or Br;

$R_1$-$R_3$ are independently selected from the group consisting of H, alkyl, alkyloxy, alkenyl or alkynyl residues having 1 to 12 carbon atoms, and aryl residues;

X represents O, S, NH, $OCH_2COO$, $OCH_2COS$, or $OCH_2CONH$;

$A^-$ represents $Cl^-$, $Br^-$, $F^-$, $I^-$, $AcO^-$, citrate, or any negative ions;

n=0, 1, 2, 3, 4, 5, 6, 7, 8, 9, 10 . . . ;

Aryl represents

Structure 7a-1
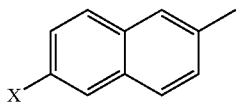

In which X represents $CH_3O$, Cl, F, $CH_3S$, $CHF_2O$

Structure 7a-2
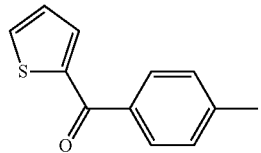

Structure 7a-3
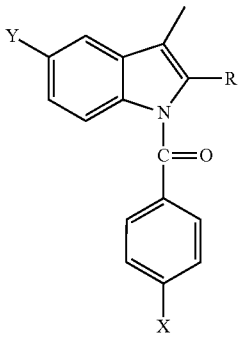

In which, Y represents $CH_3O$, F, $CH_3CO$, $(CH_3)_2N$, $CH_3$, or $CH_2$=CH—$CH_2$; X represents Cl, F, $CF_3$, $CH_3SO$, or $CH_3S$; R represents $CH_3$, $C_2H_5$, $C_3H_7$ Structure 7a-4
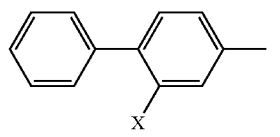

In which, X reprsents F, Cl, H

Structure 7a-3

In which, X represents Cl, Br, F, CH₃

Structure 7a-4

Structure 7a-5

In which, X represents Cl, Br, F, CH₃

Structure 7a-6

Structure 7a-7

In which, X represents Cl, F, Br

Structure 7a-8

Structure 7a-9

In which, X represents O or S, Y represents CH₂ and CO, and Z represents, CO and CH₂, R represents H, CH₃, C₂H₅.

Structure 7a-10

Structure 7a-11

In which, X represents CO or O

Structure 7a-10

In which, X represents Cl, Br, F or CH₃O

All R groups may include C, H, O, S, or N atoms and may have single, double, and treble bonds. Any $CH_2$ groups may be independently replaced with O, S, or NH.

B. Examples of HPP of 3-Aryl- and Heteroaryl Propionic Acids and Related Compounds 4,5-Diphenyl-2-oxazole propionic acid (oxaprozin), 3-(4-biphenylylcarbonyl)propionic acid (fenbufen), 5-(4-chlorophenyl)-beta-hydroxy-2-furanpropanoic acid (orpanoxin), and related compounds are members of 3-aryl and heteroarylpropionic acid group of NSAIA.

In certain embodiments, the HPP has the following Structure 8:

Structure 8 including stereoisomers and pharmaceutically acceptable salts thereof.

In certain embodiments, the HPP has the Structure 8, including stereoisomers and pharmaceutically acceptable salts thereof, wherein:

W represents H, OH, Cl, F, I, or Br;

Y, X, R, $R_1$, $R_2$, and HA are defined as supra;

Aryl- represents:

Structure 8-1a

Structure 8-2a

Structure 8-3a

-continued

Structure 8-4a

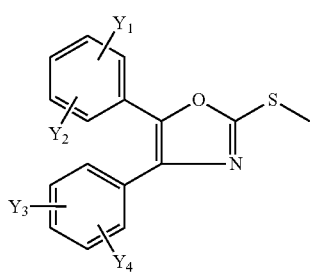

$Y_1$, $Y_2$, $Y_3$, or $Y_4$, represents independently H, HO, $CH_3COO$, $R_7COO$, HS, $NO_2$, CN, =N—OH, =$NOR_8$, $NR_5OR_8$, $NR_5OH$, $CH_3COS$, $R_7COS$, $NH_2$, $CH_3CONH$, $R_7CONH$, $CH_3$, $CH_3CH_2$, $C_3H_7$, $C_4H_9$, $CH_3O$, $CH_3CH_2O$, $C_3H_7O$, Cl, F, Br, I, $CH_3S$, $CHF_2O$, $CF_3O$, $CF_3CF_2O$, $C_3F_7O$, $CF_3$, $CF_3CF_2$, $C_3F_7$, $C_4F_9$, $CH_3SO_2$, $R_7SO_2$, $CH_3SO$, $R_7SO$, $CH_3CO$, $CH_3CH_2CO$, $C_3H_7CO$, $(CH_3)_2N$, $CH_2$=CH—$CH_2$, $CH_2$=CH—$CH_2O$, $CH_3(CH_2)_3O$, $C_3H_7O$, $C_4H_9O$, cycloalkyl, substituted cycloalkyl, cycloalkenyl, cycloalkynyl, benzyl, substituted benzyl, phenyl, 4-chlorophenyl, 4-fluorophenyl, 4-bromophenyl, 4-iodophenyl, 3-chlorophenyl, 3-fluorophenyl, 3-bromophenyl, 3-iodophenyl, 2-chlorophenyl, 2-fluorophenyl, 2-bromophenyl, 2-iodophenyl, or other substituted phenyl; $R_8$ represents $CH_3CO$, $CH_3CH_2CO$, $C_3H_7CO$, $C_4H_9CO$, $CH_3$, $CH_3CH_2$, $C_3H_7$, $C_4H_9$;

all $Y_1$, $Y_2$, $Y_3$, $Y_4$, $R_5$, $R_6$, $R_7$, $R_8$, or —$(CH_2)_n$— groups are branched or straight chains and may include C, H, O, Cl, Br, F, I, P, S, N or any other atoms which are pharmaceutically acceptable and may have single, double, or/and triple bonds.

In certain embodiments, the HPP has the following Structure 8-A:

Structure 8-a

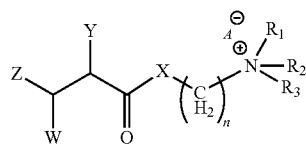

including stereoisomers and pharmaceutically acceptable salts thereof, wherein $R_1$ is H.

In certain embodiments, the HPP has the Structure 5, including stereoisomers and pharmaceutically acceptable salts thereof, wherein:

W represents H, OH, Cl, F, or Br;

$R_1$ is H;

$R_2$ and $R_3$ are independently selected from the group consisting of H, one of any alkyl, alkyloxy, alkenyl or alkynyl residues having 1 to 12 carbon atoms, or aryl residues;

X represents O, S, NH, $OCH_2COO$, $OCH_2COS$, or $OCH_2CONH$;

$A^-$ represents $Cl^\Gamma$, $Br^\Gamma$, $F^\Gamma$, $I^\Gamma$, $AcO^\Gamma$, citrate, or any negative ions;

n=0, 1, 2, 3, 4, 5, 6, 7, 8, 9, 10;

Y represents H;

Z represents

Structure 8a-1a

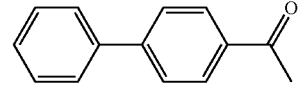

Structure 8a-2a

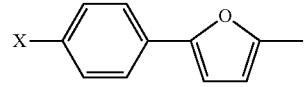

In which, X represents Cl, F, or Br

Structure 8a-3a

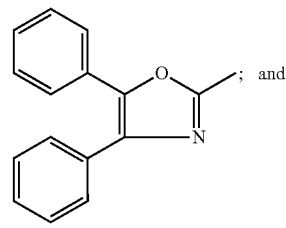

; and all R groups may include C, H, O, S, N atoms and may have single, double, and treble bonds and any $CH_2$ groups may be independently replaced with O, S, or NH.

C. HPP of Cyclized Aryl and Heteroarylpropionic Acid and Related Compounds

In certain embodiments, the HPP of cyclized aryl and heteroarylpropionic acid has Structure 8 as defined supra, including stereoisomers and pharmaceutically acceptable salts thereof, wherein:

W represents H, OH, Cl, F, I, or Br;

Y, X, R, $R_1$, $R_2$, and HA are defined as supra;

Y and Z together represent:

Structure 8-1b

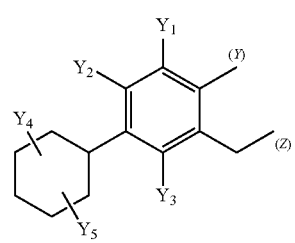

Structure 8-2b

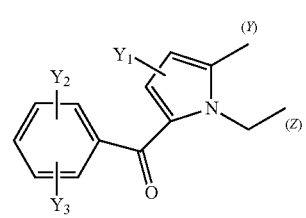

-continued

Structure 8-3b

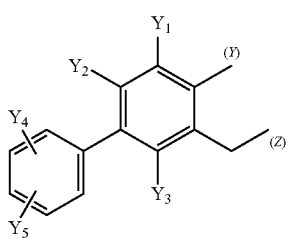

Structure 8-4b

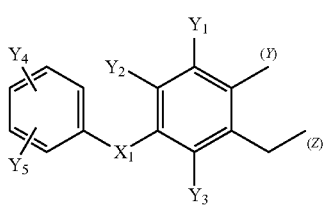

Structure 8-5b

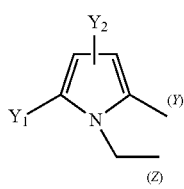

Structure 8-6b

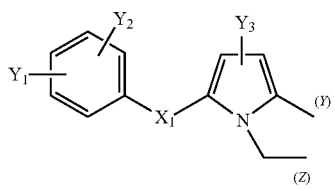

$Y_1$, $Y_2$, $Y_3$, $Y_4$, $Y_5$, or $Y_6$ represents independently H, HO, $CH_3COO$, $R_7COO$, HS, $NO_2$, CN, =N—OH, =$NOR_8$, $NR_5OR_8$, $NR_5OH$, $CH_3COS$, $R_7COS$, $NH_2$, $CH_3CONH$, $R_7CONH$, $CH_3$, $CH_3CH_2$, $C_3H_7$, $C_4H_9$, $CH_3O$, $CH_3CH_2O$, $C_3H_7O$, Cl, F, Br, I, $CH_3S$, $CHF_2O$, $CF_3O$, $CF_3CF_2O$, $C_3F_7O$, $CF_3$, $CF_3CF_2$, $C_3F_7$, $C_4F_9$, $CH_3SO_2$, $R_7SO_2$, $CH_3SO$, $R_7SO$, $CH_3CO$, $CH_3CH_2CO$, $C_3H_7CO$, $(CH_3)_2N$, $CH_2$=CH—$CH_2$, $CH_2$=CH—$CH_2O$, $CH_3(CH_2)_3O$, $C_3H_7O$, $C_4H_9O$, cycloalkyl, substituted cycloalkyl, cycloalkenyl, substituted cycloalkenyl, benzyl, substituted benzyl, phenyl, 4-chlorophenyl, 4-fluorophenyl, 4-bromophenyl, 4-iodophenyl, 3-chlorophenyl, 3-fluorophenyl, 3-bromophenyl, 3-iodophenyl, 2-chlorophenyl, 2-fluorophenyl, 2-bromophenyl, 2-iodophenyl, or other substituted phenyl;

$R_8$ represents $CH_3CO$, $CH_3CH_2CO$, $C_3H_7CO$, $C_4H_9CO$, $CH_3$, $CH_3CH_2$, $C_3H_7$, $C_4H_9$; $X_1$ represents $CH_2$, CO, O, $NR_5$, or S;

all $Y_1$, $Y_2$, $Y_3$, $Y_4$, $Y_5$, $Y_6$, R, $R_1$, $R_2$, $R_5$, $R_6$, $R_7$, $R_8$, or —$(CH_2)_n$— groups are branched or straight chains and may include C, H, O, Cl, Br, F, I, P, S, N or any other atoms which are pharmaceutically acceptable and may have single, double, or/and triple bonds.

In certain embodiments, the HPP has Structure 8-a, including stereoisomers and pharmaceutically acceptable salts thereof, wherein:
W represents H,
Y and Z together represent Structure 8a-1b

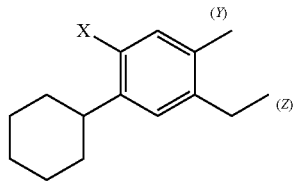

Structure 8a-2b

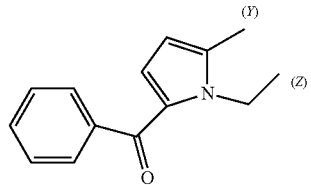

In which, X represents Cl, F, or Br and X represents Cl, F or Br.

1-6. HPP of Aryl- and Heteroaryl Acetic Acids and Related Compounds

In certain embodiments, the HPP has the following Structure 9,

Structure 9

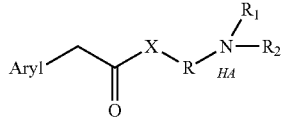

including stereoisomers and pharmaceutically acceptable salts thereof.

In certain embodiments, the HPP has the Structure 9, including stereoisomers and pharmaceutically acceptable salts thereof, wherein:

R represents a branched or straight chain —$(CH_2)_n$—, n=1, 2, 3, 4, 5, 6, 7, 8, 9, 10, 11, 12, . . . , in —$(CH_2)_n$—, any $CH_2$ may be replaced with O, S, $NR_5$, CH=CH, C=C, $CHR_5$, $CR_5R_6$, aryl or heteroaryl residues, or any other moieties which are pharmaceutically acceptable;

$R_1$ represents H, one of any alkyl, alkyloxyl, alkenyl, perfluoroalkyl, alkyl halide or alkynyl residues having 1 to 12 carbon atoms, aryl or heteroaryl moieties, wherein, any $CH_2$ may be independently replaced with O, S, CH=CH, C=C, $CHR_5$, $CR_5R_6$, aryl or heteroaryl moieties, or any other moieties which are pharmaceutically acceptable;

$R_2$ represents H, one of any alkyl, alkyloxyl, alkenyl, perfluoroalkyl, alkyl halide or alkynyl residues having 1 to 12 carbon atoms, aryl or heteroaryl moieties, wherein, any $CH_2$ may be independently replaced with O, S, CH=CH, C=C, $CHR_5$, $CR_5R_6$, aryl or heteroaryl moieties, or any other moieties which are pharmaceutically acceptable;

X represents O, $OCH_2COO$, $OCH_2COS$, $OCH_2CONR_5$, NH, $NR_5$, NHO, NHNH, S, or none;

$R_5$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

$R_6$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

$R_7$ represents one of any alkyl, alkyloxyl, alkenyl, perfluoroalkyl, alkyl halide or alkynyl residues having 1 to 12 carbon atoms, aryl or heteroaryl moieties;

HA represents none, HCl, HBr, HF, HI, HOAc, citric acid, or any acids which are pharmaceutically acceptable;

all R, $R_1$, $R_2$, $R_5$, $R_6$, $R_7$, or —$(CH_2)_n$— groups are branched or straight chains and may include C, H, O, Cl, Br, F, I, P, S, N or any other atoms which are pharmaceutically acceptable and may have single, double, or/and triple bonds Aryl- represents:

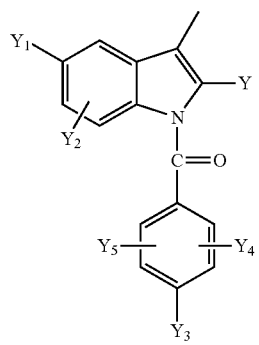

Structure 9-1

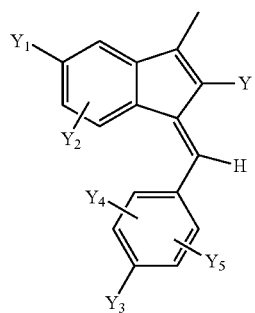

Structure 9-2

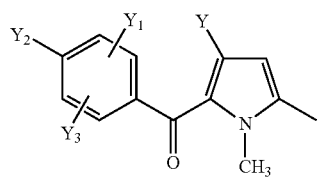

Structure 9-3

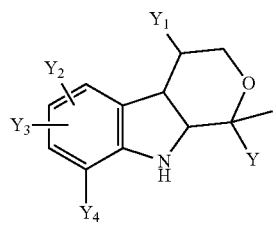

Structure 9-4

-continued

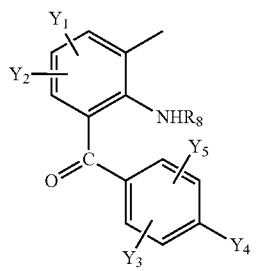

Structure 9-5

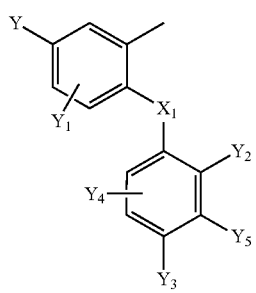

Structure 9-6

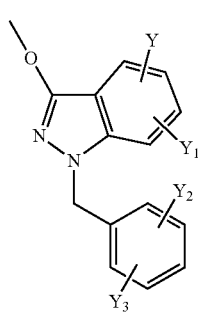

Structure 9-7

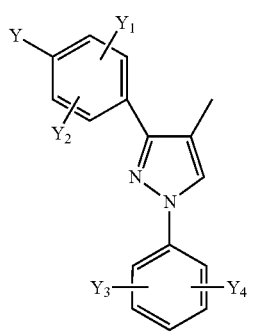

Structure 9-8

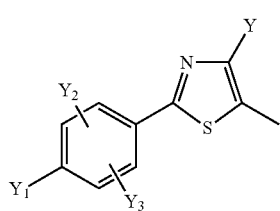

Structure 9-9

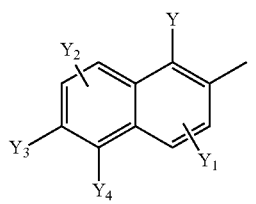

Structure 9-10

-continued

Structure 9-11
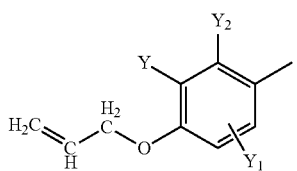

Structure 9-12
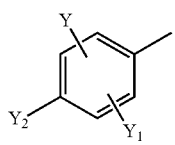

Structure 9-13
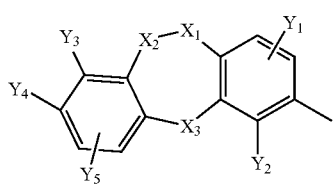

Structure 9-14
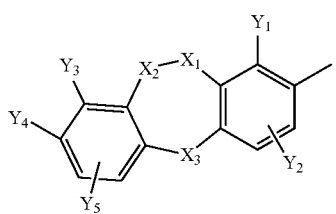

Structure 9-15
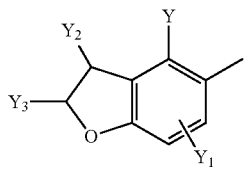

Structure 9-16
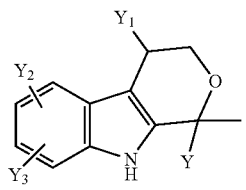

Structure 9-17
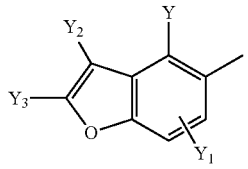

Structure 9-18
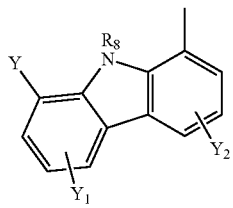

-continued

Structure 9-19
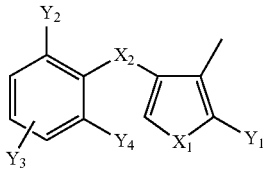

Structure 9-20
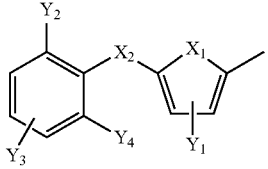

Structure 9-21
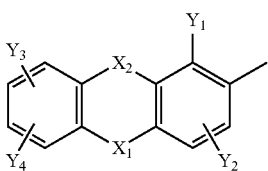

Structure 9-22
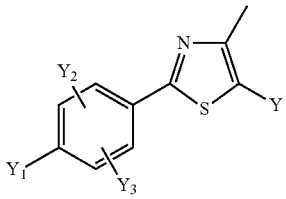

Structure 9-23
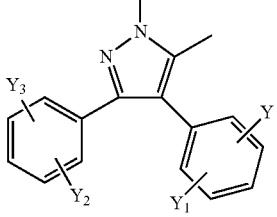

Structure 9-24
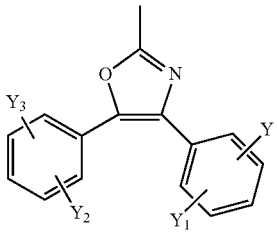

including stereoisomers and pharmaceutically acceptable salts thereof, wherein:

$Y, Y_1, Y_2, Y_3, Y_4$, or $Y_5$ represents independently H, HO, $CH_3COO$, $R_7COO$, HS, $NO_2$, CN, =N—OH, $NR_5OR_8$, $NR_5OH$, $CH_3COS$, $R_7COS$, $NH_2$, $CH_3CONH$, $R_7CONH$, $CH_3$, $CH_3CH_2$, $C_3H_7$, $C_4H_9$, $CH_3O$, $CH_3CH_2O$, $C_3H_7O$, Cl, F, Br, I, $CH_3S$, $CHF_2O$, $CF_3O$, $CF_3CF_2O$, $C_3F_7O$, $CF_3$, $CF_3CF_2$, $C_3F_7$, $C_4F_9$, $CH_3SO_2$, $R_7SO_2$, $CH_3SO$, $R_7SO$, $CH_3CO$, $CH_3CH_2CO$, $C_3H_7CO$, $(CH_3)_2N$, $CH_2=CH—CH_2$, $CH_2=CH—CH_2O$, $CH_3(CH_2)_3O$, $C_3H_7O$, $C_4H_9O$, benzyl, substituted benzyl, phenyl, 4-chlorophenyl, 4-fluorophenyl, 4-bromophenyl, 4-iodophenyl, 3-chlorophenyl, 3-fluorophenyl, 3-bromophenyl, 3-iodophenyl, 2-chlorophenyl, 2-fluorophenyl, 2-bromophenyl, 2-iodophenyl, or other substituted phenyl;

$R_8$ represents $CH_3CO$, $CH_3CH_2CO$, $C_3H_7CO$, $C_4H_9CO$, $CH_3$, $CH_3CH_2$, $C_3H_7$, $C_4H_9$;

$X_1$ represents $CH_2$, $CH=$, $CO$, $NR_5$, $O$, or $S$;

$X_2$ represents $CH_2$, $CH=$, $CO$, $NR_5$, $O$, or $S$;

$X_3$ represents $CH_2$, $CH=$, $CO$, $NR_5$, $O$, or $S$; all R, $R_1$, $R_2$, $R_5$, $R_6$, $R_7$, $R_8$, or $—(CH_2)_n—$ groups are branched or straight chains and may include C, H, O, Cl, Br, F, I, P, S, N or any other atoms which are pharmaceutically acceptable and may have single, double, or/and triple bonds.

In certain embodiments, the HPP has the following Structure 9-a:

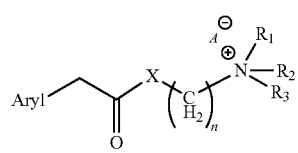

Structure 9-a including stereoisomers and pharmaceutically acceptable salts thereof, wherein:

$R_1$ is H;

$R_2$ and $R_3$ are independently selected from the group consisting of H, one of any alkyl, alkyloxy, alkenyl and alkynyl residues having 1 to 12 carbon atoms, or aryl residues;

X represents O, S, NH, $OCH_2COO$, $OCH_2COS$, or $OCH_2CONH$;

$A^-$ represents $Cl^-$, $Br^-$, $F^-$, $I^-$, $AcO^-$, citrate, or any negative ions;

n=0, 1, 2, 3, 4, 5, 6, 7, 8, 9, 10 . . . ;

Aryl represents

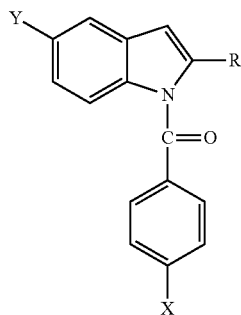

Structure 9a-1

In which, Y represents $CH_3O$, F, $CH_3CO$, $(CH_3)_2N$, $CH_3$, or $CH_2=CH—CH_2$; X represents Cl, F, $CF_3$, $CH_3SO$, or $CH_3S$; R represents $CH_3$, $C_2H_5$, $C_3H_7$

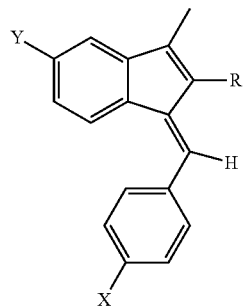

Structure 9a-1

In which, Y represents $CH_3O$, F, $CH_3CO$, $(CH_3)_2N$, $CH_3$, or $CH_2=CH—CH_2$; X represents Cl, F, $CF_3$, $CH_3SO$, or $CH_3S$; R represents $CH_3$, $C_2H_5$, $C_3H_7$

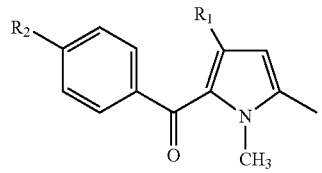

Structure 9a-3

In which, $R_1$ represents H, $CH_3$——, or $C_2H_5$; $R_2$ represents $CH_3$——, $C_2H_5$——, Br, Cl, or F

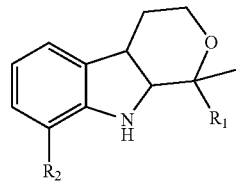

Structure 9a-4

In which, $R_1$ represents $CH_3$, $CH_3CH_2$, or $C_3H_7$, $R_2$ represents $CH_3$, $C_2H_5$, or $C_3H_7$

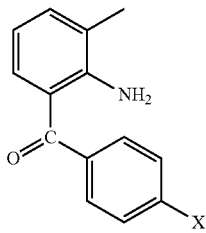

Structure 9a-5

In which, Y represents H, Br, Cl or F

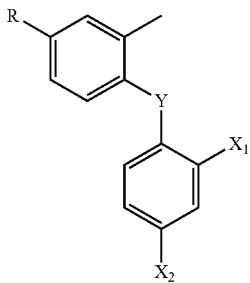

Structure 9a-6

In which, Y represents NH, O, or S; $X_1$ represents H, Br, Cl, or F; $X_2$ represents H, Br, Cl, or F; R represents H, $CH_3CO$; $C_2H_5CO$, $C_3H_7CO$, Structure 9a-7

In which, X represents H, Br, Cl or F

Structure 9a-8

In which, R$_1$ represents CH$_3$, CH$_3$CH$_2$, or C$_3$H$_7$ R$_2$ represents CH$_3$, C$_2$H$_5$, or C$_3$H$_7$ In which, X represents H, Br, Cl, F; and
Structure 9a-9 all R groups may include C, H, O, S, N atoms and may have single, double, and treble bonds. Any CH$_2$ groups may be independently replaced with O, S, or NH.

I-7. Examples of HPP of Diclofenac and Related Compounds

In certain embodiments, the HPP has the following Structure 10:

Structure 10 including stereoisomers and pharmaceutically acceptable salts thereof.

In certain embodiments, the HPP has the Structure 10, including stereoisomers and pharmaceutically acceptable salts thereof, wherein:

R represents a branched or straight chain —(CH$_2$)$_n$—, n=0, 1, 2, 3, 4, 5, 6, 7, 8, 9, 10, 11, 12, . . . , in —(CH$_2$)$_n$—, any CH$_2$ may be replaced with O, S, NR$_5$, CH═CH, C≡C, CHR$_5$, CR$_5$R$_6$, aryl or heteroaryl residues, or any other moieties which are pharmaceutically acceptable;

R1 and R2 taken alone are same or different and are H, one of any alkyl, alkyloxyl, alkenyl, perfluoroalkyl, alkyl halide or alkynyl residues having 1 to 12 carbon atoms, aryl or heteroaryl moieties or taken together are —(CH$_2$)$_n$—, wherein n=2, 3, 4, 5, 6, 7, 8, 9, 10, . . . , and any CH$_2$ may be independently replaced with O, S, NR$_5$, CH═CH, C≡C, CR$_4$R$_5$, aryl or heteroaryl moieties, or other moieties which are pharmaceutically acceptable;

X represents O, NH, NR$_5$, S, or none;

R$_5$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

R$_6$ represents H, OH, Cl, F, Br, I, one of any alkyl, alkyloxyl, alkenyl, perfluoroalkyl, alkyl halide or alkynyl residues having 1 to 12 carbon atoms, aryl or heteroaryl moieties;

HA represents none, HCl, HBr, HF, HI, HOAc, citric acid, or any acids which are pharmaceutically acceptable;

Y$_1$ Y$_2$, Y$_3$, or Y$_4$, represents independently H, HO, CH$_3$COO, R$_y$COO, HS, NO$_2$, CN, CH$_3$COS, NH$_2$, CH$_3$CONH, RCONH, CH$_3$, CH$_3$CH$_2$, C$_3$H$_7$, C$_4$H$_9$, CH$_3$O, CH$_3$CH$_2$O C$_3$H$_7$O, Cl, F, Br, I, CH$_3$S, CHF$_2$O, CF$_3$O, CF$_3$CF$_2$O, C$_3$F$_7$O, CF$_3$, CF$_3$CF$_2$, C$_3$F$_7$, C$_4$F$_9$, CH$_3$SO$_2$, R$_y$SO$_2$, CH$_3$SO, RSO, CH$_3$CO, CH$_3$CH$_2$CO. All R, R$_1$, R$_2$, R$_5$, R$_6$ or —(CH$_2$)$_n$—groups are branched or straight chains and may include C, H, O, Cl, Br, F, I, P, S, N or any other atoms which are pharmaceutically acceptable and may have single, double, or/and triple bonds.

In certain embodiments, the HPP has the following Structure 10-a:

Structure 10-a including stereoisomers and pharmaceutically acceptable salts thereof, wherein:

R$_1$ is H;

R$_2$ and R$_3$ independently represent H, one of any alkyl, alkyloxy, alkenyl or alkynyl residues having 1 to 12 carbon atoms, or aryl residues;

X represents O, S or NH; A$^r$ represents Cl$^r$, Br$^r$, F$^r$, I$^r$, AcO$^r$, citrate, or any negative ions;

n=0, 1, 2, 3, 4, 5, 6, 7, 8, 9, 10 . . . ;

all R groups may include C, H, O, S, N atoms and may have single, double, and treble bonds; and any CH$_2$ groups may be independently replaced with O, S, or NH.

1-9. HPP of N-Arylanthranilic Acids and Related Compounds

In certain embodiments, the HPP has the following Structure 11:

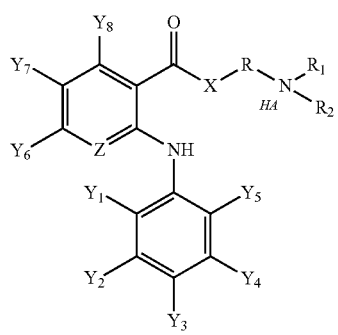

Structure 11 including stereoisomers and pharmaceutically acceptable salts thereof.

In certain embodiments, the HPP has the Structure 11, including stereoisomers and pharmaceutically acceptable salts thereof, wherein:

R represents none (0 carbon atom), linear or branched 1-20 carbon atoms alkyl, 1-20 carbon atoms alkyloxyl, 1-20 carbon atoms perfluoroalkyl, 1-20 carbon atoms alkyl halide, 2-20 carbon atoms alkenyl, 2-20 carbon atoms alkynyl, 6-20 carbon atoms aryl, or 2-20 carbon atoms heteroaryl moieties which are pharmaceutically acceptable, wherein, any $CH_2$ may be independently replaced with O, S, $NR_5$, or other groups;

$R_1$ represents H, one of any 1-20 carbon atoms alkyl, 1-20 carbon atoms alkyloxyl, 1-20 carbon atoms alkenyl, 1-20 carbon atoms perfluoroalkyl, 1-20 carbon atoms alkyl halide, 1-20 carbon atoms alkynyl, 6-20 carbon atoms aryl, or 2-20 carbon atoms heteroaryl moieties, wherein, any $CH_2$ may be independently replaced with O, S, CH=CH, C≡C, $CHR_5$, $CR_5R_6$, aryl or heteroaryl moieties, or any other moieties which are pharmaceutically acceptable;

$R_2$ represents H, one of any 1-20 carbon atoms alkyl, 1-20 carbon atoms alkyloxyl, 1-20 carbon atoms alkenyl, 1-20 carbon atoms perfluoroalkyl, 1-20 carbon atoms alkyl halide, 1-20 carbon atoms alkynyl, 6-20 carbon atoms aryl, or 2-20 carbon atoms heteroaryl moieties, wherein, any $CH_2$ may be independently replaced with O, S, CH=CH, C≡C, $CHR_5$, $CR_5R_6$, aryl or heteroaryl moieties, or any other moieties which are pharmaceutically acceptable;

X represents O, NH, $NR_5$, S, or none;

Z represents N or CH;

$R_5$ represents H, OH, Cl, F, Br, I, one of any 1-20 carbon atoms alkyl, 1-20 carbon atoms alkyloxyl, 1-20 carbon atoms alkenyl, 1-20 carbon atoms perfluoroalkyl, 1-20 carbon atoms alkyl halide, 1-20 carbon atoms alkynyl, 6-20 carbon atoms aryl, or 2-20 carbon atoms heteroaryl moieties, wherein, any $CH_2$ may be independently replaced with O, S, CH=CH, C≡C, $CHR_5$, $CR_5R_6$, aryl or heteroaryl moieties, or any other moieties which are pharmaceutically acceptable;

$R_6$ represents H, OH, Cl, F, Br, I, one of any 1-20 carbon atoms alkyl, 1-20 carbon atoms alkyloxyl, 1-20 carbon atoms alkenyl, 1-20 carbon atoms perfluoroalkyl, 1-20 carbon atoms alkyl halide, 1-20 carbon atoms alkynyl, 6-20 carbon atoms aryl, or 2-20 carbon atoms heteroaryl moieties, wherein, any $CH_2$ may be independently replaced with O, S, CH=CH, C≡C, $CHR_5$, $CR_5R_6$, aryl or heteroaryl moieties, or any other moieties which are pharmaceutically acceptable;

$R_7$ represents one of any 1-20 carbon atoms alkyl, 1-20 carbon atoms alkyloxyl, 1-20 carbon atoms alkenyl, 1-20 carbon atoms perfluoroalkyl, 1-20 carbon atoms alkyl halide, 1-20 carbon atoms alkynyl, 6-20 carbon atoms aryl, or 2-20 carbon atoms heteroaryl moieties, wherein, any $CH_2$ may be independently replaced with O, S, CH=CH, C≡C, $CHR_5$, $CR_5R_6$, aryl or heteroaryl moieties, or any other moieties which are pharmaceutically acceptable;

$Y_1, Y_2, Y_3, Y_4, Y_5, Y_6, Y_7$, or $Y_8$ represents independently H, HO, $CH_3COO$, $R_7COO$, HS, $NO_2$, CN, =N—OH, =$NOR_8$, $NR_5OR_8$, $NR_5OH$, $CH_3COS$, $R_7COS$, $NH_2$, $CH_3CONH$, $R_7CONH$, $CH_3$, $CH_3CH_2$, $C_3H_7$, $C_4H_9$, $CH_3O$, $CH_3CH_2O$, $C_3H_7O$, Cl, F, Br, I, $CH_3S$, $CHF_2O$, $CF_3O$, $CF_3CF_2O$, $C_3F_7O$, $CF_3$, $CF_3CF_2$, $C_3F_7$, $C_4F_9$, $CH_3SO_2$, $R_7SO_2$, $CH_3SO$, $R_7SO$, $CH_3CO$, $CH_3CH_2CO$, $C_3H_7CO$, $(CH_3)_2N$, $CH_2$=CH—$CH_2$, $CH_2$=CH—$CH_2O$, $CH_3(CH_2)_3$ O, $C_3H_7O$, $C_4H_9O$, cycloalkyl, cycloalkenyl, cycloalkynyl, benzyl, substituted benzyl, phenyl, 4-chlorophenyl, 4-fluorophenyl, 4-bromophenyl, 4-iodophenyl, 3-chlorophenyl, 3-fluorophenyl, 3-bromophenyl, 3-iodophenyl, 2-chlorophenyl, 2-fluorophenyl, 2-bromophenyl, 2-iodophenyl, or other substituted phenyl; $R_8$ represents $CH_3CO$, $CH_3CH_2CO$, $C_3H_7CO$, $C_4H_9CO$, $CH_3$, $CH_3CH_2$, $C_3H_7$, $C_4H_9$; HA represents none, HCl, HBr, HF, HI, HOAc, citric acid, or any acids which are pharmaceutically acceptable;

all $Y_1, Y_2, Y_3, Y_4, Y_5, Y_6, Y_7$, or $Y_8$, R, $R_1$, $R_2$, $R_5$, $R_6$, $R_7$, $R_8$, or —$(CH_2)_n$— groups are branched or straight chains and may include C, H, O, Cl, Br, F, I, P, S, N or any other atoms which are pharmaceutically acceptable and may have single, double, or/and triple bonds.

In certain embodiments, the HPP has the following Structure 11-a:

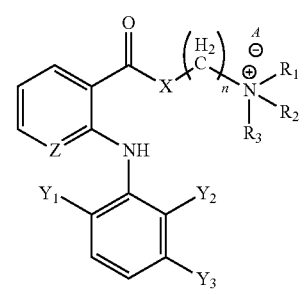

Structure 11-a including stereoisomers and pharmaceutically acceptable salts thereof, wherein:

$R_1$ is H;

$R_2$ and $R_3$ independently represent H, one of any alkyl, alkyloxy, alkenyl or alkynyl residues having 1 to 12 carbon atoms, or aryl residues;

X represents O, S, or NH; $A^Γ$ represents $Cl^Γ$, $Br^Γ$, $F^Γ$, $I^Γ$, $AcO^Γ$, citrate, or any negative ions;

$Y_1$-$Y_3$ independently represent H, Cl, F, $CH_3$, $CF_3$;

Z represents CH or N;

n=0, 1, 2, 3, 4, 5, 6, 7, 8, 9, 10 . . . ;

all R groups may include C, H, O, S, or N atoms and may have single, double, and treble bonds; and any CH₂ groups may be independently replaced with O, S, or NH.

I-10. HPP of Oxicams and Related Compounds

In certain embodiments, the HPP has the following Structure 12:

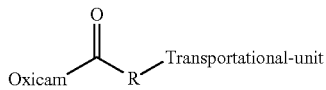

Structure 12 including stereoisomers and pharmaceutically acceptable salts thereof, wherein:

Transportational-unit has a structure selected from Group N;

R represents linear or branched 0-20 carbon atoms alkyl, 1-20 carbon atoms alkyloxyl, 1-20 carbon atoms perfluoroalkyl, 1-20 carbon atoms alkyl halide, 2-20 carbon atoms alkenyl, 2-20 carbon atoms alkynyl, 6-20 carbon atoms aryl, or 2-20 carbon atoms heteroaryl moieties which are pharmaceutically acceptable, wherein any CH₂ may be independently replaced with O, S, NR₄, or other groups;

R₁₁ represents linear or branched 0-20 carbon atoms alkyl, 1-20 carbon atoms alkyloxyl, 1-20 carbon atoms perfluoroalkyl, 1-20 carbon atoms alkyl halide, 2-20 carbon atoms alkenyl, 2-20 carbon atoms alkynyl, 6-20 carbon atoms aryl, or 2-20 carbon atoms heteroaryl moieties which are pharmaceutically acceptable, wherein any CH₂ may be independently replaced with O, S, NR₄, or other groups;

R₁₂ represents linear or branched 0-20 carbon atoms alkyl, 1-20 carbon atoms alkyloxyl, 1-20 carbon atoms perfluoroalkyl, 1-20 carbon atoms alkyl halide, 2-20 carbon atoms alkenyl, 2-20 carbon atoms alkynyl, 6-20 carbon atoms aryl, or 2-20 carbon atoms heteroaryl moieties which are pharmaceutically acceptable, wherein any CH₂ may be independently replaced with O, S, NR₄, or other groups;

R₁₃ represents linear or branched 0-20 carbon atoms alkyl, 1-20 carbon atoms alkyloxyl, 1-20 carbon atoms perfluoroalkyl, 1-20 carbon atoms alkyl halide, 2-20 carbon atoms alkenyl, 2-20 carbon atoms alkynyl, 6-20 carbon atoms aryl, or 2-20 carbon atoms heteroaryl moieties which are pharmaceutically acceptable, wherein any CH₂ may be independently replaced with O, S, NR₄, or other groups;

R₁₄ represents linear or branched 0-20 carbon atoms alkyl, 1-20 carbon atoms alkyloxyl, 1-20 carbon atoms perfluoroalkyl, 1-20 carbon atoms alkyl halide, 2-20 carbon atoms alkenyl, 2-20 carbon atoms alkynyl, 6-20 carbon atoms aryl, or 2-20 carbon atoms heteroaryl moieties which are pharmaceutically acceptable, wherein any CH₂ may be independently replaced with O, S, NR₄, or other groups;

R₁ represents H or one of any alkyl, alkyloxyl, alkenyl, perfluoroalkyl, alkyl halide, alkynyl, aryl, or heteroaryl moieties having 1 to 20 carbon atoms;

R₂ represents H or one of any alkyl, alkyloxyl, alkenyl, perfluoroalkyl, alkyl halide, alkynyl, aryl, or heteroaryl moieties having 1 to 20 carbon atoms;

R₃ represents H or one of any alkyl, alkyloxyl, alkenyl, perfluoroalkyl, alkyl halide, alkynyl, aryl, or heteroaryl moieties having 1 to 20 carbon atoms;

R₄ represents H or one of any alkyl, alkyloxyl, alkenyl, perfluoroalkyl, alkyl halide, alkynyl, aryl, or heteroaryl moieties having 1 to 20 carbon atoms;

R₅ represents H or one of any alkyl, alkyloxyl, alkenyl, perfluoroalkyl, alkyl halide, alkynyl, aryl, or heteroaryl moieties having 1 to 20 carbon atoms;

HA represents nothing, HCl, HBr, HF, HI, HOAc, citric acid, or any acids which are pharmaceutically acceptable;

oxicam- represents

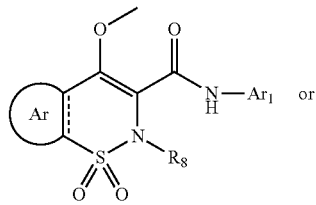

Structure 12-1 or

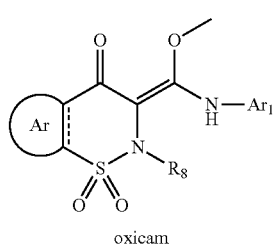

Structure 12-2 oxicam $R_8$ represents H, $CH_3$, $C_2H_5$, $C_3H_7$, $CF_3$, $C_2F_5$, or $C_3F_7$;

$Ar_1$ represents aryl or heteroaryl system, they include, but are not limited to:

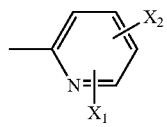

Structure 12-1a

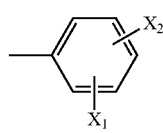

Structure 12-2a

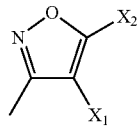

Structure 12-3a

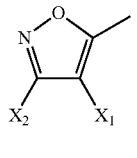

Structure 12-4a

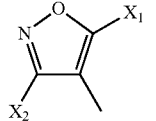

Structure 12-5a

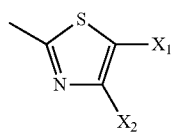

Structure 12-6a

-continued

Structure 12-7a
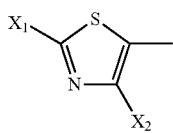

Structure 12-8a
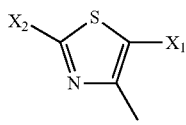

Structure 12-9a
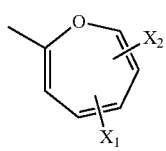

Structure 12-10a
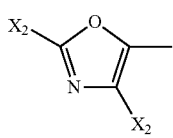

Structure 12-11a
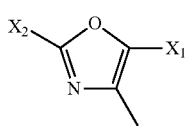

Structure 12-12a
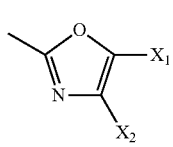

Structure 12-13a
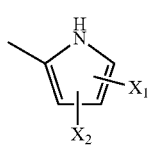

Structure 12-14a
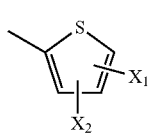

Structure 12-15a
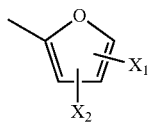

wherein, $X_1$ and $X_2$ represent H, F, Cl, Br, I, $CF_3$, $C_2F_5$, $SO_2CF_3$, $SO_2CH_3$, $NO_2$, alkyl, alkyloxyl, alkenyl or alkynyl residues having 1 to 8 carbon atoms;

represents ary or heteroaryl system, they include, but are not limited to:

Structure 12-1b
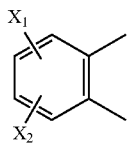

Structure 12-2b
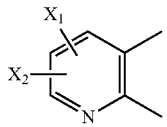

Structure 12-3b
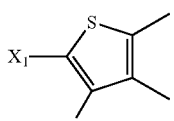

Structure 12-4b
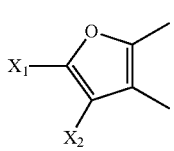

Structure 12-5b
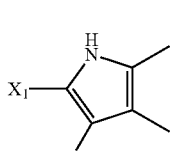

$X_1$ and $X_2$ represent H, F, Cl, Br, I, $CF_3$, $C_2F_5$, $SO_2CF_3$, $SO_2CH_3$, $NO_2$, alkyl, alkyloxyl, alkenyl or alkynyl residues having 1 to 8 carbon atoms;

all $X_1$, $X_2$, R, $R_1$, $R_2$, $R_3$, $R_4$, $R_5$, $R_8$, $R_{11}$, $R_{12}$, $R_{13}$, $R_{14}$, —$(CH_2)_n$—, groups are branched or linear chains and may include C, H, O, Cl, Br, F, I, P, S, N or any other atoms which are pharmaceutically acceptable and may have single, double, and/or triple bonds.

In certain embodiments, the HPP has the following Structure 12-a1 or Structure 12-a2:

Structure 12-a1
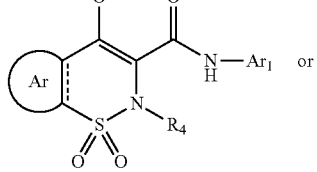

-continued

Structure 12-a2

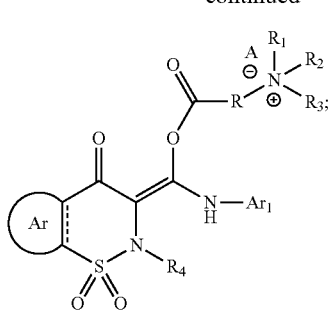

including stereoisomers and pharmaceutically acceptable salts thereof, wherein:

R represents a branched or straight chain, $—(CH_2)_n—$, wherein n=0, 1, 2, 3, 4, 5, 6, 7, 8, 9, 10 . . . , aryl residues or heteroaryl residues;

$R_1$, is H;

$R_2$ and $R_3$ independently represent H, alkyl, alkyloxy, alkenyl or alkynyl residues having 1 to 12 carbon atoms, aryl or heteroaryl residues;

$R_4$ represents H, $CH_3$, $C_2H_5$, $CF_3$, or $C_2F_5$; $A^\Gamma$ represents $Cl^\Gamma$, $Br^\Gamma$, $F^\Gamma$, $I^\Gamma$, $AcO^\Gamma$, citrate, or any negative ions; and n=0, 1, 2, 3, 4, 5, 6, 7, 8, 9, 10;

$Ar_1$ and Ar are defined the same as supra; and $X_1$ and $X_2$ represent H, F, Cl, Br, I, $CF_3$, $C_2F_5$, $SO_2CF_3$, $SO_2CF_3$, $NO_2$, alkyl, alkyloxyl, alkenyl or alkynyl residues having 1 to 8 carbon atoms. All R, $—(CH_2)_n—$, groups are branched or straight chains and may include C, H, O, S, or N atoms and may have single, double, and treble bonds. Any $CH_2$ groups may be independently replaced with O, S, or NH.

II. Pharmaceutical Compositions Comprising HPPs

Another aspect of the invention relates to a pharmaceutical composition comprising a HPP and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a HPP from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., a HPP, of the formulation and suitable for use in contact with the tissue or organ of a biological system without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of HPP in these formulations can vary widely, and will be selected primarily based on fluid volumes, viscosities, body weight and the like in accordance with the particular mode of administration selected and the biological system's needs. For example, the concentration can be 0.1% to 99.5%, 10% to 70%, 5% to 20% wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges.

Thus, a typical pharmaceutical composition for intravenous administration would be about $10^{\Gamma 9}$ g to about 100 g, about $10^{\Gamma 6}$ g to about 100 g, about 0.001 g to about 100 g, or about 0.01 g to about 10 g per subject per day. Dosages from about 0.01 mg, up to about 5 g, per subject per day may be used. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

In each embodiment, a pharmaceutical composition comprises a NSAIA-HPP according to the present invention (NSAIA-HPP composition).

III. Applications of HPPs i) Methods for Penetrating a Biological Barrier.

Another aspect of the invention relates to a method of use of a composition of the invention in penetrating one or more BBs in a biological subject. The method comprises a step of administrating to a BB a HPP or a pharmaceutical composition of the invention. In one embodiment, a HPP shows more than 100 times (>about 200 time higher, >about 300 higher) higher penetration rate through one or more BBs than its parent drug.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a layer of cells, a biological structure, an inner surface of subjects, organisms, organs or body cavities, an external surface of subjects, organisms, organs or body cavities, or any combination or plurality thereof.

Examples of biological membrane include a lipid bilayer structure, eukaryotic cell membrane, prokaryotic cell membrane, intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies. An organelle envelope may have more than two membranes.

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of cell layer of layer of cells include lining of eukaryotic cells (e.g., epithelium, lamina propria and smooth muscle or muscularis mucosa (in gastrointestinal tract), lining of prokaryotic cells (e.g., surface layer or S-layer which refers to a two dimensional structure monomolecular layer composed of identical proteins or glycoproteins. Specifically, an S-layer refers to a part of the cell envelope commonly found in bacteria and archaea), a biofilm (a structured community of microorganisms encapsulated within a self-developed polymeric matrix and adherent to a living or inert surface), plant cell layer (e.g., empidermis). The cells may be normal cells or pathological cells (e.g. disease cells, cancer cells).

Examples of biological structures include structures sealed by tight or occluding junctions which provide a barrier to the entry of toxins, bacteria and viruses from the hostile exterior, e.g. the blood milk barrier and the blood brain barrier (BBB). In particular, BBB is composed of impermeable class of endothelium, which presents both a physical barrier through tight junctions adjoining neighboring endothelial cells and a transport barrier comprised of efflux transporters. BBB is a formidable barrier, e.g., to toxins as well as drugs for neurological disease treatment. The biological structure may also include a mixture of cells, proteins and sugars (e.g. blood clots).

Examples of inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of external surface of an subjects, organisms, organs or body cavities include capillaries (e.g. capillaries in the heart tissue), mucous membranes that are continuous with skin (e.g. such as at the nostrils, the lips, the ears, the genital area, and the anus) outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani), skin, cuticle (e.g., dead layers of epidermal cells or keratinocytes or superficial layer of overlapping cells covering the hair shaft of an animal, a multi-layered structure outside the epidermis of many invertebrates, plant cuticles or polymers cutin and/or cutan), external layer of the wall of a pollen grain or the external wall layer of a spore), or a combination or plurality thereof.

In addition, a biological barrier further includes a sugar layer, a protein layer or any other biological layer, or a combination or plurality thereof. For example, skin is a biological barrier that has a plurality of biological layers. The outer surface of the skin is the epidermis, which itself contains several layers; the basal cell layer, the spinous cell layer, the granular cell layer, and the stratum corneum. The cells in the epidermis are called keratinocytes. The stratum corneum ("horny layer") is the top layer of the epidermis, wherein cells here are flat and scale-like ("squamous") in shape. These cells contain a lot of keratin and are arranged in overlapping layers that impart a tough and oilproof and waterproof character to the skin's surface.

ii) Methods for Diagnosing a Condition in a Biological System.

Another aspect of the invention relates to a method of use of a composition of the invention in diagnosing a condition in a biological system. The method comprises the following steps:

1) administrating a composition comprising a HPP to the biological subject;

2) detecting the presence, location or amount of the HPP in the biological subject; and 3) determining a condition in the biological system.

In certain embodiments, the HPP (or the agent cleaved from the HPP) aggregates in the site of action where a condition occurs. In certain embodiments, the presence, location or amount of the functional unit of the HPP is also detected. In certain embodiments, the onset, development, progress, or remission of a condition (e.g., an infection or a disease) associated is also determined.

In certain embodiments, the HPP is labeled with or conjugated to a detectable agent. Alternatively, the HPP is prepared to include radioisotopes for detection. Numerous detectable agents are available which can be generally grouped into the following categories:

(a) Radioisotopes, such as $^{35}S$, $^{14}C$, $^{13}C$, $^{15}N$, $^{125}I$, $^{3}H$, and $^{131}I$. The diagnostic agent can be labeled with the radioisotope using the techniques known in the art and radioactivity can be measured using scintillation counting; in addition, the diagnostic agent can be spin labeled for electron paramagnetic resonance for carbon and nitrogen labeling.

(b) Fluorescent agents such as BODIPY, BODIPY analogs, rare earth chelates (europium chelates), fluorescein and its derivatives, FITC, 5,6 carboxyfluorescein, rhodamine and its derivatives, dansyl, Lissamine, phycoerythrin, green fluorescent protein, yellow fluorescent protein, red fluorescent protein and Texas Red. Fluorescence can be quantified using a fluorometer.

(c) Various enzyme-substrate agents, such luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

In certain embodiments, the detectable agent is not necessarily conjugated to the diagnostic agent but is capable of recognizing the presence of the diagnostic agent and the diagnostic agent can be detected.

In certain embodiments, the HPP of the present invention can be provided in a kit, i.e., a packaged combination of reagents in predetermined amounts with instructions for performing the diagnostic assay. Where the HPP is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

iii) Methods for Screening a Substance for a Desired Character

Another aspect of the invention relates to a method of screening a HPP for a desired character.

In certain embodiments, the method comprises:
1) covalently linking the test functional unit to a transportational unit through a linker to form a test composition (or covalently linking a functional unit to a test transportational unit through a linker, or covalently linking a functional unit to a transportational unit through a test linker)
2) administrating a test composition a biological system; and
3) determining whether the test composition that has a desired character.

In one embodiment, the desired character may include, for example, 1) the ability of the test functional unit to form a high penetration composition or convert back to a parent drug, 2) the penetration ability and/or rate of the test composition, 3) the efficiency and/or efficacy of the test composition, 4) the transportational ability of the test transportational unit, 5) the cleavability of the test linker.

iv) Methods for Treating a Condition in a Biological Subject

Another aspect of the invention relates to a method of use of a composition of the invention in treating a condition in a biological system. The method comprises administrating the pharmaceutical composition to the biological system.

The term "treating" as used herein means curing, alleviating, inhibiting, or preventing. The term "treat" as used herein means cure, alleviate, inhibit, or prevent. The term "treatment" as used herein means cure, alleviation, inhibition or prevention.

The term "biological system," "biological subject" or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism. In at least some form, all organisms are capable of response to stimuli, reproduction, growth and development, and maintenance of homeostasis as a stable whole.

Some examples of the conditions the method can treat include conditions that can be treated by the parent drug of the HPP.

v). Methods of Use of a NSAIA-HPP Composition in Treatments.

Another aspect of the invention relates to a method of use of a NSAIA-HPP composition in treating a condition in a biological system by administrating a NSAIA-HPP to the biological system.

A) Conditions Treatable by the Method

Some examples of the conditions that are treated by the method include:
1) metabolism disorder, e.g. abnormal blood glucose level, abnormal blood lipid level, diabetes mellitus (type I or/and type II) and diabetes-induced complications, including diabetic retinopathy, necrobiotic ulcers, and diabetic proteinuria;
2) abnormal blood pressure, e.g. hypertension and hypotension;
3) tumor, e.g. benign tumor, breast cancer, colon-rectum cancer, oral cancer, lung or other respiratory system cancers, skin cancers, uterus cancer, pancreatic cancer, prostate cancer, genital cancer, urinary organs cancers, leukemia or other blood and lymph tissues cancer.
4) cardiovascular diseases, e.g. heart attack, unstable angina, peripheral occlusive arterial disease and stroke;
5) neurodegenerative disease, e.g. Alzheimer's diseases and Parkinson's disease;
6) skin condition, e.g. psoriasis and psoriatic disorders, acne, cystic acne, pus-filled or reddish bumps, comedones, papules, pustules, nodules, epidermoid cysts, keratosis pilaris, abnormal vascular skin lesions, birthmarks, moles (nevi), skin tags, scleroderma, vitiligo and related diseases, or aging spots (liver spots);
7) autoimmune disease, e.g. discoid lupus erythematosus, systemic lupus erythematosus (SLE), autoimmune hepatitis, cleroderma, Sjogren's syndrome, rheumatoid arthritis, polymyositis, scleroderma, Hashimoto's thyroiditis, juvenile diabetes mellitus, Addison disease, vitiligo, pernicious anemia, glomerulonephritis, pulmonary fibrosis, multiple sclerosis (MS) and Crohn's disease;
8) eye disease, e.g. glaucoma, ocular hypertension, loss of vision after ophthalmic surgery, vision of a warm-blooded animal impaired by cystoid macular edema and cataract;
9) pain;
10) injuries;
11) inflammation related conditions, e.g. prostate gland inflammation (prostatitis), prostatocystitis, prostate enlarge fibrosis, hemorrhoids, Kawasaki syndrome, gastroenteritis, type-1 membranoproliferative glomerulonephritis, Bartter's syndrome, chronic uveitis, ankylosing spondylitis, hemophilic arthropathy, inflamed hemorrhoids, post irradiation (factitial) proctitis, chronic ulcerative colitis, inflammatory bowel disease, cryptitis, periodontitis, arthritis, and an inflammatory condition in an organ selected from the group consisting of liver, lung, stomach, brain, kidney, heart, ear, eye, nose, mouth, tongue, colon, pancreas, gallbladder, duodenum, rectum stomach, colonrectum, intestine, vein, respiratory system, vascular, the anorectum and pruritus ani;
12) fever;
13) conditions related to platelet aggregation, e.g. thromboembolis after surgery, carotid endarterectomy, the recurrence of stenosis after coronary angioplasty, thromboembolis complications in chronic arterial fibrillation, aortocornonary-artery-bypass graft occlusion, heart attack, stroke, multi-infract dementia, dementia, hemodialysis shunt thrombosis and arterial embolic complications in patients' prosthetic heart valves;

14) dysmenorrheal;
15) allergy;
16) asthma;
17) preeclamptic toxemia in high-risk women,
18) IUD-associated uterine bleeding,
19) radiation-induced conditions, and
20) bone disease, e.g. osteoporosis, Paget's disease and bone metastases.

In certain embodiments, the method of treating a condition amelioratable or treatable with Aspirin or Aspirin related compounds comprising administering a HPP of aspirin or aspirin related compounds to a subject. Examples of the condition include, for instance, gouty arthritis, pain and inflammation of arthritic and other inflammatory conditions, inflammatory bowel disease, heart attack (C. H. Hennekens, et al., N. Engl. J. Med., 321, 129(1989)]; stroke (T. A. Gossel, U.S. Pharmacist, February, 1988, p. 34.], tumor (e.g. colon cancer (M. J. Thun, et al., N. Engl. J. Med., 325, 1393(1991)], rectal cancer), Kawasaki syndrome, thromboembolism after surgery, unstable angina, gastroenteritis, aortocoronary-artery-bypass graft occlusion, thromboembolic complications in chronic arterial fibrillation, platelet aggregatioartrial in carotid endarterectomy, cataracts, recurrence of stenosis after coronary angioplasty, multi-infract dementia, diabetes mellitus and diabetes-induced complications (e.g. diabetic retinopathy, necrobiotic ulcers, and diabetic proteinuria), cardiovascular disease, hemodialysis shunt thrombosis, renal disease (e.g. type-1 membranoproliferative glomerulonephritis), peripheral occlusive arterial disease, arterial embolic complications in patients' prosthetic heart valves, pregnancy-induced hypertension and preeclamptic toxemia in high-risk women.

In certain embodiments, the method of treating a condition amelioratable or treatable with salicylate or salicyte related compounds (e.g., diflunisal or diflunisal related compounds) comprising administering a HPP of salicylate or salicyte related compounds to a subject. Examples of the condition include, for instance, pain, inflammation (e.g. osteoarthritis, gout and rheumatoid arthritis) dysmenorrheal, eye disease (e.g. the loss of vision due to ophthalmic surgery (Hirsch-Kauffmann, Dan J., U.S. Pat. No. 5,134,165), and the vision of a warm-blooded animal impaired by cystoid macular edema (Yung-Yu Hung, et al., U.S. Pat. No. 6,593,365).)

In certain embodiments, the method of treating a condition amelioratable or treatable with ibuprofen or ibuprofen related compounds comprising administering a HPP of ibuprofen related compounds to a subject. Examples of the condition include, for instance, inflammation, fever, dysmenorrhea, Bartter's syndrome, chronic uveitis, both anterior and posterior, IUD-associated uterine bleeding, radiation-induced vomiting in patients receiving pelvic irradiation, diabetic and related conditions, pain, hemophilic arthropathy, bone loss (Jee; Webster S. S. U.S. Pat. No. 5,604,259), and sunburn (Sunshine: Abraham. U.S. Pat. No. 5,100,918)

In certain embodiments, the method of treating a condition amelioratable or treatable with ketoprofen or ketoprofen related compounds comprising administering a HPP of ketoprofen or ketoprofen related compounds to a subject. Examples of the condition include, for instance, rheumatoid arthritis and osteoarthritis, dysmenorrhea, acute biliary colic, pain, fever. (PDR Generics, 1996, second edition, Medical Economics, Montvale, N.J., pg 1812), and bone regeneration (Alfano, M. C.; Troullos, E. S., U.S. Pat. No. 5,902,110).

In certain embodiments, the method of treating a condition amelioratable or treatable with fenoprofen or fenoprofen related compounds comprising administering a HPP of fenoprofen or fenoprofen related compounds to a subject. Examples of the condition include, for instance, pain, osteoarthritis and rheumatoid arthritis, gout (PDR Generics, 1996, second edition, Medical Economics, Montvale, N.J., pg 1290) and shock (Toth, P. D., U.S. Pat. No. 4,472,431).

In certain embodiments, the method of treating a condition amelioratable or treatable with aryl- and heteroarylpropionic acids comprising administering a HPP of aryl- and heteroarylpropionic acids to a subject. Examples of the condition include, for instance, rheumatoid arthritis, osteoarthritis, dysmenorrhea, gouty arthritis ankylosing spondylitis, and dementia (McGeer; Patrick L. et al. U.S. Pat. No. 5,192,753). In certain embodiments, the parent drug of aryl- and heteroarylpropionic acids the HPP is selected from the group consisting naproxen, suprofen, α-methyl-(p-chlorobenzoyl)-5-methoxy-2-methyl indole 3-acetic acid, flurbiprofen, carprofen, pranoprofen, benoxaprofen, alminoprofen, tiaprofenic acid, pirprofen, zaltoprofen, bermoprofen, loxoprofen, indoprofen, fenclorac, oxaprozin, fenbufen, orpanoxin, ketorolac, and clidanac.

In certain embodiments, the method of treating a condition amelioratable or treatable with aryl- and heteroarylacetic acids or related compounds thereof, comprising administering a HPP of aryl- and heteroarylacetic acids or related compounds thereof to a subject. Examples of the condition include, for instance, rheumatoid arthritis, osteoarthritis, dysmenorrheal, gouty arthritis, ankylosing spondylitis and dementia (McGeer; Patrick L. et al. U.S. Pat. No. 5,192,753).

In certain embodiments, the method of treating a condition amelioratable or treatable with N-aryl anthranilic acid or related compounds thereof, comprising administering a HPP of N-aryl anthranilic acid or related compounds thereof to a subject. Examples of the condition include, for instance, gouty arthritis and ankylosing spondylitis.

In certain embodiments, the method of treating a condition amelioratable or treatable with oxicam or related compounds thereof, comprising administering a HPP of oxicam or related compounds thereof to a subject. Examples of the condition include, for instance, rheumatoid arthritis and osteoarthritis.

In one embodiment, a NSAIA-HPP shows better analgesic activities comparing to its parent drug. In certain embodiments, a NSAIA-HPP shows better or similar antipyretic activities comparing to its parent drug. In certain embodiments, a NSAIA-HPP demonstrates better anti-inflammatory activities comparing to its parent drug. In certain embodiments, a NSAIA-HPP is used to treat asthma (Bianco, Sebastiano, U.S. Pat. No. 5,570,559) by spraying into the mouth or nose of a host.

In certain embodiments, a NSAIA-HPP reduces the undesired conditions of skin such as acne, roughness, freckles, moles, dark spots and other discolorations, fine lines, wrinkles with improved skin elasticity, firmness, texture and tone, and other endothelia dysfunctions that are treatable by anti-inflammatory agents.

In certain embodiments, administration of a NSAIA-HPP on cancer subjects reduces tumor size of the subjects without significant weight loss of the subjects.

In certain embodiments, a NSAIA-HPP lowers the blood glucose levels and blood lipid levels of diabetic biological subjects while the NSAIA-HPP do not affecting the blood glucose levels of normal subjects.

In certain embodiments, a NSAIA-HPP is capable of treating thrombotic activity and embolization-associated thrombus propagation in biological subjects, e.g. stroke.

In certain embodiments, a NSAIA-HPP is used to treat autoimmune diseases, e.g. psoriasis, discoid lupus erythematosus, systemic lupus erythematosus (SLE).

In certain embodiments, a NSAIA-HPP is effective to treat lesions similar to psoriasis of biological subjects.

In certain embodiments, a NSAIA-HPP shows effective anti-hypertensive activity. In certain embodiments, a NSAIA-HPP shows anti-Parkinson's disease activity. In certain embodiments, a NSAIA-HPP shows anti-Alzheimer disease activity. In certain embodiments, a NSAIA-HPP shows anti-glaucoma activity. In certain embodiments, a NSAIA-HPP is used to treat spinal cord injury in which the healing is stopped by the protected scars around the injured spinal cord. In certain embodiments, a NSAIA-HPP is effective in treating wounds with shrunk scar after healing.

B) Administration of the Compositions According to the Present Invention.

The HPP or the HPP composition can be administered to a biological system by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

The HPP or the HPP composition can be given to a subject in the form of formulations or preparations suitable for each administration route. The formulations useful in the methods of the present invention include one or more HPPs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a HPP which can be combined with a carrier material to produce a pharmaceutically effective dose will generally be that amount of a HPP which produces a therapeutic effect. Generally, out of one hundred percent, this amount will range from about 1 percent to about ninety-nine percent of the HPP, preferably from about 20 percent to about 70 percent.

Methods of preparing these formulations or compositions include the step of bringing into association a HPP with one or more pharmaceutically acceptable carriers and, optionally, one or more accessory ingredients. In general, the formulations are prepared by uniformly and intimately bringing into association a HPP with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a HPP as an active ingredient. A compound may also be administered as a bolus, electuary, or paste.

In solid dosage forms for oral administration (e.g., capsules, tablets, pills, dragees, powders, granules and the like), the HPP is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a HPP therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPP(s) only, or preferentially, in a certain portion of the gastrointestinal tract, optionally, in a delayed manner. Examples of embedding compositions which can be used include polymeric substances and waxes. The HPP can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the HPP, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the HPP, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPPs with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of a HPP composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the HPP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPP composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The HPP composition can be alternatively administered by aerosol. This is accomplished by preparing an aqueous aerosol, liposomal preparation or solid particles containing the HPPs. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver HPP compositions to an infection site. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Formulations suitable for parenteral administration comprise a HPP in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of a HPP or in biodegradable polymers such as polylactide-polyglycolide. Depending on the ratio of the HPP to polymer, and the nature of the particular polymer employed, the rate of drug release can be controlled. Examples of other biodegradable polymers include poly (orthoesters) and poly (anhydrides). Depot injectable formulations are also prepared by entrapping the HPP in liposomes or microemulsions which are compatible with body tissue.

In an embodiment of the invention, a HPP composition is delivered to a disease or infection site in a therapeutically effective dose. As is known in the art of pharmacology, the precise amount of the pharmaceutically effective dose of a HPP that will yield the most effective results in terms of efficacy of treatment in a given patient will depend upon, for example, the activity, the particular nature, pharmacokinetics, pharmacodynamics, and bioavailability of a particular HPP, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of a disease caused by pathogenic target microbial organisms, to name a few. However, the above guidelines can be used as the basis for fine-tuning the treatment, e.g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins PA, USA) (2000).

In certain embodiments, a NSAIA-HPP composition is administered to a biological system through any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration.

IV. Advantages

In certain embodiments, since the HPP of the present invention is capable of crossing one or more biological barriers, the HPP can be administered locally (e.g., typically or transdermally) to reach a location where a condition occurs without the necessity of a systematic administration (e.g., oral or parenteral administration). The local administration and penetration of the HPP allows the HPP to reach the same level of local concentration of an agent or drug with much less amount or dosage of HPP in comparison to a systematic administration of a parent agent or drug, alternatively, a higher level of local concentration which may not be afforded in the systematic administration, or if possible, requires significantly higher dosage of an agent in the systematic administration. The high local concentration of the HPP or its parent agent if being cleaved enables the treatment of a condition more effectively or much faster than a systematically delivered parent agent and the treatment of new conditions that may not be possible or observed before. The local administration of the HPP may allow a biological subject to reduce potential sufferings from a systemic administration, e.g., adverse reactions associated with the systematic exposure to the agent, gastrointestinal/renal effects. Additionally, the local administration may allow the HPP to cross a plurality of biological barriers and reach systematically through, for example, general circulation and thus avoid the needs for systematic administration (e.g., injection) and obviate the pain associated with the parenteral injection.

In certain embodiments, the HPP according to the present invention can be administered systematically (e.g., orally or parenterally). The HPP or the active agent (e.g., drug or metabolite) of the HPP may enter the general circulation with a faster rate than the parent agent and gain faster access to the action site a condition. Additionally, the HPP can cross a biological barrier (e.g., BBB) which has not been penetrated if a parent agent is administered and thus offer novel treatment of conditions that may not be possible or observed before.

For example, the HPPs of NSAIA in the present invention demonstrate high penetration rate through a biological barrier (e.g., >about 100 times, >about 200 times, >about 300 times higher that the NSAIA alone). No gastroduodenal bleeding was observed from the subjects that took HPP of a NSAIA, while gastroduodenal bleeding was observed from the subjects that took the parent NSAIA at the similar dosage.

V. Examples

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

Example 1. Preparation of a HPP from a Parent Drug i) Preparation of a HPP from a Parent Drug which Contains at Least One Carboxylic Group In certain embodiments, the parent compound having the following Structure C:

Structure C is converted to a HPP having Structure A:

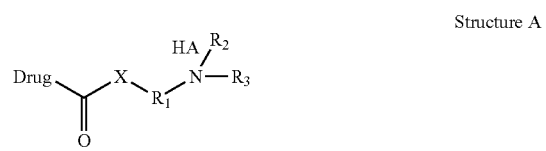

Structure A including stereoisomers and pharmaceutically acceptable salts thereof, wherein:

X is selected from the group consisting of nothing, O, $P(O)OR_1$, NH, $NR_1$ and S; and each $R_1$, $R_2$, $R_3$ and $R_4$ are independently selected from the group consisting of nothing, H, $CH_2COOR_6$, substituted and unsubstituted alkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl groups, wherein any $CH_2$ in $R_1$, $R_2$, $R_3$ and $R_4$ may be further independently replaced with O, S, P, $NR_1$, or any other pharmaceutically acceptable groups.

In certain embodiments of the invention, the HPP having Structure A are prepared according to the conventional organic synthesis by reacting the parent compounds or derivatives of the parent compounds having Structure D (e.g. acid halides, mixed anhydrides of the parent compounds, etc.):

Structure D wherein Y is selected from the group consisting of OH, halogen, alkoxycarbonyl and substituted aryloxycarbonyloxy, with compounds of Structure E:

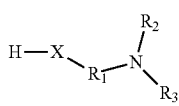

Structure E

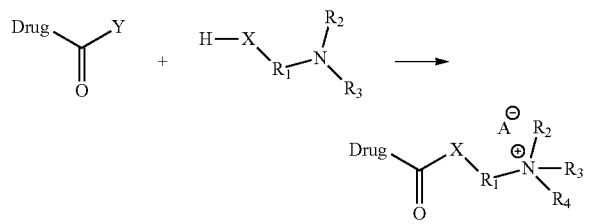

Scheme 1. Preparation of a HPP from a compound having a carboxyl group.

As used herein, the term "pharmaceutically acceptable" means approved by a regulatory agency of the Federal or a state government or listed in the U.S. Pharmacopoeia or other generally recognized pharmacopoeia for use in animals, and more particularly in humans.

As used herein, the term "pharmaceutically acceptable salt" means those salts of compounds of the invention that are safe and effective for application in a subject and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,11-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1977), incorporated herein by reference.

Preparation of Diethylaminoethyl Acetylsalicylate.AcOH 18 g (0.1 mol) of o-acetylsalicylic was dissolved in 180 ml of chloroform. 12.5 g of Sodium bicarbonate (0.15 mol) was added into the solution. Water (20 ml) was added with stirring. After the mixture had been stirred for 30 minutes, anhydrous sodium sulfate (200 g) was added. 39 g (0.15 mol) of diethylaminoethyl bromide.HBr was added into the mixture and the mixture was stirred for 5 hours at RT. 8.2 g (0.1 mol) of sodium acetate was added into the reaction mixture with stirring. The mixture is stirred for 2 hours. The solid was removed by filtration and washed with chloroform (3×50 ml). The solution is concentrated in vacuo to 100 ml. Then 300 ml of hexane was added into the solution. The solid product was collected by filtration and washed with hexane (3×100 ml). After drying, it yielded 31 g of the desired product (91%). Hygroscopic product; Solubility in water: 300 mg/ml; Elementary analysis: C17H25N06; MW: 339.38. Calculated % C: 60.07; H: 7.44; N: 4.15; O: 28.22. Found % C: 60.16; H: 7.42; N: 4.13; O: 28.29. $^1$H-NMR (400 MHz, CDCL3): delta: 1.55 (t, 6H), 2.08 (s, 3H), 2.20 (s, 3H), 3.28 (m, 4H); 3.70 (m, 2H), 4.68 (m, 2H), 6.5 (b, 1H), 7.17 (m, 1H), 7.19 (m, 1H), 7.45 (m, 1H), 7.94 (m, 1H).

Preparation of dimethylaminoethyl acetylsalicylate.AcOH 19.9 g (0.1 mol) of o-acetoxybenzoyl chloride was dissolved in 100 ml of chloroform. The mixture was cooled to 0° C. 15 ml of triethylamine and 8.9 g of dimethylaminoethanol were added into the reaction mixture. The mixture is stirred for 3 hours at RT. 6 g of acetic acid is added into the reaction mixture with stirring. The solid side product was removed by filtration and washed with chloroform (3×30 ml). The organic solution was evaporated off. After drying, it yielded 29 g of the desired product (93%). Hygroscopic product; Solubility in water: 350 mg/ml; Elementary analysis: C15H21N06; MW: 311.33. Calculated % C: 57.87; H: 6.80; N: 4.50; O: 30.83. Found % C: 57.82; H: 6.85; N: 4.48; O: 30.85. $^1$H-NMR (400 MHz, CDCL3): delta: 2.09 (s, 3H) 2.21 (s, 3H), 2.90 (s, 6H); 3.71 (m, 2H), 4.69 (m, 2H), 6.9 (b, 1H), 7.18 (m, 1H), 7.20 (m, 1H), 7.47 (m, 1H), 7.93 (m, 1H).

Preparation of diethylaminoethyl acetylsalicylate.acetylsalicylic acid 180 g of 2-acetylsalicyclic acid was dissolved in 1000 ml of chloroform. The mixture was cooled to 5° C. 103 g of 1,3-Dicyclohexylcarbodiimide was added into the mixture. The mixture is stirred for 2 h at RT. The solid waste is removed by filtration and washed with chloroform (3×300 ml). 59 g of diethylaminoethanol were added into the reaction mixture. The mixture was stirred for 3 hours at RT. The organic solution was evaporated off. After drying, it yielded 220 g of the desired product (96%). Elementary analysis: $C_{24}H_{29}NO_8$; MW: 459.18. Calculated % C: 62.73; H: 6.36; N: 3.05; O: 27.86. Found % C: 62.70; H: 6.40; Cl: N: 3.01; O: 27.90.

Preparation of S-dimethylaminoethyl acetylthiosalicylate.AcOH 19.9 g (0.1 mol) of o-acetoxybenzoyl chloride was dissolved in 100 ml of chloroform. The mixture was cooled to 0° C. 15 ml of triethylamine and 9.3 g of dimethylaminoethyl mercaptan were added into the reaction mixture. The mixture was stirred for 3 hours at RT. 6 g of acetic acid was added into the reaction mixture with stirring. The solid side product was removed by filtration and washed with chloroform (3×30 ml). The organic solution was evaporated off. After drying, it yielded 28 g of the desired product (87%). Hygroscopic product; Solubility in water: 320 mg/ml; Elementary analysis: C15H21N05S; MW: 327.4. Calculated % C: 55.03; H: 6.47; N: 4.28; O: 24.43 S: 9.79. Found % C: 55.02; H: 6.45; N: 4.35; O: 24.49; 9.69. $^1$H-NMR (400 MHz, CDCL3): delta: 2.09 (s, 3H) 2.21 (s, 3H), 2.90 (s, 6H); 3.31 (t, 2H), 3.91 (m, 2H), 6.9 (b, 1H), 7.26 (m, 1H), 7.28 (m, 1H), 7.55 (m, 1H), 7.94 (m, 1H).

Preparation of N-dimethylaminoethyl acetylsalicylamide.AcOH 19.9 g (0.1 mol) of o-acetoxybenzoyl chloride was dissolved in 100 ml of chloroform. The mixture was cooled to 0° C. 15 ml of triethylamine and 8.9 g of dimethylaminoethylamine were added into the reaction mixture. The mixture was stirred for 3 hours at RT. 6 g of acetic acid was added into the reaction mixture with stirring. The solid side product was removed by filtration and washed with chloroform (3×30 ml). The organic solution was evaporated off. After drying, yielded 28 g of the desired product (90.2%). Hygroscopic product; Solubility in water: 350 mg/ml; Elementary analysis: C15H22N2O5; MW: 310.35. Calculated % C: 58.05; H: 7.15; N: 9.03; O: 25.78. Found % C: 58.02; H: 7.18; N: 8.98; O: 25.83. $^1$H-NMR (400 MHz, CDCL3): delta: 2.09 (s, 3H) 2.21 (s, 3H), 2.90 (s, 6H); 3.54 (m, 2H), 3.64 (t, 2H), 6.9 (b, 1H), 7.8 (b, 1H); 7.25 (m, 1H), 7.26 (m, 1H), 7.48 (m, 1H), 7.92 (m, 1H).

Preparation of S-diethylaminoethyl proplonylthiosalicylate.AcOH 18 g (0.1 mol) of o-acetylsalicylic acid was dissolved in 100 ml of dichloromethane (DCM). The mixture was cooled to 0° C. 20.6 g of 1,3-Dicyclohexylcarbodiimid was added into the reaction mixture. The mixture was stirred for 30 minutes at 0° C. 14.8 g (0.1 mol) of diethylaminopropyl mercaptan was added into the reaction mixture. The mixture was stirred for 3 h at RT. 6 g of acetic acid was added into the reaction mixture with stirring. The solid side product was removed by filtration and washed with chloroform (3×50 ml). The organic solution was evaporated off. After drying, it yielded 32 g of the desired product (86.6%). Hygroscopic product; Solubility in water: 280 mg/ml; Elementary analysis: C18H27NO5S; MW: 369.48. Calculated % C: 58.51; H: 7.37; N: 3.79; O: 21.65; S: 8.68. Found % C: 58.53; H: 7.39; N: 3.75; O: 21.68; S: 8.65. $^1$H-NMR (400 MHz, CDCl3): delta: 1.09 (t, 3H), 1.56 (t, 6H), 2.21 (s, 3H), 2.27 (m, 2H) 3.28 (m, 4H), 3.31 (m, 2H); 3.91 (m, 2H), 6.8 (b, 1H), 7.25 (m, 1H), 7.26 (m, 1H), 7.48 (m, 1H), 7.92 (m, 1H).

Preparation of N-diethylaminopropyl acetylsalicylamide.AcOH 18 g (0.1 mol) of o-acetylsalicylic acid was dissolved in 100 ml of acetonitrile 32.1 g of O-(Benzotriazol-1-yl)-N,N,N',N'-tetramethyluronium tetrafluoroborate and 30 ml of triethylamine were added into the reaction mixture. 13.1 g of dimethylaminopropylamine was added into the reaction mixture. The mixture was stirred for 3 hours at RT. The solvents were evaporated off. 250 ml of ethyl acetate was added into the reaction mixture and the mixture was washed with water (3×100 ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration. After drying, it yielded 32 g of the desired product (90.8%). Hygroscopic product; Solubility in water: 280 mg/ml; Elementary analysis: C18H28N2O5; MW: 352.43. Calculated % C: 61.34; H: 8.01; N: 7.95; O: 22.70. Found % C: 61.25; H: 8.05; N: 7.96; O: 22.74. 1H-NMR (400 MHz, CDCL3): delta: 1.56 (t, 6H) 2.03 (m, 2H) 2.09 (s, 3H), 2.21 (s, 3H), 3.24 (m, 2H), 3.20 (m, 2H); 3.24 (m, 2H), 6.9 (b, 1H), 7.8 (b, 1H); 7.25 (m, 1H), 7.26 (m, 1H), 7.48 (m, 1H), 7.92 (m, 1H).

Preparation of dipropylaminoethyl acetylsalicylate.AcOH 20.3 g (0.1 mol) of sodium o-acetylsalicylate was suspended in 180 ml of chloroform. 28.8 g (0.1 mol) of dipropylaminoethyl bromide.HBr was added into the mixture and the mixture was stirred for 5 hours at RT. 8.2 g (0.1 mol) of sodium acetate was added into the reaction mixture with stirring. The mixture is stirred for 2 hours. The solid was removed by filtration and washed with chloroform (3×50 ml). The solution is concentrated in vacuo to 100 ml. Then 300 ml of hexane was added into the solution. The solid product was collected by filtration and washed with hexane (3×100 ml). After drying, it yielded 30 g of the desired product (81.6%). Hygroscopic product; Solubility in water: 300 mg/ml; Elementary analysis: C17H25NO6; MW: 367.44. Calculated % C: 62.11; H: 7.96; N: 3.81; O: 26.13. Found % C: 62.07; H: 7.99; N: 3.78; O: 26.17. $^1$H-NMR (400 MHz, CDCl3): delta: 0.97 (t, 6H), 1.77 (m, 4H), 2.20 (s, 3H), 3.25 (m, 4H); 3.70 (m, 2H), 4.69 (m, 2H), 6.8 (b, 1H), 7.17 (m, 1H), 7.19 (m, 1H), 7.45 (m, 1H), 7.94 (m, 1H).

Preparation of dipropylaminoethyl acetylsalicylate.AcOH 60 g of Polymer-bound triethylamine (3 mmol/g, 100-200 mesh) was suspended in 180 ml of chloroform. 18 g (0.1 mol) of o-acetylsalicylic acid was added into the into the mixture and the mixture was stirred for 5 hours at RT. The polymer is removed by filtration and washed with tetrahydrofuran (3×50 ml). 8.2 g (0.1 mol) of sodium acetate was added into the reaction mixture with stirring. The mixture is stirred for 2 h. The solid was removed by filtration and washed with chloroform (3×50 ml). The solution is concentrated in vacuo to 100 ml. Then 300 ml of hexane was added into the solution. The solid product was collected by filtration and washed with hexane (3×100 ml). After drying, it yielded 31 g of the desired product (91%). Hygroscopic product; Solubility in water: 300 mg/ml; Elementary analysis: C17H25NO6; MW: 339.38. Calculated % C: 60.07; H: 7.44; N: 4.15; O: 28.22. Found % C: 60.16; H: 7.42; N: 4.13; O: 28.29. $^1$H-NMR (400 MHz, CDCl3): delta: 1.55 (t, 6H), 2.08 (s, 3H), 2.20 (s, 3H), 3.28 (m, 4H); 3.70 (m, 2H), 4.68 (m, 2H), 6.5 (b, 1H), 7.17 (m, 1H), 7.19 (m, 1H), 7.45 (m, 1H), 7.94 (m, 1H).

Preparation of diethylaminoethyl 5-(2,4-difluorophenyl) salicylate.AcOH 31.1 g (0.1 ml) of 5-(2,4-difluorophenyl) acetylsalicyl chloride was dissolved in 100 ml of chloroform. The mixture was cooled to 0° C. 15 ml of triethylamine and 11.7 g (0.1 mol) of diethylaminoethanol were added into the reaction mixture. The mixture is stirred for 3 hours at RT. The solvents are evaporated off. The residue is dissolved in methanol (300 ml), 5% sodium bicarbonate (200 ml) is added into the reaction mixture. The mixture is refluxed for 2 hr. The mixture is evaporated to dryness. Methanol (300 ml) is added into the residue with stirring. Solid is removed by filtration and washed with methanol. The solution is evaporated to dryness and the residue is dissolved in chloroform (200 ml). 6 g of acetic acid is added into the reaction mixture with stirring. Some solid is removed by filtration. Another 6 g of acetic acid is added into the reaction mixture with stirring. The organic solution was evaporated off. After drying, it yielded 36 g of the desired product (88%). Hygroscopic product; Solubility in water: 400 mg/ml; Elementary analysis: $C_{21}H_{25}F_2NO_5$; MW: 409.42. Calculated % C: 61.60; H: 6.15; F: 9.28; N: 3.42; O: 19.54. Found % C: 61.56; H: 6.18; F: 9.27; N: 3.40; O: 19.59. $^1$H-NMR (400 MHz, CDCl$_3$): δ: 1.56 (t, 6H), 2.21 (s, 3H), 3.27 (m, 4H), 3.70 (m, 2H), 4.69 (t, 2H), 4.9 (b, 1H), 6.74 (m, 1H), 6.84 (m, 1H), 7.0 (b, H), 7.06 (b, 1H), 7.15 (m, 1H), 7.44 (m, 1H), 7.86 (m, 1H).

Preparation of diethylaminoethyl salicylsalicylate.AcOH 31.8 g (0.1 mol) of acetylsalicylsalicyl chloride was dissolved in 100 ml of chloroform. The mixture was cooled to 0° C. 15 ml of triethylamine and 8.9 g (0.1 mol) of diethylaminoethanol were added into the reaction mixture. The mixture is stirred for 3 hours at RT. The solvents are evaporated off. The residue is dissolved in methanol (300 ml), 5% sodium bicarbonate (200 ml) is added into the reaction mixture. The mixture is stirred for 3 hr. The mixture is evaporated to dryness. Methanol (300 ml) is added into the residue with stirring. Solid is removed by filtration and washed with methanol. The solution is evaporated to dryness and the residue is dissolved in chloroform (200 ml). 6 g of acetic acid is added into the reaction mixture with stirring. Some solid is removed by filtration. Another 6 g of acetic acid is added into the reaction mixture with stirring. The organic solution was evaporated off. After drying, it yielded 32 g of the desired product (82%). Hygroscopic product; Solubility in water: 400 mg/ml; Elementary analysis: $C_{20}H_{23}NO_7$; MW: 389.40. Calculated % C: 61.69; H: 5.95; N: 3.60; O: 28.76. Found % C: 61.66; H: 5.98; N: 3.58; O: 28.78. $^1$H-NMR (400 MHz, $CDCl_3$): δ: 2.21 (s, 3H), 2.90 (s, 6H), 3.70 (m, 2H), 4.69 (t, 2H), 4.9 (b, 1H), 6.74 (b, 1H), 6.88 (m, 1H), 7.0 (b, H), 7.26 (b, 1H), 7.27 (m, 1H), 7.35 (m, 1H) 7.54 (m, 1H), 7.97 (m, 1H), 8.06 (m, 1H).

Preparation of dimethylaminoethyl salicylate.AcOH 19.9 g (0.1 mol) of acetylsalicyl chloride was dissolved in 100 ml of chloroform. The mixture was cooled to 0° C. 15 ml of triethylamine and 8.9 g (0.1 mol) of dimethylaminoethanol was added into the reaction mixture. The mixture is stirred for 3 hours at RT. The solvents are evaporated off. The residue is dissolved in methanol (300 ml), 5% sodium bicarbonate (200 ml) is added into the reaction mixture. The mixture is refluxed for 2 hr. The mixture is evaporated to dryness. Methanol (300 ml) is added into the residue with stirring. Solid is removed by filtration and washed with methanol. The solution is evaporated to dryness and the residue is dissolved in chloroform (200 ml). 6 g of acetic acid is added into the reaction mixture with stirring. Some solid is removed by filtration. Another 6 g of acetic acid is added into the reaction mixture with stirring. The organic solution was evaporated off. After drying, it yielded 23 g of the desired product (88%). Hygroscopic product; Solubility in water: 350 mg/ml; Elementary analysis: $C_{13}H_{19}NO_5$; MW: 269.29. Calculated % C: 57.98; H: 7.11; N: 5.20; O: 29.71. Found % C: 57.96; H: 7.13; N: 5.17; O: 29.74. $^1$H-NMR (400 MHz, $CDCl_3$): δ: 2.21 (s, 3H), 2.90 (s, 6H), 3.70 (m, 2H), 4.69 (t, 2H), 4.9 (b, 1H), 6.74 (b, 1H), 6.84 (m, 1H), 6.93 (b, 1H), 6.98 (b, 1H), 7.30 (b, 1H).

Preparation of S-dimethylaminoethyl 5-(2,4-difluorophenyl) thiosalicylate.AcOH 31.1 g (0.1 mol) of 5-(2,4-difluorophenyl) acetylsalicyl chloride was dissolved in 100 ml of chloroform. The mixture was cooled to 0° C. 15 ml of triethylamine and 9.3 g of dimethylaminoethyl mercaptan were added into the reaction mixture. The mixture is stirred for 3 h at RT. The solvents are evaporated off. The residue is dissolved in methanol (300 ml), 5% sodium bicarbonate (200 ml) is added into the reaction mixture. The mixture is refluxed for 2 hr. The mixture is evaporated to dryness. Methanol (300 ml) is added into the residue with stirring. Solid is removed by filtration and washed with methanol. The solution is evaporated to dryness and the residue is dissolved in chloroform (200 ml). 6 g of acetic acid is added into the reaction mixture with stirring. Some solid is removed by filtration. Another 6 g of acetic acid is added into the reaction mixture with stirring. The organic solution was evaporated off. After drying, it yielded 32 g of the desired product (80.5%). Hygroscopic product; Solubility in water: 400 mg/ml; Elementary analysis: $C_{19}H_{21}F_2NO_4S$; MW: 397.44. Calculated % C: 57.42; H: 5.33; F: 9.56; N: 3.52; O: 16.10, S: 8.07. Found % C: 57.40; H: 5.35; F: 9.53; N: 3.51; O: 16.15; S: 8.06. $^1$H-NMR (400 MHz, $CDCl_3$): δ: 2.20 (s, 3H), 2.90 (s, 6H), 3.31 (t, 2H), 3.91 (t, 2H), 5.0 (b, 1H), 6.7 (b, 1H), 6.74 (m, 1H), 6.84 (m, 1H); 7.14 (m, 1H), 7.23 (m, 1H). 7.44 (m, 1H), 7.87 (m, 1H).

Preparation of N-dimethylaminoethyl 5-(2,4-difluorophenyl) salicylamide.AcOH 31.1 g (0.1 mol) of 5-(2,4-difluorophenyl) acetylsalicyl chloride was dissolved in 100 ml of chloroform. The mixture was cooled to 0° C. 15 ml of triethylamine and 8.8 g (0.1 mol) of dimethylaminoethylamine was added into the reaction mixture. The mixture is stirred for 3 h at RT. The solvents are evaporated off. The residue is dissolved in methanol (300 ml), 5% sodium bicarbonate (200 ml) is added into the reaction mixture. The mixture is refluxed for 2 hr. The mixture is evaporated to dryness. Methanol (300 ml) is added into the residue with stirring. Solid is removed by filtration and washed with methanol. The solution is evaporated to dryness and the residue is dissolved in chloroform (200 ml). 6 g of acetic acid is added into the reaction mixture with stirring. Some solid is removed by filtration. Another 6 g of acetic acid is added into the reaction mixture with stirring. The organic solution was evaporated off. After drying, it yielded 33 g of the desired product (86.8%). Hygroscopic product; Solubility in water: 400 mg/ml; Elementary analysis: $C_{19}H_{22}F_2N_2O_4$; MW: 380.39. Calculated % C: 59.99; H: 5.83; F: 9.99; N: 7.36; O: 16.82. Found % C: 59.97; H: 5.85; F: 9.98; N: 7.35; O: 16.85. $^1$H-NMR (400 MHz, $CDCl_3$): δ: 2.20 (s, 3H), 2.90 (s, 6H), 3.54 (t, 2H), 3.64 (t, 2H), 5.0 (b, 1H), 6.7 (b, 1H), 6.73 (m, 1H), 6.80 (m, 1H); 7.15 (m, 1H), 7.22 (m, 1H). 7.44 (m, 1H), 7.87 (m, 1H), 8.01 (b, 1H).

Preparation of S-diethylaminoethyl thiosalicylate.AcOH 18 g (0.1 mol) of acetylsalicylic acid was dissolved in 100 ml of dichloromethane (DCM). The mixture was cooled to 0° C. 20.6 g of 1,3-Dicyclohexylcarbodiimid was added into the reaction mixture. The mixture was stirred for 30 minutes at 0° C. 13.4 g (0.1 mol) of diethylaminoethyl mercaptan was added into the reaction mixture. The mixture was stirred for 3 h at RT. The solvents are evaporated off. The residue is dissolved in methanol (300 ml), 5% sodium bicarbonate (200 ml) is added into the reaction mixture. The mixture is stirred for 20 h at RT. The mixture is evaporated to dryness. Methanol (300 ml) is added into the residue with stirring. Solid is removed by filtration and washed with methanol. The solution is evaporated to dryness and the residue is dissolved in chloroform (200 ml). 6 g of acetic acid is added into the reaction mixture with stirring. Some solid is removed by filtration. Another 6 g of acetic acid is added into the reaction mixture with stirring. The organic solution was evaporated off. After drying, it yielded 29 g of the desired product (92.5%). Hygroscopic product; Solubility in water: 400 mg/ml; Elementary analysis: $C_{15}H_{23}NO_4S$; MW: 313.41. Calculated % C: 57.48; H: 7.40; N: 4.47; O: 20.42, S: 10.23. Found % C: 57.43; H: 7.42; N: 4.46; O: 20.47; S: 10.21. $^1$H-NMR (400 MHz, $CDCl_3$): 1.56 (t, 6H) 2.20 (s, 3H), 3.26 (m, 4H), 3.31 (t, 2H), 3.91 (t, 2H), 5.0 (b, 1H), 6.8 (b, 1H), 6.92 (d, 1H), 7.41 (d, 1H), 7.81 (d, 1H).

Preparation of ethyl 3-N, N-diethylaminopropionyl 5-(2,4-difluorophenyl) salicylate.AcOH 27.8 g (0.1 mol) of ethyl 5-(2,4-difluorophenyl) salicylate was dissolved in 100 ml of chloroform (100 ml). The mixture was cooled to 0° C. 21 ml (0.2 mol) of triethylamine and 20.0 g (0.1 mol) of 3-N, N-diethylaminopropionyl chloride hydrochloride were added into the reaction mixture. The mixture is stirred for 3 h at RT. The solid is removed by filtration. Acetic acid (6 g) was added into the reaction mixture with stirring. Hexane (200 ml) was added. The solid product was collected by filtration. After drying, it yielded 40 g of the desired product (85.9%). Hygroscopic product; Solubility in water: 400 mg/ml; Elementary analysis: $C_{24}H_{29}F_2NO_6$; MW: 465.49. Calculated % C: 61.93; H: 6.28; F: 8.16; N: 3.01; O: 20.62. Found % C: 61.90; H: 6.30; F: 8.15; N: 3.00; O: 20.65. $^1$H-NMR (400 MHz, $CDCl_3$): δ: 1.30 (t, 3H), 1.56 (t, 6H), 2.20 (s, 3H), 2.67 (t, 2H); 3.28 (m, 4H), 3.50 (m, 2H), 4.29 (m, 2H), 6.8 (b, 1H), 6.70 (m, 1H), 6.81 (m, 1H), 7.40 (m, 2H), 7.44 (d, 1H), 7.9 (d, 1H).

Preparation of ethyl 3-N, N-dimethylaminopropionyl salicylsalicylate.AcOH 28.6 g (0.1 mol) of ethyl salicylsalicylate was dissolved in 100 ml of chloroform (100 ml). The mixture was cooled to 0° C. 21 ml (0.2 mol) of triethylamine and 17.2 g (0.1 mol) of 3-N, N-dimethylaminopropionyl chloride hydrochloride were added into the reaction mixture. The mixture is stirred for 3 h at RT. The solid is removed by filtration. Acetic acid (6 g) was added into the reaction mixture with stirring. Hexane (200 ml) was added. The solid product was collected by filtration. After drying, it yielded 42 g of the desired product (88.7%). Hygroscopic product; Solubility in water: 380 mg/ml; Elementary analysis: $C_{25}H_{31}NO_8$; MW: 473.52. Calculated % C: 63.41; H: 6.60; N: 2.96; O: 27.03. Found % C: 63.40; H: 6.62; N: 2.93; O: 27.05. $^1$H-NMR (400 MHz, CDCl3): σ: 1.30 (t, 3H), 1.57 (t, 6H); 2.20 (s, 3H), 2.68 (t, 2H); 3.28 (m, 4H), 3.50 (m, 2H), 4.29 (m, 2H), 6.8 (b, 1H), 7.21 (m, 2H), 7.26 (m, 1H), 7.27 (m, 1H), 7.49 (m, 1H), 7.54 (m, 1H); 8.05 (m, 1H); 8.12 (m, 1H).

Preparation of ethyl 3-N, N-dimethylaminopropionyl salicylate.AcOH 16.6 g (0.1 mol) of ethyl salicylate was dissolved in 100 ml of chloroform (100 ml). The mixture was cooled to 0° C. 21 ml (0.2 mol) of triethylamine and 17.2 g (0.1 mol) of 3-N, N-dimethylaminopropionyl chloride hydrochloride were added into the reaction mixture. The mixture is stirred for 3 h at RT. The solid is removed by filtration. Acetic acid (6 g) was added into the reaction mixture with stirring. Hexane (200 ml) was added. The solid product was collected by filtration. After drying, it yielded 28 g of the desired product (85.9%). Hygroscopic product; Solubility in water: 400 mg/ml; Elementary analysis: $C_{16}H_{23}NO_6$; MW: 325.36. Calculated % C: 59.06; H: 7.13; N: 4.31; O: 29.50. Found % C: 59.03; H: 7.15; N: 4.30; O: 29.52. $^1$H-NMR (400 MHz, $CDCl_3$): δ: 1.31 (t, 3H), 2.20 (s, 3H), 2.68 (t, 2H); 2.92 (m, 4H), 3.50 (m, 2H), 4.30 (m, 2H), 6.8 (b, 1H), 7.18 (m, 2H), 7.44 (m, 1H), 7.92 (m, 1H).

Preparation of diethylaminoethyl 2-(ρ-isobutylphenyl) propionate.AcOH 22.5 g (0.1 mol) of 2-(ρ-isobutylphenyl) propionyl chloride was dissolved in 100 ml of chloroform. The mixture was cooled to 0° C. 15 ml of triethylamine and 11.7 g of diethylaminoethanol were added into the reaction mixture. The mixture is stirred for 3 hours at RT. The solid side product was removed by filtration and washed with chloroform (3×30 ml). 6 g of acetic acid is added into the chloroform solution with stirring. The organic solution was evaporated off. After drying, it yielded 35 g of the desired product (92%). Hygroscopic product; Solubility in water: 400 mg/ml; Elementary analysis: $C_{21}H_{35}NO_4$; MW: 365.51. Calculated % C: 69.01; H: 9.65; N: 3.83; O: 17.51; Found % C: 68.98; H: 9.68; N: 3.82; O: 17.52. $^1$H-NMR (400 MHz, $CDCl_3$): δ: 1.10 (d, 6H), 1.52 (d, 3H), 1.56 (t, 6H), 2.21 (s, 3H), 2.22 (m, 1H); 2.51 (d, 2H), 3.28 (m, 4H), 3.52 (m, 2H), 3.78 (m, 1H), 4.52 (t, 2H), 6.8 (b, 1H), 7.06 (d, 2H), 7.07 (d, 2H).

Preparation of dimethylaminoethyl 2-(ρ-isobutylphenyl) propionate.AcOH 22.5 g (0.1 mol) of 2-(ρ-isobutylphenyl) propionyl chloride was dissolved in 100 ml of chloroform. The mixture was cooled to 0° C. 15 ml of triethylamine and 8.9 g of dimethylaminoethanol were added into the reaction mixture. The mixture is stirred for 3 hours at RT. 6 g of acetic acid is added into the reaction mixture with stirring. The solid side product was removed by filtration and washed with chloroform (3×30 ml). The organic solution was evaporated off. After drying, it yielded 31 g of the desired product (92%). Hygroscopic product; Solubility in water: 300 mg/ml; Elementary analysis: $C_{19}H_{31}NO_4$; MW: 337.45. Calculated % C: 67.63; H: 9.26; N: 4.15; O: 18.96; Found % C: 67.60; H: 7.28; N: 4.14; O: 18.98. $^1$H-NMR (400 MHz, $CDCl_3$): δ: 1.01 (d, 6H), 1.52 (d, 3H), 2.21 (s, 3H), 2.22 (m, 1H); 2.51 (d, 2H), 2.90 (s, 6H), 3.52 (m, 2H), 3.78 (m, 1H), 4.52 (t, 2H), 6.8 (b, 1H), 7.06 (d, 2H), 7.07 (d, 2H).

Preparation of dipropylaminoethyl 2-(ρ-isobutylphenyl) propionate.AcOH 22.3 g (0.1 mol) of sodium 2-(ρ-isobutylphenyl) propionate was suspended in 180 ml of chloroform. 28.8 g (0.1 mol) of dipropylaminoethyl bromide.HBr was added into the mixture and the mixture was stirred for 5 hours at RT. 8.2 g (0.1 mol) of sodium acetate was added into the reaction mixture with stirring. The mixture is stirred for 2 hours. The solid was removed by filtration and washed with chloroform (3×50 ml). The solution is concentrated in vacuo to 100 ml. Then 300 ml of hexane was added into the solution. The solid product was collected by filtration and washed with hexane (3×100 ml). After drying, it yielded 35 g of the desired product (88.9%). Hygroscopic product; Solubility in water: 300 mg/ml; Elementary analysis: $C_{23}H_{39}NO_4$; MW: 393.56. Calculated % C: 70.19; H: 9.99; N: 3.56; O: 16.26. Found % C: 70.14; H: 10.03; N: 3.55; O: 16.28. $^1$H-NMR (400 MHz, $CDCl_3$): δ: 0.96 (d, 6H), δ: 1.10 (d, 6H), 1.52 (d, 3H), 1.77 (m, 4H), 2.21 (s, 3H), 2.22 (m, 1H); 2.51 (d, 2H), 3.24 (m, 4H), 3.52 (m, 2H), 3.78 (m, 1H), 4.52 (t, 2H), 6.8 (b, 1H), 7.06 (d, 2H), 7.07 (d, 2H).

Preparation of dipropylaminoethyl 2-(ρ-isobutylphenyl) propionate.AcOH 60 g of Polymer-bound triethylamine (3 mmol/g, 100-200 mesh) was suspended in 180 ml of chloroform. 20.6 g (0.1 mol) of 2-(ρ-isobutylphenyl) propionic acid was added into the mixture with stirring. 43 g (0.15 mol) of dipropylaminoethyl bromide.HBr was added into the mixture and the mixture was stirred for 5 hours at RT. The polymer was removed by filtration and washed with tetrahydrofuran (3×50 ml). 8.2 g (0.1 mol) of sodium acetate was added into the reaction mixture with stirring. The mixture was stirred for 2 h. The solid was removed by filtration and washed with chloroform (3×50 ml). The solution was concentrated in vacuo to 100 ml. Then 300 ml of hexane was added into the solution. The solid product was collected by filtration and washed with hexane (3×100 ml). After drying, it yielded 36 g of the desired product (91.5%). Hygroscopic product; Solubility in water: 300 mg/ml; Elementary analysis: $C_{23}H_{39}NO_4$; MW: 393.56. Calculated % C: 70.19; H: 9.99; N: 3.56; O: 16.26. Found % C: 70.14; H: 10.03; N: 3.55; O: 16.28. $^1$H-NMR (400 MHz, CDCl$_3$): δ: 0.96 (d, 6H), δ: 1.10 (d, 6H), 1.52 (d, 3H), 1.77 (m, 4H), 2.21 (s, 3H), 2.22 (m, 1H); 2.51 (d, 2H), 3.24 (m, 4H), 3.52 (m, 2H), 3.78 (m, 1H), 4.52 (t, 2H), 6.8 (b, 1H), 7.06 (d, 2H), 7.07 (d, 2H).

Preparation of 3-piperidinemethyl 2-(ρ-isobutylphenyl) propionate.AcOH 60 g of Polymer-bound triethylamine (3 mmol/g, 100-200 mesh) was suspended in 180 ml of chloroform. 20.6 g (0.1 mol) of 2-(ρ-isobutylphenyl) propionic acid was added into the mixture with stirring. 39 g (0.15 mol) of 3-piperidinemethyl bromide.HBr was added into the mixture and the mixture was stirred for 5 hours at RT. The polymer is removed by filtration and washed with acetone (3×50 ml). 300 ml of 5% $Na_2CO_3$ was added into the solution with stirring. The mixture is stirred for 30 min. The chloroform solution is washed with water (3×100 ml) and dried over $Na_2SO_4$. Sodium sulfate is removed by filtration and washed with chloroform (3×100 ml). 6 g of acetic acid was added into the mixture. The solution is concentrated in vacuo to 100 ml. Then 300 ml of hexane was added into the solution. The solid product was collected by filtration and washed with hexane (3×100 ml). After drying, it yielded 35 g of the desired product (96%). Elementary analysis: $C_{21}H_{33}NO_4$; MW: 363.49 Calculated % C: 69.39; H: 9.15; N: 3.85; O: 17.61. Found % C: 69.35; H: 9.18; N: 3.83; O: 17.64.

Preparation of S-dimethylaminoethyl 2-(ρ-isobutylphenyl) thiopropionate.AcOH 22.5 g (0.1 mol) of 2-(ρ-isobutylphenyl) propionyl chloride was dissolved in 100 ml of chloroform. The mixture was cooled to 0° C. 15 ml of triethylamine and 9.3 g of dimethylaminoethyl mercaptan were added into the reaction mixture. The mixture was stirred for 3 hours at RT. 6 g of acetic acid was added into the reaction mixture with stirring. The solid side product was removed by filtration and washed with chloroform (3×30 ml). The organic solution was evaporated off. After drying, it yielded 32 g of the desired product (90.5%). Hygroscopic product; Solubility in water: 300 mg/ml; Elementary analysis: $C_{19}H_{31}NO_3S$; MW: 353.52. Calculated % C: 64.55; H: 8.84; N: 3.96; O: 13.58, S: 9.07. Found % C: 64.52; H: 8.86; N: 3.95; O: 13.62; S: 9.05. $^1$H-NMR (400 MHz, CDCl$_3$): δ: 1.01 (d, 6H), 1.52 (d, 3H), 2.20 (s, 3H), 2.22 (m, 1H); 2.50 (d, 2H), 2.90 (s, 6H), 3.31 (t, 2H), 3.81 (t, 1H), 3.91 (t, 2H), 6.8 (b, 1H), 7.06 (d, 2H), 7.07 (d, 2H).

Preparation of S-diethylaminoethyl 2-(ρ-isobutylphenyl) thiopropionat.AcOH 20.6 g (0.1 mol) of 2-(ρ-isobutylphenyl) propionic acid was dissolved in 100 ml of dichloromethane (DCM). The mixture was cooled to 0° C. 20.6 g of 1,3-Dicyclohexylcarbodiimid was added into the reaction mixture. The mixture was stirred for 30 minutes at 0° C. 13.4 g (0.1 mol) of diethylaminoethyl mercaptan was added into the reaction mixture. The mixture was stirred for 3 h at RT. 6 g of acetic acid was added into the reaction mixture with stirring. The solid side product was removed by filtration and washed with chloroform (3×50 ml). The organic solution was evaporated off. After drying, it yielded 34 g of the desired product (89.1%). Hygroscopic product; Solubility in water: 300 mg/ml; Elementary analysis: $C_{21}H_{35}NO_3S$; MW: 381.57. Calculated % C: 66.10; H: 9.25; N: 3.67; O: 12.58, S: 8.40. Found % C: 66.07; H: 9.29; N: 3.66; O: 12.60; S: 8.38. $^1$H-NMR (400 MHz, CDCl$_3$): δ: 1.01 (d, 6H), 1.52 (d, 3H), 1.56 (t, 6H) 2.20 (s, 3H), 2.22 (m, 1H); 2.50 (d, 2H), 3.26 (m, 4H), 3.31 (t, 2H), 3.81 (t, 1H), 3.91 (t, 2H), 6.8 (b, 1H), 7.06 (d, 2H), 7.07 (d, 2H).

Preparation of N-dimethylaminoethyl 2-(ρ-isobutylphenyl) propionamide.AcOH 22.5 g (0.1 mol) of 2-(ρ-isobutylphenyl) propionyl chloride was dissolved in 100 ml of chloroform. The mixture was cooled to 0° C. 15 ml of triethylamine and 8.9 g of dimethylaminoethylamine were added into the reaction mixture. The mixture was stirred for 3 hours at RT. 6 g of acetic acid was added into the reaction mixture with stirring. The solid side product was removed by filtration and washed with chloroform (3×30 ml). The organic solution was evaporated off. After drying, yielded 30 g of the desired product (89.1%). Hygroscopic product; Solubility in water: 300 mg/ml; Elementary analysis: $C_{19}H_{32}N_2O_3$; MW: 336.47. Calculated % C: 67.82; H: 9.59; N: 8.33; O: 14.27. Found % C: 67.80; H: 9.61; N: 8.31; O: 14.26. $^1$H-NMR (400 MHz, CDCl$_3$): δ: 1.01 (d, 6H), 1.52 (d, 3H), 2.20 (s, 3H), 2.22 (m, 1H); 2.50 (d, 2H), 2.90 (s, 6H), 3.50 (t, 2H), 3.64 (t, 2H), 3.89 (m, 1H), 6.8 (b, 1H), 7.06 (d, 2H), 7.07 (d, 2H), 7.8 (b, 1H).

Preparation of N-dimethylaminopropyl 2-(ρ-isobutylphenyl) propionamide.AcOH 20.6 g (0.1 mol) of 2-(ρ-isobutylphenyl) propionic acid was dissolved in 100 ml of acetonitrile. 32.1 g of O-(Benzotriazol-1-yl)-N,N,N',N'-tetramethyluronium tetrafluoroborate and 30 ml of triethylamine were added into the reaction mixture. 13.1 g of dimethylaminopropylamine was added into the reaction mixture. The mixture was stirred for 3 hours at RT. The solvents were evaporated off. 250 ml of ethyl acetate was added into the reaction mixture and the mixture was washed with water (3×100 ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration.

After drying, it yielded 32 g of the desired product (91.2%). Hygroscopic product; Solubility in water: 320 mg/ml; Elementary analysis: $C_{20}H_{34}N_2O_3$; MW: 350.5. Calculated % C: 68.54; H: 9.78; N: 7.99; O: 13.69. Found % C: 68.51; H: 9.80; N: 7.98; O: 13.71. $^1$H-NMR (400 MHz, CDCl$_3$): δ: 1.01 (d, 6H), 1.52 (d, 3H), 1.98 (m, 2H), 2.20 (s, 3H), 2.22 (m, 1H); 2.50 (d, 2H), 2.90 (s, 6H), 3.20 (m, 2H), 3.24 (m, 2H), 3.89 (m, 1H), 6.8 (b, 1H), 7.06 (d, 2H), 7.07 (d, 2H), 7.8 (b, 1H).

Preparation of diethylaminoethyl (Z)-5-fluoro-2-methyl-1-[(4-methylsulfinyl) phenylmethylene]-1H-indene-3-acetate.AcOH 1.3 g (0.2 mol) of (Z)-5-fluoro-2-methyl-1-[(4-methylsulfinyl) phenylmethylene]-1H-indene-3-acetic acid was dissolved in 500 ml of chloroform. DCC (R0283, 21) is added into the reaction mixture and the mixture was stirred for 2 h at 25 C. The solid was removed by filtration and washed with chloroform (3×100 ml). 11.7 g (0.1 mol) of diethylaminoethanol was added into the reaction mixture. The mixture was stirred for overnight at RT. The solution was concentrated to 100 ml. 300 ml of hexanes was added into the residue. The solid was collected by filtration and washed with hexanes. After drying, it yielded 75 g of the desired product (92.3%). Elementary analysis: $C_{46}H_{47}F_2NO_6S_2$; MW: 812.00. Calculated % C: 68.04; H: 5.83; F: 4.68; N: 1.72; O: 11.82; S: 7.90. Found % C: 68.07; H: 5.85; F: 4.63; N: 1.72; O: 11.87; S: 7.86.

Preparation of diethylaminoethyl 1-methyl-5-(4-methylbenzoyl)-1H-pyrrole-2-acetate.AcOH 8.6 g (0.1 mol) of 1-methyl-5-(4-methylbenzoyl)-1H-pyrrole-2-acetyl chloride was dissolved in 100 ml of chloroform. The mixture was cooled to 0° C. 15 ml of triethylamine and 8.9 g (0.1 mol) of dimethylaminoethanol were added into the reaction mixture. The mixture is stirred for 3 hours at RT. The solvents are evaporated off. The residue is dissolved in methanol (300 ml), 5% sodium bicarbonate (200 ml) is added into the reaction mixture. The mixture is stirred for 3 hr. The mixture is evaporated to dryness. Methanol (300 ml) is added into the residue with stirring. Solid is removed by filtration and washed with methanol. The solution is evaporated to dryness and the residue is dissolved in chloroform (200 ml). 6 g of acetic acid is added into the reaction mixture with stirring. Some solid is removed by filtration. Another 6 g of acetic acid is added into the reaction mixture with stirring. The organic solution was evaporated off. After drying, it yielded 37 g of the desired product (88.8%). Elementary analysis: $C_{23}H_{32}N_2O_5$; MW: 416.51. Calculated % C: 66.32; H: 7.74; N: 6.73; O: 19.21. Found % C: 66.29; H: 7.76; N: 6.73; O: 19.22.

Preparation of S-dimethylaminoethyl 1-(p-chlorobenzoyl)-5-methoxy-2-methylindole 3-acetate.AcOH 0.4 g (0.1 mol) of dimethylaminoethyl mercaptan was dissolved in 10% sodium bicarbonate (200 ml) and acetone (100 ml). 37.6 g (0.1 mol) of 1-(p-chlorobenzoyl)-5-methoxy-2-methylindole 3-acetyl chloride was added into the reaction mixture. The mixture is stirred for 3 hours at RT. The solvents are evaporated off. The residue is suspended in ethyl acetate (500 ml). 5% sodium bicarbonate (200 ml) is added into the reaction mixture with stirring. Ethyl acetate layer is collected and washed with water (3×500 ml). The ethyl acetate solution was dried over anhydrous sodium sulfate. Sodium sulfate is removed by filtration. 6 g of acetic acid is added into the reaction mixture with stirring. The organic solution was evaporated off. After drying, it yielded 46 g of the desired product (86.3%). Elementary analysis: $C_{27}H_{33}ClN_2O_5S$; MW: 533.08. Calculated % C: 60.83; H: 6.24; Cl: 6.65; N: 5.26; O: 15.01; S: 6.02. Found % C: 60.80; H: 6.26; Cl: 6.66; N: 5.25, O: 15.02; S: 6.01.

Preparation of N-dimethylaminoethyl 5-(4-Chlorobenzoyl)-1,4-dimethyl-1H-pyrrole-2-acetamide-.AcOH 8.8 g (0.1 mol) of dimethylaminoethylamine was dissolved in 10% sodium bicarbonate (200 ml) and acetone (100 ml). 31 g (0.1 mol) of 2-(3-benzoyphenyl) propionyl chloride was added into the reaction mixture. The mixture is stirred for 3 hours at RT. The solvents are evaporated off. The residue is suspended in ethyl acetate (500 ml). 5% sodium bicarbonate (200 ml) is added into the reaction mixture with stirring. Ethyl acetate layer is collected and washed with water (3×500 ml). The ethyl acetate solution was dried over anhydrous sodium sulfate. Sodium sulfate is removed by filtration. 6 g of acetic acid is added into the reaction mixture with stirring. The organic solution was evaporated off. After drying, it yielded 33 g of the desired product (85.9%). Elementary analysis: $C_{23}H_{32}ClN_3O_4$; MW: 449.97. Calculated % C: 61.39; H: 7.17; Cl: 7.88; N: 9.34; O: 14.22. Found % C: 61.37; H: 7.18; Cl: 7.89; N: 9.32; O: 14.24.

Preparation of N-dimethylaminoethyl 1,8-diethyl-1,3,4,9-tetrahydropyrano-[3,4-b]indole-1-acetamide-.AcOH 8.9 g (0.1 mol) of 1,8-diethyl-1,3,4,9-tetrahydropyrano-[3,4-b]indole-1-acetic acid was dissolved in 100 ml of acetonitrile. 32.1 g of O-(Benzotriazol-1-yl)-N,N,N',N'-tetramethyluronium tetrafluoroborate and 30 ml of triethylamine were added into the reaction mixture. 11.7 g of dimethylaminoethylamine was added into the reaction mixture. The mixture was stirred for 3 hours at RT. The solvents were evaporated off. 250 ml of ethyl acetate was added into the reaction mixture and the mixture was washed with water (3×100 ml). The organic solution was dried over anhydrous sodium sulfate. Sodium sulfate was removed by filtration. 6 g of acetic acid was added into the reaction mixture with stirring. Flexane (200 ml) was added. The solid product was collected by filtration. After drying, it yielded 40 g of the desired product (89.4%). $C_{25}H_{41}N_3O_4$; MW: 447.61. Calculated % C: 67.08; H: 9.23; N: 9.39; O: 14.30. Found % C: 67.05; H: 9.25; N: 9.38; O: 14.32.

Preparation of diethylaminoethyl 3-chloro-4-(2-propenyloxy) benzeneacetate.AcOH 0 g of Polymer-bound triethylamine (3 mol/g, 100-200 mesh) was suspended in 180 ml of chloroform. 22.7 g (0.1 mol) of 3-chloro-4-(2-propenyloxy) benzeneacetic acid was added into the mixture with stirring. 43 g (0.15 mol) of diethylaminoethyl bromide.HBr was added into the mixture and the mixture was stirred for 5 hours at RT. The polymer was removed by filtration and washed with tetrahydrofuran (3×50 ml). 8.2 g (0.1 mol) of sodium acetate was added into the reaction mixture with stirring. The mixture was stirred for 2 h. The solid was removed by filtration and washed with chloroform (3×50 ml). The solution was concentrated in vacuo to 100 ml. Then 300 ml of hexane was added into the solution. The solid product was collected by filtration and washed with hexane (3×100 ml). After drying, it yielded 34 g of the desired product (88.3%). Hygroscopic product; Elementary analysis: $C_{19}H_{29}ClN_2O_4$; MW: 384.9. Calculated % C: 59.29; H: 7.59; Cl: 9.21, N: 7.28; O: 16.63. Found % C: 59.26; H: 7.61; Cl: 9.22; N: 7.26; O: 16.65.

Preparation of diethylaminoethyl 2[(2, 6-dichlorophenyl)amino]benzene acetate.AcOH 35.1 g (0.1 mol) of 2[(2,6-dichlorophenyl)amino]benzene acetyl chloride hydrochloride was dissolved in 100 ml of chloroform. The mixture was cooled to 0° C. 30 ml of triethylamine and 11.7 g of diethylaminoethanol were added into the reaction mixture. The mixture is stirred for 3 hours at RT. The solid side product was removed by filtration and washed with chloroform (3×30 ml). 6 g of acetic acid is added into the reaction mixture with stirring. The organic solution was evaporated off. After drying, it yielded 39 g of the desired product (85.6%). Hygroscopic product; Solubility in water: 400 mg/ml; Elementary analysis: $C_{22}H_{28}Cl_2N_2O_4$; MW: 455.37. Calculated % C: 58.03; H: 6.20; Cl: 15.57; N: 6.15; O: 14.05. Found % C: 58.01; H: 6.22; Cl: 15.55, N: 6.14; O: 14.09. $^1$H-NMR (400 MHz, CDCl$_3$): δ: 1.56 (t, 6H), 2.21 (s, 3H), 3.28 (m, 4H), 3.50 (s, 2H), 3.52 (m, 2H), 3.81 (b, 1H), 4.51 (t, 2H), 6.32 (d, 1H), 6.50 (m, 2H), 6.78 (b, 1H), 6.82 (m, 2H), 6.91 (d, 2H).

Preparation of dimethylaminoethyl 2[(2,6-dichlorophenyl)amino] benzene acetate.AcOH 2[(2,6-Dichlorophenyl)amino]benzene acetyl chloride hydrochloride (35.1 g, 0.1 mol) was dissolved in 100 ml of acetone. The mixture was cooled to 0° C. Dimethylaminoethanol (8.9 g, 0.1 mol) were added into the reaction mixture. Sodium bicarbonate (20 g) and water (100 ml) are added into the mixture. The mixture is stirred for 3 hours at RT. The solution is evaporated to dryness. Acetone (100 ml) is added into the residue. The solid side product was removed by filtration and washed with acetone (3×30 ml). 6 g of acetic acid is added into the reaction mixture with stirring. The organic solution was evaporated off. After drying, it yielded 38 g of the desired product (88.9%). Hygroscopic product; Solubility in water: 410 mg/ml; Elementary analysis: $C_{20}H_{24}Cl_2N_2O_4$; MW: 427.32. Calculated % C: 56.21; H: 5.66; Cl: 16.59, N: 6.56; O: 14.98. Found % C: 56.18; H: 5.68; Cl: 16.56, N: 6.55; O: 15.03. $^1$H-NMR (400 MHz, CDCl$_3$): δ: 2.21 (s, 3H), 2.91 (s, 6H), 3.50 (s, 2H), 3.52 (m, 2H), 3.81 (b, 1H), 4.51 (t, 2H), 6.32 (d, 1H), 6.50 (m, 2H), 6.78 (b, 1H), 6.82 (m, 2H), 6.91 (d, 2H).

Preparation of S-dimethylaminoethyl 2[(2,6-dichlorophenyl)amino] benzene acetate.AcOH 2[(2,6-Dichlorophenyl)amino]benzene acetyl chloride hydrochloride (35.1 g, 0.1 mol) was dissolved in 100 ml of acetone. The mixture was cooled to 0° C. Dimethylaminoethyl mercaptan (9.3 g, 0.1 mol) were added into the reaction mixture. Sodium bicarbonate (20 g) and water (100 ml) are added into the mixture. The mixture is stirred for 3 hours at RT. The solution is evaporated to dryness. Acetone (100 ml) is added into the residue. The solid side product was removed by filtration and washed with acetone (3×30 ml). 6 g of acetic acid is added into the reaction mixture with stirring. The organic solution was evaporated off. After drying, it yielded 40 g of the desired product (90.2%). Hygroscopic product; Solubility in water: 410 mg/ml; Elementary analysis: $C_{20}H_{24}Cl_2N_2O_3S$; MW: 443.39. Calculated % C: 54.18; H: 5.46; Cl: 15.99, N: 6.32; O: 10.83, S: 7.22. Found % C: 54.16; H: 5.48; Cl: 15.97, N: 6.31; O: 10.86, S: 7.23. $^1$H-NMR (400 MHz, CDCl$_3$): δ: 2.21 (s, 3H), 2.91 (s, 6H), 3.31 (t, 2H), 3.66 (s, 2H), 3.91 (m, 2H), 3.93 (b, 1H), 6.32 (d, 1H), 6.50 (m, 2H), 6.78 (b, 1H), 6.82 (m, 2H), 6.91 (d, 2H).

Preparation of N-dimethylaminoethyl 2[(2,6-dichlorophenyl)amino] benzene acetamide.AcOH 2[(2,6-Dichlorophenyl)amino]benzene acetyl chloride hydrochloride (35.1 g, 0.1 mol) was dissolved in 100 ml of acetone. The mixture was cooled to 0° C. Dimethylaminoethylamine (8.9 g) added into the reaction mixture. Sodium bicarbonate (20 g) and water (100 ml) are added into the mixture. The mixture is stirred for 3 hours at RT. The solution is evaporated to dryness. Acetone (100 ml) is added into the residue. The solid side product was removed by filtration and washed with acetone (3×30 ml). 6 g of acetic acid is added into the reaction mixture with stirring. The organic solution was evaporated off. After drying, it yielded 40 g of the desired product (93.8%). Hygroscopic product; Solubility in water: 450 mg/ml; Elementary analysis: $C_{20}H_{25}Cl_2N_3O_3$; MW: 426.34. Calculated % C: 56.34; H: 5.91; Cl: 16.63, N: 9.86; O: 11.26. Found % C: 56.31; H: 5.5.94; Cl: 16.61, N: 9.84; O: 11.30. $^1$H-NMR (400 MHz, CDCl$_3$): δ: 2.21 (s, 3H), 2.91 (s, 6H), 3.44 (s, 2H), 3.51 (t, 2H), 3.64 (t, 2H), 3.93 (b, 1H), 6.32 (d, 1H), 6.50 (m, 2H), 6.78 (b, 1H), 6.82 (m, 2H), 6.91 (d, 2H), 8.0 (b, 1H).

Preparation of dipropylaminoethyl 2[(2,6-dichlorophenyl)amino] benzene acetate.AcOH 31.8 g (0.1 mol) of sodium 2[(2,6-dichlorophenyl)amino] benzene acetate was suspended in 180 ml of chloroform. 28.8 g (0.1 mol) of dipropylaminoethyl bromide.HBr was added into the mixture and the mixture was stirred for 5 hours at RT. 8.2 g (0.1 mol) of sodium acetate was added into the reaction mixture with stirring. The mixture is stirred for 2 hours. The solid was removed by filtration and washed with chloroform (3×50 ml). The solution is concentrated in vacuo to 100 ml. Then 300 ml of hexane was added into the solution. The solid product was collected by filtration and washed with hexane (3×100 ml). After drying, it yielded 41 g of the desired product (87%). Hygroscopic product; Solubility in water: 300 mg/ml; Elementary analysis: $C_{24}H_{32}Cl_2N_2O_4$; MW: 483.43 Calculated % C: 59.63; H: 6.67; Cl: 14.67; N: 5.79; O: 13.24. Found % C: 59.60; H: 6.70; Cl: 14.65, N: 5.78; O: 13.27. $^1$H-NMR (400 MHz, CDCl$_3$): δ: 0.97 (t, 6H), 1.78 (m, 4H), 2.21 (s, 3H), 3.24 (t, 4H), 3.50 (s, 2H), 3.52 (m, 2H), 3.81 (b, 1H), 4.51 (t, 2H), 6.34 (d, 1H), 6.50 (m, 2H), 6.78 (b, 1H), 6.82 (m, 2H), 6.91 (d, 2H).

Preparation of dipropylaminoethyl dipropylaminoethyl 2[(2,6-dichlorophenyl)amino] benzene acetate.AcOH 60 g of Polymer-bound triethylamine (3 mmol/g, 100-200 mesh) was suspended in 180 ml of chloroform. 31.8 g (0.1 mol) of 2[(2,6-dichlorophenyl)amino]benzene acetic acid was added into the mixture with stirring. 43 g (0.15 mol) of dipropylaminoethyl bromide.HBr was added into the mixture and the mixture was stirred for 5 hours at RT. The polymer is removed by filtration and washed with tetrahydrofuran (3×50 ml). 8.2 g (0.1 mol) of sodium acetate was added into the reaction mixture with stirring. The mixture is stirred for 2 h. The solid was removed by filtration and washed with chloroform (3×50 ml). The solution is concentrated in vacuo to 100 ml. Then 300 ml of hexane was added into the solution. The solid product was collected by filtration and washed with hexane (3×100 ml). After drying, it yielded 45 g of the desired product (93.2%). Hygroscopic product; Solubility in water: 300 mg/ml; Elementary analysis: $C_{24}H_{32}Cl_2N_2O_4$; MW: 483.43 Calculated % C: 59.63; H: 6.67; Cl: 14.67; N: 5.79; O: 13.24. Found % C: 59.60; H: 6.70; Cl: 14.65, N: 5.78; O: 13.27. $^1$H-NMR (400 MHz, CDCl$_3$): δ: 0.97 (t, 6H), 1.78 (m, 4H), 2.21 (s, 3H), 3.24 (t, 4H), 3.50 (s, 2H), 3.52 (m, 2H), 3.81 (b, 1H), 4.51 (t, 2H), 6.34 (d, 1H), 6.50 (m, 2H), 6.78 (b, 1H), 6.82 (m, 2H), 6.91 (d, 2H).

Preparation of 1-piperidinepropyl
2[(2,6-dichlorophenyl)amino]benzene acetate.AcOH 31.8 g (0.1 mol) of sodium 2[(2,6-dichlorophenyl)amino] benzene acetate was suspended in 180 ml of chloroform. 28.6 g (0.1 mol) of 1-piperidinepropyl bromide.HBr was added into the mixture and the mixture was stirred for 5 hours at RT. The mixture is washed with 5% Na$_2$CO$_3$ (1×300 ml) and water (3×100 ml). The mixture is dried over anhydrous Na$_2$SO$_4$. Sodium sulfate was removed by filtration and washed with chloroform (3×50 ml). 6 g of acetic acid was added into the solution. The solution is concentrated in vacuo to 100 ml. Then 300 ml of hexane was added into the solution. The solid product was collected by filtration and washed with hexane (3×100 ml). After drying, it yielded 40 g of the desired product (86%). Elementary analysis: $C_{24}H_{30}Cl_2N_2O_4$; MW: 481.43 Calculated % C: 59.88; H: 6.28; Cl: 14.73; N: 5.82; O: 13.29. Found % C: 59.83; H: 6.32; Cl: 14.71, N: 5.79; O: 13.35.

Preparation of diethylaminoethyl
2-(3-benzoyphenyl) propionate.AcOH 11.7 g (0.1 mol) of diethylaminoethanol was dissolved in 10% sodium bicarbonate (200 ml) and acetone (100 ml). 27.3 g (0.1 mol) of 2-(3-benzoyphenyl) propionyl chloride was added into the reaction mixture. The mixture is stirred for 3 hours at RT. The solvents are evaporated off. The residue is suspended in ethyl acetate (500 ml). 5% sodium bicarbonate (200 ml) is added into the reaction mixture with stirring. Ethyl acetate layer is collected and washed with water (3×500 ml). The ethyl acetate solution was dried over anhydrous sodium sulfate. Sodium sulfate is removed by filtration. 6 g of acetic acid is added into the reaction mixture with stirring. The organic solution was evaporated off. After drying, it yielded 36 g of the desired product (87%). Hygroscopic product; Solubility in water: 400 mg/ml; Elementary analysis: $C_{24}H_{31}NO_5$; MW: 413.51. Calculated % C: 69.71; H: 7.56; N: 3.39; O: 19.35; Found % C: 69.69; H: 7.59; N: 3.36; O: 19.36. $^1$H-NMR (400 MHz, CDCl$_3$): δ: 1.51 (d, 3H), δ: 1.56 (t, 6H), 2.21 (s, 3H), 3.27 (m, 4H), 3.52 (m, 2H), 3.78 (m, 1H), 4.52 (t, 2H), 7.0 (b, 1H), 7.31 (m, 2H), 7.36 (m, 2H), 7.45 (m, 1H), 7.51 (m, 1H), 7.56 (m, 1H), 7.70 (m, 2H).

Preparation of dimethylaminoethyl
2-(3-phenoxyphenyl) propionate.AcOH 26.1 g (0.1 mol) of 2-(3-phenoxyphenyl) propionyl chloride was dissolved in 100 ml of chloroform. The mixture was cooled to 0° C. 15 ml of triethylamine and 8.9 g (0.1 mol) of dimethylaminoethanol were added into the reaction mixture. The mixture is stirred for 3 hours at RT. The solvents are evaporated off. The residue is dissolved in methanol (300 ml), 5% sodium bicarbonate (200 ml) is added into the reaction mixture. The mixture is stirred for 3 hr. The mixture is evaporated to dryness. Methanol (300 ml) is added into the residue with stirring. Solid is removed by filtration and washed with methanol. The solution is evaporated to dryness and the residue is dissolved in chloroform (200 ml). 6 g of acetic acid is added into the reaction mixture with stirring. Some solid is removed by filtration. Another 6 g of acetic acid is added into the reaction mixture with stirring. The organic solution was evaporated off. After drying, it yielded 32 g of the desired product (85.7%). Hygroscopic product; Solubility in water: 500 mg/ml; Elementary analysis: $C_{21}H_{27}NO_5$; MW: 373.44. Calculated % C: 67.54; H: 7.29; N: 3.75; O: 21.42. Found % C: 67.51; H: 7.30; N: 3.74; O: 21.45. $^1$H-NMR (400 MHz, CDCl$_3$): δ: 1.51 (d, 3H), δ: 2.21 (s, 3H), 2.91 (s, 6H), 3.52 (m, 2H), 3.78 (m, 1H), 4.51 (t, 2H), 6.70 (b, 1H), 6.74 (m, 1H), 6.78 (m, 1H), 6.84 (m, 1H), 6.92 (m, 2H), 6.98 (m, 1H), 7.17 (m, 1H), 7.22 (m, 2H).

Preparation of S-dimethylaminoethyl
2-(3-phenoxyphenyl) thiopropionate.AcOH 10.4 g (0.1 mol) of dimethylaminoethyl mercaptan was dissolved in 10% sodium bicarbonate (200 ml) and acetone (100 ml). 27.3 g (0.1 mol) of 2-(3-phenoxyphenyl) propionyl chloride was added into the reaction mixture. The mixture is stirred for 3 hours at RT. The solvents are evaporated off. The residue is suspended in ethyl acetate (500 ml). 5% sodium bicarbonate (200 ml) is added into the reaction mixture with stirring. Ethyl acetate layer is collected and washed with water (3×500 ml). The ethyl acetate solution was dried over anhydrous sodium sulfate. Sodium sulfate is removed by filtration. 6 g of acetic acid is added into the reaction mixture with stirring. The organic solution was evaporated off. After drying, it yielded 34 g of the desired product (87.3%). Hygroscopic product; Solubility in water: 400 mg/ml; Elementary analysis: $C_{21}H_{27}NO_4S$; MW: 389.51. Calculated % C: 64.75; H: 6.99; N: 3.60; O: 16.43; S: 8.23. Found % C: 64.73; H: 6.98; N: 3.61; O: 16.46; S: 8.22. $^1$H-NMR (400 MHz, CDCl$_3$): δ: 1.52 (d, 3H), δ: 2.20 (s, 3H), 2.91 (s, 6H), 3.31 (t, 2H), 3.81 (m, 1H), 3.91 (t, 2H), 6.70 (b, 1H), 6.74 (m, 1H), 6.78 (m, 1H), 6.84 (m, 1H), 6.92 (m, 2H), 6.98 (m, 1H), 7.17 (m, 1H), 7.22 (m, 2H).

Preparation of N-dimethylaminoethyl
2-(3-benzoyphenyl) propionate.AcOH 8.8 g (0.1 mol) of dimethylaminoethylamine was dissolved in 10% sodium bicarbonate (200 ml) and acetone (100 ml). 27.3 g (0.1 mol) of 2-(3-benzoyphenyl) propionyl chloride was added into the reaction mixture. The mixture is stirred for 3 hours at RT. The solvents are evaporated off. The residue is suspended in ethyl acetate (500 ml). 5% sodium bicarbonate (200 ml) is added into the reaction mixture with stirring. Ethyl acetate layer is collected and washed with water (3×500 ml). The ethyl acetate solution was dried over anhydrous sodium sulfate. Sodium sulfate is removed by filtration. 6 g of acetic acid is added into the reaction mixture with stirring. The organic solution was evaporated off. After drying, it yielded 33 g of the desired product (85.9%). Hygroscopic product; Solubility in water: 400 mg/ml; Elementary analysis: $C_{22}H_{28}N_2O_5$; MW: 384.20. Calculated % C: 68.73; H: 7.34; N: 7.29; O: 16.65; Found % C: 68.70; H: 7.35; N: 7.29; O: 16.66. $^1$H-NMR (400 MHz, CDCl$_3$): δ: 1.51 (d, 3H), 2.21 (s, 3H), 2.90 (s, 6H), 3.50 (t, 2H), 3.65 (t, 2H), 3.89 (m, 1H), 7.0 (b, 1H), 7.33 (m, 2H), 7.37 (m, 2H), 7.47 (m, 1H), 7.52 (m, 1H), 7.57 (m, 1H), 7.72 (m, 2H), 7.80 (b, 1H).

Preparation of N-dimethylaminoethyl 2-(3-benzoyphenyl) propionate.AcOH 25.7 g (0.1 mol) of 2-(3-benzoyphenyl) propionic acid was dissolved in 100 ml of acetonitrile. 32.1 g of O-(Benzotriazol-1-yl)-N,N,N',N'-tetramethyluronium tetrafluoroborate and 30 ml of triethylamine were added into the reaction mixture. 11.7 g of dimethylaminoethylamine was added into the reaction mixture. The mixture was stirred for 3 hours at RT. The solvents were evaporated off. 250 ml of ethyl acetate was added into the reaction mixture and the mixture was washed with water (3×100 ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration. After drying, it yielded 32 g of the desired product (83.3%). Hygroscopic product; Solubility in water: 400 mg/ml; Elementary analysis: $C_{22}H_{28}N_2O_5$; MW: 384.20. Calculated % C: 68.73; H: 7.34; N: 7.29; O: 16.65. Found % C: 68.70; H: 7.35; N: 7.29; O: 16.66. $^1$H-NMR (400 MHz, CDCl$_3$): δ: 1.51 (d, 3H), 2.21 (s, 3H), 2.90 (s, 6H), 3.50 (t, 2H), 3.65 (t, 2H), 3.89 (m, 1H), 7.0 (b, 1H), 7.33 (m, 2H), 7.37 (m, 2H), 7.47 (m, 1H), 7.52 (m, 1H), 7.57 (m, 1H), 7.72 (m, 2H), 7.80 (b, 1H).

Preparation of diethylaminoethyl 2-(3-benzoyphenyl) propionate.AcOH 60 g of Polymer-bound triethylamine (3 mol/g, 100-200 mesh) was suspended in 180 ml of chloroform. 25.7 g (0.1 mol) of 2-(3-benzoyphenyl) propionic acid was added into the mixture with stirring. 43 g (0.15 mol) of diethylaminoethyl bromide.HBr was added into the mixture and the mixture was stirred for 5 hours at RT. The polymer was removed by filtration and washed with tetrahydrofuran (3×50 ml). 8.2 g (0.1 mol) of sodium acetate was added into the reaction mixture with stirring. The mixture was stirred for 2 h. The solid was removed by filtration and washed with chloroform (3×50 ml). The solution was concentrated in vacuo to 100 ml. Then 300 ml of hexane was added into the solution. The solid product was collected by filtration and washed with hexane (3×100 ml). After drying, it yielded 36 g of the desired product (87%). Hygroscopic product; Solubility in water: 400 mg/ml; Elementary analysis: $C_{24}H_{31}NO_5$; MW: 413.51. Calculated % C: 69.71; H: 7.56; N: 3.39; O: 19.35. Found % C: 69.69; H: 7.59; N: 3.36; O: 19.36. $^1$H-NMR (400 MHz, CDCl$_3$): δ: 1.51 (d, 3H), δ: 1.56 (t, 6H), 2.21 (s, 3H), 3.27 (m, 4H), 3.52 (m, 2H), 3.78 (m, 1H), 4.52 (t, 2H), 7.0 (b, 1H), 7.31 (m, 2H), 7.36 (m, 2H), 7.45 (m, 1H), 7.51 (m, 1H), 7.56 (m, 1H), 7.70 (m, 2H).

Preparation of diethylaminoethyl 2-(6-methoxy-2-naphthyl) propionate.AcOH 11.7 g (0.1 mol) of diethylaminoethanol was dissolved in 10% sodium bicarbonate (200 ml) and acetone (100 ml). 24.9 g (0.1 mol) of 2-(6-methoxy-2-naphthyl) propionyl chloride was added into the reaction mixture. The mixture is stirred for 3 hours at RT. The solvents are evaporated off. The residue is suspended in ethyl acetate (500 ml). 5% sodium bicarbonate (200 ml) is added into the reaction mixture with stirring. Ethyl acetate layer is collected and washed with water (3×500 ml). The ethyl acetate solution was dried over anhydrous sodium sulfate. Sodium sulfate is removed by filtration. 6 g of acetic acid is added into the reaction mixture with stirring. The organic solution was evaporated off. After drying, it yielded 36 g of the desired product (89.9%). Hygroscopic product; Solubility in water: 300 mg/ml; Elementary analysis: $C_{22}H_{31}NO_5$; MW: 389.49. Calculated % C: 67.84; H: 8.02; N: 3.60; O: 20.54; Found % C: 67.82; H: 8.04; N: 3.58; O: 20.56. $^1$H-NMR (400 MHz, D$_2$O): δ: 1.36 (t, 6H), 1.50 (d, 3H), 2.11 (s, 3H), 3.20 (m, 4H), 3.47 (m, 2H), 3.70 (s, 3H), 3.78 (m, 1H), 4.48 (t, 2H), 6.88 (b, 1H), 6.98 (s, 1H), 7.03 (d, 1H), 7.18 (d, 1H), 7.43 (s, 1H), 7.50 (d, 1H), 7.54 (d, 1H).

Preparation of diethylaminoethyl α-methyl-4-(2-thienylcarbonyl) benzeneacetate.AcOH 28.1 g (0.1 mol) of α-methyl-4-(2-thienylcarbonyl) benzeneacetyl chloride was dissolved in 100 ml of chloroform. The mixture was cooled to 0° C. 15 ml of triethylamine and 11.7 g (0.1 mol) of diethylaminoethanol were added into the reaction mixture. The mixture is stirred for 3 hours at RT. The solvents are evaporated off. The residue is dissolved in methanol (300 ml), 5% sodium bicarbonate (200 ml) is added into the reaction mixture. The mixture is stirred for 3 hr. The mixture is evaporated to dryness. Methanol (300 ml) is added into the residue with stirring. Solid is removed by filtration and washed with methanol. The solution is evaporated to dryness and the residue is dissolved in chloroform (200 ml). 6 g of acetic acid is added into the reaction mixture with stirring. Some solid is removed by filtration. Another 6 g of acetic acid is added into the reaction mixture with stirring. The organic solution was evaporated off. After drying, it yielded 35 g of the desired product (83.2%). Hygroscopic product; Solubility in water: 400 mg/ml; Elementary analysis: $C_{22}H_{31}NO_5S$; MW: 419.53. Calculated % C: 62.68; H: 7.41; N: 3.32; O: 18.98; S: 7.61. Found % C: 62.63; H: 7.45; N: 3.31; O: 19.01; S: 7.60. $^1$H-NMR (400 MHz, D$_2$O): δ: 1.36 (t, 6H), 1.45 (d, 3H), 2.11 (s, 3H), 3.20 (m, 4H), 3.47 (m, 2H), 3.78 (m, 1H), 4.48 (t, 2H), 6.88 (b, 1H), 6.98 (s, 1H), 7.31 (d, 2H), 7.05 (m, 1H), 7.43 (m, 2H), 7.70 (d, 2H).

Preparation of S-dimethylaminoethyl 2-(2-fluoro-4-biphenylyl) propionate.AcOH 13.2 g (0.1 mol) of diethylaminoethyl mercaptan was dissolved in 10% sodium bicarbonate (200 ml) and acetone (100 ml). 26.3 g (0.1 mol) of 2-(2-fluoro-4-biphenylyl) propionyl chloride was added into the reaction mixture. The mixture is stirred for 3 hours at RT. The solvents are evaporated off. The residue is suspended in ethyl acetate (500 ml). 5% sodium bicarbonate (200 ml) is added into the reaction mixture with stirring. Ethyl acetate layer is collected and washed with water (3×500 ml). The ethyl acetate solution was dried over anhydrous sodium sulfate. Sodium sulfate is removed by filtration. 6 g of acetic acid is added into the reaction mixture with stirring. The organic solution was evaporated off. After drying, it yielded 36 g of the desired product (85.8%). Hygroscopic product; Solubility in water: 400 mg/ml; Elementary analysis: $C_{23}H_{30}FNO_3S$; MW: 419.55. Calculated % C: 65.84; H: 7.21; F: 4.53; N: 3.34; O: 11.44; S: 7.64. Found % C: 65.80; H: 7.23; F: 4.55; N: 3.32, O: 11.47; S: 7.63. $^1$H-NMR (400 MHz, $D_2O$): δ: 1.35 (t, 6H), 1.44 (d, 3H), 2.11 (s, 3H), 3.20 (m, 4H), 3.30 (t, 2H), 3.80 (m, 1H), 3.88 (t, 2H), 6.88 (b, 1H), 6.88 (m, 1H), 6.95 (m, 1H), 7.22 (m, 1H), 7.32 (m, 2H), 7.41 (m, 1H), 7.48 (m, 2H).

Preparation of N-dimethylaminoethyl diethylaminoethyl 5-benzoyl-2, 3-dihydro-1H-pyrrolizine-1-carboxylamide.AcOH.AcOH 11.7 g (0.1 mol) of diethylaminoethylamine was dissolved in 10% sodium bicarbonate (200 ml) and acetone (100 ml). 27.4 g (0.1 mol) of 5-benzoyl-2, 3-dihydro-1H-pyrrolizine-1-carboxylyl chloride was added into the reaction mixture. The mixture is stirred for 3 hours at RT. The solvents are evaporated off. The residue is suspended in ethyl acetate (500 ml). 5% sodium bicarbonate (200 ml) is added into the reaction mixture with stirring. Ethyl acetate layer is collected and washed with water (3×500 ml). The ethyl acetate solution was dried over anhydrous sodium sulfate. Sodium sulfate is removed by filtration. 6 g of acetic acid is added into the reaction mixture with stirring. The organic solution was evaporated off. After drying, it yielded 35 g of the desired product (84.8%). Hygroscopic product; Solubility in water: 400 mg/ml; Elementary analysis: $C_{23}H_{31}N_3O_4$; MW: 412.50. Calculated % C: 66.81; H: 7.56; N: 10.16; O: 15.48. Found % C: 66.90; H: 7.38; N: 10.18; O: 15.54. $^1$H-NMR (400 MHz, $D_2O$): δ: 1.39 (t, 6H), 2.10 (s, 3H), 2.27 (m, 2H), 3.22 (m, 4H), 3.50 (t, 2H), 3.60 (t, 2H), 3.80 (m, 2H), 3.71 (m, 1H), 5.85 (m, 1H), 6.70 (m, 1H), 6.85 (b, 1H), 7.32 (b, 1H), 7.40 (m, 1H), 7.45 (m, 2H), 7.78 (m, 2H).

Preparation of N-diethylaminoethyl 4, 5-Diphenyl-2-oxazole propionamide.AcOH 29.3 g (0.1 mol) of 4, 5-Diphenyl-2-oxazole propionic acid was dissolved in 100 ml of acetonitrile. 32.1 g of O-(Benzotriazol-1-yl)-N,N,N',N'-tetramethyluronium tetrafluoroborate and 30 ml of triethylamine were added into the reaction mixture. 11.6 g of diethylaminoethylamine was added into the reaction mixture. The mixture was stirred for 3 hours at RT. The solvents were evaporated off. 250 ml of ethyl acetate was added into the reaction mixture and the mixture was washed with water (3×100 ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration. After drying, it yielded 40 g of the desired product (88.6%). Hygroscopic product; Solubility in water: 400 mg/ml; Elementary analysis: $C_{26}H_{33}N_3O_4$; MW: 451.56. Calculated % C: 69.16; H: 7.37; N: 9.31; O: 14.17. Found % C: 69.11; H: 7.40; N: 9.30; O: 14.19. $^1$H-NMR (400 MHz, $D_2O$): δ: 1.41 (t, 6H), 2.10 (s, 3H), 2.45 (t, 2H), 2.76 (t, 2H), 3.22 (m, 4H), 3.49 (t, 2H), 3.60 (t, 2H), 6.87 (b, 1H), 7.22 (b, 1H), 7.22 (m, 2H), 7.32 (m, 4H), 7.47 (m, 4H).

Preparation of diethylaminoethyl 6-chloro-α-methyl-9H-carbazole-2-acetate.AcOH 60 g of Polymer-bound triethylamine (3 mol/g, 100-200 mesh) was suspended in 180 ml of chloroform. 27.4 g (0.1 mol) of 6-chloro-α-methyl-9H-carbazole-2-acetic acid was added into the mixture with stirring. 43 g (0.15 mol) of diethylaminoethyl bromide.HBr was added into the mixture and the mixture was stirred for 5 hours at RT. The polymer was removed by filtration and washed with tetrahydrofuran (3×50 ml). 8.2 g (0.1 mol) of sodium acetate was added into the reaction mixture with stirring. The mixture was stirred for 2 h. The solid was removed by filtration and washed with chloroform (3×50 ml). The solution was concentrated in vacuo to 100 ml. Then 300 ml of hexane was added into the solution. The solid product was collected by filtration and washed with hexane (3×100 ml). After drying, it yielded 38 g of the desired product (87.8%). Hygroscopic product; Solubility in water: 400 mg/ml; Elementary analysis: $C_{23}H_{29}ClN_2O_4$; MW: 432.94. Calculated % C: 63.81; H: 6.75; Cl: 8.19, N: 6.47; O: 14.78. Found % C: 63.85; H: 6.78; Cl: 8.17; N: 6.44; O: 14.76. $^1$H-NMR (400 MHz, $D_2O$): δ: 1.39 (t, 6H), 1.47 (d, 3H), 2.11 (s, 3H), 3.21 (m, 4H), 3.49 (m, 2H), 3.77 (m, 1H), 4.48 (t, 2H), 6.80 (b, 1H), 6.85 (m, 1H), 7.10 (m, 1H), 7.05 (m, 1H), 7.26 (m, 1H), 7.34 (m, 1H), 7.50 (m, 1H), 7.52 (m, 1H).

Preparation of N-diethylaminoethyl 2-[(2,3-dimethylphenyl) amino]benzoamide.AcOH 24.1 g (0.1 mol) of 2-[(2,3-dimethylphenyl)amino]benzoic acid was dissolved in 100 ml of acetonitrile. 32.1 g of O-(Benzotriazol-1-yl)-N,N,N',N'-tetramethyluronium tetrafluoroborate and 30 ml of triethylamine were added into the reaction mixture. 11.6 g of dimethylaminoethylamine was added into the reaction mixture. The mixture was stirred for 3 hours at RT. The solvents were evaporated off. 250 ml of ethyl acetate was added into the reaction mixture and the mixture was washed with water (3×100 ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration. After drying, it yielded 37 g of the desired product (92.5%). Hygroscopic product; Solubility in water: 400 mg/ml; Elementary analysis: $C_{23}H_{33}N_3O_4$; MW: 399.53. Calculated % C: 69.14; H: 8.33; N: 10.52; O: 12.01. Found % C: 69.11; H: 8.35; N: 10.51; O: 12.03. $^1$H-NMR (400 MHz, $D_2O$): δ: 1.41 (t, 6H), 2.10 (s, 3H), 2.30 (s, 3H), 2.31 (s, 3H), 3.22 (m, 4H), 3.54 (m, 2H), 3.60 (m, 2H), 6.15 (m, 1H), 6.30 (m, 1H), 6.57 (m, 1H), 6.72 (m, 1H), 7.20 (m, 2H), 7.70 (m, 1H), 7.80 (b, 1H).

Preparation of N-diethylaminoethyl 2-[(2,6-dichloro-3-methylphenyl)amino]benzoamide.AcOH 29.6 g (0.1 mol) of 2-[(2,6-dichloro-3-methylphenyl) amino]benzoic acid was dissolved in 300 ml of chloroform. 20.6 g of N, N'-Dicyclohexylcarbodiimide was added into the reaction mixture. 11.7 g of diethylaminoethylamine was added into the reaction mixture. The mixture was stirred for 3 hours at RT. The solid is removed by filtration. The chloroform solution was washed with 5% $NaHCO_3$ (2×100 ml) and water (3×100 ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration. After drying, it yielded 39 g of the desired product (85.8%). Hygroscopic product; Solubility in water: 400 mg/ml; Elementary analysis: $C_{22}H_{29}Cl_2N_3O_3$; MW: 454.39. Calculated % C: 58.15; H: 6.43; Cl: 15.60; N: 9.25, O: 10.56. Found % C: 58.10; H: 6.46; Cl: 15.62; N: 9.22, O: 10.60. $^1$H-NMR (400 MHz, $D_2O$): δ: 1.43 (t, 6H), 2.11 (s, 3H), 2.28 (s, 3H), 3.23 (m, 4H), 3.49 (m, 2H), 3.63 (m, 2H), 6.30 (d, 1H), 6.57 (m, 1H), 6.72 (d, 1H), 6.80 (m, 1H), 7.20 (m, 1H), 7.68 (m, 1H), 7.70 (b, 1H).

Preparation of S-dimethylaminoethyl 2-[[(3-trifluoromethyl)phenyl]amino]benzoate.AcOH 28.1 g (0.1 mol) of 2-[[(3-trifluoromethyl)phenyl]amino] benzoic acid was dissolved in 300 ml of chloroform. N, N'-Dicyclohexylcarbodiimide was added into the reaction mixture. 11.7 g of dimethylaminoethyl mercaptan was added into the reaction mixture. The mixture was stirred for 3 hours at RT. The solid is removed by filtration. The chloroform solution was washed with 5% $NaHCO_3$ ($2 \times 100$ ml) and water ($3 \times 100$ ml). The organic solution was dried over anhydrous sodium sulfate. Sodium sulfate was removed by filtration. 6 g of acetic acid was added into the reaction mixture with stirring. Hexane (200 ml) was added. The solid product was collected by filtration. After drying, it yielded 39 g of the desired product (88.5%). Hygroscopic product; Solubility in water: 400 mg/ml; Elementary analysis: $C_{21}H_{26}F_3N_3O_3S$; MW: 456.52. Calculated % C: 57.88; H: 5.96; F: 12.48; N: 6.14, O: 10.51; S: 7.02. Found % C: 57.84; H: 5.99; F: 12.45; N: 6.15, O: 10.56, S: 7.01. $^1$H-NMR (400 MHz, $D_2O$): δ: 1.44 (t, 6H), 2.11 (s, 3H), 3.23 (m, 4H), 3.30 (m, 2H), 3.90 (m, 2H), 6.46 (m, 1H), 6.65 (m, 2H), 6.77 (m, 2H), 6.90 (m, 1H), 7.30 (m, 1H), 7.78 (m, 1H).

Preparation of diethylaminoethyl 2-[[3-(trifluoromethyl)phenyl]amino]-3-pyridinecarboxylate.AcOH 28.2 g (0.1 mol) of 2-[[3-(trifluoromethyl)phenyl]amino]-3-pyridinecarboxylic acid was dissolved in 200 ml of 10% $NaHCO_3$. 100 ml of acetone and 43 g (0.15 mol) of diethylaminoethyl bromide.HBr was added into the mixture and the mixture was stirred for 5 hours at RT. The mixture is extracted with ethyl acetate ($2 \times 300$ ml). The ethyl acetate solution is dried over anhydrous sodium sulfate. 6 g of acetic acid is added into the solution. The solution was concentrated in vacuo to 100 ml. Then 300 ml of hexane was added into the solution. The solid product was collected by filtration and washed with hexane ($3 \times 100$ ml). After drying, it yielded 38 g of the desired product (86.1%). Hygroscopic product; Solubility in water: 400 mg/ml; Elementary analysis: $C_{21}H_{26}F_3N_3O_4$; MW: 441.44. Calculated % C: 57.14; H: 5.94; F: 12.91, N: 9.52; O: 14.50. Found % C: 57.11; H: 5.97; F: 12.92; N: 9.50; O: 14.50. $^1$H-NMR (400 MHz, $D_2O$): δ: 1.44 (t, 6H), 2.11 (s, 3H), 3.23 (m, 4H), 3.70 (m, 2H), 4.60 (m, 2H), 6.46 (m, 1H), 6.65 (s, 1H), 6.77 (m, 1H), 6.83 (m, 1H), 6.90 (m, 1H), 8.00 (m, 1H), 8.38 (m, 1H).

Preparation of diethylaminoethyl 2-[[2-methyl-3-(trifluoromethyl)phenyl]amino]-3-pyridinecarboxylate.AcOH 60 g of Polymer-bound triethylamine (3 mol/g, 100-200 mesh) was suspended in 180 ml of chloroform. 29.6 g (0.1 mol) of 2-[[2-methyl-3-(trifluoromethyl)phenyl]amino]-3-pyridinecarboxylic acid was added into the mixture with stirring. 43 g (0.15 mol) of diethylaminoethyl bromide.HBr was added into the mixture and the mixture was stirred for 5 hours at RT. The polymer was removed by filtration and washed with tetrahydrofuran ($3 \times 50$ ml). 8.2 g (0.1 mol) of sodium acetate was added into the reaction mixture with stirring. The mixture was stirred for 2 h. The solid was removed by filtration and washed with chloroform ($3 \times 50$ ml). The solution was concentrated in vacuo to 100 ml. Then 300 ml of hexane was added into the solution. The solid product was collected by filtration and washed with hexane ($3 \times 100$ ml). After drying, it yielded 40 g of the desired product (87.8%). Hygroscopic product; Solubility in water: 400 mg/ml; Elementary analysis: $C_{22}H_{28}F_3N_3O_4$; MW: 455.47. Calculated % C: 58.01; H: 6.20; F: 12.51, N: 9.23; O: 14.05. Found % C: 57.98; H: 6.23; F: 12.50; N: 9.21; O: 14.08. $^1$H-NMR (400 MHz, $D_2O$): δ: 1.45 (t, 6H), 2.11 (s, 3H), 2.35 (s, 3H), 3.23 (m, 4H), 3.70 (m, 2H), 4.60 (m, 2H), 6.36 (m, 1H), 6.65 (m, 1H), 6.77 (m, 1H), 6.83 (m, 1H), 8.00 (m, 1H), 8.38 (m, 1H).

ii) Preparation of a HPP from a Parent Drug which Contains at Least One Non-Carbonyl Group In certain embodiments, the parent compound having the following Drug-$X_1$H Structure F is converted to a HPP of Structure

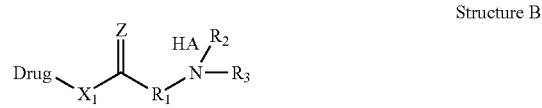

Structure B including stereoisomers and pharmaceutically acceptable salts thereof, wherein:

$X_1$ is selected from the group consisting of O, P(O)O$R_1$, NH, N$R_1$ and S;

Z is selected from the group consisting of O and S. (Scheme 2)

Scheme 2. Preparation of a HPP from a compound.

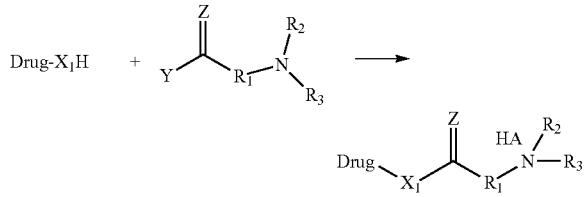

In one embodiment of the invention, a HPP having Structure B is prepared according to the conventional organic synthesis by reacting the parent drug or derivatives of the parent compounds of Structure 7 (e.g. acid halides, mixed anhydrides of the parent compounds, etc.):

Drug-$X_1$H

Structure G wherein X1 is defined as supra, with compounds of Structure H:

Structure H wherein Y, Z, $R_1$, $R_2$, and $R_3$ are defined as supra.

Preparation of 4-N,N-dimethylaminobutyryloxy-2-methyl-N-2-pyridinyl-2H, 1,2-benzothiazine-3-carboxamide 1,1-dioxide.HCl 33.1 g (0.1 mol) of 4-hydroxy-2-methyl-N-2-pyridinyl-2H, 1,2-benzothiazine-3-carboxamide 1,1-dioxide was dissolved in 200 ml of acetone and 250 ml of 10% $NaHCO_3$. 22.3 g (0.12 mol) of dimethylaminobutyryl chloride hydrochloride was added into the mixture. The mixture was stirred for 3 hours at RT. The solvents were evaporated off. 500 ml of ethyl acetate was added into the reaction mixture and the mixture was washed with 5% $NaHCO_3$ (1×200 ml) and water (3×100 ml). The organic solution was dried over anhydrous sodium sulfate. Sodium sulfate was removed by filtration. HCl gas (4 g) is bubbled into the solution. The solid product was collected by filtration. After drying, it yielded 40 g of the hygroscopic desired product (83.2%). Solubility in water: 250 mg/ml; Elementary analysis: $C_{21}H_{25}ClN_4O_5S$; MW: 480.96. Calculated % C: 52.44, H: 5.24, Cl: 7.37, N: 11.65, O: 16.63, S: 6.67. Found % C: 52.40, H: 5.27, Cl: 7.42, N: 11.60; O: 16.70, S: 6.61. $^1$H-NMR (400 MHz, $D_2O$): δ: 2.00 (m, 2H), 2.23 (m, 2H), 2.46 (s, 3H), 2.85 (s, 6H), 3.18 (m, 2H), 6.60-6.70 (m, 2H), 7.20 (m, 1H), 7.40-7.44 (m, 2H), 7.56 (m, 1H), 7.80 (m, 1H), 8.10 (m, 1H).

Preparation of N-(2-thiazolyl)-4-N,N-dimethylaminobutyryloxy-2-methyl-2H, 1,2-benzothiazine-3-carboxamide 1,1-dioxide.HCl 32.5 g (0.1 mol) of N-(2-thiazolyl)-4-hydroxy-2-methyl-2H, 1,2-benzothiazine-3-carboxamide 1,1-dioxide and 16 g (0.1 mol) of diethylaminobutyric acid were dissolved in 300 ml of dichloromethylene. The mixture is cooled to 0° C. with ice bath. 20.6 g (0.1 mol) of N, N'-Dicyclohexylcarbodiimide was added into the reaction mixture. The mixture was stirred for 1 hour at 0° C. and 2 hours at RT. The solid is removed by filtration. The dichloromethylene solution was washed with 5% $NaHCO_3$ (2×100 ml) and water (3×100 ml). The organic solution was dried over anhydrous sodium sulfate. Sodium sulfate was removed by filtration. HCl gas (4 g) is bubbled into the solution. The solid product was collected by filtration. After drying, it yielded 37 g of the hygroscopic desired product (76%). Solubility in water: 250 mg/ml; elementary analysis: $C_{19}H_{23}ClN_4O_5S_2$; MW: 486.99. Calculated % C: 46.86, H: 4.76, Cl: 7.28, N: 11.50, O: 16.43, S: 13.17. Found % C: 46.83, H: 4.78, Cl: 7.31, N: 11.52, O: 16.41, S: 13.15. $^1$H-NMR (400 MHz, $D_2O$): δ: 2.01 (m, 2H), 2.22 (m, 2H), 2.44 (s, 3H), 2.85 (s, 6H), 3.18 (m, 2H), 6.50 (m, 1H), 7.20 (m, 1H), 7.40 (m, 1H), 7.50 (m, 1H), 7.58 (m, 1H), 7.85 (m, 1H).

Preparation of 6-chloro-4-N,N-dimethylaminobutyryloxy-2-methyl-N-2-pyridinyl-2H-thieno[2,3-e]-1,2-thiazine-3-carboxamide 1,1-dioxide.HCl 36 g (0.1 mol) of 6-chloro-4-hydroxy-2-methyl-N-2-pyridinyl-2H-thieno[2,3-e]-1,2-thiazine-3-carboxamide 1,1-dioxide.HCl was dissolved in 200 ml of acetone and 200 ml of 10% $NaHCO_3$. 22.3 g (0.12 mol) of dimethylaminobutyryl chloride hydrochloride was added into the mixture and the mixture was stirred for 3 hours at RT. The solvents were evaporated off. 500 ml of ethyl acetate was added into the reaction mixture and the mixture was washed with 10% $NaHCO_3$ (1×500 ml) and water (3×100 ml). The organic solution was dried over anhydrous sodium sulfate. Sodium sulfate was removed by filtration. HCl gas is bubbled into the solution. The solid product was collected by filtration. After drying, it yielded 42 g of the hygroscopic desired product (80.5%). Solubility in water: 250 mg/ml; Elementary analysis: $C_{19}H_{22}Cl_2N_4O_5S_2$; MW: 521.44. Calculated % C: 43.76, H: 4.25, Cl: 13.60, N: 10.74, O: 15.34, S: 12.30. Found % C: 43.72, H: 4.27, Cl: 13.67, N: 10.70; O: 15.37, S: 12.27. $^1$H-NMR (400 MHz, $D_2O$): δ: 2.02 (m, 2H), 2.21 (m, 2H), 2.47 (s, 3H), 2.86 (s, 6H), 3.18 (m, 2H), 6.60-6.70 (m, 2H), 7.10 (s, 1H), 7.44 (m, 1H), 8.10 (m, 1H).

Preparation of 4-N,N-dimethylaminobutyryloxy-2-methyl-N-2-pyridinyl-2H-thieno[2,3-e]-1,2-thiazine-3-carboxamide 1,1-dioxide.HCL 32.5 g (0.1 mol) of 4-hydroxy-2-methyl-N-2-pyridinyl-2H-thieno[2,3-e]-1,2-thiazine-3-carboxamide 1,1-dioxide and 16 g (0.1 mol) of diethylaminobutyric acid were dissolved in 300 ml of dichloromethylene. The mixture is cooled to 0° C. with ice bath. 20.6 g (0.1 mol) of N, N'-Dicyclohexylcarbodiimide was added into the reaction mixture. The mixture was stirred for 1 hour at 0° C. and 2 hours at RT. The solid is removed by filtration. The dichloromethylene solution was washed with 5% $NaHCO_3$ (2×100 ml) and water (3×100 ml). The organic solution was dried over anhydrous sodium sulfate. Sodium sulfate was removed by filtration. HCl gas (4 g) is bubbled into the solution. The solid product was collected by filtration. After drying, it yielded 39 g of the hygroscopic desired product (80.1%). Solubility in water: 250 mg/ml; Elementary analysis: $C_{19}H_{23}ClN_4O_5S_2$; MW: 486.99. Calculated % C: 46.86, H: 4.76, Cl: 7.28, N: 11.50, O: 16.43, S: 13.17. Found % C: 46.82, H: 4.77, Cl: 7.30, N: 11.47; O: 16.47, S: 13.15. $^1$H-NMR (400 MHz, $D_2O$): δ: 2.02 (m, 2H), 2.21 (m, 2H), 2.47 (s, 3H), 2.86 (s, 6H), 3.18 (m, 2H), 6.61-6.70 (m, 2H), 7.30 (d, 1H), 7.45 (m, 1H), 7.60 (d, 1H), 8.11 (m, 1H).

Preparation of 4-N,N-dimethylaminobutyryloxy-2-methyl-N-[5-Methyl-3-isoxolyl-2H-1,2-benzothiazine-3-carboxamide 1,1-dioxide].HCl 32.5 g (0.1 mol) of 4-hydroxy-2-methyl-N-[5-Methyl-3-isoxolyl-2H-1,2-benzothiazine-3-carboxamide 1,1-dioxide].HCl and 16 g (0.1 mol) of diethylaminobutyric acid were dissolved in 300 ml of dichloromethylene. The mixture is cooled to 0° C. with ice bath. 20.6 g (0.1 mol) of N, N'-Dicyclohexylcarbodiimide was added into the reaction mixture. The mixture was stirred for 1 hour at 0° C. and 2 hours at RT. The solid is removed by filtration. The dichloromethylene solution was washed with 5% $NaHCO_3$ (2×100 ml) and water (3×100 ml). The organic solution was dried over anhydrous sodium sulfate. Sodium sulfate was removed by filtration. HCl gas (4 g) is bubbled into the solution. The solid product was collected by filtration. After drying, it yielded 37 g of the hygroscopic desired product (78.7%). Solubility in water: 250 mg/ml; Elementary analysis: $C_{19}H_{23}ClN_4O_6S$; MW: 470.93. Calculated % C: 48.46, H: 4.92, Cl: 7.53, N: 11.90, O: 20.38, S: 6.81. Found % C: 48.43, H: 4.94, Cl: 7.57, N: 11.86, O: 20.41, S: 6.79. $^1$H-NMR (400 MHz, $D_2O$): δ: 2.01 (m, 2H), 2.22 (m, 2H), 2.44 (s, 3H), 2.85 (s, 6H), 3.18 (m, 2H), 6.40 (m, 1H), 7.20 (m, 1H), 7.40 (m, 1H), 7.52 (m, 1H), 7.58 (m, 1H), 7.85 (m, 1H).

Example 2. The HPPs have Higher Aqueous Solubility Comparing to their Parent Drugs HPPs have higher aqueous solubility comparing to their parent drugs (Table 1).

TABLE 1

| Solubility of NSAIAs and NSAIA-HPPs | | | |
|---|---|---|---|
| HPP | (g/L) | Parent Drug | (g/L) |
| diethylaminoethyl acetylsalicylate•AcOH in pH 7 phosphate buffer | >300 | Aspirin | 0.01 |
| diethylaminoethyl 5-(2,4-difluorophenyl) salicylate•AcOH in water | >400 | Diflunisal | 0.05 |
| diethylaminoethyl salicylsalicylate•AcOH | >350 | Salsalate | 0.07 |
| diethylaminoethyl salicylate•AcOH | >400 | salicylic acid | 0.1 |
| diethylaminoethyl 2-(p-isobutylphenyl) propionate•AcOH in water | >300 | Ibuprofen | 0.05 |
| diethylaminoethyl 2-(3-benzoylphenyl) propionate•AcOH in water | >450 | Ketoprofen | 0.1 |
| diethylaminoethyl 2-(3-phenoxyphenyl) propionate•AcOH | >450 | Fenoprofen | 0.1 |
| diethylaminoethyl 2-(6-methoxy-2-naphthyl)propionate•AcOH | >450 | Naproxen | 0.1, |
| diethylaminoethyl α-methyl-4-(2-thienylcarbonyl)benzeneacetate•AcOH, | >400 | Suprofen | 0.1 |
| diethylaminoethyl α-methyl-(p-chlorobenzoyl)-5-methoxy-2-methylindole 3-acetate•AcOH, | >450 | α-methyl-(p-chlorobenzoyl)-5-methoxy-2-methylindole 3-acetic acid | 0.2 |
| diethylaminoethyl 2-(2-fluoro-4-biphenylyl) propionate•AcOH, | >450 | Flurbiprofen | 0.2 |
| diethylaminoethyl 6-chloro-α-methyl-9H-carbazole-2-acetate•AcOH, | >350 | Carprofen | 0.1 |
| diethylaminoethyl α-methyl-5H-[1]benzopyrano[2,3-b]pyridine-7-acetate•AcOH, | >450 | Pranoprofen | 0.2 |
| diethylaminoethyl 2-(4-chlorophenyl)-α-methyl-5-benzoxazoleacetate•AcOH | >400 | Benoxaprofen | 0.1 |
| diethylaminoethyl α-methyl-4-[(2-methyl-2-propenyl)amino]benzeneacetate•AcOH, | >450 | Alminoprofen | 0.1 |
| diethylaminoethyl 5-benzoyl-α-methyl-2-thiopheneacetate•AcOH, | >400 | Tiaprofenic acid | 0.1 |
| diethylaminoethyl 3-chloro-4-(2,5-dihydro-1H-pyrrol-1-yl)-α-methyl benzeneacetate•AcOH, | >450 | Pirprofen | 0.1 |
| diethylaminoethyl 2-(10,11-dihydro-10-oxodibenzo(b,f)thiepin-2-yl)propionate•AcOH, | >350 | Zaltoprofen | 0.1 |
| diethylaminoethyl 2-(8-methyl-10,11-dihydro-11-oxodibenz(b,f)oxepin-2-yl)propionate•AcOH, | >400 | Bermoprofen | 0.1 |
| diethylaminoethyl 2-[4-(2-oxocyclopentyl-methyl)phenyl]propionate•AcOH, | >350 | Loxoprofen | 0.1 |
| diethylaminoethyl 4-(1,3-dihydro-1-oxo-2H-isoindol-2-yl)-α-methylbenzeneacetate•AcOH, | >400 | Indoprofen | 0.1 |
| diethylaminoethyl α,3-dichloro-4-cyclohexylbenzeneacetate•AcOH, | >350 | Fenclorac | 0.2 |
| diethylaminoethyl 4,5-Diphenyl-2-oxazole propionate•AcOH, | >400 | Oxaprozin | 0.1 |
| diethylaminoethyl 3-(4-biphenylylcarbonyl)propionate•AcOH, | >400 | Fenbufen | 0.1 |
| diethylaminoethyl 5-(4-chlorophenyl)-beta-hydroxy-2-furanpropionate•AcOH, | >350 | Orpanoxin | 0.1 |
| diethylaminoethyl 5-benzoyl-2,3-dihydro-1H-pyrrolizine-1-carboxylate•AcOH, | >450 | Ketorolac | 0.1 |
| diethylaminoethyl 6-chloro-5-cyclohexyl-2,3-dihydro-1H-indene-1-carboxylate•AcOH | >350 | Clidanac | 0.1 |
| diethylaminoethyl 1-(p-chlorobenzoyl)-5-methoxy-2-methylindole 3-acetate•AcOH | >250 | Indomethacin | 0.1 |
| diethylaminoethyl (Z)-5-fluoro-2-methyl-1-[(4-methylsulfinyl) phenylmethylene]-1H-indene-3-acetate•AcOH, | >200 | Sulindac | 0.1 |
| diethylaminoethyl 1-methyl-5-(4-methylbenzoyl)-1H-pyrrole-2-acetate•AcOH, | >250 | Tolmetin | 0.2 |
| diethylaminoethyl 5-(4-Chlorobenzoyl)-1,4-dimethyl-1H-pyrrole-2-acetate•AcOH, | >250 | Zomepirac | 0.2 |
| diethylaminoethyl 1,8-diethyl-1,3,4,9-tetrahydropyrano-[3,4-b]indole-1-acetate•AcOH, | >250 | Etodolac | 0.1 |
| diethylaminoethyl 2-amino-3-benzoylbenzeneacetate•AcOH, | >250 | Amfenac | 0.2 |
| diethylaminoethyl 2-amino-3-(4-bromo-benzoyl)benzeneacetate•AcOH, | >200 | Bromofenac | 0.1 |

TABLE 1-continued

Solubility of NSAIAs and NSAIA-HPPs

| HPP | (g/L) | Parent Drug | (g/L) |
|---|---|---|---|
| diethylaminoethyl 3-chloro-4-(2-propenyloxy)benzeneacetate•AcOH, | >200 | Alclofenac | 0.1 |
| diethylaminoethyl 2-(2,4-dichlorophenoxy)benzeneacetate•AcOH, | >200 | Fenclofenac | 0.1 |
| diethylaminoethyl 1-(4-chlorobenzoyl-5-methoxy-2-methyl-1H-indole-3-acetoxyacetate•AcOH, | >250 | Acemetacin | 0.1 |
| diethylaminoethyl 4-(4-chlorophenyl)-2-phenyl-5-thiazoleacetate•AcOH, | >150 | Fentiazac | 0.1 |
| diethylaminoethyl 3-(4-chlorophenyl)-1-phenyl-1H-pyrazole-4-acetate•AcOH, | >200 | Lonazolac | 0.1 |
| diethylaminoethyl [(1-benzyl-1H-indazol-3-yl)oxy]acetate•AcOH, | >250 | Bendazac | 0.1 |
| diethylaminoethyl 6-methoxyl-2-naphthalene-2-acetate•AcOH, | >200 | 6MNA | 0.1 |
| diethylaminoethyl ρ-isobutylphenylacetate•AcOH, | >250 | Ibufenac | 0.1 |
| diethylaminoethyl 2[(2,6-dichlorophenyl)amino]benzene acetate•AcOH in water | >300 | Diclofenac | 0.1 |
| diethylaminoethyl 2-[(2,3-dimethylphenyl)amino]benzoate•AcOH, | >400 | Mefenamic acid, | <0.1 |
| diethylaminoethyl 2-[(2,6-dichloro-3-methylphenyl)amino]benzoate•AcOH, | >400 | Meclofenamic acid | <0.1 |
| diethylaminoethyl 2-[[(3-(trifluoromethyl)phenyl)amino]benzoate•AcOH | >400 | Flufenamic acid | <0.1 |
| diethylaminoethyl 2-[[3-(trifluoromethyl)phenyl]amino]-3-pyridinecarboxylate•AcOH | >400 | Niflumic acid, | <0.1 |
| diethylaminoethyl 2-[[2-methyl-3-(trifluoromethyl)phenyl]amino]-3-pyridinecarboxylate•AcOH, | >400 | flunixin, | <0.1 |
| diethylaminoethyl 2-[(3-chloro-2-methylphenyl)amino]benzoate, | >400 | tolfenamic acid, | <0.1 |
| 4-N,N-dimethylaminobutyryloxy-2-methyl-N-2-pyridinyl-2H,1,2-benzothiazine-3-carboxamide 1,1-dioxide•HCl, | >300 | Piroxicam | <0.1 |
| N-(2-thiazolyl)-4-N,N-dimethylaminobutyryloxy-2-methyl-2H,1,2-benzothiazine-3-carboxamide 1,1-dioxide•HCl, | >300 | Sudoxiam | <0.1 |
| 6-chloro-4-N,N-dimethylaminobutyryloxy-2-methyl-N-2-pyridinyl-2H-thieno[2,3-e]-1,2-thiazine-3-carboxamide 1,1-dioxide•HCl, | >300 | lomoxicam | <0.1 |
| 4-N,N-dimethylaminobutyryloxy-2-methyl-N-2-pyridinyl-2H-thieno[2,3-e]-1,2-thiazine-3-carboxamide 1,1-dioxide•HCl, | >300 | Tenoxicam | <0.1 |
| 8-chloro-(4-N,N-dimethylaminobutyryloxy-pyridine-2-ylamino-methylidene)-3-methyl-2,2-dioxo-2$\lambda^{6,7}$-dithia-3-azabicyclo[4,3,0]nona-8,10-dien-5-one•HCl | >300 | Lomoxicam | <0.1 |
| 4-N,N-dimethylaminobutyryloxy-2-methyl-N-[5-Methyl-3-isoxolyl-2H-1,2-benzothiazine-3-carboxamide 1,1-dioxide]•HCl | >300 | Isoxicam | <0.1 |
| 4-N,N-dimethylaminobutyryloxy-2-methyl-N-(5-methyl-2-thiazolyl)-2H-1,2-benzothiazine-3-carboxamide-1,1-dioxide•HCl | >300 | meloxicam | <0.1 |

Example 3. HPPs have Higher In Vitro Penetration Rates Across Human Skin Comparing to their Parent Drugs The penetration rates of HPPs and their parent drugs through human skin are measured in vitro by modified Franz cells. The Franz cells have two chambers, the top sample chamber and the bottom receptor chamber. The human skin tissue (360-400 μm thick) that separates the top and the receptor chambers is isolated from the anterior or posterior thigh areas.

The compound tested (2 mL, 20% in 0.2 M phosphate buffer, pH. 7.4) are added to the sample chamber of a Franz cell. The receptor chamber contains 10 ml of 2% bovine serum albumin in saline which is stirred at 600 rpm. The amount of the tested compound penetrating the skin is determined by high-performance liquid chromatography (HPLC) method. The results are shown in FIG. 1a-1i. The apparent flux values of the tested compounds are calculated from the slopes in FIGS. 1a-1i and summarized in Table 2.

Because the lowest detectable apparent flux values in this method is 1 μg/cm$^2$/h, parent drugs that shows a apparent flux value less than 1 μg/cm$^2$/h are considered as not detectable for penetrating across the skin tissue. The HPPs of these parent drugs (e.g. aspirin, diflunisal, salsalate, salicylic acid, ketoprofen, fenoprofen, piroxicam, sudoxiam, lomoxicam, tenoxicam, lomoxicam, isoxicam and meloxicam) have detectable penetration across the skin tissue. For the parent drugs that have detectable apparent flux value, their HPPs have higher apparent flux value.

TABLE 2

In vitro Penetration Rate of Prodrug Compounds and their Parent Compounds

| Prodrug compounds | µg/cm$^2$/h | Parent compounds | µg/cm$^2$/h |
|---|---|---|---|
| diethylaminoethyl acetylsalicylate•AcOH | 1000 | Aspirin | <1 |
| diethylaminoethyl 5-(2,4-difluorophenyl)salicylate•AcOH | 100 | Diflunisal | <1 |
| diethylaminoethyl salicylsalicylate•AcOH | 80 | Salsalate | <1 |
| diethylaminoethyl salicylate•AcOH | 60 | salicylic acid | <1 |
| diethylaminoethyl 2-(p-isobutylphenyl)propionate•AcOH | 1250 | Ibuprofen | 50 |
| diethylaminoethyl 2-(3-benzoylphenyl)propionate•AcOH | 1150 | Ketoprofen | <1 |
| diethylaminoethyl 2-(3-phenoxyphenyl)propionate•AcOH | 1250 | Fenoprofen | <1 |
| diethylaminoethyl 2-(6-methoxy-2-naphthyl)propionate•AcOH, | 3500 | naproxen | 30 |
| diethylaminoethyl α-methyl-4-(2-thienylcarbonyl)benzeneacetate•AcOH, | 3000 | suprofen | 30 |
| diethylaminoethyl α-methyl-(p-chlorobenzoyl)-5-methoxy-2-methylindole 3-acetate•AcOH, | 4000 | α-methyl-(p-chlorobenzoyl)-5-methoxy-2-methylindole 3-acetic acid | 30 |
| diethylaminoethyl 2-(2-fluoro-4-biphenylyl)propionate•AcOH, | 3500 | flurbiprofen | 30 |
| diethylaminoethyl 6-chloro-α-methyl-9H-carbazole-2-acetate•AcOH, | 4000 | carprofen | 40 |
| diethylaminoethyl α-methyl-5H-[1]benzopyrano[2,3-b]pyridine-7-acetate•AcOH, | 3800 | pranoprofen | 30 |
| diethylaminoethyl 2-(4-chlorophenyl)-α-methyl-5-benzoxazoleacetate•AcOH, | 4000 | benoxaprofen | 40 |
| diethylaminoethyl α-methyl-4-[(2-methyl-2-propenyl)amino]benzeneacetate•AcOH, | 3500 | alminoprofen | 30 |
| diethylaminoethyl 5-benzoyl-α-methyl-2-thiopheneacetate•AcOH, | 4200 | tiaprofenic acid | 30 |
| diethylaminoethyl 3-chloro-4-(2,5-dihydro-1H-pyrrol-1-yl)-α-methyl benzeneacetate•AcOH, | 3500 | pirprofen | 30 |
| diethylaminoethyl 2-(10,11-dihydro-10-oxodibenzo(b,f)thiepin-2-yl)propionate•AcOH, | 3700 | zaltoprofen | 30 |
| diethylaminoethyl 2-(8-methyl-10,11-dihydro-11-oxodibenz(b,f)oxepin-2-yl)propionate•AcOH, | 4100 | bermoprofen | 40 |
| diethylaminoethyl 2-[4-(2-oxocyclopentyl-methyl)phenyl]propionate•AcOH, | 3400 | loxoprofen | 30 |
| diethylaminoethyl 4-(1,3-dihydro-1-oxo-2H-isoindol-2-yl)-α-methylbenzeneacetate•AcOH, | 4200 | indoprofen | 30 |
| diethylaminoethyl α,3-dichloro-4-cyclohexylbenzeneacetate•AcOH, | 3800 | fenclorac | 40 |
| diethylaminoethyl 4,5-Diphenyl-2-oxazole propionate•AcOH, | 4000 | oxaprozin | 30 |
| diethylaminoethyl 3-(4-biphenylylcarbonyl)propionate•AcOH, | 3600 | fenbufen | 40 |
| diethylaminoethyl 5-(4-chlorophenyl)-beta-hydroxy-2-furanpropionate•AcOH, | 4100 | orpanoxin | 30 |
| diethylaminoethyl 5-benzoyl-2,3-dihydro-1H-pyrrolizine-1-carboxylate•AcOH, | 3800 | ketorolac | 30 |
| diethylaminoethyl 6-chloro-5-cyclohexyl-2,3-dihydro-1H-indene-1-carboxylate•AcOH, | 4000 | clidanac | 40 |
| diethylaminoethyl 1-(p-chlorobenzoyl)-5-methoxy-2-methylindole 3-acetate•AcOH | 1100 | Indomethacin | 10 |
| diethylaminoethyl (Z)-5-fluoro-2-methyl-1-[(4-methylsulfinyl) phenylmethylene]-1H-indene-3-acetate•AcOH, | 900 | Sulindac | 10 |
| diethylaminoethyl 1-methyl-5-(4-methylbenzoyl)-1H-pyrrole-2-acetate•AcOH, | 1000 | Tolmetin | 10 |
| diethylaminoethyl 5-(4-Chlorobenzoyl)-1,4-dimethyl-1H-pyrrole-2-acetate•AcOH, | 1200 | Zomepirac | 10 |
| diethylaminoethyl 1,8-diethyl-1,3,4,9-tetrahydropyrano-[3,4-b]indole-1-acetate•AcOH, | 1300 | Etodolac | 10 |
| diethylaminoethyl 2-amino-3-benzoylbenzeneacetate•AcOH, | 800 | Amfenac | 10 |

TABLE 2-continued

In vitro Penetration Rate of Prodrug Compounds and their Parent Compounds

| Prodrug compounds | µg/cm$^2$/h | Parent compounds | µg/cm$^2$/h |
|---|---|---|---|
| diethylaminoethyl 2-amino-3-(4-bromo-benzoyl)benzeneacetate•AcOH, | 1100 | Bromofenac | 10 |
| diethylaminoethyl 3-chloro-4-(2-propenyloxy)benzeneacetate•AcOH, | 1000 | Alclofenac | 10 |
| diethylaminoethyl 2-(2,4-dichlorophenoxy)benzeneacetate•AcOH, | 1500 | Fenclofenac | 10 |
| diethylaminoethyl 1-(4-chlorobenzoyl-5-methoxy-2-methyl-1H-indole-3-acetoxyacetate•AcOH, | 1200 | Acemetacin | 10 |
| diethylaminoethyl 4-(4-chlorophenyl)-2-phenyl-5-thiazoleacetate•AcOH, | 1300 | Fentiazac | 10 |
| diethylaminoethyl 2[(2,6-dichlorophenyl)amino]benzene acetate•AcOH | 5000 | Diclofenac | 20 |
| diethylaminoethyl 2-[(2,3-dimethylphenyl)amino]benzoate•AcOH, | 2100 | Mefenamic acid | 10 |
| diethylaminoethyl 2-[(2,6-dichloro-3-methylphenyl)amino]benzoate•AcOH, | 2000 | meclofenamic acid | 10 |
| diethylaminoethyl 2-[[(3-(trifluoromethyl)phenyl)amino]benzoate•AcOH | 2200 | flufenamic acid, | 10 |
| diethylaminoethyl 2-[[3-(trifluoromethyl)phenyl]amino]-3-pyridinecarboxylate•AcOH | 1800 | niflumic acid, | 10 |
| diethylaminoethyl 2-[[2-methyl-3-(trifluoromethyl)phenyl]amino]-3-pyridinecarboxylate•AcOH, | 1700 | flunixin | 10 |
| 4-N,N-dimethylaminobutyryloxy-2-methyl-N-2-pyridinyl-2H,1,2-benzothiazine-3-carboxamide 1,1-dioxide•HCl, | 1700 | Piroxicam | <1 |
| N-(2-thiazolyl)-4-N,N-dimethylaminobutyryloxy-2-methyl-2H,1,2-benzothiazine-3-carboxamide 1,1-dioxide•HCl, | 1500 | Sudoxiam | <1 |
| 6-chloro-4-N,N-dimethylaminobutyryloxy-2-methyl-N-2-pyridinyl-2H-thieno[2,3-e]-1,2-thiazine-3-carboxamide 1,1-dioxide•HCl, | 1600 | lomoxicam | <1 |
| 4-N,N-dimethylaminobutyryloxy-2-methyl-N-2-pyridinyl-2H-thieno[2,3-e]-1,2-thiazine-3-carboxamide 1,1-dioxide•HCl, | 1800 | Tenoxicam | <1 |
| 8-chloro-(4-N,N-dimethylaminobutyryloxy-pyridine-2-ylamino-methylidene)-3-methyl-2,2-dioxo-2λ$^{6,7}$-dithia-3-azabicyclo[4,3,0]nona-8,10-dien-5-one•HCl | 1700 | Lomoxicam | <1 |
| 4-N,N-dimethylaminobutyryloxy-2-methyl-N-[5-Methyl-3-isoxolyl-2H-1,2-benzothiazine-3-carboxamide 1,1-dioxide]•HCl | 1800 | Isoxicam | <1 |
| 4-N,N-dimethylaminobutyryloxy-2-methyl-N-(5-methyl-2-thiazolyl)-2H-1,2-benzothiazine-3-carboxamide-1,1-dioxide•HCl | 1900 | meloxicam | <1 |

Example 4. In Vivo Transportation of Prodrug

A. Transportation of HPPs into Plasma

Tested compounds (20% solution or suspension in 1 mL isopropanol) are administered transdermally to the skin of intact hairless mice. The plasma levels of the parent compounds are determined by HPLC. The results show that HPP are converted to their parent drugs within a short period of time after administration. The peak levels of the active compounds in plasma are reached in less than 60 minutes after the transdermal administration of the HPPs (FIGS. 2a-2j), which is shorter than the time required to reach the plasma peak levels of the parent drugs when the parent drugs are taken orally. The Peak plasma levels of the prodrug compounds and the parent compounds are summarized in Table 3-a.

TABLE 3-a

Plasma concentration of the parent compounds after administration of prodrug compounds and parent compounds.

| Prodrug compound | t min | mg/L | Parent Compound | t (h) | mg/L |
| --- | --- | --- | --- | --- | --- |
| diethylaminoethyl acetylsalicylate•AcOH | 20 | 30 | Aspirin | ~2 | 0.1 |
| Diethylaminoethyl 5-(2,4-difluorophenyl) salicylate•AcOH | 30 | 50 | Diflunisal | 1-2 | 0.2 |
| diethylaminoethyl salicylsalicylate•AcOH | 30 | 40 | Salsalate | 1-2 | 0.1 |
| diethylaminoethyl salicylate•AcOH | 30 | 40 | salicylic acid | 1-2 | 0.1 |
| diethylaminoethyl 2-(p-isobutylphenyl) propionate•AcOH | 30 | 120 | Ibuprofen | 1-2 | 2 |
| diethylaminoethyl 2-(3-benzoylphenyl) propionate•AcOH | 40 | 20 | Ketoprofen | 1-2 | 1 |
| diethylaminoethyl 2-(3-phenoxyphenyl) propionate•AcOH | 40 | 20 | Fenoprofen | 1-2 | 1 |
| diethylaminoethyl 2-(6-methoxy-2-naphthyl)propionate•AcOH, | 50 | 2000 | naproxen | 2-4 | 10 |
| diethylaminoethyl α-methyl-4-(2-thienylcarbonyl)benzeneacetate•AcOH, | 50 | 2000 | suprofen | 2-4 | 10 |
| diethylaminoethyl α-methyl-(p-chlorobenzoyl)-5-methoxy-2-methylindole 3-acetate•AcOH, | 50 | 2000 | α-methyl-(p-chloro-benzoyl)-5-methoxy-2-methylindole 3-acetic acid | 2-4 | 10 |
| diethylaminoethyl 2-(2-fluoro-4-biphenylyl)propionate•AcOH, | 50 | 2000 | flurbiprofen | 2-4 | 10 |
| diethylaminoethyl 6-chloro-α-methyl-9H-carbazole-2-acetate•AcOH, | 50 | 2000 | carprofen | 2-4 | 10 |
| diethylaminoethyl α-methyl-5H-[1]benzopyrano[2,3-b]pyridine-7-acetate•AcOH, | 50 | 2000 | pranoprofen | 2-4 | 10 |
| diethylaminoethyl 2-(4-chlorophenyl)-α-methyl-5-benzoxazoleacetate•AcOH, | 50 | 2000 | benoxaprofen | 2-4 | 10 |
| diethylaminoethyl α-methyl-4-[(2-methyl-2-propenyl)amino]benzeneacetate•AcOH, | 50 | 2000 | alminoprofen | 2-4 | 10 |
| diethylaminoethyl 5-benzoyl-α-methyl-2-thiopheneacetate•AcOH, | 50 | 2000 | tiaprofenic acid | 2-4 | 10 |
| diethylaminoethyl 3-chloro-4-(2,5-dihydro-1H-pyrrol-1-yl)-α-methyl benzeneacetate•AcOH, | 50 | 2000 | pirprofen | 2-4 | 10 |
| diethylaminoethyl 2-(10,11-dihydro-10-oxodibenzo(b,f)thiepin-2-yl)propionate•AcOH, | 50 | 2000 | zaltoprofen | 2-4 | 10 |
| diethylaminoethyl 2-(8-methyl-10,11-dihydro-11-oxodibenz(b,f)oxepin-2-yl)propionate•AcOH, | 50 | 2000 | bermoprofen | 2-4 | 10 |
| diethylaminoethyl 2-[4-(2-oxocyclopentyl-methyl)phenyl]propionate•AcOH, | 50 | 2000 | loxoprofen | 2-4 | 10 |
| diethylaminoethyl 4-(1,3-dihydro-1-oxo-2H-isoindol-2-yl)-α-methylbenzeneacetate•AcOH, | 50 | 2000 | indoprofen | 2-4 | 10 |
| diethylaminoethyl α,3-dichloro-4-cyclohexylbenzeneacetate•AcOH, | 50 | 2000 | fenclorac | 2-4 | 10 |
| diethylaminoethyl 4,5-Diphenyl-2-oxazole propionate•AcOH, | 50 | 2000 | oxaprozin | 2-4 | 10 |
| diethylaminoethyl 3-(4-biphenylyl-carbonyl)propionate•AcOH, | 50 | 2000 | fenbufen | 2-4 | 10 |
| diethylaminoethyl 5-(4-chlorophenyl)-beta-hydroxy-2-furanpropionate•AcOH, | 50 | 2000 | orpanoxin | 2-4 | 10 |
| diethylaminoethyl 5-benzoyl-2,3-dihydro-1H-pyrrolizine-1-carboxylate•AcOH, | 50 | 2000 | ketorolac | 2-4 | 10 |
| diethylaminoethyl 6-chloro-5-cyclohexyl-2,3-dihydro-1H-indene-1-carboxylate•AcOH, | 50 | 2000 | Clidanac | 2-4 | 10 |
| diethylaminoethyl 1-(p-chlorobenzoyl)-5-methoxy-2-methylindole 3-acetate•AcOH | 50 | 20 | Indomethacin | 1-2 | 0.1 |
| diethylaminoethyl (Z)-5-fluoro-2-methyl-1-[(4-methylsulfinyl) phenylmethylene]-1H-indene-3-acetate•AcOH, | 50 | 20 | Sulindac | 1-2 | 0.1 |
| diethylaminoethyl 1-methyl-5-(4-methylbenzoyl)-1H-pyrrole-2-acetate•AcOH, | 50 | 20 | Tolmetin | 1-2 | 0.1 |
| diethylaminoethyl 5-(4-Chlorobenzoyl)-1,4-dimethyl-1H-pyrrole-2-acetate•AcOH, | 50 | 20 | Zomepirac | 1-2 | 0.1 |
| diethylaminoethyl 1,8-diethyl-1,3,4,9-tetrahydropyrano-[3,4-b]indole-1- | 50 | 20 | Etodolac | 1-2 | 0.1 |

TABLE 3-a-continued

Plasma concentration of the parent compounds after administration of prodrug compounds and parent compounds.

| Prodrug compound | t min | mg/L | Parent Compound | t (h) | mg/L |
|---|---|---|---|---|---|
| acetate•AcOH, | | | | | |
| diethylaminoethyl 2-amino-3-benzoylbenzeneacetate•AcOH, | 50 | 20 | Amfenac | 1-2 | 0.1 |
| diethylaminoethyl 2-amino-3-(4-bromo-benzoyl)benzeneacetate•AcOH, | 50 | 20 | Bromofenac | 1-2 | 0.1 |
| diethylaminoethyl 3-chloro-4-(2-propenyloxy)benzeneacetate•AcOH, | 50 | 20 | Alclofenac | 1-2 | 0.1 |
| diethylaminoethyl 2-(2,4-dichlorophenoxy)benzeneacetate•AcOH, | 50 | 20 | Fenclofenac | 1-2 | 0.1 |
| diethylaminoethyl 1-(4-chlorobenzoyl-5-methoxy-2-methyl-1H-indole-3-acetoxyacetate•AcOH, | 50 | 20 | Acemetacin | 1-2 | 0.1 |
| diethylaminoethyl 4-(4-chlorophenyl)-2-phenyl-5-thiazoleacetate•AcOH, | 50 | 20 | Fentiazac | 1-2 | 0.1 |
| diethylaminoethyl 3-(4-chlorophenyl)-1-phenyl-1H-pyrazole-4-acetate•AcOH, | 50 | 20 | Lonazolac | 1-2 | 0.1 |
| diethylaminoethyl [(1-benzyl-1H-indazol-3-yl)oxy]acetate•AcOH, | | | Bendazac | 1-2 | 0.1 |
| diethylaminoethyl 2[(2,6-dichloro-phenyl)amino]benzene acetate•AcOH | 40 | 2100 | Diclofenac | 1-2 | 1 |
| diethylaminoethyl 2-[(2,3-dimethylphenyl)amino]benzoate•AcOH, | 50 | 20 | Mefenamic acid, | 2-4 | 0.1 |
| diethylaminoethyl 2-[(2,6-dichloro-3-methylphenyl)amino]benzoate•AcOH, | 50 | 20 | meclofenamic acid, | 2-4 | 0.1 |
| diethylaminoethyl 2-[[(3-(trifluoro-methyl)phenyl)amino]benzoate•AcOH | 50 | 20 | flufenamic acid, | 2-4 | 0.1 |
| diethylaminoethyl 2-[[3-(trifluoro-methyl)phenyl]amino]-3-pyridinecarboxylate•AcOH | 50 | 20 | niflumic acid, | 2-4 | 0.1 |
| diethylaminoethyl 2-[[2-methyl-3-(trifluoro-methyl)phenyl]amino]-3-pyridinecarboxylate•AcOH, | 50 | 20 | flunixin, | 2-4 | 0.1 |
| 4-N,N-dimethylaminobutyryloxy-2-methyl-N-2-pyridinyl-2H,1,2-benzothiazine-3-carboxamide 1,1-dioxide•HCl, | 50 | 20 | Piroxicam | 2-4 | 0.1 |
| N-(2-thiazolyl)-4-N,N-dimethylaminobutyryloxy-2-methyl-2H,1,2-benzothiazine-3-carboxamide 1,1-dioxide•HCl, | 50 | 20 | Sudoxiam | 2-4 | 0.1 |
| 6-chloro-4-N,N-dimethylaminobutyryloxy-2-methyl-N-2-pyridinyl-2H-thieno[2,3-e]-1,2-thiazine-3-carboxamide 1,1-dioxide•HCl, | 50 | 20 | lomoxicam | 2-4 | 0.1 |
| 4-N,N-dimethylaminobutyryloxy-2-methyl-N-2-pyridinyl-2H-thieno[2,3-e]-1,2-thiazine-3-carboxamide 1,1-dioxide•HCl, | 50 | 20 | Tenoxicam | 2-4 | 0.1 |
| 8-chloro-(4-N,N-dimethylaminobutyryloxy-pyridine-2-ylamino-methylidene)-3-methyl-2,2-dioxo-2$\lambda^{6}$,7-dithia-3-azabicyclo[4,3,0]nona-8,10-dien-5-one•HCl | 50 | 20 | Lomoxicam | 2-4 | 0.1 |
| 4-N,N-dimethylaminobutyryloxy-2-methyl-N-[5-Methyl-3-isoxolyl-2H-1,2-benzothiazine-3-carboxamide 1,1-dioxide]•HCl | 50 | 20 | Isoxicam | 2-4 | 0.1 |
| 4-N,N-dimethylaminobutyryloxy-2-methyl-N-(5-methyl-2-thiazolyl)-2H-1,2-benzothiazine-3-carboxamide-1,1-dioxide•HCl | 50 | 20 | meloxicam | 2-4 | 0.1 |

B) Transportation of HPPs Through GI Tract.

The in vivo rates of GI tract penetration of 2-(ρ-isobutylphenyl) propionic acid (IBPP) and diethylaminoethyl 2-(ρ-isobutylphenyl) propionate.AcOH (DEAE-IBPP) were compared. The donor consisted of either a 10% suspension of 2-(ρ-isobutylphenyl) propionic acid (IBPP) or 10% solution of diethylaminoethyl 2-(ρ-isobutylphenyl) propionate.AcOH (DEAE-IBPP) in 1 mL of pH 7.4 phosphate buffer were administrated orally to rats. Plasma levels of ibuprofen and diethylaminoethyl 2-(ρ-isobutylphenyl) propionate were determined by a specific high-performance liquid chromatography method. The results were shown in FIG. 2j.

The results show that diethylaminoethyl 2-(ρ-isobutylphenyl) propionate.AcOH penetrates the GI tract is much faster than that ibuprofen does. It takes ~2 hours for ibuprofen to reach the peak ibuprofen level when it is taken orally, however, it takes only ~15 min. for diethylaminoethyl 2-(ρ-isobutylphenyl) propionate.AcOH to reach the peak ibuprofen level when it is taken orally.

C) Transportation of HPPs Through the Intercellular and Intracellular Fluids.

Wistar rats were killed with $CO_2$ and 50 mg/kg of diethylaminoethyl salicylic acid citric acid salt was applied to the back (hairs were shaved off) of the died rat which was kept at 37° C. and shaken for 3 h. The organ tissue (~1 g) was taken out and homogenized immediately in 5 ml of methanol, using a tissue tearor at 30,000 rpm (about 2 min.). The mixture was centrifuged for 5 minutes at 16,000 rpm. The supernatant (2 ml) was collected and evaporated to dryness. The residue was diluted to 0.1 ml and the amounts of diethylaminoethyl acetylsalicylate (DEAE-ASA), diethylaminoethyl salicylate (DEAE-SA), aspirin, and salicylic acid were determined with HPLC. The results are shown in Table 3-b.

TABLE 3-b

The distribution of diethylaminoethyl acetylsalicylate•citric acid salt and its metabolites in rats' body tissues and plasma.

| Prodrug or metabolites | Plasma | Liver | Bone | Brain |
|---|---|---|---|---|
| DEAE-ASA | 8 ± 4 μg/ml | 7 ± 4 μg/g | 6 ± 4 μg/g | 5 ± 3 μg/g |
| Aspirin | 2 ± 1 μg/ml | 3 ± 2 μg/g | 3 ± 1 μg/g | 2 ± 1 μg/g |
| DEAE-SA | 10 ± 3 μg/ml | 11 ± 4 μg/g | 5 ± 2 μg/g | 11 ± 2 μg/g |
| Salicylic acid | 65 ± 10 μg/ml | 45 ± 8 μg/g | 35 ± 6 μpg/g | 30 ± 6 μg/g |

D) Transportation of HPP Through Blood-Milk Barrier 1 hour after 50 mg/kg of diethylaminoethyl 2-(ρ-isobutylphenyl)propionate. citric acid salt (ibuprofenamine citric acid salt, 10% aqueous solution) were applied to the back (30 cm$^2$) of sheep, 55±8 μg/ml of ibuprofen and 10±5 μg/ml of ibuprofenamine were found out in the milk.

Example 5. Acute Toxicity of HPP and Parent Drug

The acute toxicity of the prodrug compounds and parent compounds are measured by $LD_{50}$ of rat. The results (Table 4) show that the prodrug compounds are less toxic than the corresponding parent compounds.

TABLE 4

The acute toxicity of HPP and their parent drugs in rats($LD_{50}$).

| HPP | $LD_{50}$ (g/kg) | Parent Drug | $LD_{50}$ (g/kg) |
|---|---|---|---|
| diethylaminoethyl acetylsalicylate•AcOH | 2.3 | Aspirin | 1.5 |
| dimethylaminoethyl acetylsalicylate•AcOH | 2.2 | Aspirin | 1.5 |
| diethylaminoethyl 5-(2,4-difluorophenyl) salicylate•AcOH | 1.0 | Diflunisal | 0.5 |
| diethylaminoethyl salicylsalicylate•AcOH | 2.0 | Salsalate | 1.5 |
| diethylaminoethyl salicylate•AcOH | 1.6 | salicylic acid | 1.3 |
| diethylaminoethyl 2-(ρ-isobutylphenyl) propionate•AcOH | 1.8 | Ibuprofen | 1.5 |
| dimethylaminoethyl 2-(ρ-isobutylphenyl) propionate•AcOH | 1.6 | Ibuprofen | 1.5 |
| diethylaminoethyl 2-(3-benzoylphenyl) propionate•AcOH | 0.3 | Ketoprofen | 0.1 |
| diethylaminoethyl 2-(3-phenoxyphenyl) propionate•AcOH | 1.5 | Fenoprofen | 0.8 |
| diethylaminoethyl 2-(6-methoxy-2-naphthyl) propionate•AcOH | 2.2 | Naproxen | 1.2 |
| diethylaminoethyl α-methyl-4-(2-thienylcarbonyl)benzene-acetate•AcOH | 0.8 | Suprofen | 0.59 |
| diethylaminoethyl 6-chloro-α-methyl-9H-carbazole-2-acetate•AcOH | 0.7 | Carprofen | 0.40 |
| diethylaminoethyl α-methyl-5H-[1]benzopyrano[2,3-b]pyridine-7-acetate•AcOH | 0.75 | Pranoprofen | 0.45 |
| Diethylaminoethyl 2-(4-chlorophenyl)-α-methyl-5-benzoxazoleacetate•AcOH | 1.3 | Benoxaprofen | 0.80 |
| Diethylaminoethyl 4-(1,3-dihydro-1-oxo-2H-isoindol-2-yl)-α-methylbenzeneacetate•AcOH | 3.5 | Alminoprofen | 2.40 |
| diethylaminoethyl α-methyl-4-[(2-methyl-2-propenyl)amino]benzeneacetate•AcOH | 1.1 | Indoprofen | 0.70 |
| diethylaminoethyl α,3-dichloro-4-cyclohexylbenzeneacetate•AcOH | 0.6 | Fenclorac | 0.43 |
| diethylaminoethyl 6-chloro-5-cyclohexyl-2,3-dihydro-1H-indene-1-carboxylate•AcOH | 0.2 | Clidanac | 0.035 |
| diethylaminoethyl 1-(p-chlorobenzoyl)-5-methoxy-2-methylindole 3-acetate•AcOH | 0.1 | Indomethacin | 0.013 |
| diethylaminoethyl (Z)-5-fluoro-2-methyl-1-[(4-methylsulfinyl) phenylmethylene]-1H-indene-3-acetate•AcOH, | 0.5 | Sulindac | 0.26 |
| diethylaminoethyl 1-methyl-5-(4-methylbenzoyl)-1H-pyrrole-2-acetate•AcOH, | 0.6 | Tolmetin | 0.35 |
| Diethylaminoethyl 5-(4-Chlorobenzoyl)-1,4-dimethyl-1H-pyrrole-2-acetate•AcOH, | 0.2 | Zomepirac | 0.027 |
| diethylaminoethyl 1,8-diethyl-1,3,4,9-tetrahydropyrano-3,4-b]indole-1-acetate•AcOH, | 0.6 | Etodolac | 0.46 |
| diethylaminoethyl 2-amino-3-benzoylbenzeneacetate•AcOH, | 1.0 | Amfenac | 0.31 |
| diethylaminoethyl 2-amino-3-(4-bromo-benzoyl)benzeneacetate•AcOH, | 1.6 | Bromofenac | |
| Diethylaminoethyl 3-chloro-4-(2-propenyloxy)benzeneacetate•AcOH, | 3.0 | Alclofenac | 1.05 |
| diethylaminoethyl 2-(2,4-dichlorophenoxy)benzeneacetate•AcOH, | 0.2 | Fenclofenac | 2.28 |
| diethylaminoethyl 1-(4-chlorobenzoyl-5-methoxy-2-methyl-1H-indole-3-acetoxyacetate•AcOH, | 1.2 | Acemetacin | 0.024 |
| diethylaminoethyl 4-(4-chlorophenyl)-2-phenyl-5-thiazoleacetate•AcOH, | 1.2 | Fentiazac | 0.70 |
| diethylaminoethyl 3-(4-chlorophenyl)-1-phenyl-1H-pyrazole-4-acetate•AcOH, | 1.2 | Lonazolac | 1.0 |
| diethylaminoethyl 2[(2,6-dichloro-phenyl)amino]benzene acetate•AcOH | 0.80 | Diclofenac | 0.45 |
| dimethylaminoethyl 2[(2,6-dichlorophenyl)amino]benzene acetate•AcOH | 0.7 | Diclofenac | 0.45 |
| diethylaminoethyl 2-[(2,3- | 0.9 | Mefenamic acid | 0.6 |

TABLE 4-continued

The acute toxicity of HPP and their parent drugs in rats($LD_{50}$).

| HPP | $LD_{50}$ (g/kg) | Parent Drug | $LD_{50}$ (g/kg) |
|---|---|---|---|
| dimethylphenyl)amino]benzoate•AcOH, | | | |
| diethylaminoethyl 2-[(2,6-dichloro-3-methylphenyl)amino]benzoate•AcOH, | 1.0 | Meclofenamic acid | |
| diethylaminoethyl 2-[[(3-(trifluoromethyl)phenyl)amino]benzoate•AcOH | 0.8 | Flufenamic acid | 0.72 |
| diethylaminoethyl 2-[[3-(trifluoro-methyl)phenyl]amino]-3-pyridinecarboxylate•AcOH | 0.75 | Niflumic acid, | 0.65 |
| diethylaminoethyl 2-[[2-methyl-3-(trifluoro-methyl)phenyl]amino]-3-pyridinecarboxylate•AcOH, | 1.1 | flunixin, | |
| 4-N,N-dimethylaminobutyryloxy-2-methyl-N-2-pyridinyl-2H,1,2-benzothiazine-3-carboxamide 1,1-dioxide•HCl, | 0.55 | Piroxicam | 0.36 |
| N-(2-thiazolyl)-4-N,N-dimethylaminobutyryloxy-2-methyl-2H,1,2-benzothiazine-3-carboxamide 1,1-dioxide•HCl, | 0.67 | Sudoxiam | |
| 6-chloro-4-N,N-dimethylaminobutyryloxy-2-methyl-N-2-pyridinyl-2H-thieno[2,3-e]-1,2-thiazine-3-carboxamide 1,1-dioxide•HCl, | 0.58 | lomoxicam | |
| 4-N,N-dimethylaminobutyryloxy-2-methyl-N-2-pyridinyl-2H-thieno[2,3-e]-1,2-thiazine-3-carboxamide 1,1-dioxide•HCl, | 0.50 | Tenoxicam | |
| 8-chloro-(4-N,N-dimethylaminobutyryloxy-pyridine-2-ylamino-methylidene)-3-methyl-2,2-dioxo-$2\lambda^{6,7}$-dithia-3-azabicyclo[4,3,0]nona-8,10-dien-5-one•HCl | 0.61 | Lomoxicam | |
| 4-N,N-dimethylaminobutyryloxy-2-methyl-N-[5-Methyl-3-isoxolyl-2H-1,2-benzothiazine-3-carboxamide 1,1-dioxide]•HCl | 0.57 | Isoxicam | |
| 4-N,N-dimethylaminobutyryloxy-2-methyl-N-(5-methyl-2-thiazolyl)-2H-1,2-benzothiazine-3-carboxamide-1,1-dioxide•HCl | 0.59 | meloxicam | |

Example 6. Gastroduodenal Bleeding Caused by Oral Administration of HPPs and their Parent Drugs Rats (10 rats for each compound tested) are orally administered with 100 mg/kg of one HPP or parent drug every day for 21 days. The parent drug groups generate average of 2-5 mg of fecal blood per gram of feces and the HPP groups generate no fecal blood. Results show that no gastroduodenal bleeding is observed from rats that take prodrug compounds, while gastroduodenal bleeding is observed from all rats that take parent compounds at the similar dosage.

Example 7. Analgesic Activities of HPPs and their Parent Drugs

The analgesic activities of the prodrug compounds and parent compounds are determined using the D'Amour-Smith Method (J. Pharmacol. Exp. Ther., 72, 74(1941)).

After the tested compounds are administered (the dosages for each test compounds are specified in FIGS. 3a-3h, prodrug compounds are administered orally and transdermally respectively in different groups, while parent compounds are administered orally) to a group of mice (six mice every group), the tails of mice are exposed to heat and the prolongation time of pain threshold is determined. The results show that the same dosage of prodrug compounds has stronger analgesic activities than the corresponding parent compounds. The prodrug compounds show similar analgesic activities when the same dosages are administered orally or transdermally. (FIGS. 3a-3h).

Acetic acid solution is administered intraperitoneally to a group of mice (6 mice every group) 30 minutes after a test compound administered to the mice at the dosage specified in the tables below. The prodrug compounds are administered either transdermally or orally. The parent compounds are administered orally. The number of writhing that occurred when mice are administered the acetic acid solution are counted, and the rate of inhibition based on the control group which was not pretreated with any test compounds is calculated. The results show that the prodrug compounds have better analgesic activities comparing to their corresponding parent compounds.

Aspirin (ASA, 50 mg/kg and 100 g) was administered to groups B1 and B2 of mice and diethylaminoethyl acetylsalicylate.AcOH (DEAE-ASA, 50 mg and 100 mg/kg) was administered orally to groups C1 and C2. Diethylaminoethyl acetylsalicylate.AcOH (DEAE-ASA, 50 mg and 100 mg/kg) was administered transdermally to groups D1 and D2. The A group is the control group. The test compounds were administered to the mice 30 minutes before the acetic acid solution was administered. The results are shown in Tables 4-12.

TABLE 4

The rate of writhing inhibition by aspirin and its HPP.

| Group | A | B1 | B2 | C1 | C2 | D1 | D2 |
|---|---|---|---|---|---|---|---|
| Dose (mg/kg) | 0 | 50 | 100 | 50 | 100 | 50 | 100 |
| No. of Writhing | 33.2 | 18.2 | 13.2 | 15.4 | 11.0 | 14.5 | 10.1 |
| % | — | 45 | 60 | 54 | 67 | 56 | 70 |

Diflunisal (50 mg/kg and 100 mg/kg) was administered to groups B1 and B2 of mice, diethylaminoethyl 5-(2,4-difluorophenyl) salicylate.AcOH (50 mg/kg and 100 mg/kg) was administered transdermally to groups C1 and C2 of mice, diethylaminoethyl salicylsalicylate.AcOH (50 mg/kg and 100 mg/kg) was administered transdermally to groups D1 and D2 of mice, and diethylaminoethyl salicylate.AcOH (50 mg and 100 mg/kg) was administered transdermally to groups E1 and E2. The A group is the control group. The test compounds were administered to the mice 30 minutes before the acetic acid solution was administered. The results are shown in Table 5.

TABLE 5

The rate of writhing inhibition by diflunisal and its HPP.

| Group | A | B1 | B2 | C1 | C2 | D1 | D2 | E1 | E2 |
|---|---|---|---|---|---|---|---|---|---|
| Dose (mg/kg) | 0 | 50 | 100 | 50 | 100 | 50 | 100 | 50 | 100 |
| No. of Writhing | 35.0 | 18.1 | 13.2 | 13.2 | 10.2 | 14.2 | 12.0 | 14.0 | 11.9 |
| % | — | 48 | 62 | 62 | 71 | 59 | 65 | 60 | 66 |

Ibuprofen (IBPP, 50 mg/kg and 100 mg) was administered to groups B1 and B2 of mice and diethylaminoethyl 2-(ρ-isobutylphenyl) propionate.AcOH (DEAE-IBPP, 50 mg and 100 mg/kg) was administered orally to groups C1 and C2. Diethylaminoethyl 2-(ρ-isobutylphenyl) propionate.AcOH (DEAE-IBPP, 50 mg and 100 mg/kg) was administered transdermally to groups D1 and D2. The A group is the control group. The test compounds were administered to the mice 30 minutes before the acetic acid solution was administered. The results are shown in Table 6.

TABLE 6

The rate of writhing inhibition by ibuprofen and its HPPs.

| Group | A | B1 | B2 | C1 | C2 | D1 | D2 |
|---|---|---|---|---|---|---|---|
| Dose (mg/kg) | 0 | 50 | 100 | 50 | 100 | 50 | 100 |
| No. of writhing | 34.2 | 17.2 | 13.1 | 14.1 | 10.2 | 13.3 | 9.8 |
| % | — | 50 | 62 | 59 | 70 | 61 | 71 |

Ketoprofen (50 mg/kg) was administered to groups B of mice, fenoprofen (50 mg/kg) was administered to groups C of mice, diethylaminoethyl 2-(3-benzoylphenyl) propionate.AcOH (50 mg/kg) was administered transdermally to groups D of mice, and diethylaminoethyl 2-(3-phenoxyphenyl) propionate.AcOH (50 mg/kg) was administered transdermally to groups E of mice. The A group is the control group. The test compounds were administered to the mice 30 minutes before the acetic acid solution was administered. The results are shown in Table 7.

TABLE 7

The rate of writhing inhibition by fenoprofen, ketoprofen and their HPPs.

| Group | A | B | C | D | E |
|---|---|---|---|---|---|
| Dose (mg/kg) | 0 | 50 | 50 | 50 | 50 |
| No. of Writhing | 35.0 | 18.1 | 13.2 | 14.2 | 14.0 |
| % | — | 48 | 62 | 59 | 60 |

Diethylaminoethyl 2-(6-methoxy-2-naphthyl)propionate.AcOH (100 mg/kg, B), diethylaminoethyl α-methyl-4-(2-thienylcarbonyl)benzeneacetate.AcOH (100 mg/kg, C), diethylaminoethyl α-methyl-(p-chlorobenzoyl)-5-methoxy-2-methylindole 3-acetate.AcOH (100 mg/kg, D), diethylaminoethyl 2-(2-fluoro-4-biphenylyl)propionate.AcOH (100 mg/kg, E), diethylaminoethyl 6-chloro-α-methyl-9H-carbazole-2-acetate.AcOH (100 mg/kg, F), diethylaminoethyl α-methyl-5H-[1]benzopyrano[2,3-b]pyridine-7-acetate.AcOH (100 mg/kg, G), diethylaminoethyl 2-(4-chlorophenyl)-α-methyl-5-benzoxazoleacetate.AcOH (100 mg/kg, H), diethylaminoethyl α-methyl-4-[(2-methyl-2-propenyl)amino]benzeneacetate.AcOH (100 mg/kg, I), diethylaminoethyl 5-benzoyl-α-methyl-2-thiopheneacetate.AcOH (100 mg/kg, J), diethylaminoethyl 3-chloro-4-(2,5-dihydro-1H-pyrrol-1-yl)-α-methyl benzeneacetate.AcOH (100 mg/kg, K), diethylaminoethyl 2-(10, 11-dihydro-10-oxodibenzo(b,f)thiepin-2-yl)propionate.AcOH (100 mg/kg, L), diethylaminoethyl 2-(8-methyl-10,11-dihydro-11-oxodibenz(b,f)oxepin-2-yl)propionate.AcOH (100 mg/kg, M), diethylaminoethyl 2-[4-(2-oxocyclopentyl-methyl)phenyl]propionate.AcOH (100 mg/kg, N), diethylaminoethyl 4-(1,3-dihydro-1-oxo-2H-isoindol-2-yl)-α-methylbenzeneacetate.AcOH (100 mg/kg, 0), diethylaminoethyl α,3-dichloro-4-cyclohexylbenzeneacetate.AcOH (100 mg/kg, P), diethylaminoethyl 4,5-Diphenyl-2-oxazole propionate.AcOH (100 mg/kg, Q), diethylaminoethyl 3-(4-biphenylylcarbonyl)propionate.AcOH (100 mg/kg, R), diethylaminoethyl 5-(4-chlorophenyl)-beta-hydroxy-2-furanpropionate.AcOH (100 mg/kg, S), diethylaminoethyl 5-benzoyl-2,3-dihydro-1H-pyrrolizine-1-carboxylate.AcOH (100 mg/kg, T), diethylaminoethyl 6-chloro-5-cyclohexyl-2,3-dihydro-1H-indene-1-carboxylate.AcOH (100 mg/kg, U) were administered transdermally the mice 30 minutes before the acetic acid solution was administered. The A group is the control group. The results are shown in Table 8.

TABLE 8

The rate of writhing inhibition by aryl- and heteroarylpropionic acids and their HPPs.

| Group | Dose (mg/kg) | No. of Writhing | % |
|---|---|---|---|
| A | 0 | 35.0 | — |
| B | 100 | 17.1 | 51 |
| C | 100 | 15.7 | 55 |
| D | 100 | 13.8 | 61 |
| E | 100 | 15.6 | 55 |
| F | 100 | 14.2 | 59 |
| G | 100 | 16.1 | 54 |
| H | 100 | 17.1 | 51 |
| I | 100 | 15.6 | 55 |
| J | 100 | 13.2 | 62 |
| K | 100 | 14.0 | 60 |
| L | 100 | 14.2 | 59 |
| M | 100 | 13.8 | 61 |
| N | 100 | 15.7 | 55 |
| O | 100 | 13.2 | 62 |
| P | 100 | 15.2 | 57 |
| Q | 100 | 15.7 | 55 |
| R | 100 | 14.2 | 59 |
| S | 100 | 15.6 | 55 |
| T | 100 | 16.1 | 54 |
| U | 100 | 15.2 | 57 |

Diethylaminoethyl 1-(p-chlorobenzoyl)-5-methoxy-2-methylindole 3-acetate.AcOH (100 mg/kg, B), diethylaminoethyl (Z)-5-fluoro-2-methyl-1-[(4-methylsulfinyl) phenylmethylene]-1H-indene-3-acetate.AcOH (100 mg/kg, C), diethylaminoethyl 1-methyl-5-(4-methylbenzoyl)-1H-pyrrole-2-acetate.AcOH (100 mg/kg, D), diethylaminoethyl 5-(4-Chlorobenzoyl)-1,4-dimethyl-1H-pyrrole-2-acetate.AcOH (100 mg/kg, E), diethylaminoethyl 1,8-diethyl-1,3,4,9-tetrahydropyrano-[3,4-b]indole-1-acetate.AcOH (100 mg/kg, F), diethylaminoethyl 2-amino-3-benzoylbenzeneacetate.AcOH (100 mg/kg, G), diethylaminoethyl 2-amino-3-(4-bromo-benzoyl)benzeneacetate.AcOH (100 mg/kg, H), diethylaminoethyl 3-chloro-4-(2-propenyloxy)benzeneacetate.AcOH (100 mg/kg, I), diethylaminoethyl 2-(2,4-dichlorophenoxy)benzeneacetate.AcOH (100 mg/kg, J), diethylaminoethyl 1-(4-chlorobenzoyl-5-methoxy-2-methyl-1H-indole-3-acetoxyacetate.AcOH (100 mg/kg, K), diethylaminoethyl 4-(4-chlorophenyl)-2-phenyl-5-thiazoleacetate.AcOH (100 mg/kg, L), or diethylaminoethyl 3-(4-chlorophenyl)-1-phenyl-1H-pyrazole-4-acetate.AcOH (100 mg/kg, M) were administered transdermally the mice 30 minutes before the acetic acid solution was administered.

The A group is the control group. The results are shown in Table 9.

TABLE 9

The rate of writhing inhibition by aryl- and heteroarylacetic acids and their HPPs.

| Group | Dose (mg/kg) | No. of Writhing | % |
|---|---|---|---|
| A | 0 | 35.0 | — |
| B | 100 | 15.6 | 55 |
| C | 100 | 14.2 | 59 |
| D | 100 | 17.1 | 51 |
| E | 100 | 15.6 | 55 |
| F | 100 | 14.0 | 60 |
| G | 100 | 13.8 | 61 |
| H | 100 | 13.2 | 62 |
| I | 100 | 15.7 | 55 |
| J | 100 | 14.2 | 59 |
| K | 100 | 15.6 | 55 |
| L | 100 | 16.1 | 54 |
| M | 100 | 15.2 | 57 |

[Diclofenac (10 mg and 20 mg/kg) was administered to groups B1 and B2 of mice and diethylaminoethyl 2[(2,6-dichlorophenyl)amino]benzene acetate.AcOH (10 mg and 20 mg/kg) was administered orally to groups C1 and C2. Diethylaminoethyl 2[(2,6-dichlorophenyl)amino]benzene acetate.AcOH (10 mg and 20 mg/kg) was administered transdermally to groups D1 and D2. The A group is the control group. The test compounds were administered to the mice 30 minutes before the acetic acid solution was administered. The results are shown in Table 10.

TABLE 10

The rate of writhing inhibition by diclofenac and its HPP.

| Group | A | B1 | B2 | C1 | C2 | D1 | D2 |
|---|---|---|---|---|---|---|---|
| Dose (mg/kg) | 0 | 10 | 20 | 10 | 20 | 10 | 20 |
| No. of writhing | 34.2 | 14.2 | 10.1 | 12.1 | 9.2 | 10.3 | 8.8 |
| % | — | 58.5 | 70.5 | 64.6 | 73.1 | 69.9 | 74.3 |

Diethylaminoethyl 2-[(2,3-dimethylphenyl)amino]benzoate.AcOH (100 mg/kg, B), diethylaminoethyl 2-[(2,6-dichloro-3-methylphenyl)amino]benzoate.AcOH (100 mg/kg, C), diethylaminoethyl 2-[[(3-(trifluoromethyl)phenyl)amino]benzoate.AcOH (100 mg/kg, D), diethylaminoethyl 2-[[3-(trifluoromethyl)phenyl]amino]-3-pyridinecarboxylate.AcOH (100 mg/kg, E), diethylaminoethyl 2-[[2-methyl-3-(trifluoromethyl)phenyl]amino]-3-pyridinecarboxylate.AcOH (100 mg/kg, F) were administered transdermally the mice 60 minutes before the acetic acid solution was administered. The group A is the control group. The results are shown in Table 11.

TABLE 11

The rate of writhing inhibition by arylanthranilic acids and their HPPs.

| Group | Dose (mg/kg) | No. of Writhing | % |
|---|---|---|---|
| A | 0 | 35.0 | — |
| B | 100 | 15.6 | 55 |
| C | 100 | 14.2 | 59 |
| D | 100 | 16.1 | 54 |
| E | 100 | 15.2 | 57 |
| F | 100 | 15.7 | 55 |

4-N,N-dimethylaminobutyryloxy-2-methyl-N-2-pyridinyl-2H,1,2-benzothiazine-3-carboxamide 1,1-dioxide.HCl (50 mg/kg, B), N-(2-thiazoyl)-4-N,N-dimethylaminobutyryloxy-2-methyl-2H, 1,2-benzothiazine-3-carboxamide 1,1-dioxide.HCl (50 mg/kg, C), 6-chloro-4-N,N-dimethylaminobutyryloxy-2-methyl-N-2-pyridinyl-2H-thieno[2,3-e]-1,2-thiazine-3-carboxamide 1,1-dioxide.HCl (50 mg/kg, D), 4-N,N-dimethylaminobutyryloxy-2-methyl-N-2-pyridinyl-2H-thieno[2,3-e]-1,2-thiazine-3-carboxamide 1,1-dioxide.HCl (50 mg/kg, E), 8-chloro-(4-N,N-dimethylaminobutyryloxy-pyridine-2-ylamino-methylidene)-3-methyl-2,2-dioxo-2$\lambda^6$'7-dithia-3-azabicyclo[4,3,0]nona-8,10-dien-5-one.HCl (50 mg/kg, F), 4-N,N-dimethylaminobutyryloxy-2-methyl-N-[5-Methyl-3-isoxolyl-2H-1,2-benzothiazine-3-carboxamide 1,1-dioxide].HCl (50 mg/kg, G), and 4-N,N-dimethylaminobutyryloxy-2-methyl-N-(5-methyl-2-thiazolyl)-2H-1, 2-benzothiazine-3-carboxamide-1,1-dioxide.HCl (50 mg/kg, H) were administered transdermally the mice 60 minutes before the acetic acid solution was administered. The group A is the control group. The results are shown in Table 12.

TABLE 12

The rate of writhing Inhibition by Oxicams and their HPPs.

| Group | Dose (mg/kg) | No. of Writhing | % |
|---|---|---|---|
| A | 0 | 35.0 | — |
| B | 50 | 15.6 | 55 |
| C | 50 | 15.7 | 55 |
| D | 50 | 16.5 | 53 |
| E | 50 | 16.9 | 53 |
| F | 50 | 17.5 | 50 |
| G | 50 | 15.8 | 55 |
| H | 50 | 18.2 | 48 |

Example 8. Antipyretic Activities of Prodrug Compounds Comparing to their Parent Compounds Rats are administered with sterilized *E. coli* suspension as a pyrogen. Each group of rats are administered with a prodrug compounds or parent compounds at a dosage specified below. The prodrug compounds are administered either orally or transdermally. The parent compounds are administered orally. Results show that the prodrug compounds have same or better antipyretic activities than their corresponding parent compounds (Tables 13-21).

The control group is group A. 2 hours later, Aspirin (ASA, B1 for 100 mg/kg and B2 for 150 mg/kg) and diethylaminoethyl acetylsalicylate.AcOH (DEAE-ASA, $C_1$ for 100 mg/kg and $C_2$ for 150 mg) were administered orally and diethylaminoethyl acetylsalicylate.AcOH (DEAE-ASA, D1 for 100 mg and D2 for 150 mg/kg) were administered transdermally. The body temperature of rats was taken at 90 min. intervals before and after the administration of the test compounds. The results are shown in the following Table 13.

TABLE 13

Antipyretic activity of aspirin and its HPP.

| Compound | t = 0 min | t = 90 min | t = 180 min | t = 270 min |
|---|---|---|---|---|
| Control group(A) | 37.32 ± 0.05 | 37.35 ± 0.04 | 37.12 ± 0.05 | 37.08 ± 0.04 |
| ASA (100 mg/kg, B1) | 37.22 ± 0.05 | 36.80 ± 0.05 | 36.85 ± 0.05 | 36.81 ± 0.05 |

TABLE 13-continued

Antipyretic activity of aspirin and its HPP.

| Compound | t = 0 min | t = 90 min | t = 180 min | t = 270 min |
|---|---|---|---|---|
| ASA (150 mg/kg, B2) | 37.30 ± 0.06 | 36.50 ± 0.05 | 36.59 ± 0.05 | 36.55 ± 0.05 |
| DEAE-ASA (100 mg/kg, C1, orally) | 37.25 ± 0.09 | 36.40 ± 0.15 | 36.50 ± 0.09 | 36.40 ± 0.15 |
| DEAE-ASA (150 mg/kg, C2, orally) | 37.18 ± 0.07 | 36.30 ± 0.15 | 36.28 ± 0.07 | 36.20 ± 0.09 |
| DEAE-ASA (100 mg/kg, D1, transdermally) | 37.19 ± 0.07 | 36.40 ± 0.05 | 36.38 ± 0.05 | 36.40 ± 0.15 |
| DEAE-ASA (150 mg/kg, D2, transdermally) | 37.33 ± 0.05 | 36.27 ± 0.15 | 36.26 ± 0.07 | 36.22 ± 0.08 |

The control group is group A. 2 hours later, diflunisal (B1 for 100 mg/kg and B2 for 150 mg/kg) was administered orally and diethylaminoethyl 5-(2,4-difluorophenyl) salicylate.AcOH (C1 for 100 mg/kg and C2 for 150 mg), diethylaminoethyl salicylsalicylate.AcOH (D1 for 100 mg/kg and D2 for 150 mg), and diethylaminoethyl salicylate.AcOH (E1 for 100 mg/kg and E2 for 150 mg) were administered transdermally. The body temperature of rats was taken at 90 min. intervals before and after the administration of the test compounds. The results are shown in Table 14.

TABLE 14

Antipyretic activity of diflunisal and its HPP.

| Compound | t = 0 min. | t = 90 min. | t = 180 min. | t = 270 min. |
|---|---|---|---|---|
| A, Control group | 37.33 ± 0.05 | 37.26 ± 0.07 | 37.32 ± 0.05 | 37.34 ± 0.08 |
| B1 (100 mg/kg) | 37.25 ± 0.06 | 36.81 ± 0.05 | 36.82 ± 0.08 | 36.78 ± 0.07 |
| B2 (150 mg/kg) | 37.35 ± 0.09 | 36.61 ± 0.07 | 36.56 ± 0.06 | 36.57 ± 0.05 |
| C1 (100 mg/kg) | 37.22 ± 0.07 | 36.42 ± 0.06 | 36.40 ± 0.05 | 36.47 ± 0.08 |
| C2 (150 mg/kg) | 37.26 ± 0.08 | 36.20 ± 0.05 | 36.30 ± 0.07 | 36.31 ± 0.08 |
| D1 (100 mg/kg) | 37.28 ± 0.06 | 36.75 ± 0.06 | 36.78 ± 0.08 | 36.80 ± 0.07 |
| D2 (150 mg/kg) | 37.26 ± 0.05 | 36.45 ± 0.05 | 36.40 ± 0.07 | 36.50 ± 0.05 |
| E1 (100 mg/kg) | 37.28 ± 0.06 | 36.85 ± 0.06 | 36.88 ± 0.08 | 36.86 ± 0.07 |
| E2 (150 mg/kg) | 37.26 ± 0.05 | 36.55 ± 0.05 | 36.60 ± 0.07 | 36.65 ± 0.05 |

The control group is group A. 2 hours later, ibuprofen (IBPP, B1 for 100 mg/kg and B2 for 150 mg/kg) and diethylaminoethyl 2-(p-isobutylphenyl) propionate.AcOH (DEAE-IBPP, C1 for 100 mg/kg and C2 for 150 mg) were administered orally and diethylaminoethyl 2-(p-isobutylphenyl) propionate.AcOH (DEAE-IBPP, D1 for 100 mg and D2 for 150 mg/kg) was administered transdermally. The body temperatures of the rats were taken at 90 min. intervals before and after the administration of the test compounds. The results are shown in Table 15.

TABLE 15

Antipyretic activity of ibuprofen and its HPP.

| Compound | t = 0 min. | t = 90 min. | t = 180 min. | t = 270 min. |
|---|---|---|---|---|
| Control group(A) | 37.35 ± 0.05 | 37.25 ± 0.07 | 37.33 ± 0.05 | 37.32 ± 0.08 |
| IBPP (100 mg/kg, B1) | 37.25 ± 0.06 | 36.83 ± 0.05 | 36.80 ± 0.08 | 36.78 ± 0.07 |
| IBPP (150 mg/kg, B2) | 37.35 ± 0.09 | 36.59 ± 0.07 | 36.53 ± 0.06 | 36.55 ± 0.05 |
| DEAE-IBPP (100 mg/kg, C1, orally) | 37.22 ± 0.07 | 36.40 ± 0.06 | 36.50 ± 0.05 | 36.45 ± 0.08 |
| DEAE-IBPP (150 mg/kg, C2, orally) | 37.24 ± 0.08 | 36.30 ± 0.05 | 36.35 ± 0.07 | 36.38 ± 0.08 |
| DEAE-IBPP (100 mg/kg, D1, transdermally) | 37.27 ± 0.06 | 36.30 ± 0.06 | 36.35 ± 0.08 | 36.31 ± 0.07 |
| DEAE-IBPP (150 mg/kg, D2, transdermally) | 37.26 ± 0.05 | 36.25 ± 0.05 | 36.30 ± 0.07 | 36.20 ± 0.05 |

The control group is group A. 2 hours later, ketoprofen (50 mg/kg, B) and fenoprofen (50 mg/kg, C) were administered orally and diethylaminoethyl 2-(3-benzoyphenyl) propionate.AcOH (50 mg/kg, D) and diethylaminoethyl 2-(3-phenoxyphenyl) propionate.AcOH (50 mg/kg, E) were administered transdermally. The body temperature of rats was taken at 90 min. intervals before and after the administration of the test compounds. The results are shown in Table 16.

TABLE 16

Antipyretic Activity of ketoprofen and related compounds.

| Compound | t = 0 min. | t = 90 min. | t = 180 min. | t = 270 min. |
|---|---|---|---|---|
| A, Control group | 37.33 ± 0.05 | 37.26 ± 0.07 | 37.32 ± 0.05 | 37.34 ± 0.08 |
| B (50 mg/kg) | 37.25 ± 0.06 | 36.81 ± 0.05 | 36.82 ± 0.08 | 36.78 ± 0.07 |
| C (50 mg/kg) | 37.22 ± 0.07 | 36.82 ± 0.06 | 36.80 ± 0.05 | 36.77 ± 0.08 |
| D (50 mg/kg) | 37.28 ± 0.06 | 36.65 ± 0.06 | 36.58 ± 0.08 | 36.60 ± 0.07 |
| E (50 mg/kg) | 37.28 ± 0.06 | 36.65 ± 0.06 | 36.58 ± 0.08 | 36.56 ± 0.07 |

The control group is group A. 2 hours later, diethylaminoethyl 2-(6-methoxy-2-naphthyl)propionate.AcOH (100 mg/kg, B), diethylaminoethyl α-methyl-4-(2-thienylcarbonyl)benzeneacetate.AcOH (100 mg/kg, C), diethylaminoethyl α-methyl-(p-chlorobenzoyl)-5-methoxy-2-methylindole 3-acetate.AcOH (100 mg/kg, D), diethylaminoethyl 2-(2-fluoro-4-biphenylyl)propionate.AcOH (100 mg/kg, E), diethylaminoethyl 6-chloro-α-methyl-9H-carbazole-2-acetate.AcOH (100 mg/kg, F), diethylaminoethyl α-methyl-5H-[1]benzopyrano[2,3-b]pyridine-7-acetate.AcOH (100 mg/kg, G), diethylaminoethyl 2-(4-chlorophenyl)-α-methyl-5-benzoxazoleacetate.AcOH (100 mg/kg, H), diethylaminoethyl α-methyl-4-[(2-methyl-2-propenyl)amino]benzeneacetate.AcOH (100 mg/kg, I), diethylaminoethyl 5-benzoyl-α-methyl-2-thiopheneacetate.AcOH (100 mg/kg, J), diethylaminoethyl 3-chloro-4-(2,5-dihydro-1H-pyrrol-1-yl)-α-methyl benzeneacetate.AcOH (100 mg/kg, K), diethylaminoethyl 2-(10,11-dihydro-10-oxodibenzo(b,f)thiepin-2-yl) propionate.AcOH (100 mg/kg, L), diethylaminoethyl 2-(8- methyl-10,11-dihydro-11-oxodibenz(b,f)oxepin-2-yl) propionate.AcOH (100 mg/kg, M), diethylaminoethyl 2-[4-(2-oxocyclopentyl-methyl)phenyl]propionate.AcOH (100 mg/kg, N), diethylaminoethyl 4-(1,3-dihydro-1-oxo-2H-isoindol-2-yl)-α-methylbenzeneacetate.AcOH (100 mg/kg, O), diethylaminoethyl α,3-dichloro-4-cyclohexylbenzeneacetate.AcOH (100 mg/kg, P), diethylaminoethyl 4,5-Diphenyl-2-oxazole propionate.AcOH (100 mg/kg, Q), diethylaminoethyl 3-(4-biphenylylcarbonyl)propionate.AcOH (100 mg/kg, R), diethylaminoethyl 5-(4-chlorophenyl)-beta-hydroxy-2-furanpropionate.AcOH (100 mg/kg, S), diethylaminoethyl 5-benzoyl-2,3-dihydro-1H-pyrrolizine-1-carboxylate.AcOH (100 mg/kg, T), diethylaminoethyl 6-chloro-5-cyclohexyl-2,3-dihydro-1H-indene-1-carboxylate.AcOH (100 mg/kg, U) were administered transdermally. The body temperature of rats was taken at 90 min. intervals before and after the administration of the test compounds. The results are shown in Table 17.

TABLE 17

Antipyretic Activity of aryl- and heteroarylpropionic acids and their HPPs.

| Compound | t = 0 min. | t = 90 min. | t = 180 min. | t = 270 min. |
|---|---|---|---|---|
| A (Control group) | 37.34 ± 0.05 | 37.36 ± 0.07 | 37.37 ± 0.05 | 37.44 ± 0.08 |
| B (100 mg/kg) | 37.33 ± 0.07 | 36.80 ± 0.06 | 36.72 ± 0.05 | 36.50 ± 0.08 |
| C (100 mg/kg) | 37.28 ± 0.06 | 36.65 ± 0.06 | 36.58 ± 0.08 | 36.45 ± 0.07 |
| D (100 mg/kg) | 37.35 ± 0.06 | 36.71 ± 0.05 | 36.60 ± 0.08 | 36.59 ± 0.07 |
| E (100 mg/kg) | 37.29 ± 0.07 | 36.82 ± 0.06 | 36.70 ± 0.05 | 36.67 ± 0.08 |
| F (100 mg/kg) | 37.28 ± 0.06 | 36.68 ± 0.05 | 36.62 ± 0.08 | 36.58 ± 0.07 |
| G (100 mg/kg) | 37.27 ± 0.06 | 36.76 ± 0.05 | 36.65 ± 0.06 | 36.49 ± 0.08 |
| H (100 mg/kg) | 37.25 ± 0.07 | 36.82 ± 0.06 | 36.70 ± 0.05 | 36.50 ± 0.08 |
| I (100 mg/kg) | 37.23 ± 0.06 | 36.69 ± 0.06 | 36.52 ± 0.08 | 36.40 ± 0.07 |
| J (100 mg/kg) | 37.26 ± 0.06 | 36.65 ± 0.06 | 36.58 ± 0.08 | 36.36 ± 0.07 |
| K (100 mg/kg) | 37.27 ± 0.06 | 36.68 ± 0.05 | 36.62 ± 0.08 | 36.58 ± 0.07 |
| L (100 mg/kg) | 37.25 ± 0.06 | 36.71 ± 0.05 | 36.65 ± 0.08 | 36.64 ± 0.07 |
| M (100 mg/kg) | 37.26 ± 0.07 | 36.80 ± 0.06 | 36.70 ± 0.05 | 36.57 ± 0.08 |
| N (100 mg/kg) | 37.25 ± 0.06 | 36.71 ± 0.05 | 36.65 ± 0.08 | 36.64 ± 0.07 |
| O (100 mg/kg) | 37.28 ± 0.06 | 36.65 ± 0.06 | 36.58 ± 0.08 | 36.56 ± 0.07 |
| P (100 mg/kg) | 37.25 ± 0.06 | 36.75 ± 0.05 | 36.62 ± 0.08 | 36.58 ± 0.07 |
| Q (100 mg/kg) | 37.24 ± 0.07 | 36.82 ± 0.06 | 36.70 ± 0.05 | 36.67 ± 0.08 |
| R (100 mg/kg) | 37.23 ± 0.06 | 36.81 ± 0.05 | 36.65 ± 0.08 | 36.61 ± 0.07 |
| S (100 mg/kg) | 37.29 ± 0.07 | 36.82 ± 0.06 | 36.60 ± 0.05 | 36.67 ± 0.08 |
| T (100 mg/kg) | 37.22 ± 0.06 | 36.65 ± 0.06 | 36.58 ± 0.08 | 36.51 ± 0.07 |
| U (100 mg/kg) | 37.25 ± 0.06 | 36.63 ± 0.06 | 36.55 ± 0.08 | 36.51 ± 0.07 |

The control group is group A. 2 hours later, diethylaminoethyl 1-(p-chlorobenzoyl)-5-methoxy-2-methylindole 3-acetate.AcOH (100 mg/kg, B), diethylaminoethyl (Z)-5-fluoro-2-methyl-1-[(4-methylsulfinyl) phenylmethylene]-1H-indene-3-acetate.AcOH (100 mg/kg, C), diethylaminoethyl 1-methyl-5-(4-methylbenzoyl)-1H-pyrrole-2-acetate.AcOH (100 mg/kg, D), diethylaminoethyl 5-(4-Chlorobenzoyl)-1,4-dimethyl-1H-pyrrole-2-acetate.AcOH (100 mg/kg, E), diethylaminoethyl 1,8-diethyl-1,3,4,9-tetrahydropyrano-[3,4-b]indole-1-acetate.AcOH (100 mg/kg, F), diethylaminoethyl 2-amino-3-benzoylbenzeneacetate.AcOH (100 mg/kg, G), diethylaminoethyl 2-amino-3-(4-bromo-benzoyl)benzeneacetate.AcOH (100 mg/kg, H), diethylaminoethyl 3-chloro-4-(2-propenyloxy)benzeneacetate.AcOH (100 mg/kg, I), diethylaminoethyl 2-(2,4-dichlorophenoxy)benzeneacetate.AcOH (100 mg/kg, J), diethylaminoethyl 1-(4-chlorobenzoyl-5-methoxy-2-methyl-1H-indole-3-acetoxyacetate.AcOH (100 mg/kg, K), diethylaminoethyl 4-(4-chlorophenyl)-2-phenyl-5-thiazoleacetate.AcOH (100 mg/kg, L), or diethylaminoethyl 3-(4-chlorophenyl)-1-phenyl-1H-pyrazole-4-acetate.AcOH (100 mg/kg, M) were administered transdermally. The body temperature of rats was taken at 90 min. intervals before and after the administration of the test compounds. The results are shown in Table 18.

TABLE 18

Antipyretic Activity of aryl- and heteroarylacetic acids and their HPPs.

| Compound | t = 0 min. | t = 90 min. | t = 180 min. | t = 270 min. |
|---|---|---|---|---|
| A (Control group) | 37.33 ± 0.05 | 37.26 ± 0.07 | 37.32 ± 0.05 | 37.34 ± 0.08 |
| B (100 mg/kg) | 37.35 ± 0.06 | 36.91 ± 0.05 | 36.85 ± 0.08 | 36.79 ± 0.07 |
| C (100 mg/kg) | 37.28 ± 0.06 | 36.65 ± 0.05 | 36.62 ± 0.08 | 36.58 ± 0.07 |
| D (100 mg/kg) | 37.27 ± 0.06 | 36.71 ± 0.05 | 36.65 ± 0.08 | 36.59 ± 0.07 |
| E (100 mg/kg) | 37.21 ± 0.07 | 36.82 ± 0.06 | 36.70 ± 0.05 | 36.70 ± 0.08 |
| F (100 mg/kg) | 37.23 ± 0.06 | 36.65 ± 0.06 | 36.58 ± 0.08 | 36.60 ± 0.07 |
| G (100 mg/kg) | 37.22 ± 0.06 | 36.65 ± 0.05 | 36.62 ± 0.08 | 36.58 ± 0.07 |
| H (100 mg/kg) | 37.25 ± 0.06 | 36.71 ± 0.05 | 36.65 ± 0.08 | 36.64 ± 0.07 |
| I (100 mg/kg) | 37.23 ± 0.07 | 36.80 ± 0.06 | 36.70 ± 0.05 | 36.67 ± 0.08 |
| J (100 mg/kg) | 37.22 ± 0.06 | 36.65 ± 0.06 | 36.58 ± 0.08 | 36.56 ± 0.07 |
| K (100 mg/kg) | 37.21 ± 0.06 | 36.75 ± 0.05 | 36.62 ± 0.08 | 36.58 ± 0.07 |
| L (100 mg/kg) | 37.23 ± 0.06 | 36.81 ± 0.05 | 36.75 ± 0.08 | 36.71 ± 0.07 |
| M (100 mg/kg) | 37.22 ± 0.07 | 36.82 ± 0.06 | 36.80 ± 0.05 | 36.77 ± 0.08 |

The control group is group A. 2 hours later, diclofenac (B1 for 10 mg/kg and B2 for 20 mg/kg) was administered orally and diethylaminoethyl 2[(2,6-dichlorophenyl)amino] benzene acetate.AcOH was administered orally (C1 for 10 mg/kg and C2 for 20 mg/kg) and transdermally (D1 for 10 mg/kg and D2 for 20 mg/kg). The body temperatures of rats were taken at 90 min. intervals before and after the administration of the test compounds. The results are shown in Table 19.

TABLE 19

Antipyretic activity of diclofenac and its HPP.

| Compound | t = 0 min. | t = 90 min. | t = 180 min. | t = 270 min. |
|---|---|---|---|---|
| Control group(A) | 37.56 ± 0.05 | 37.55 ± 0.07 | 37.53 ± 0.05 | 37.52 ± 0.08 |
| (10 mg/kg, B1) | 37.56 ± 0.06 | 36.90 ± 0.05 | 36.91 ± 0.08 | 36.92 ± 0.07 |
| (20 mg/kg, B2) | 37.55 ± 0.09 | 36.60 ± 0.07 | 36.53 ± 0.06 | 36.55 ± 0.05 |
| (10 mg/kg, C1, orally) | 37.52 ± 0.07 | 36.50 ± 0.06 | 36.60 ± 0.05 | 36.55 ± 0.08 |
| (20 mg/kg, C2, orally) | 37.54 ± 0.08 | 36.30 ± 0.05 | 36.35 ± 0.07 | 36.38 ± 0.08 |
| (10 mg/kg, D1, transdermally) | 37.58 ± 0.06 | 36.30 ± 0.06 | 36.35 ± 0.08 | 36.31 ± 0.07 |
| (20 mg/kg, D2, transdermally) | 37.59 ± 0.05 | 36.25 ± 0.05 | 36.30 ± 0.07 | 36.20 ± 0.05 |

The control group is group A. 2 hours later, diethylaminoethyl 2-[(2,3-dimethylphenyl)amino]benzoate.AcOH (100 mg/kg, B), diethylaminoethyl 2-[(2,6-dichloro-3-methylphenyl)amino]benzoate.AcOH (100 mg/kg, C), diethylaminoethyl 2-[[(3-(trifluoromethyl)phenyl)amino]benzoate.AcOH (100 mg/kg, D), diethylaminoethyl 2-[[3-(trifluoromethyl)phenyl]amino]-3-pyridinecarboxylate.AcOH (100 mg/kg, E), diethylaminoethyl 2-[[2-methyl-3-(trifluoromethyl)phenyl]amino]-3-pyridinecarboxylate.AcOH (100 mg/kg, F) were administered transdermally. The body temperature of rats was taken at 90 min. intervals before and after the administration of the test compounds. The results are shown in Table 20.

TABLE 20

Antipyretic Activity of arylanthranilic acids and their HPPs.

| Compound | t = 0 min. | T = 90 min. | t = 180 min. | t = 270 min. |
|---|---|---|---|---|
| A (Control group) | 37.34 ± 0.05 | 37.36 ± 0.07 | 37.37 ± 0.05 | 37.44 ± 0.08 |
| B (100 mg/kg) | 37.35 ± 0.06 | 36.71 ± 0.05 | 36.60 ± 0.08 | 36.59 ± 0.07 |
| C (100 mg/kg) | 37.28 ± 0.06 | 36.68 ± 0.05 | 36.62 ± 0.08 | 36.58 ± 0.07 |
| D (100 mg/kg) | 37.27 ± 0.06 | 36.76 ± 0.05 | 36.65 ± 0.06 | 36.49 ± 0.07 |
| E (100 mg/kg) | 37.25 ± 0.07 | 36.82 ± 0.06 | 36.70 ± 0.05 | 36.50 ± 0.08 |
| F (100 mg/kg) | 37.23 ± 0.06 | 36.69 ± 0.06 | 36.52 ± 0.08 | 36.40 ± 0.07 |

The control group is group A. 2 hours later, 4-N,N-dimethylaminobutyryloxy-2-methyl-N-2-pyridinyl-2H, 1,2-benzothiazine-3-carboxamide 1,1-dioxide.HCl (25 mg/kg, B), N-(2-thiazoyl)-4-N,N-dimethylaminobutyryloxy-2-methyl-2H, 1,2-benzothiazine-3-carboxamide 1,1-dioxide-.HCl (25 mg/kg, C), 6-chloro-4-N,N-dimethylaminobutyryloxy-2-methyl-N-2-pyridinyl-2H-thieno[2,3-e]-1,2-thiazine-3-carboxamide 1,1-dioxide.HCl (25 mg/kg, D), 4-N,N-dimethylaminobutyryloxy-2-methyl-N-2-pyridinyl-2H-thieno[2,3-e]-1,2-thiazine-3-carboxamide 1,1-dioxide-.HCl (25 mg/kg, E), 8-chloro-(4-N,N-dimethylaminobutyryloxy-pyridine-2-ylamino-methylidene)-3-methyl-2,2-dioxo-$2\lambda^{6'}7$-dithia-3-azabicyclo[4,3,0]nona-8,10-dien-5-one.HCl (25 mg/kg, F), 4-N,N-dimethylaminobutyryloxy-2-methyl-N-[5-Methyl-3-isoxolyl-2H-1,2-benzothiazine-3-carboxamide 1,1-dioxide].HCl (25 mg/kg, G), and 4-N,N-dimethylaminobutyryloxy-2-methyl-N-(5-methyl-2-thiazolyl)-2H-1,2-benzothiazine-3-carboxamide-1,1-dioxide.HCl (25 mg/kg, H) were administered transdermally. The body temperature of the rats was taken at 90 min. intervals before and after the administration of the test compounds. The results are shown in Table 21.

TABLE 21

Antipyretic activity of oxicams and their HPPs.

| Compound | t = 0 min. | t = 90 min. | t = 180 min. | t = 270 min. |
|---|---|---|---|---|
| A (Control group) | 37.54 ± 0.05 | 37.66 ± 0.07 | 37.67 ± 0.05 | 37.64 ± 0.08 |
| B (25 mg/kg) | 37.57 ± 0.06 | 36.51 ± 0.05 | 36.40 ± 0.06 | 36.45 ± 0.07 |
| C (25 mg/kg) | 37.50 ± 0.07 | 36.61 ± 0.04 | 36.50 ± 0.07 | 36.60 ± 0.05 |
| D (25 mg/kg) | 37.55 ± 0.05 | 36.66 ± 0.06 | 36.60 ± 0.06 | 36.61 ± 0.07 |
| E (25 mg/kg) | 37.54 ± 0.06 | 36.61 ± 0.06 | 36.58 ± 0.08 | 36.55 ± 0.05 |
| F (25 mg/kg) | 37.53 ± 0.05 | 36.57 ± 0.05 | 36.52 ± 0.07 | 36.51 ± 0.06 |
| G (25 mg/kg) | 37.52 ± 0.06 | 36.62 ± 0.07 | 36.53 ± 0.06 | 36.60 ± 0.05 |
| H (25 mg/kg) | 37.57 ± 0.07 | 36.53 ± 0.08 | 36.52 ± 0.08 | 36.50 ± 0.07 |

Example 9. Anti-Inflammatory Activities of HPPs and their Parent Drugs

A carrageenin solution is administered subcutaneously to the foot pads of a group of rats 60 min. after the rats are administered with a test compound. HPP is administered transdermally or orally, and its corresponding parent drug is administered orally. The volume of the hind paw was measured at every hour after the administration of the carrageenin, and the rate of increase in the volume of the paw was calculated and designated as the rate of swelling (%). The results show that HPPs have better anti-inflammatory activities than that of the corresponding parent drugs (FIGS. 4a-4h). Other compounds of the general "Structure 1" shown similar anti-inflammatory activity.

50 mg/kg of diethylaminoethyl acetylsalicylate.AcOH was administered orally or transdermally to rats and 50 mg/kg of aspirin was administered orally. 60 minutes later, a carrageenin solution was administered subcutaneously to the foot pads of the rats. The volume of the hind paw was measured at every hour after the administration of the carrageenin, and the rate of increase in the volume of the paw was calculated and designated as the rate of swelling (%). The results obtained are shown in FIG. 4a.

50 mg/kg of diethylaminoethyl 5-(2,4-difluorophenyl) salicylate.AcOH was administered orally or transdermally to rats and 50 mg/kg of diflunisal was administered orally. 60 minutes later, a carrageenin solution was administered subcutaneously to the foot pads of the rats. The volume of the hind paw was measured at every hour after the administration of the carrageenin, and the rate of increase in the volume of the paw was calculated and designated as the rate of swelling (%). The results obtained are shown in FIG. 4b.

50 mg/kg of diethylaminoethyl 2-(p-isobutylphenyl) propionate.AcOH was administered orally or transdermally to rats and 50 mg/kg of ibuprofen was administered orally. 60 minutes later, a carrageenin solution was administered subcutaneously to the foot pads of the rats. The results obtained are shown in FIG. 4c.

10 mg/kg of diethylaminoethyl 2[(2,6-dichlorophenyl)amino]benzene acetate.AcOH was administered orally or transdermally to rats and 10 mg/kg of diclofenac was administered orally. 60 minutes later, a carrageenin solution was administered subcutaneously to the foot pads of the rats. The volume of the hind paw was measured at every hour after the administration of the carrageenin, and the rate of increase in the volume of the paw was calculated and designated as the rate of swelling (%). The results obtained are shown in FIG. 4g.

50 mg/kg of diethylaminoethyl 2-(3-benzoyphenyl) propionate.AcOH was administered orally or transdermally to rats and 50 mg/kg of ketoprofen was administered orally. 60 minutes later, a carrageenin solution was administered subcutaneously to the foot pads of the rats. The volume of the hind paw was measured at every hour after the administration of the carrageenin, and the rate of increase in the volume of the paw was calculated and designated as the rate of swelling (%). The results obtained are shown in FIG. 4d.

Diethylaminoethyl 2-(6-methoxy-2-naphthyl)propionate.AcOH (100 mg/kg, B), diethylaminoethyl α-methyl-4-(2-thienylcarbonyl)benzeneacetate.AcOH (100 mg/kg, C), diethylaminoethyl α-methyl-(p-chlorobenzoyl)-5-methoxy-2-methylindole 3-acetate.AcOH (100 mg/kg, D), diethylaminoethyl 2-(2-fluoro-4-biphenylyl)propionate.AcOH (100 mg/kg, E), diethylaminoethyl 6-chloro-α-methyl-9H-carbazole-2-acetate.AcOH (100 mg/kg, F), diethylaminoethyl α-methyl-5H-[1]benzopyrano[2,3-b]pyridine-7-acetate.AcOH (100 mg/kg, G), diethylaminoethyl 2-(4-chlorophenyl)-α-methyl-5-benzoxazoleacetate.AcOH (100 mg/kg, H), diethylaminoethyl α-methyl-4-[(2-methyl-2-propenyl)amino]benzeneacetate.AcOH (100 mg/kg, I), diethylaminoethyl 5-benzoyl-α-methyl-2-thiopheneacetate.AcOH (100 mg/kg, J), diethylaminoethyl 3-chloro-4-(2,5-dihydro-1H-pyrrol-1-yl)-α-methyl benzeneacetate.AcOH (100 mg/kg, K), diethylaminoethyl 2-(10, 11-dihydro-10-oxodibenzo(b,f)thiepin-2-yl)propionate.AcOH (100 mg/kg, L), diethylaminoethyl 2-(8-methyl-10,11-dihydro-11-oxodibenz(b,f)oxepin-2-yl)propionate.AcOH (100 mg/kg, M), diethylaminoethyl 2-[4-(2-oxocyclopentyl-methyl)phenyl]propionate.AcOH (100 mg/kg, N), diethylaminoethyl 4-(1, 3-dihydro-1-oxo-2H-isoindol-2-yl)-α-methylbenzeneacetate.AcOH (100 mg/kg, O), diethylaminoethyl α,3- dichloro-4-cyclohexylbenzeneacetate.AcOH (100 mg/kg, P), diethylaminoethyl 4,5-Diphenyl-2-oxazole propionate.AcOH (100 mg/kg, Q), diethylaminoethyl 3-(4-biphenylylcarbonyl)propionate.AcOH (100 mg/kg, R), diethylaminoethyl 5-(4-chlorophenyl)-beta-hydroxy-2-furanpropionate.AcOH (100 mg/kg, S), diethylaminoethyl 5-benzoyl-2,3-dihydro-1H-pyrrolizine-1-carboxylate.AcOH (100 mg/kg, T), diethylaminoethyl 6-chloro-5-cyclohexyl-2,3-dihydro-1H-indene-1-carboxylate.AcOH (100 mg/kg, U) were administered transdermally. Group A is the controlled group. 60 minutes later, a carrageenin solution was administered subcutaneously to the foot pads of the rats. The volume of the hind paw was measured at every hour after the administration of the carrageenin, and the rate of increase in the volume of the paw was calculated and designated as the rate of swelling (%). The results obtained are shown in FIGS. 4e-1-4e-4.

1 hour before the carrageenin injection, diethylaminoethyl 1-(p-chlorobenzoyl)-5-methoxy-2-methylindole 3-acetate.AcOH (100 mg/kg, B), diethylaminoethyl (Z)-5-fluoro-2-methyl-1-[(4-methylsulfinyl) phenylmethylene]-1H-indene-3-acetate.AcOH (100 mg/kg. C), diethylaminoethyl 1-methyl-5-(4-methylbenzoyl)-1H-pyrrole-2-acetate.AcOH (100 mg/kg. D), diethylaminoethyl 5-(4-Chlorobenzoyl)-1,4-dimethyl-1H-pyrrole-2-acetate.AcOH (100 mg/kg, E), diethylaminoethyl 1,8-diethyl-1,3,4,9-tetrahydropyrano-[3.4-b]indole-1-acetate.AcOH (100 mg/kg, B, diethylaminoethyl 2-amino-3-benzoylbenzeneacetate.AcOH (100 mg/kg, G). diethylaminoethyl 2-amino-3-(4-bromo-benzoyl)benzeneacetate.AcOH (100 mg/kg, H), diethylaminoethyl 3-chloro-4-(2-propenyloxy)benzeneacetate.AcOH (100 mg/kg, I), diethylaminoethyl 2-(2,4-dichlorophenoxy)benzeneacetate.AcOH (100 mg/kg, J), diethylaminoethyl 1-(4-chlorobenzoyl-5-methoxy-2-methyl-1H-indole-3-acetoxyacetate.AcOH (100 mg/kg, K), diethylaminoethyl 4-(4-chlorophenyl-2-phenyl-5-thiazoleacetate.AcOH (100 mg/kg, L), or diethylaminoethyl 3-(4-chlorophenyl-1-phenyl-1H-pyrazole-4-acetate.AcOH (100 mg/kg, M), were administered transdermally. A group is the control group. (FIGS. 4f-1-4f-2)

Diethylaminoethyl 2-[(2,3-dimethylphenyl)amino]benzoate.AcOH (100 mg/kg, B), diethylaminoethyl 2-[(2,6-dichloro-3-methylphenyl)amino]benzoate.AcOH (100 mg/kg, C), diethylaminoethyl 2-[[(3-(trifluoromethyl)phenyl)amino]benzoate.AcOH (100 mg/kg, D), diethylaminoethyl 2-[[3-(trifluoromethyl)phenyl]amino]-3-pyridinecarboxylate.AcOH (100 mg/kg, E), diethylaminoethyl 2-[[2-methyl-3-(trifluoromethyl)phenyl]amino]-3-pyridinecarboxylate.AcOH (100 mg/kg, F) were administered transdermally. Group A is the controlled group. 60 minutes later, a carrageenin solution was administered subcutaneously to the feet pads of the rats. The volume of the hind paw was measured at every hour after the administration of the carrageenin, and the rate of increase in the volume of the paw was calculated and designated as the rate of swelling (%). The results obtained are shown in FIG. 4h.

Example 10. Antiasthmatic Activities of the Prodrug Compounds

It is also known that a high dose of oral acetylsalicylic acid shows an antireactive-antiasthmatic activity by inhibition of the cyclooxygenase activity (Bianco, Sebastiano, U.S. Pat. No. 5,570,559), Due to their very high membrane penetration rate, these pro-drugs can be used in treating asthma by spraying into the mouth or nose of a host. They can also be used to treat acne due to their anti-inflammatory properties. They can be used for the treatment and prevention of endothelia dysfunction as well.

Example 11. Application of the HPPs in Treating Skin Conditions

HPPs can also be used to treat psoriasis, acne, sunburn or other skin conditions due to inhibition of the cyclooxygenase activity and very high skin penetration rate.

Diethylaminoethyl acetylsalicylate.AcOH is applied to subjects' the sun damaged skin. The treated skin demonstrates an 97% reduction of acne, an 89% reduction in roughness, an 85% reduction in the look of freckles, moles, dark spots, and other discolorations, an 85% reduction in the appearance of fine lines and wrinkles. 92% of the subjects treated experienced improved elasticity and firmness, and 95% experienced overall improvement in texture and tone. The results shown that HPPs of aspirin and related compounds may be used to treat skin conditions.

Example 12. Application of HPPs in Treating Cancer i) Breast Cancer.

Human breast cancer cells (BCAP-37, 2-3 mm$^3$ of tumor tissue was used in each mouse) are subcutaneously xenografted into the front leg of nude mice (BALB, 12 groups, 7 mice each group). After 14 days, the tumors grow to the size of 50±10 mm$^3$ (0.05 ml). Then 30 μl of 5% (equal to 1.5 mg of the HPPs) diethylaminoethyl acetylsalicylate.acetylsalicylic acid salt (P-1, in acetone); 1-piperidinepropyl 2[(2,6-dichlorophenyl)amino]benzene acetate.AcOH (P-2, in water), 1-pyrrolidinepropyl 2-(3-benzoylphenyl) propionate.AcOH (P-3, in water), 4-piperidinemethyl 2-(3-phenoxyphenyl)propionate.AcOH (P-4, in water), 3-piperidinemethyl 2-(ρ-isobutylphenyl) propionate.AcOH (P-5, in water), diethylaminoethyl 1-(p-chlorobenzoyl)-5-methoxy-2-methylindole 3-acetate.AcOH (P-11, in water), 2-(4-morpholinyl)ethyl (Z)-5-fluoro-2-methyl-1-[(4-methylsulfinyl) phenylmethylene]-1H-indene-3-acetate.AcOH (P-12, in water), diethylaminoethyl 2-(2,4-dichlorophenoxy)benzeneacetate.AcOH (P-19, in water), diethylaminoethyl 2-(8-methyl-10,11-dihydro-11-oxodibenz(b,f)oxepin-2-yl)propionate.AcOH (P-37, in water), 1-pyrrolidinepropyl 2-[[(3-(trifluoromethyl)phenyl)amino]benzoate.AcOH (P-48, in water), 4-N,N-dimethylaminobutyryloxy-2-methyl-N-2-pyridinyl-2H, 1,2-benzothiazine-3-carboxamide 1,1-dioxide.HCl (P-51, in acetone) is topically applied to the human breast cancer cells-implanted area every 8 hours. On day 42, the tumors sizes and weight of the mice are shown in Table 22.

TABLE 22

The tumors size and the weights of the control group
and the drug-treated groups of nude mice on day 42.

| HPP | Control | P-1 | P-2 | P-3 | P-4 | P-5 |
|---|---|---|---|---|---|---|
| Tumor size (mm$^3$) | 800 ± 100 | 150 ± 50 | 180 ± 50 | 200 ± 50 | 180 ± 50 | 190 ± 50 |
| Mouse weight (g) | 22 ± 2 | 22 ± 3 | 22 ± 2 | 21 ± 3 | 22 ± 3 | 23 ± 2 |
| HPP | P-11 | P-12 | P-19 | P-37 | P-48 | P-51 |
| Tumor size (mm$^3$) | 210 ± 100 | 250 ± 50 | 280 ± 50 | 250 ± 50 | 290 ± 50 | 390 ± 50 |
| Mouse weight (g) | 21 ± 2 | 23 ± 3 | 21 ± 2 | 23 ± 3 | 22 ± 3 | 23 ± 2 | ii) Colon Cancer.

Human colon cancer cells (LS174J, 2-3 mm$^3$ of tumor tissue was used in each mouse) are subcutaneously xenografted into the front leg of nude mice (BALB). After 7 days, the tumors grow to the size of 55±10 mm$^3$ (0.055 ml). Then about 30 µl of 5% (equal to 1.5 mg of the pro-drugs) diethylaminoethyl acetylsalicylate.acetylsalicylic acid salt (P-1, in acetone); 1-piperidinepropyl 2[(2,6-dichlorophenyl)amino]benzene acetate.AcOH (P-2, in water), 1-pyrrolidinepropyl 2-(3-benzoylphenyl) propionate.AcOH (P-3, in water), 4-piperidinemethyl 2-(3-phenoxyphenyl)propionate.AcOH (P-4, in water), 3-piperidinemethyl 2-(p-isobutylphenyl) propionate.AcOH (P-5, in water), diethylaminoethyl 1-methyl-5-(4-methylbenzoyl)-1H-pyrrole-2-acetate.AcOH (P-13, in water), 2-(4-morpholinyl)ethyl 2-amino-3-benzoylbenzeneacetate.AcOH (P-16, in water), diethylaminoethyl 2-(10,11-dihydro-10-oxodibenzo(b,f)thiepin-2-yl)propionate.AcOH (P-36), diethylaminoethyl 2-[(2,3-dimethylphenyl)amino]benzoate.AcOH (P-46, in water), diethylaminoethyl 2-[(2,6-dichloro-3-methylphenyl)amino]benzoate.AcOH (P-47, in water), N-(2-thiazoyl)-4-N,N-dimethylaminobutyryloxy-2-methyl-2H, 1,2-benzothiazine-3-carboxamide 1,1-dioxide.HCl (P-52, in acetone) is topically applied to the human colon cancer cells-implanted area every 8 hours. On day 30, the tumors size and mouse weight are shown in Table 23.

TABLE 23 the tumors size and the weight of the control
group and the HPP-treated groups on day 30.

| HPP | Control | P-1 | P-2 | P-3 | P-4 | P-5 |
|---|---|---|---|---|---|---|
| Tumor size (mm$^3$) | 1300 ± 300 | 420 ± 100 | 480 ± 180 | 500 ± 150 | 480 ± 120 | 390 ± 110 |
| Mouse weight (g) | 21 ± 2 | 22 ± 3 | 22 ± 2 | 21 ± 3 | 22 ± 3 | 23 ± 2 |
| HPP | P-13 | P-16 | P-36 | P-46 | P-47 | P-52 |
| Tumor size (mm$^3$) | 610 ± 200 | 550 ± 150 | 480 ± 180 | 650 ± 250 | 490 ± 150 | 690 ± 250 |
| Mouse weight (g) | 21 ± 2 | 23 ± 3 | 21 ± 2 | 23 ± 3 | 22 ± 3 | 23 ± 2 |

The results show that NSAIA-HPPs have very strong anti-tumor activity and have little effect in reducing the treated subjects' body weight.

Example 13. Hypoglycemic Effect of NSAIA-HPPs

HPPs lower blood glucose level in rat models (SLAC/GK, type 2 diabetes, n=7). 50% acetone solution of diethylaminoethyl acetylsalicylate.acetylsalicylic acid salt (P-1, in acetone); 4-acetamidophenyl salicylyldimethylaminobutyrate.HCl (P-6), diethylaminoethyl 5-(2,4-difluorophenyl) acetylsalicylate.5-(2,4-difluorophenyl).acetylsalicylic acid salt (P-8), diethylaminoethyl salicylsalicylate.AcOH (P-9), diethylaminoethyl salicylate.AcOH (P-10), diethylaminoethyl 5-acetamido-acetylsalicylate (P-58), diethylaminoethyl acetylsalicylsalicylate.acetylsalicylsalicylic acid salt (P-59), diethylaminoethyl acetylsalicylsalicylate.acetylsalicylsalicylic acid salt (P-60) (equal to of 20 mg/kg of NSAIAs) are administered transdermally to the backs (about 1.5 cm$^2$) of rats (fur was shaved) once per day (at 8 am) for 5 weeks. The blood glucose levels are measured once every 3 days at 3 pm (no fasting) from the second week to the fifth week (Table 24). The blood lipid levels are measured at the end of the fifth week (Table 25).

The results showed that HPP-NSAIAs lowered blood lipid levels (total cholesterol and triglycerides) in diabetes rat models effectively and do not affect HDL levels.

20% acetone solution of diethylaminoethyl acetylsalicylate.acetylsalicylic acid salt (P-1, in acetone); 4-acetamidophenyl salicylyldimethylaminobutyrate.HCl (P-6), diethylaminoethyl 5-(2,4-difluorophenyl) acetylsalicylate.5-(2,4-difluorophenyl) acetylsalicylic acid salt (P-8), diethylaminoethyl salicylsalicylate.AcOH (P-9), diethylaminoethyl salicylate.AcOH (P-10), diethylaminoethyl 5-acetamido-acetylsalicylate (P-58), diethylaminoethyl acetylsalicylsalicylate. acetylsalicylsalicylic acid salt (P-59), diethylaminoethyl acetylsalicylsalicylate. acetylsalicylsalicylic acid salt (P-60) (equal to of 20 mg/kg of NSAIAs) were mixed with food and were orally administered to the rats (SLAC/GK, type 2 diabetes, n=7) with food every day for 5 weeks. The blood glucose levels were measured once every 3 days at 3 pm (no fasting) from the second week to the fifth week. The results are shown in Table 26. The blood lipid levels were measured at the end of the fifth week. The results are shown in Table 27.

TABLE 24

Anti-diabetes activity of the pro-drugs of NSAIAs

| HPP | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
|---|---|---|---|---|---|---|---|---|---|
| Baseline | 15.6 ± 3 | 16.1 ± 3 | 16.7 ± 4 | 17.1 ± 3 | 16.5 ± 4 | 15.8 ± 3 | 17.1 ± 3 | 16.3 ± 3 | 15.5 ± 3 |
| Average | 15.9 ± 3 | 6.5 ± 1 | 8.5 ± 2 | 8.1 ± 1 | 8.4 ± 1 | 8.2 ± 1 | 8.4 ± 1 | 8.7 ± 1 | 8.6 ± 1 |
| Baseline | 6.5 ± 1 | 6.4 ± 1 | 6.8 ± 1 | 7.1 ± 1 | 6.5 ± 1 | 6.8 ± 1 | 6.9 ± 1 | 7.2 ± 1 | 6.6 ± 1 |
| Average | 6.6 ± 1 | 6.3 ± 1 | 6.5 ± 1 | 6.8 ± 1 | 6.7 ± 1 | 6.9 ± 1 | 7.1 ± 1 | 7.3 ± 1 | 7.5 ± 1 |

The results showed that the NSAIA-HPPs lower blood glucose levels in diabetes rat models effectively and do not affect the blood glucose levels in normal rats. The blood glucose levels of the rats stay at normal level (7-8 mmol/L, no fasting) after the treatment is stopped for 30 days. This means that the HPPS not only lower blood glucose levels, but also may cure diabetes.

TABLE 25

Blood lipid-lowering activity of NSAIA-HPPs.

| Prodrug | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
|---|---|---|---|---|---|---|---|---|---|
| Cholesterol (total) | | | | | | | | | |
| Baseline | 7.6 ± 0.5 | 7.7 ± 0.4 | 7.3 ± 0.5 | 7.6 ± 0.6 | 7.7 ± 0.5 | 7.1 ± 0.5 | 7.8 ± 0.5 | 7.6 ± 0.6 | 7.3 ± 0.6 |
| Average | 7.9 ± 0.5 | 4.0 ± 0.3 | 4.7 ± 0.4 | 5.3 ± 0.3 | 4.8 ± 0.4 | 4.9 ± 0.4 | 5.6 ± 0.4 | 5.1 ± 0.3 | 5.6 ± 0.3 |
| Cholesterol (HDL) | | | | | | | | | |
| Baseline | 1.4 ± 0.1 | 1.4 ± 0.2 | 1.3 ± 0.1 | 1.6 ± 0.2 | 1.3 ± 0.1 | 1.6 ± 0.2 | 1.3 ± 0.1 | 1.6 ± 0.2 | 1.3 ± 0.2 |
| Average | 1.3 ± 0.1 | 1.5 ± 0.2 | 1.3 ± 0.2 | 1.5 ± 0.2 | 1.4 ± 0.2 | 1.5 ± 0.1 | 1.4 ± 0.2 | 1.6 ± 0.2 | 1.5 ± 0.2 |
| Triglycerides | | | | | | | | | |
| Baseline | 5.2 ± 0.7 | 5.4 ± 0.5 | 5.3 ± 0.5 | 5.6 ± 0.6 | 5.3 ± 0.5 | 5.6 ± 0.6 | 5.3 ± 0.5 | 5.6 ± 0.5 | 5.3 ± 0.6 |
| Average | 5.5 ± 0.6 | 1.5 ± 0.2 | 2.3 ± 0.2 | 1.9 ± 0.2 | 2.4 ± 0.2 | 2.5 ± 0.2 | 2.4 ± 0.2 | 1.9 ± 0.2 | 2.5 ± 0.2 |

TABLE 26

Anti-diabetes activity of the NSAIA-HPPs

| Prodrug | | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
|---|---|---|---|---|---|---|---|---|---|---|
| Diabetic rats | Baseline | 15.3 ± 3 | 16.5 ± 3 | 16.1 ± 4 | 16.1 ± 3 | 16.5 ± 4 | 15.6 ± 3 | 17.0 ± 3 | 15.3 ± 3 | 16.5 ± 3 |
| | Average | 15.6 ± 3 | 6.5 ± 1 | 7.5 ± 2 | 7.3 ± 1 | 7.6 ± 1 | 7.8 ± 1 | 8.4 ± 1 | 8.6 ± 1 | 7.9 ± 1 |
| Normal rats | Baseline | 6.6 ± 1 | 6.3 ± 1 | 6.5 ± 1 | 7.0 ± 1 | 6.3 ± 1 | 6.7 ± 1 | 6.9 ± 1 | 7.5 ± 1 | 6.8 ± 1 |
| | Average | 6.5 ± 1 | 6.5 ± 1 | 6.4 ± 1 | 6.8 ± 1 | 6.6 ± 1 | 6.9 ± 1 | 7.2 ± 1 | 7.3 ± 1 | 7.3 ± 1 |

The results showed that the pro-drugs of NSAIAs lowered blood glucose levels in diabetic rat models very effectively and did not affect the blood glucose levels of normal rats when the pro-drugs were taken orally and the dosages are much smaller than that of the parent drugs.

TABLE 27

Blood lipid-lowering activity of the pro-drugs of NSAIAs

| Prodrug | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
|---|---|---|---|---|---|---|---|---|---|
| Cholesterol (total) | | | | | | | | | |
| Baseline | 7.8 ± 0.6 | 7.6 ± 0.4 | 7.5 ± 0.4 | 7.8 ± 0.6 | 7.9 ± 0.5 | 7.6 ± 0.5 | 7.9 ± 0.5 | 7.7 ± 0.6 | 7.5 ± 0.5 |
| Average | 7.9 ± 0.5 | 4.1 ± 0.3 | 4.9 ± 0.4 | 5.7 ± 0.3 | 5.6 ± 0.4 | 5.2 ± 0.5 | 5.8 ± 0.4 | 5.7 ± 0.3 | 5.5 ± 0.3 |
| Cholesterol (HDL) | | | | | | | | | |
| Baseline | 1.6 ± 0.1 | 1.5 ± 0.2 | 1.5 ± 0.1 | 1.4 ± 0.2 | 1.5 ± 0.1 | 1.6 ± 0.2 | 1.8 ± 0.1 | 1.9 ± 0.2 | 1.5 ± 0.2 |
| Average | 1.5 ± 0.1 | 1.6 ± 0.2 | 1.4 ± 0.2 | 1.3 ± 0.2 | 1.4 ± 0.2 | 1.7 ± 0.1 | 1.6 ± 0.2 | 1.8 ± 0.2 | 1.6 ± 0.2 |
| Triglycerides | | | | | | | | | |
| Baseline | 5.5 ± 0.6 | 5.7 ± 0.5 | 5.5 ± 0.5 | 5.6 ± 0.7 | 5.8 ± 0.6 | 5.7 ± 0.6 | 5.5 ± 0.5 | 5.4 ± 0.6 | 5.2 ± 0.5 |
| Average | 5.5 ± 0.6 | 1.4 ± 0.2 | 1.8 ± 0.2 | 1.8 ± 0.2 | 2.7 ± 0.2 | 2.6 ± 0.2 | 1.8 ± 0.2 | 2.7 ± 0.2 | 2.5 ± 0.2 |

The results showed that the pro-drugs of NSAIAs lowered blood lipid levels (total cholesterol and triglycerides) in diabetic rat models very effectively when the pro-drugs were taken orally and the dosages are much smaller than that of the parent drugs.

The pro-drugs in this invention lower blood glucose levels in mouse models (SLAC:NOD-IDDM, type 1 diabetes, n=7). 50% acetone solution of diethylaminoethyl acetylsalicylate.acetylsalicylic acid salt (P-1, in acetone); 4-acetamidophenyl salicylyldimethylaminobutyrate.HCl (P-6), diethylaminoethyl 5-(2,4-difluorophenyl) acetylsalicylate.5-(2,4-difluorophenyl) acetylsalicylic acid salt (P-8), diethylaminoethyl salicylsalicylate.AcOH (P-9), diethylaminoethyl salicylate.AcOH (P-10), diethylaminoethyl 5-acetamido-acetylsalicylate (P-58), diethylaminoethyl acetylsalicylate. acetylsalicylsalicylic acid salt (P-59), diethylaminoethyl acetylsalicylsalicylate. acetylsalicylsalicylic acid salt (P-60) (equal to of 30 mg/kg of NSAIAs) were administered transdermally to the backs (about 1.5 cm$^2$) of mice (fur was shaved) once per day (at 8 am) for 7 weeks. The blood glucose levels were measured once every 3 days at 3 pm (no fasting) from the fourth week to the seventh week. The results are shown in table 28.

TABLE 28

Anti-diabetes (type I) activity of the pro-drugs of NSAIAs

| Prodrug | Control mmol/L | P-1 mmol/L | P-6 mmol/L | P-8 mmol/L | P-9 mmol/L | P-10 mmol/L | P-58 mmol/L | P-59 mmol/L | P-60 mmol/L |
|---|---|---|---|---|---|---|---|---|---|
| Baseline | 28.6 ± 5 | 26.1 ± 5 | 27.7 ± 4 | 29.1 ± 5 | 26.5 ± 4 | 25.8 ± 3 | 27.1 ± 3 | 24.3 ± 3 | 25.5 ± 3 |
| Average | 32.9 ± 5 | 6.5 ± 1 | 9.5 ± 2 | 9.1 ± 1 | 9.4 ± 1 | 8.2 ± 1 | 7.9 ± 1 | 8.7 ± 1 | 8.6 ± 1 |

The results showed that the pro-drugs of NSAIAs lowered blood glucose levels in diabetic (type I) mouse models effectively.

Example 14. NSAIA-HPPs Treat Psoriasis, Discoid Lupus Erythematosus, Systemic Lupus Erythematosus (SLE), Multiple Sclerosis (MS) in Biological System Heavy suspensions of *Malassezia* [Rosenberg, E. W., et al., Mycopathologia, 72, 147-154 (1980)] were applied to the shaved skin on the backs of the Chinese white rabbits (n=4×6) twice (at 7 am and 7 pm) per day for 2 weeks, lesions similar to psoriasis resulted. Then a 5% aqueous solution of 3-piperidinemethyl 2-(ρ-isobutylphenyl) propionate.AcOH (P-5), diethylaminoethyl 1-methyl-5-(4-methylbenzoyl)-1H-pyrrole-2-acetate.AcOH (P-13), diethylaminoethyl 5-(4-Chlorobenzoyl)-1,4-dimethyl-1H-pyrrole-2-acetate.AcOH (P-14), diethylaminoethyl 1,8-diethyl-1,3,4,9-tetrahydropyrano-[3,4-b]indole-1-acetate.AcOH (P-15), diethylaminoethyl 2-amino-3-(4-bromo-benzoyl)benzeneacetate.AcOH (P-17) diethylaminoethyl 3-chloro-4-(2-propenyloxy)benzeneacetate.AcOH (P-18), diethylaminoethyl 1-(4-chlorobenzoyl-5-methoxy-2-methyl-1H-indole-3-acetoxyacetate.AcOH (P-20), diethylaminoethyl 4-(4-chlorophenyl)-2-phenyl-5-thiazoleacetate.AcOH (P-21), diethylaminoethyl 3-(4-chlorophenyl)-1-phenyl-1H-pyrazole-4-acetate.AcOH (P-22) were applied to the same areas 3 hours (10 am and 10 pm) after the application of heavy suspensions of *Malassezia* (7 am and 7 pm). 10 days after the application of these pro-drugs, the lesions were resolved.

For evaluation of anti-lupus erythematosus activity, 5% diethylaminoethyl acetylsalicylate.acetylsalicylic acid salt (P-1, in acetone, 30 mg/kg) or 3-piperidinemethyl 2-(ρ-isobutylphenyl) propionate.AcOH (P-5, in water, 30 mg/kg) were topically applied to the skin on the backs of mice (MRL/LPR, n=5×3) with discoid lupus erythematosus and systemic lupus erythematosus twice per day. After 6 weeks, all skin lesions and lupus nephritis were resolved in the pro-drug treated mice, but the condition of the control mice were getting worse.

These results suggest that these pro-drugs of NSAIAs are promising agents for the treatment of psoriasis, discoid lupus erythematosus, systemic lupus erythematosus (SLE), multiple sclerosis (MS) and other autoimmune diseases in human.

Example 15. NSAIA-HPPs Treat Thrombotic Activity and Embolization-Associated Thrombus Propagation in Biological Subject Eighteen Chinese White rabbits weighing between 3.0 and 3.5 kg (aged 6-7 months) were selected and divided into three groups (control, P-1 and P-10 groups, n=6). One hour before the experiment, thrombi were made by aspirating venous blood (1 ml) into a sterilized bottle to clot. To avoid fragmentation and slow lysis, the autologous blood clots were stabilized in temperature-controlled (70□) distilled water for 10 min. After anesthesia, the femoral veins were exposed and distally isolated, and autologous blood clots (0.05 g/kg) were injected through an indwelling catheter (20 GA), which had been placed in the femoral vein isolated earlier. 50% acetone solution of diethylaminoethyl acetylsalicylate.acetylsalicylic acid salt (P-1, in acetone, 20 mg/kg) and diethylaminoethyl acetylsalicylsalicylate. acetylsalicylsalicylic acid salt (P-59, 20 mg/kg) were topically applied to the back of the rabbits. After 2 days, rabbits were euthanized with an excessive intravenous injection of sodium amobarbital (60 mg/kg). The lungs and hearts were isolated to observe whether thrombi were present in the pulmonary arteries. The lungs were immersed in 10% formalin for 24 h. Consecutive transverse sections along the obstructed pulmonary arteries were paraffin-embedded and stained with hematoxylin-eosine. In the control group, platelet thrombus and mixed thrombus surrounded the infused clots, which were present in large-sized vessels as well and stretched the vessel walls in both proximal and distal directions. There was excessive proliferation of endothelial cells and fibrocytes in these vessels. Additionally, there was acute pulmonary congestion. In the P-1 and P-59 groups, both lung tissue and vascular walls were normal. The results showed that thrombotic activity and that embolization-associated thrombus propagation can be prevented by these pro-drugs of NSAIAs. These pro-drugs can be very useful for preventing and treating blood clots—a major cause of strokes, heart attacks and organ transplant rejection.

Thrombosis was induced by electrical stimulation (1 mA for 3 minutes) of the carotid artery in spontaneously hypertensive and stroke prone rats (SLAC/SHRSP) by using a thrombosis formation instrument (YLS-14A, Shandong Academy of Medical Sciences, Shandong, China). The rats (Spragu Dawley, 25 weeks old, 380-450 g) were divided into 3 groups randomly, group A is the control group, groups B and C are aspirinamine-treated group. In group B, 100 mg/kg of aspirinamine citric acid salt (10% in water) was applied to the rats' back skin (~5 $cm^2$, fur was cut off) 2 hour before the operation and 1 hour after the operation, then 50 mg/kg of the drug was applied to the back of rats twice per day. In group C, 50 mg/kg of aspirinamine was applied to the back of rats twice per day starting from 24 hours after the operation. The recovery of motor functions of rats was evaluated every day. The operation process is outlined in the Method section in the supporting online materials. The HPP of aspirin is effective to protect rats from stroke without bleeding problem (Table 29), the HPP of aspirin is also capable of reversing paralysis from post-stroke rat without bleeding problem (Table 30). The HPP of aspirin is the first drug which can reverses paralysis from post-stroke.

TABLE 29

Anti-stroke activity by aspirinamine

|  | Stroke-free rats (2 hours) | Stroke-free rats (1 day) | Stroke-free rats (7 days) |
| --- | --- | --- | --- |
| Control group (A) | 0/10 | 0/8 | 0/8 (1 died) |
| Treated group (B) | 8/10 | 9/10 | 10/10 |

TABLE 30

Alleviation of the effects of strokes by aspirinamine

| | Stroke-free rats (3 hrs) | Stroke-free rats (2 day) | Weight Loss (3 days) | Stroke-free rats (7 day) | Weight Loss (7 days) | Stroke-free rats (14 days) | Weight Loss (14 days) |
|---|---|---|---|---|---|---|---|
| Control group | 0/10 | 0/10 | −25 +/− 8% (2 died) | 0/10 | −22 +/− 5% (1 more died) | 1/10 | −18 +/− 6% |
| Treated group | 0/10 | 4/10 | −13 +/− 7% | 9/10 | −7 +/− 4% | 10/10 | −4 +/− 2% |

Example 15. Anti-Hypertensive Activity of HPP-NSAIA

20 Spontaneously hypertensive rats (SLAC/SHR, 19 weeks old, 300-350 g) were divided into 2 groups randomly. In group A, pure water (0.5 ml) was applied to the rats' back skin (~5 cm², fur was cut off) once per day for 6 weeks. In groups B, 50 mg/kg of aspirinamine citric acid salt (10% in water) was applied to the rats' back skin (~5 cm², fur was cut off) once per day. The aspirin-HPP shows anti-hypertensive activities. (Table 31). And the other NSAIA-HPPs have the same anti-hypertensive activities.

TABLE 31

Anti-hypertensive activity of diethylaminoethyl acetylsalicylate•citric acid

| | Blood pressure (mmHg) (week 0) | | Blood pressure (mmHg) (week 2 to week 6) | |
|---|---|---|---|---|
| | Systolic | diastolic | Systolic | diastolic |
| Group A | 181.4 ± 16.7 | 115.2 ± 15.1 | 183.1 ± 15.7 | 116.2 ± 13.3 |
| Group B | 184.6 ± 15.1 | 118.2 ± 13.1 | 115.4 ± 14.6 | 83.5 ± 12.1 |

Hypertension patients' blood pressure is controlled by transdermally administering 100 mg of atenolol HCl salt in 1 ml of pure water per day without side effect of hypotention. 20 Hypertension patents were divided to 2 groups. Group A is control group (n=10, 1 ml of water was administrated to the chest of patients once per day) and group B is atenolol treated group (n=10, 100 mg of atenolol HCl salt was administrated to the chest of patients once per day) (Table 32).

TABLE 32

Anti-hypertension effect of atenolol which was administrated transdermally

| | Blood Pressure (mmHg) (before treatment) | Blood pressure(mmHg) (2 weeks after treatment) |
|---|---|---|
| Group A | 162 ± 27/110 ± 21 | 128 ± 15/81 ± 12 |
| Group B | 160 ± 22/110 ± 20 | 163 ± 28/113 ± 23 |

Example 16. Anti-Parkinson's Disease Activity of NSAIA-HPP

30 Male $C_{57}$/BL6 mice (24-26 g) were divided into 3 groups. Group A mice were i.p. injected 0.4% sodium carboxymethylcellulos (15 ml/kg per day) for 7 days. Group B and C mice were i.p. injected N-methyl-4-phenyl-1,2,3, 6-tetrahydropyridine (MPTP, 30 mg/kg per day) for 7 days. The mice were divided into 2 groups. In groups A and B, 0.1 ml of pure water was applied transdermally to the neck of mice once per day for 14 days. In group C, 30 mg/kg of diethylaminoethyl acetylsalicylate.citric acid (aspirinamine) in 0.1 ml of water was applied transdermally to the neck of mice once per day for 14 days. All mice were killed after the last treatment and the brain tissues were quickly frozen at −80° C. The contents of dopamine (DA) in the striatum were determined with spectrofluorophotometer ($\lambda_{Ex}$=310 nm, $\lambda_{Em}$=390 nm, RF-5000), 5-HT ($\lambda_{Ex}$=355 nm, $\lambda_{Em}$=495 nm), and noradrenaline (NA) ($\lambda_{Ex}$=400 nm, $\lambda_{Em}$=500 nm). The contents of malondialdehyde (MDA) in the SN were measured with the thiobarbituric acid-reaction to indicate the LPO, and contents of glutathione (GSH) in the substantia nigra (SN) were based on the dithionitrobenzonic acid (DTNB) determination. The contents of GABA and Glu in the striatum and SN were shown by high performance amino acid auto-analyser. The results are shown in Table 33. Effects of diethylaminoethyl acetylsalicylate.citric acid on the contents of DA, NA, and 5-HT The content of DA, NA, and 5-HT in the striatum was significantly decreased in MPTP group compared with control group (P<0.05, n=10). Diethylaminoethyl acetylsalicylate.citric acid (30 mg/kg transdermally) increased DA, NA, and 5-HT contents compared with model group (P<0.05, n=10) (Table 33).

TABLE 33

Effects of diethylaminoethyl acetylsalicylate•citric acid on the concentration DA, NA, and 5-HT in the striatum of PD mice induced by MPTP.

| Group | DA μg/g wet tissue | NA | 5-FIT |
|---|---|---|---|
| Control | 885 ± 86 | 618 ± 55 | 306 ± 17 |
| MPTP + water | 515 ± 103 | 419 ± 57 | 248 ± 22 |
| MPTP + aspirinamine (30 mg/kg) | 817 ± 89 | 602 ± 55 | 302 ± 29 | n = 10.
Mean ± SD.
$^b$P < 0.05 vs the control group.
$^e$P < 0.05 vs MPTP group.

Effects of Diethylaminoethyl Acetylsalicylate.Citric Acid on the Contents of MDA and GSH.

The level of nigral GSH in model group was markedly decreased (P<0.01, n=10) and the contents of nigral MDA was increased compared with those in control group (P<0.01, n=10). Diethylaminoethyl acetylsalicylate.citric acid markedly lowered the MDA level while relatively increased the GSH level in PD model (P<0.01, n=10). The results were shown in Table 34.

TABLE 34

Effects of diethylaminoethyl acetylsalicylate•citric acid on the concentration GSH (μg/g protein) and MDA (μmol/g protein) in the substantia nigra of PD mice induced by MPTP.

| Group | GSH | MDA |
|---|---|---|
| Control | 152 ± 12 | 13 ± 3 |
| MPTP + water | 101 ± 17 | 21 ± 4 |
| MPTP + aspirinamine (30 mg/kg) | 143 ± 13 | 14 ± 4 | n = 10.
Mean ± SD.
P < 0.01 vs control group
P < 0.01 vs MPTP group.

Effect of Diethylaminoethyl Acetylsalicylate.Citric Acid on the Contents of GABA and Glu.

MPTP increased the striatal GABA level (P<0.01, n=10) while decreased GABA in the SN (P<0.05, n=10) compared with control group, which were reversed by diethylaminoethyl acetylsalicylate.citric acid (30 mg/kg). However, modafinil did not change the increase of nigrostriatal Glu release induced by MPTP (Table 35).

TABLE 35

Effects of diethylaminoethyl acetylsalicylate•citric acid on the concentration of GABA (μmol/g wet tissue) and Glu in the substantia nigra and striatum of PD mouse induced by MPTP.

| | Substantia nigra | | Striatum | |
|---|---|---|---|---|
| Group | GABA | Glu | GABA | Glu |
| Control | 5.1 ± 0.5 | 27.1 ± 2.5 | 4.7 ± 1.7 | 24.1 ± 2.6 |
| MPTP + water | 2.2 ± 0.4 | 34.5 ± 2.7 | 8.4 ± 1.7 | 33.2 ± 4.5 |
| MPTP + aspirinamine(30 mg/kg) | 4.7 ± 0.5 | 29.5 ± 2.4 | 4.9 ± 1.6 | 26.5 ± 2.7 | n = 10.
Mean ± SD.
P < 0.01 vs control group.
P > 0.05, P < 0.05, P < 0.01 vs MPTP group.

The contents of striatal NA and 5-HT in the MPTP mice were markedly lower than those of the normal mice, and the NSAIA-HPP treatment increased striatal DA, NA, and 5-HT levels. It can improve or reverse the progress of Parkinson's disease. The NSAIA-HPP also inhibited striatal GABA release in PD model. The NSAIA-HPP prevent the neurotoxicity of MPTP by anti-oxidation and modulation of the striatal NA and 5-HT and nigrostriate GABAergic activity. Therefore a NSAIA-HPP may be used for the treatment of Parkinson's disease.

Example 17. Anti-Alzheimer Disease Activity of Diethylaminopropyl Acetylsalicylate.HCl was Tested with Tg2576 Mouse Model of Alzheimer Disease The pathology of Alzheimer's disease (AD) shows a significant correlation between β-amyloid peptide (AβP) conformation and the clinical severity of dementia. For many years, efforts have been focused on the development of inhibitors of β-amyloid (A β) formation and its related neurotoxic effects. To determine the effect of diethylaminopropyl acetylsalicylate.HCl on in vivo Aβ accumulation, we administered transdermally diethylaminopropyl acetylsalicylate.HCl (50 mg/kg in water) to the Tg2576 mouse model of AD over 2 months resulted in a significant, non-overlapping 70-80% reduction in the number of senile plaques, one of the pathological hallmarks of AD. Three-month-old female transgenic mice overexpressing the human APP gene containing the Swedish mutation that causes familial AD (Tg2576 line) were used for testing the effects of diethylaminopropyl acetylsalicylate.HCl in vivo. 20 Tg2576 mice were divided into 2 groups. In group A (n=10), 0.2 ml of pure water was applied transdermally to the back of mouse once per day for 2 months. In group B (n=10), 50 mg/kg of diethylaminopropyl acetylsalicylate.HCl in 0.2 ml of pure water was applied to the back of mouse once per day for 2 months. Then the animals were killed and their brains were removed for analysis. For Aβ analysis, hemibrains were dounce homogenized in 70% formic acid at 150 mg tissue/ml formic acid solution. Homogenates were transferred to a chilled ultracentrifuge and were then spun at 100,000 g for 1 h at 4° C. Supernatants were collected and neutralized with formic acid neutralization buffer (1.0 M Tris base, 0.5 M $NaH_2PO_4$, and 0.05% $NaN_3$; 1:20) for Aβ quantitation by ELISA. Aβ 40 and Aβ 42 were assayed by ELISA. Four individual experiments were performed. To compare across studies, the values for an individual study were normalized using the values obtained for the control animals included in each study. Values represent the mean±SE for the n number shown, after normalizing. As shown in table 36. The transdermal treatment of diethylaminopropyl acetylsalicylate.HCl (50 mg/kg) resulted in a significant reduction (70%) in Aβ 42 concentration in the brain.

TABLE 36

The effect of diethylaminopropyl acetylsalicylate•HCl on the AR42 concentration.

| Group | Control (only water) | diethylaminopropyl acetylsalicylate•HCl (50 mg/kg) |
|---|---|---|
| Aβ 42 concentration (pmol/g tissue) | 7.8 ± 0.4 | 2.3 ± 0.3 |

Studies in the Tg2576 mouse model have indicated that transdermally administered 50 mg/kg of diethylaminopropyl acetylsalicylate.HCl results in a significant reduction (70%) the amount of Aβ detected in the brains of these animals at 2 months administration. To determine if the transdermal administration of diethylaminopropyl acetylsalicylate.HCl has beneficial functional consequences, we tested 2 months of diethylaminopropyl acetylsalicylate.HCl (50 mg/kg) in the transgenic model for Alzheimer's disease in which mice develop learning deficits as amyloid accumulates. The results show that diethylaminopropyl acetylsalicylate.HCl protects transgenic mice from the learning and age-related memory deficits that normally occur in this mouse model for Alzheimer's disease. In the diethylaminopropyl acetylsalicylate.HCl (50 mg/kg) treated group, all mice performed superbly on the radial-arm water-maze test of working memory and untreated transgenic mice show memory deficits. The diethylaminopropyl acetylsalicylate.HCl treated transgenic mice showed cognitive performance superior to that of the control transgenic mice and, ultimately, performed as well as nontransgenic mice. This therapeutic approach can thus prevent and treat Alzheimer's dementia.

Example 18. Anti-Glaucoma Activity of NSAIA-HPP

The ability of diethylaminoethyl acetylsalicylate.HCl to reduce intraocular pressure (IOP) was evaluated in cats with ocular hypertension produced by previously done laser trabeculoplastry. IOP was determined with a pneumatonometer after light corneal anesthesia with dilute proparacaine. 14 Cats were divided into 2 groups. Baseline IOP was determined prior to treatment with the test compound aqueous solution. In group A, 0.5 ml of water was applied transdermally to the area around eye (outside) of cat twice per day for 10 days. In group B, 30 mg/kg of diethylaminoethyl acetylsalicylate.HCl the area around eye (outside) of cat twice per day for 10 days. The results are shown in Table 37.

TABLE 37

Intraocular pressure reduction by diethylaminoethyl acetylsalicylate•HCl.

| Group | Base-line | End of treatment (day 10) |
|---|---|---|
| A (only water) | 23.2 ± 0.6 | 22.2 ± 0.5 |
| B (drug treated) | 24.1 ± 0.7 | 16.1 ± 0.5 |

Diethylaminoethyl acetylsalicylate•HCl shows very strong anti-glaucoma activity in animal model.

Example 19. NSAIA-HPP can be Used to Treat Spinal Cord Injury in which the Healing is Stopped by the Protected Scars Around the Injured Spinal Cord A group of rat was anesthetized with chloral hydrate, the spinal cord of rats was hit to induce spinal cord injury. At the next day, 20 completely paralyzed rats were divided into 2 groups. In group A (n=10), 0.2 ml of pure water was applied transdermally to the area of injury (~2×3 cm$^2$) twice per day for 1 months. In group B (n=10), 5 mg of diethylaminopropyl acetylsalicylate.HCl in 0.2 ml of pure water was applied to the area of injury (~2×3 cm$^2$) twice per day for 1 months. After the treatment, all rats (10/10) in control group (group A) were still completely paralyzed. We were excited to see that all rats (10/10) in the diethylaminopropyl acetylsalicylate.HCl treated group (group B) could walk. 4 Rats of them were completely normal and other 6 rats walked more slowly and less confidently than their injury. This therapeutic approach can treat spinal cord injury in humans and animals.

Example 20. The NSAIA-HPP is Effective in Treating Wounds with Shrunk Scar after Healing 25 Chinese white rabbits were divided into 5 groups and hairs on the back of rabbits were removed (5×5 cm$^2$). After anesthesia, The average scar area of the pro-drugs of NSAIAs (5% aqueous solution of 3-piperidinemethyl 2-(p-isobutylphenyl) propionate.HCl, diethylaminoethyl 1-methyl-5-(4-methylbenzoyl)-1H-pyrrole-2-acetate.HCl, diethylaminoethyl 5-(4-Chlorobenzoyl)-1,4-dimethyl-1H-pyrrole-2-acetate.HCl, diethylaminoethyl 1,8-diethyl-1,3,4,9-tetrahydropyrano-[3,4-b]indole-1-acetate.HCl, diethylaminoethyl 2-amino-3-(4-bromo-benzoyl)benzeneacetate.HCl, diethylaminoethyl 3-chloro-4-(2-propenyloxy)benzeneacetate.HCl, diethylaminoethyl 1-(4-chlorobenzoyl-5-methoxy-2-methyl-1H-indole-3-acetoxyacetate.HCl, diethylaminoethyl 4-(4-chlorophenyl)-2-phenyl-5-thiazoleacetate.HCl, or diethylaminoethyl 3-(4-chlorophenyl)-1-phenyl-1H-pyrazole-4-acetate.HCl were applied to the nearby area of wounds) areas treated rabbits is only a third of that of the control rabbits from same size cuts wounds in the Chinese white rabbit model and the scars are as soft as normal unscarred tissues.

The invention claimed is:

1. A method for treating an ibuprofen-treatable condition in a subject in need thereof comprising:
transdermally administering to the subject a pharmaceutical composition,
wherein the ibuprofen-treatable condition is selected from fever, pain, and inflammation; and
wherein the pharmaceutical composition comprises a therapeutically effective amount of at least one compound of Structure 1:

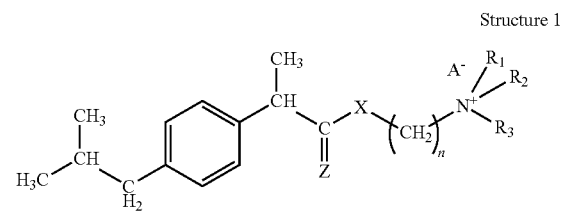

Structure 1 or a stereoisomers, wherein:

$R_1$ and $R_2$ are independently selected from H, $C_1$-$C_{12}$ alkyl, $C_1$-$C_{12}$ alkyloxyl, $C_2$-$C_{12}$ alkenyl, $C_2$-$C_{12}$ alkynyl, and aryl;

$R_3$ is H;

X is O, S or NH;

Z is S or O;

$A^-$ is a pharmaceutically acceptable counter ion; and n=1, 2, 3, 4, 5, 6, 7, 8, 9, or 10.

2. The method according to claim 1, wherein $A^-$ is selected from $Cl^-$, $Br^-$, $F^-$, $I^-$, and $AcO^-$.

3. The method according to claim 1, wherein the condition treatable by ibuprofen is rheumatoid arthritis or osteoarthritis.

4. The method according to claim 1, wherein the composition is formulated as a solution, suspension, spray, lotion, emulsion or gel.

5. The method according to claim 4, wherein the composition is formulated as a spray.

6. The method according to claim 1, wherein the subject is a human or animal.

7. The method according to claim 1, wherein the compound is:

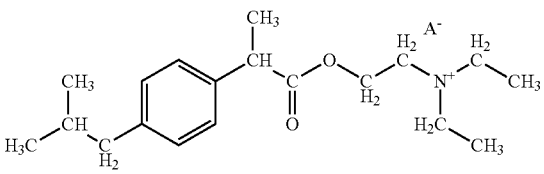

wherein $A^-$ is selected from $Cl^-$, $Br^-$, $F^-$, $I^-$, $AcO^-$, acetylsalicylate, oxalate and citrate.

8. The method according to claim 7, wherein $A^-$ is $Cl^-$ or $Br^-$.

9. The method according to claim 1, wherein the composition further comprises a pharmaceutically acceptable carrier selected from buffered saline, water, acetone and alcohol.

10. The method according to claim 1, wherein the compound is:

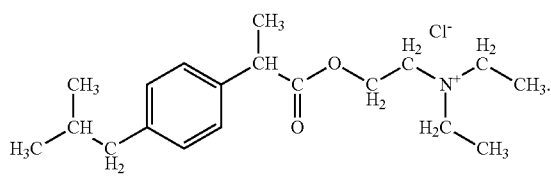 [SMILES: CC[NH+](CC)CCOC(=O)C(C)c1ccc(CC(C)C)cc1 ; [Cl-]]

11. The method according to claim 1, wherein the compound is selected from:
dipropylaminoethyl 2-(p-isobutylphenyl) propionate.AcOH;
diethylaminoethyl 2-(p-isobutylphenyl) propionate.AcOH;
N-dimethylaminopropyl 2-(p-isobutylphenyl) propionamide.AcOH;
S-diethylaminoethyl 2-(p-isobutylphenyl) thiopropionat.AcOH;
N-dimethylaminoethyl 2-(p-isobutylphenyl) propionamide.AcOH;
S-dimethylaminoethyl 2-(p-isobutylphenyl) thiopropionate.AcOH;
2-(Diethylamino)ethyl-2-(4-isobutylphenyl)propionate hydrochloride; and
dimethylaminoethyl 2-(p-isobutylphenyl) propionate.AcOH.

12. A method for treating an ibuprofen-treatable condition in a subject in need thereof comprising:
applying to the subject a transdermal therapeutic application system,
wherein the ibuprofen-treatable condition is selected from fever, pain and inflammation; and
wherein the system is a bandage or a patch comprising an active substance-containing matrix layer and an impermeable backing layer, and
wherein the transdermal therapeutic application system comprises a pharmaceutical composition comprising at least one compound of Structure 1:

Structure 1

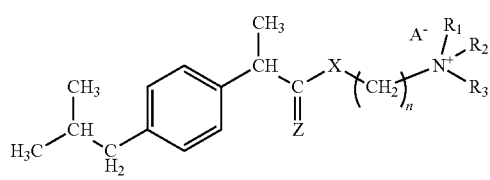

or a stereoisomer, wherein:
$R_1$ and $R_2$ are independently selected from H, $C_1$-$C_{12}$ alkyl, $C_1$-$C_{12}$ alkyloxyl, $C_2$-$C_{12}$ alkenyl, $C_2$-$C_{12}$ alkynyl, and aryl;
$R_3$ is H;
X is O, S or NH;
Z is S or O;
$A^-$ is a pharmaceutically acceptable counter ion; and
n=1, 2, 3, 4, 5, 6, 7, 8, 9, or 10.

13. The method according to claim 12, wherein the system comprises an active substance reservoir which has a permeable bottom facing the skin.

14. The method according to claim 12, wherein the system is an active substance reservoir comprising a permeable bottom facing the skin, wherein by controlling the rate of release, the system enables ibuprofen to reach therapeutic blood levels to increase effectiveness and reduce the side effects of ibuprofen.

15. The method according to claim 12, wherein the composition further comprises a pharmaceutically acceptable carrier selected from buffered saline, water, acetone and alcohol.

16. The method according to claim 12 wherein the composition is formulated as a solution, suspension, spray, lotion, emulsion or gel.

17. The method according to claim 12, wherein the condition treatable by ibuprofen is rheumatoid arthritis or osteoarthritis.

18. The method according to claim 12, wherein the compound is selected from:
dipropylaminoethyl 2-(p-isobutylphenyl) propionate.AcOH;
diethylaminoethyl 2-(p-isobutylphenyl) propionate.AcOH;
N-dimethylaminopropyl 2-(p-isobutylphenyl) propionamide.AcOH;
S-diethylaminoethyl 2-(p-isobutylphenyl) thiopropionat.AcOH;
N-dimethylaminoethyl 2-(p-isobutylphenyl) propionamide.AcOH;
S-dimethylaminoethyl 2-(p-isobutylphenyl) thiopropionate.AcOH;
2-(Diethylamino)ethyl-2-(4-isobutylphenyl)propionate hydrochloride; and
dimethylaminoethyl 2-(p-isobutylphenyl) propionate.AcOH.

19. The method according to claim 12, wherein $A^-$ is selected from $Cl^-$, $Br^-$, $F^-$, $I^-$, $AcO^-$, acetylsalicylate, citrate, and oxalate.

20. The method according to claim 12, wherein the compound is:

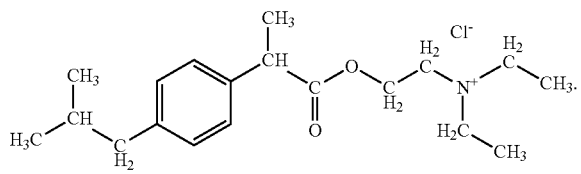 [SMILES: CC[NH+](CC)CCOC(=O)C(C)c1ccc(CC(C)C)cc1 ; [Cl-]]

* * * * *